United States Patent
Polinsky et al.

(10) Patent No.: US 10,208,032 B2
(45) Date of Patent: Feb. 19, 2019

(54) BENZAMIDE AND NICOTINAMIDE COMPOUNDS AND METHODS OF USING SAME

(71) Applicant: Onco Tartis Inc., Buffalo, NY (US)

(72) Inventors: Alexander Polinsky, Brookline, MA (US); Lioubov Korotchkina, Amherst, NY (US); Slavoljub Vujcic, Amherst, NY (US); Olga Chernova, Orchard Park, NY (US)

(73) Assignee: ONCOTARTIS INC., Buffalo, NY (US)

( * ) Notice: Subject to any disclaimer, the term of this patent is extended or adjusted under 35 U.S.C. 154(b) by 0 days.

(21) Appl. No.: 15/107,792

(22) PCT Filed: Dec. 23, 2014

(86) PCT No.: PCT/US2014/072150
§ 371 (c)(1),
(2) Date: Jun. 23, 2016

(87) PCT Pub. No.: WO2015/100322
PCT Pub. Date: Jul. 2, 2015

(65) Prior Publication Data
US 2016/0347748 A1    Dec. 1, 2016

Related U.S. Application Data

(60) Provisional application No. 61/920,672, filed on Dec. 24, 2013.

(51) Int. Cl.
| | | |
|---|---|---|
| *C07D 401/12* | (2006.01) | |
| *C07D 403/12* | (2006.01) | |
| *C07D 471/04* | (2006.01) | |
| *A61K 31/4155* | (2006.01) | |
| *C07D 231/12* | (2006.01) | |
| *A61K 31/5355* | (2006.01) | |
| *C07D 401/14* | (2006.01) | |
| *C07D 405/14* | (2006.01) | |
| *C07D 413/14* | (2006.01) | |
| *C07D 233/61* | (2006.01) | |
| *C07D 403/14* | (2006.01) | |
| *C07D 413/12* | (2006.01) | |
| *C07D 417/12* | (2006.01) | |
| *C07D 417/14* | (2006.01) | |
| *C07D 451/06* | (2006.01) | |
| *C07D 487/08* | (2006.01) | |
| *C07D 233/64* | (2006.01) | |

(52) U.S. Cl.
CPC ........ *C07D 471/04* (2013.01); *A61K 31/4155* (2013.01); *A61K 31/5355* (2013.01); *C07D 231/12* (2013.01); *C07D 233/61* (2013.01); *C07D 233/64* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C07D 413/14* (2013.01); *C07D 417/12* (2013.01); *C07D 417/14* (2013.01); *C07D 451/06* (2013.01); *C07D 487/08* (2013.01)

(58) Field of Classification Search
CPC . C07D 401/12; C07D 403/12; A61K 31/4439
USPC ................ 546/275.4; 514/341; 548/312.4
See application file for complete search history.

(56) References Cited

U.S. PATENT DOCUMENTS

| | | |
|---|---|---|
| 4,916,145 A | 4/1990 | Tilley et al. |
| 5,557,434 A | 9/1996 | Winker |
| 5,892,098 A | 4/1999 | Christensen, IV et al. |
| 6,103,720 A | 8/2000 | Lubisch et al. |
| 6,214,822 B1 | 4/2001 | Treiber et al. |
| 6,352,981 B1 | 3/2002 | Treiber et al. |
| 6,451,810 B1* | 9/2002 | Coleman ............ A61K 31/4745 514/293 |
| 7,326,791 B2 | 2/2008 | Gillard et al. |
| 8,183,239 B2 | 5/2012 | Bonaventure et al. |
| 2002/0103203 A1 | 8/2002 | Bender |
| 2003/0144274 A1 | 7/2003 | Bunker et al. |
| 2008/0132459 A1 | 6/2008 | Moradei et al. |
| 2008/0221195 A1* | 9/2008 | Wortmann ........... C07D 209/16 514/415 |
| 2009/0215823 A1 | 8/2009 | Roulston |

(Continued)

FOREIGN PATENT DOCUMENTS

| | | |
|---|---|---|
| CN | 1353609 A | 6/2002 |
| JP | H10195063 A | 7/1998 |
| JP | 2008530218 A | 8/2008 |

(Continued)

OTHER PUBLICATIONS

Loaiza, P.R. et al.: Click chemistry based solid phase supported synthesis of dopaminergic phenylacetylenes. Bioorg. & Medicnal Chem., vol. 15, pp. 7248-7257, 2007.*

(Continued)

*Primary Examiner* — Charanjit Aulakh
(74) *Attorney, Agent, or Firm* — Hodgson Russ LLP

(57) ABSTRACT

The present disclosure provides benzamide and nicotinamide compounds and pharmaceutical uses of the compounds. The compounds can be used to treat, for example, cancers such hematopoietic cancers (e.g., leukemia). The preferred compounds of the invention contain a phenylethynyl moiety as well as an amine-based heterocyclyl or heteroaryl moiety attached to the benzamide or nicotinamide compound.

12 Claims, 2 Drawing Sheets

(56) References Cited

U.S. PATENT DOCUMENTS

2011/0053975 A1 3/2011 Tazi et al.
2011/0212969 A1 9/2011 Blackburn et al.

FOREIGN PATENT DOCUMENTS

| JP | 2013509444 A | 3/2013 |
|---|---|---|
| WO | 02/078702 | 10/2002 |
| WO | 2006044823 A2 | 4/2006 |
| WO | 2009003998 A2 | 1/2009 |
| WO | 2010104307 A2 | 9/2010 |
| WO | 2010124047 A1 | 10/2010 |
| WO | 2013009830 A1 | 1/2013 |
| WO | 2014049578 A1 | 4/2014 |
| WO | 2014145022 A1 | 9/2014 |

OTHER PUBLICATIONS

Wei et al., Next-Generation NAMPT Inhibitors for All Identified by Sequential High-Throughput Phenotypic Chemical and Functional Genomic Screens, Blood, vol. 122, No. 21, 171. Nov. 2013.

Matheny et al., Next-Generation NAMPT Inhibitors Identified by Sequential High-Throughput Phenotypic Chemical and Functional Genomic Screens, Chemistry & Biology, vol. 20, No. 11, pp. 1352-1363. Nov. 2013.

Tilley, J.W., et al., Biphenylcarboxamide Derivatives as Antagonists of Platelet-Activating Factor, J. Med. Chem., 1989, vol. 32, pp 1814-1820.

CAS Reg No. 1318008-21-7, STN Entry Date Aug. 15, 2011; Benzamide, 4-(3,5-dimethyl-1H-pyrazol-1-yl)-N-[1-(5-phenyl-1Himidazol-2-yl)propyl]—Aug. 15, 2011.

CAS Reg No. 880418-34-8, STN Entry Date Apr. 14, 2006; Benzamide, 3-iodo-N-[1-(2-methylpropyl)-1H-pyrazol-5-yl]—Apr. 14, 2006.

CAS Reg No. 93669-29-5, STN Entry Date Dec. 18, 1984; Benzamide, 3-bromo-N-[3-(1H-imidazol-1-yl)propyl]—Dec. 18, 1984.

CAS Reg No. 93-98-1, STN Entry Date Nov. 16, 1984; Benzamide, N-phynyl—Nov. 16, 1984.

CAS Reg No. 1071925-58-0, STN Entry Date Nov. 11, 2008; Benzamide, N-phynl-4-(3-pyridinyl)—Nov. 11, 2008.

\* cited by examiner

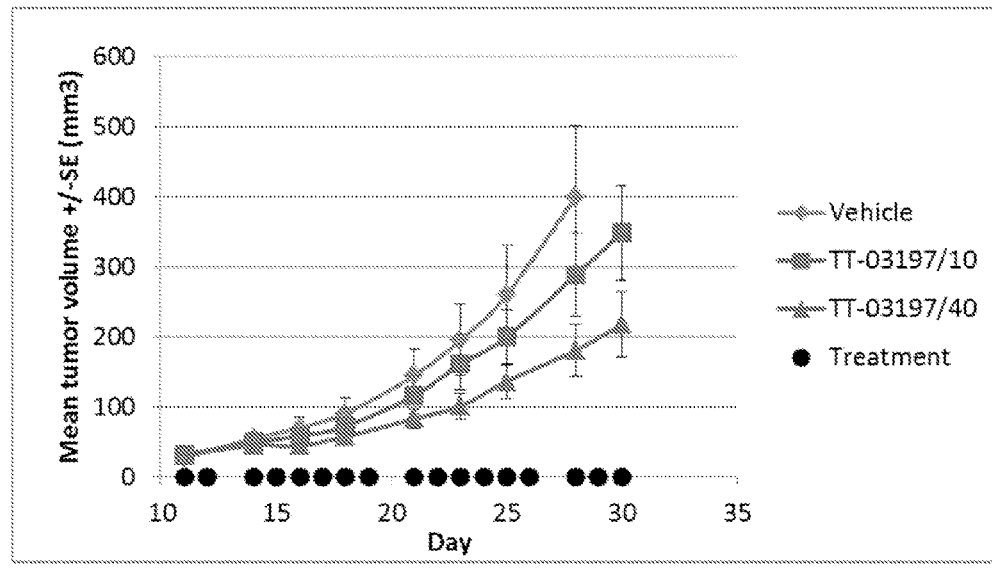
Figure 1
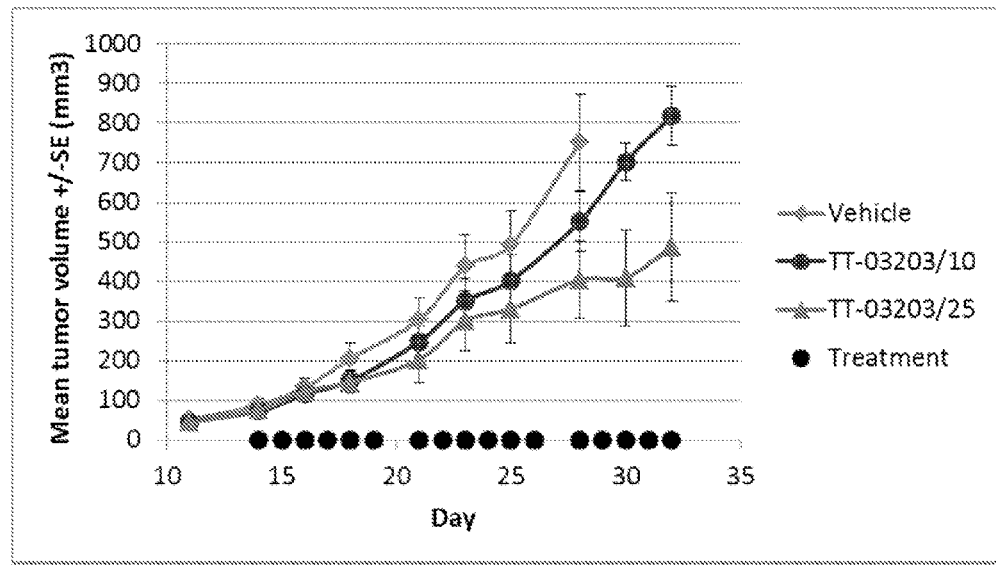
Figuure 2

BENZAMIDE AND NICOTINAMIDE COMPOUNDS AND METHODS OF USING SAME

CROSS-REFERENCE TO RELATED APPLICATIONS

This application claims priority to provisional patent application No. 61/920,672 filed Dec. 24, 2014, the disclosure of which is hereby incorporated by reference.

BACKGROUND OF THE DISCLOSURE

Cancer continues to be a major health problem in the United States and world-wide. In 2014, in the United States, there are expected to be more than 1.5 million new cancer cases and more than 580,000 cancer deaths. Cancer-related deaths account for nearly ¼ of all deaths in the U.S. Most common childhood cancers are leukemias, lymphomas, brain tumors, and bone cancer, while adult cancers are more likely to be lung, colon, breast, prostate, and pancreas. Although enhanced early-stage tumor diagnosis and management have significantly increased patient survival, development and discovery of new anticancer therapies are still needed, in part because some patients exhibit insensitivity to current anticancer drugs or develop drug-resistance after a period of treatment.

Leukemia is one of the most common hematologic malignancies in humans which usually begins in the bone marrow and results in high numbers of abnormal white blood cells. Among acute leukemia, acute lymphoblastic leukemia (ALL) is a predominant cause of childhood leukemia, while acute myeloid leukemia (AML) represents about 90% of all adult leukemia and the second most common pediatric leukemia. While imatinib has improved therapy of chronic myelogenic leukemia due to specificity to its target the bcr-abl fusion gene product, the current treatment of ALL and AML includes cells proliferation affecting drugs that are not selective for hematologic malignancies, such as vincristine, anthracycline, cyclophosphamide etc. Such treatments often lead to severe side effects, development of resistance, and low survival rates.

BRIEF SUMMARY OF THE DISCLOSURE

In an aspect, the present disclosure provides benzamide and nicotinamide compounds. The compounds can be used to selectively kill cancer cells (e.g., blood cancers). The compounds can be present In various embodiments, the compounds have the following structure:

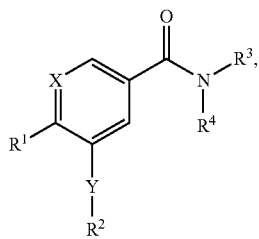

In these various embodiments, X is a carbon atom or nitrogen atom, Y is a single or triple bond, $R^1$ is selected from the group consisting of a hydrogen atom, a substituted or unsubstituted five to eight membered heterocyclic ring, six membered aryl ring, five or six membered heteroaryl ring, $C_3$ to $C_8$ cycloalkyl group, $C_1$ to $C_6$ alkyl group,

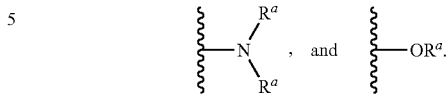

$R^2$ is selected from the group consisting of a hydrogen atom, a substituted or unsubstituted five or six membered heteroaryl ring, a five or six membered aryl ring, $C_3$ to $C_6$ cycloalkyl group, eight to ten membered heterocyclic ring system, and

$R^3$ is selected from the group consisting of a substituted or unsubstituted $C_2$ to $C_8$ alkylheteroaryl group, $C_2$ to $C_8$ alkyleneheteroaryl group, $C_6$ to $C_{10}$ aryl group, $C_2$ to $C_5$ heteroaryl group, $C_7$ to $C_{13}$ alkylaryl group, $C_7$ to $C_{13}$ alkylenearyl group, $C_2$ to $C_8$ alkylhetrocyclyl group, $C_2$ to $C_8$ alkylenehetrocyclyl group, $C_4$ to $C_8$ alkylcycloalkyl group, $C_4$ to $C_8$ alkylenecycloalkyl group, or taken together with $R^4$ and the nitrogen atom to which they are attached form a five to seven membered substituted or unsubstituted heterocyclic ring. $R^4$ is selected from the group consisting of a hydrogen atom and substituted or unsubstituted $C_1$ to $C_6$ alkyl group. $R^a$ is a substituted or unsubstituted $C_1$ to $C_6$ alkyl group or $C_5$ to $C_6$ aryl group.

In an aspect, the present invention provides methods of using the compounds. The compounds can be used, for example, to treat cancer.

In an embodiment, a method of treating cancer in an individual diagnosed with or suspected of having cancer comprises administering to the individual a therapeutically effective amount of one or more of the compounds. In an embodiment, the cancer is a hematopoietic cancer. The hematopoietic cancer is, for example, leukemia.

BRIEF DESCRIPTION OF THE FIGURES

FIG. 1. Example of growth of tumors in MV4-11 xenograft model of AML in SCID mice treated with vehicle control and TT-03197 at 10 mg/kg and 40 mg/kg administered intraperitoneally. Mice were treated 6 days per week as indicated on the figure. Results are Mean±SE (n=14-16).

FIG. 2. Example of growth of tumors in MV4-11 xenograft model of AML in SCID mice treated with vehicle control and TT-03203 at 10 mg/kg and 25 mg/kg administered orally. Mice were treated 6 days per weeks as indicated on the figure. Results are Mean±SE (n=17-20)

DETAILED DESCRIPTION OF THE DISCLOSURE

Figure 3:
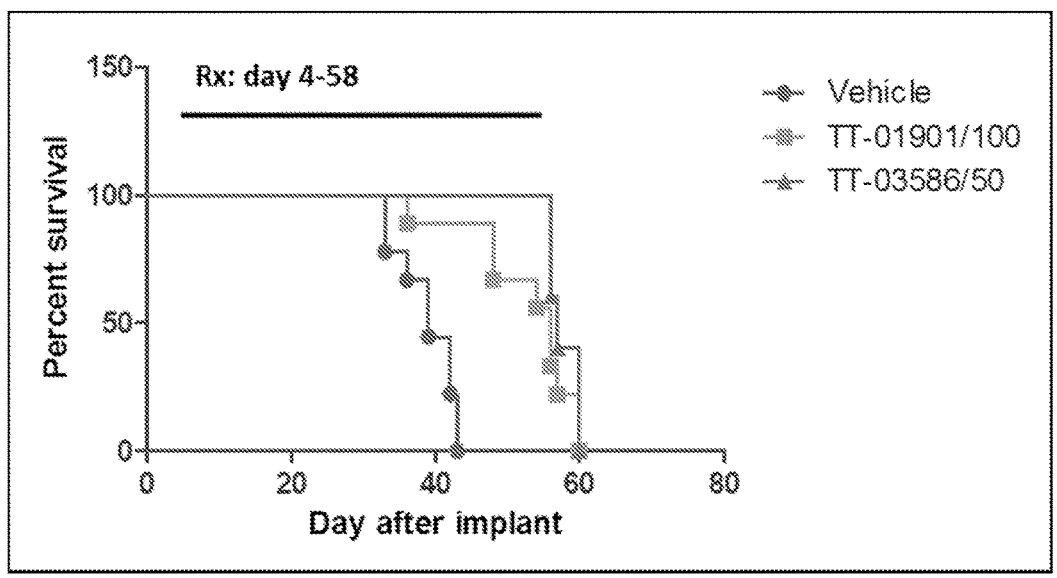
FIG. 3. Example of survival of SCID mice inoculated via IV route with MV4-11 cells and treated via oral gavage with vehicle control, TT-01901 at 100 mg/kg and TT-03586 at 50 mg/kg 6 days per week on days 4-58. Mice were sacrificed according to IACUC regulations after losing more than 20% of body weight or becoming moribund and paralyzed.

In an aspect, the present disclosure provides benzamide and nicotinamide compounds. The compounds can be used to selectively kill cancer cells (e.g., blood cancers).

In an embodiment, the present disclosure provides compounds having the following structure (I):

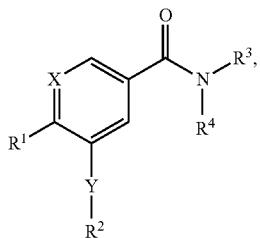 (I)

where X is a carbon atom or nitrogen atom, Y is a single or triple bond, $R^1$ is selected from the group consisting of a hydrogen atom, a substituted or unsubstituted five to eight membered heterocyclic ring, six membered aryl ring, five or six membered heteroaryl ring, $C_3$ to $C_8$ cycloalkyl group, $C_1$ to $C_6$ alkyl group,

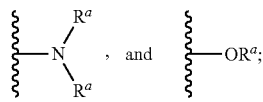

$R^2$ is selected from the group consisting of a hydrogen atom, a substituted or unsubstituted five or six membered heteroaryl ring, a five or six membered aryl ring, $C_3$ to $C_6$ cycloalkyl group, eight to ten membered heterocyclic ring system, and

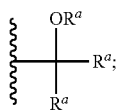

$R^3$ is selected from the group consisting of a substituted or unsubstituted $C_2$ to $C_8$ alkylheteroaryl group, $C_2$ to $C_8$ alkyleneheteroaryl group, $C_6$ to $C_{10}$ aryl group, $C_2$ to $C_5$ heteroaryl group, $C_7$ to $C_{13}$ alkylaryl group, $C_7$ to $C_{13}$ alkylenearyl group, $C_2$ to $C_8$ alkylhetrocyclyl group, $C_2$ to $C_8$ alkylenehetrocyclyl group, $C_4$ to $C_8$ alkylcycloalkyl group, $C_4$ to $C_8$ alkylenecycloalkyl group, or taken together with $R^4$ and the nitrogen atom to which they are attached form a five to seven membered substituted or unsubstituted heterocyclic ring; $R^4$ is selected from the group consisting of a hydrogen atom and substituted or unsubstituted $C_1$ to $C_6$ alkyl group; and $R^a$ is a substituted or unsubstituted $C_1$ to $C_6$ alkyl group or $C_5$ to $C_6$ aryl group.

As used herein, the term "alkyl group," unless otherwise stated, refers to branched or unbranched hydrocarbons. Examples of such alkyl groups include methyl groups, ethyl groups, propyl groups, butyl groups, isopropyl groups, tert-butyl groups, and the like. For example, the alkyl group can be a $C_1$ to $C_6$ alkyl group including all integer numbers of carbons and ranges of numbers of carbons therebetween. The alkyl group can be unsubstituted or substituted with various substituents (e.g., as described herein).

As used herein, the term "alkylene," unless otherwise stated refers to an alkyl group containing one or more double bonds.

As used herein, the term "aryl group," unless otherwise stated refers to an aromatic carbocyclic group of 6 carbon atoms having a single ring (e.g., phenyl). The aryl group is substituted with 0, 1, 2, 3, 4, or 5 substituents. The aryl group can be unsubstituted or substituted with various substituents (e.g., as described herein).

As used herein, the term "heteroaryl group," unless otherwise stated refers to an aromatic cyclic ring (i.e., fully unsaturated) having 1, 2, 3, or 4 carbon atoms and 1, 2, 3, or 4 heteroatoms selected from oxygen, nitrogen, and sulfur. Examples of heteroaryl groups include thiophene, furan, and pyridine. The heteroaryl group is substituted with 0, 1, 2, 3, or substituents. The heteroaryl group can be unsubstituted or substituted with various substituents as described herein.

As used herein, the term "cycloalkyl group," unless otherwise stated, refers to a to a saturated or partially unsaturated carbocyclic group (not aromatic) of from 3 carbons to 6 carbons having a single cyclic ring or multiple condensed rings. For example, the cycloalkyl groups can be cyclopropane, cyclobutane, cyclopentane, cyclohexane, cyclohexene, cycloheptane, cycloheptene, bicyclo[2.1.1]hexane, bicyclo[2.2.1]heptane, bicyclo[2.2.2]octane, bicyclo[3.3.0]octane, bicyclo[4.4.0]octane, and the like. Cycloalkyl also includes carbocyclic groups to which is fused an aryl or heteroaryl ring, for example indane and tetrahydronaphthalene. The cycloalkyl group can be unsubstituted or substituted with various substituents (e.g., as described herein).

As used herein, the term "heterocycle" or "heterocyclic ring," unless otherwise stated, refers to a cyclic compound having a ring where at least one or more of the atoms forming the ring is a heteroatom (e.g., oxygen, nitrogen, sulfur, etc.). The heterocyclic ring can be aromatic or nonaromatic, and include compounds that are saturated, partially unsaturated, and fully unsaturated. Examples of such groups include azetidine, pyrrolidine, piperdine, azepane, azocane, dihydropyrdinone, dihydropyridazinone, dihydrooxepinone, dihydroazepinone, pyrazolone, pyrrolone, isoxazolone, pyranone, dihydrodiazepineone, furan, thiophene, oxazole, isoxazole, thiazole, oxadiazole, thiadiazole, triazole, tetrazole, oxazoline, lactam, lactone, dihydrofuran, tetrahydrofuran, furanone, oxazolone, pyridinone, pyrimidinone, dihydropyridazine, pyranone, oxazinone, and the like. For example, the heterocyclic ring can be a 3, 4, 5, 6, 7, 8, 9 or 10 membered ring containing a number of carbon atoms ranging between 1 and 7 and a number of heteroatoms ranging between 1 and 7. The ring can be bonded to other rings to form ring systems. The heterocyclic ring can be unsubstituted or substituted with various substituents (e.g., as described herein).

As used herein, the term "alkylheteroaryl group," unless otherwise stated refers to an alkyl group, as defined herein, linked to a heteroaryl group as defined herein.

As used herein, the term "alkyleneheteroaryl group," unless otherwise stated refers to an alkylene group, as defined herein, linked to a heteroaryl group as defined herein.

As used herein, the term "alkylaryl group," unless otherwise stated refers to an alkyl group, as defined herein, linked to a aryl group as defined herein.

As used herein, the term "alkylenearyl group," unless otherwise stated refers to an alkylene group, as defined herein, linked to a aryl group as defined herein.

As used herein, the term "alkylhetrocyclyl group," unless otherwise stated refers to an alkyl group, as defined herein, linked to a heterocyclic ring as defined herein.

As used herein, the term "alkylenehetrocyclyl group," unless otherwise stated refers to an alkylene group, as defined herein, linked to a heterocyclic ring as defined herein.

As used herein, the term "alkylcycloalkyl group," unless otherwise stated refers to an alkyl group, as defined herein, linked to a cycloalkyl group as defined herein.

As used herein, the term "alkylenecycloalkyl group," unless otherwise stated refers to an alkylene group, as defined herein, linked to a cycloalkyl group as defined herein.

As used herein, the term "substituents," unless otherwise stated refer to one or more of the following groups: alkyl groups, amines, alcohol groups, alkoxy groups, halogen atoms, alkylhalides, alkylheteroaryl groups, alkoxy groups, hydroxyl groups, alkylalcohols, alkyl ethers, alkylamides, alkylamines, ketones, carbamates, PEG (polyethylene glycol) groups, cycloalkyl groups, alkyl esters, heteroaryl groups, aryl groups, nitriles, azido groups, amides, alkyenyl groups, alkynyl groups, thiol groups, heterocyclyl groups, alkyleneheteroaryl groups, alkylaryl groups, alkylenearyl groups, alkylhetrocyclyl groups, alkylenehetrocyclyl groups, alkylcycloalkyl groups, and alkylenecycloalkyl groups.

In an embodiment, the disclosure provides compounds having the following structure (II):

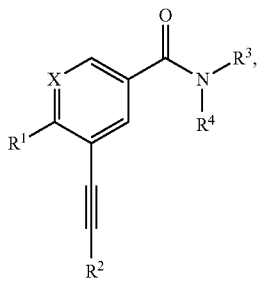

(II)

where X, R$^1$, R$^2$, R$^3$, and R$^4$ are as defined herein.

In an embodiment, the disclosure provides compounds having the following structure (III):

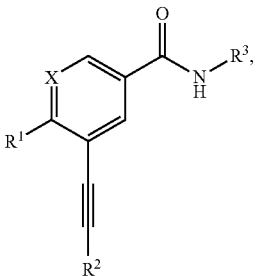

(III)

where X, R$^1$, R$^2$, and R$^3$ are as defined herein.

In an embodiment, the disclosure provides compounds having the following structure (IV):

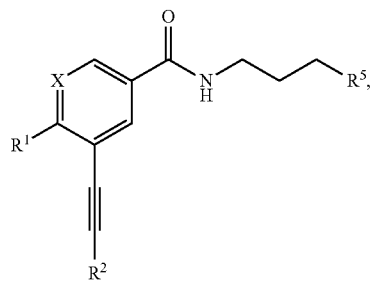

(IV)

where R$^5$ is a C$_2$ to C$_5$ heteroaryl group and X, R$^1$, and R$^2$ are as defined herein.

In an embodiment, the disclosure provides compounds having the following structure (V):

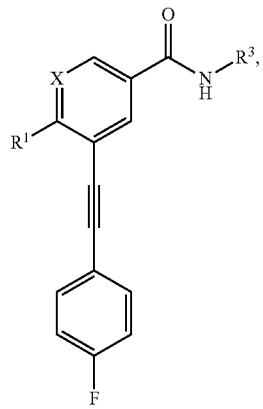

(V)

where X, R$^1$, and R$^3$ are as defined herein.

In an embodiment, the disclosure provides compounds having the following structure (VI):

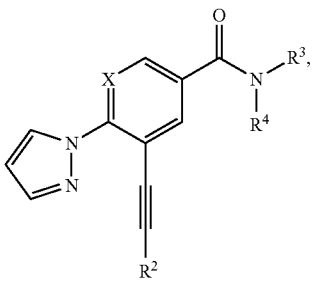

(VI)

where X, R$^2$, R$^3$, and R$^4$ are as defined herein.

In an embodiment, the disclosure provides compounds having the following structures (VII) and (VIII):

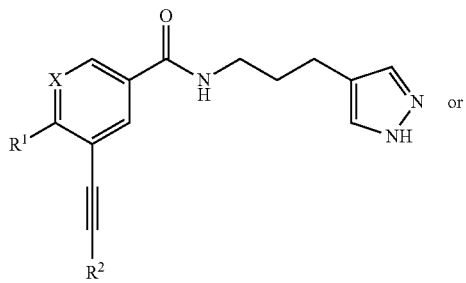
(VII)

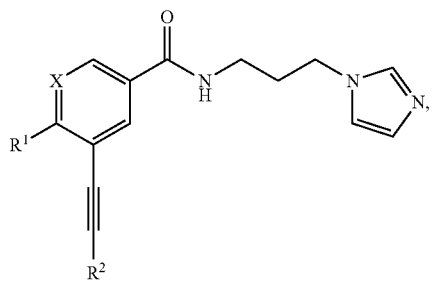
(VIII)

where X, R¹, and R² are as defined herein.

In an embodiment, the disclosure provides compounds having the following structures (IX) and (X):

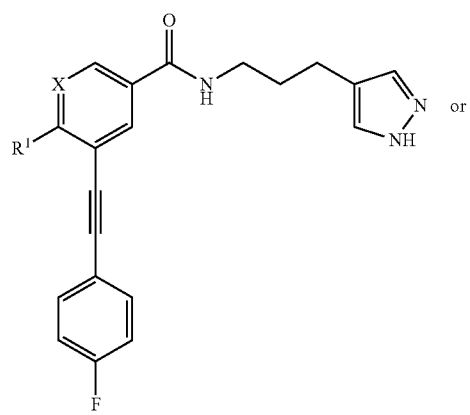
(IX)

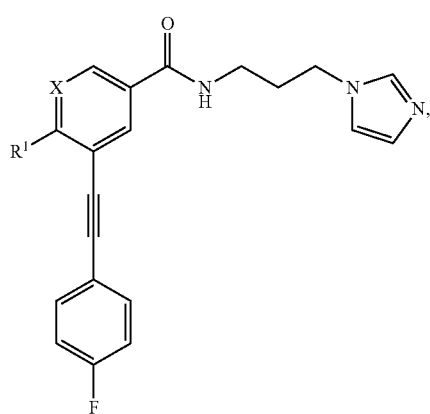
(X)

where X and R¹ are as defined herein.

In an embodiment, the disclosure provides compounds having the following structures (XI) and (XII):

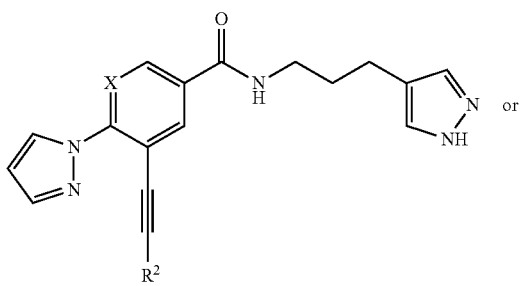
(XI)

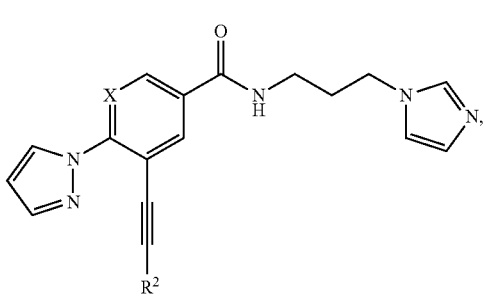
(XII)

where X and R² are as defined herein.

In certain embodiments, R¹ is selected from the following groups:

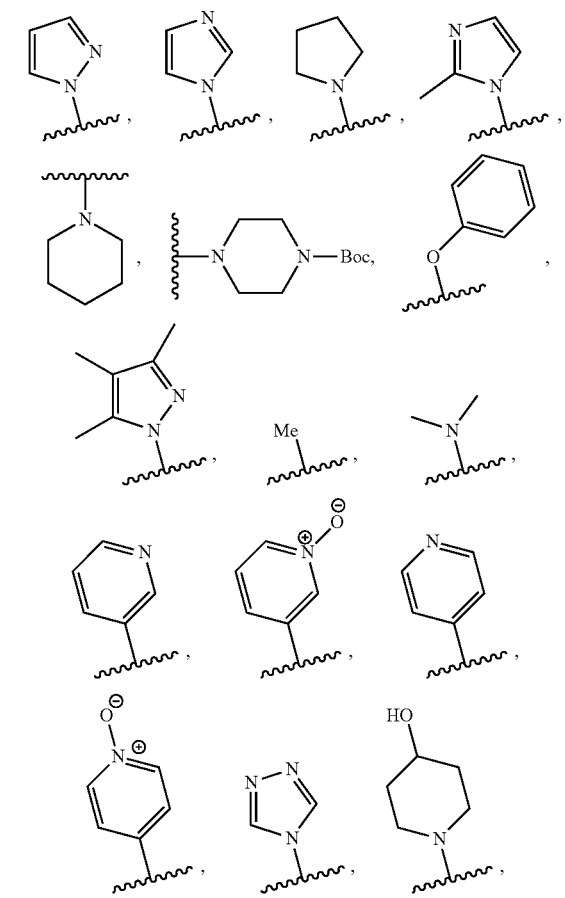

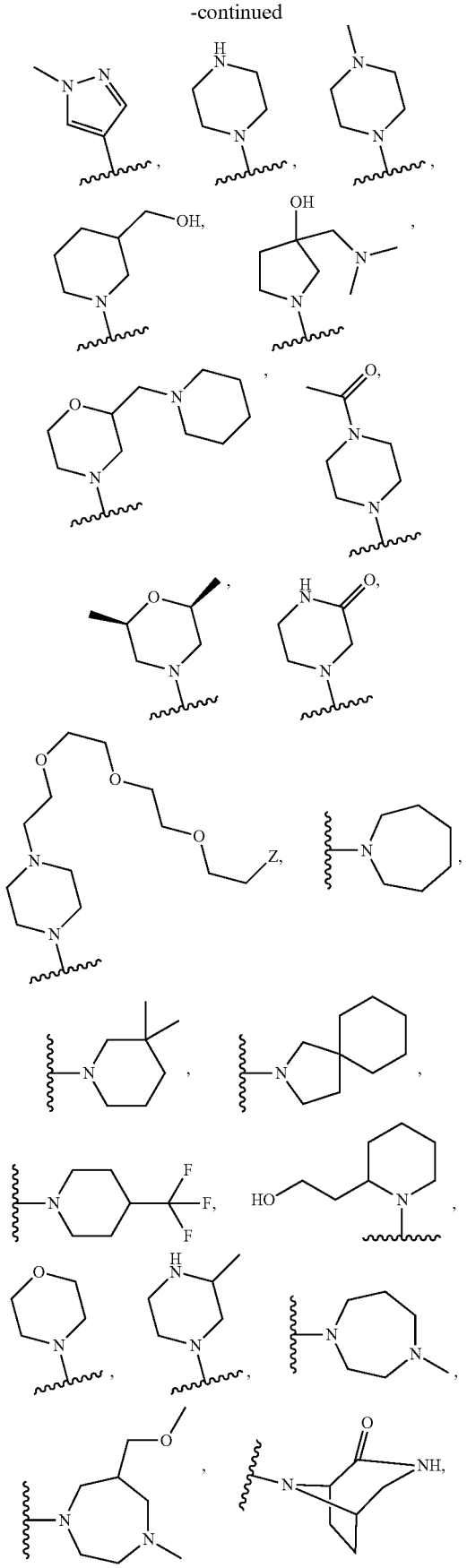
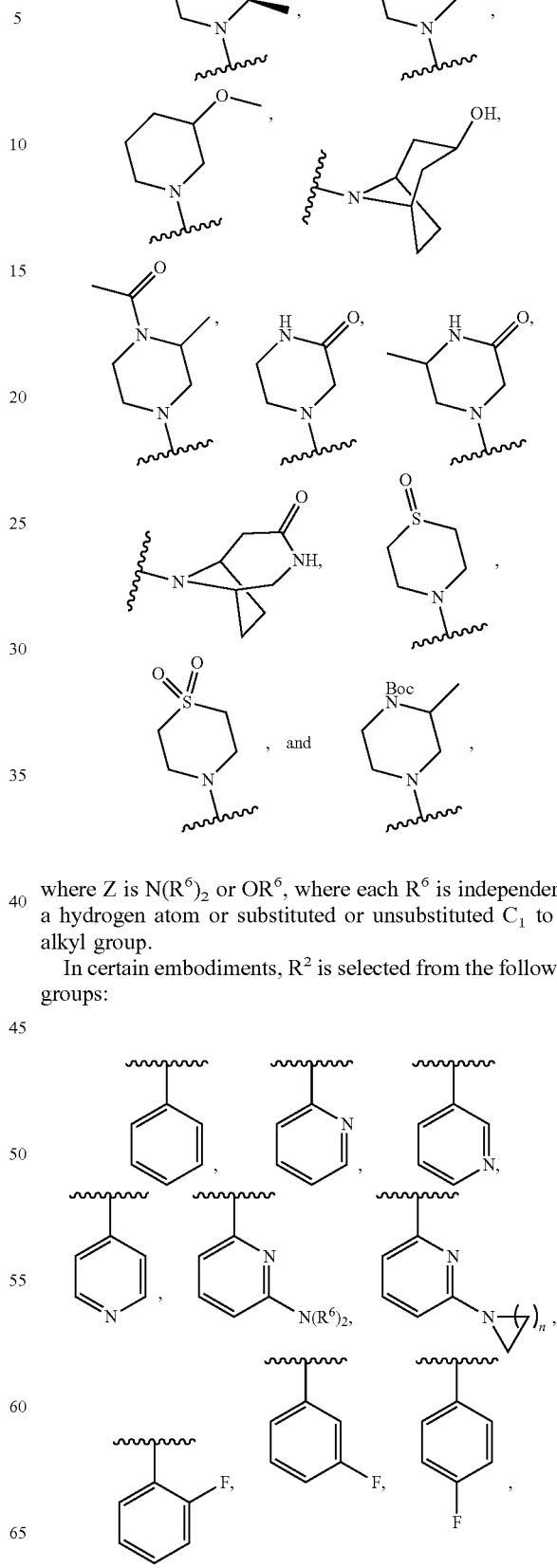
where Z is $N(R^6)_2$ or $OR^6$, where each $R^6$ is independently a hydrogen atom or substituted or unsubstituted $C_1$ to $C_6$ alkyl group.
In certain embodiments, $R^2$ is selected from the following groups:

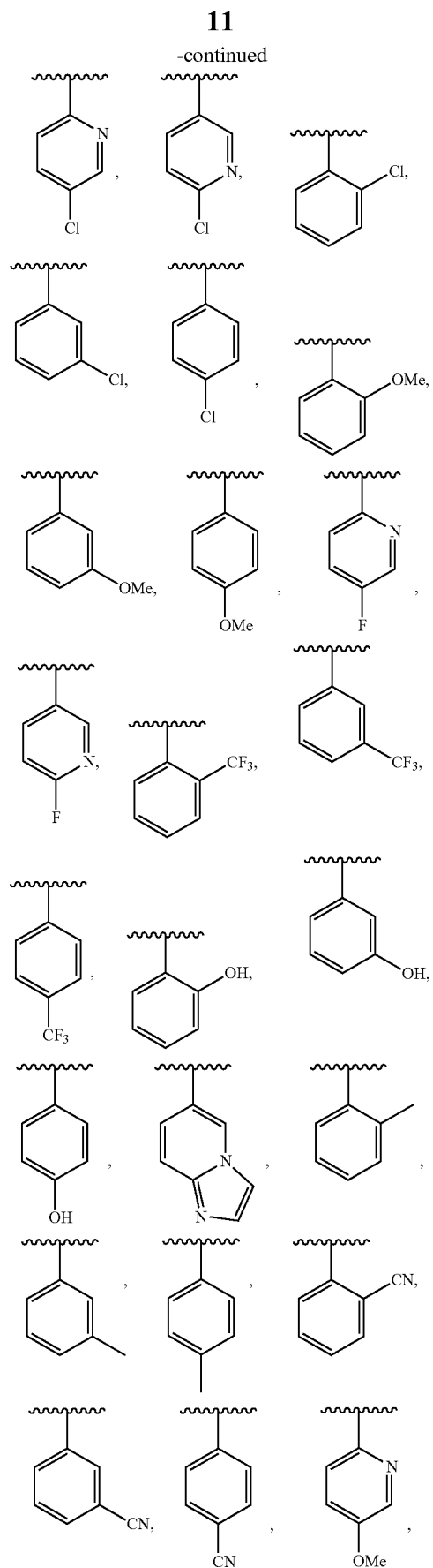
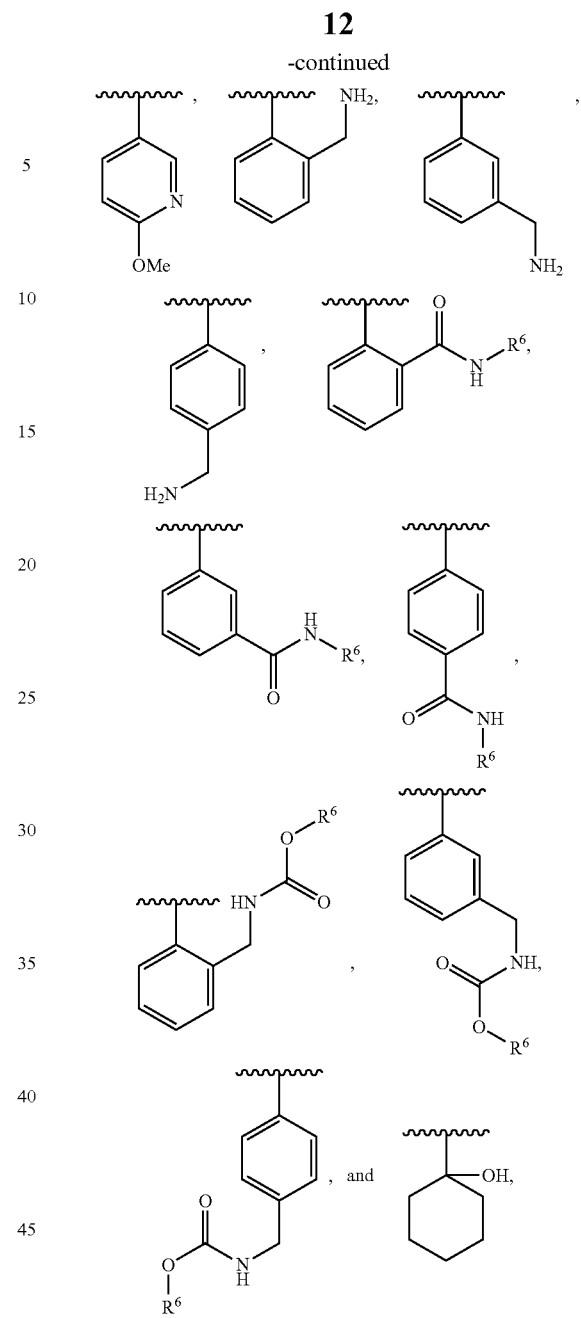
where each $R^6$ is independently a hydrogen atom or substituted or unsubstituted $C_1$ to $C_6$ alkyl group and n is 1, 2, 3, or 4.
In certain embodiments, the ring formed by $R^3$—N—$R^4$ is selected from the following structures:
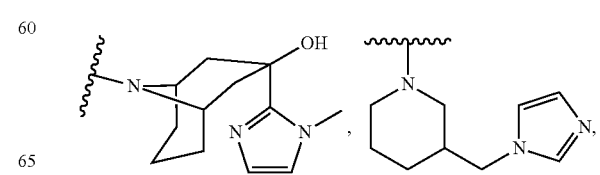

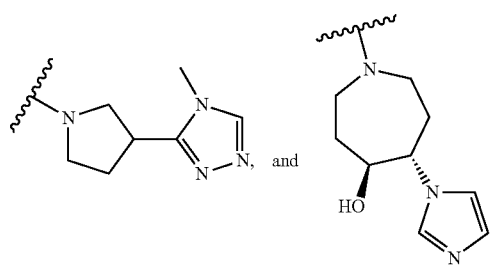
In certain embodiments, R³ is selected from the following groups:
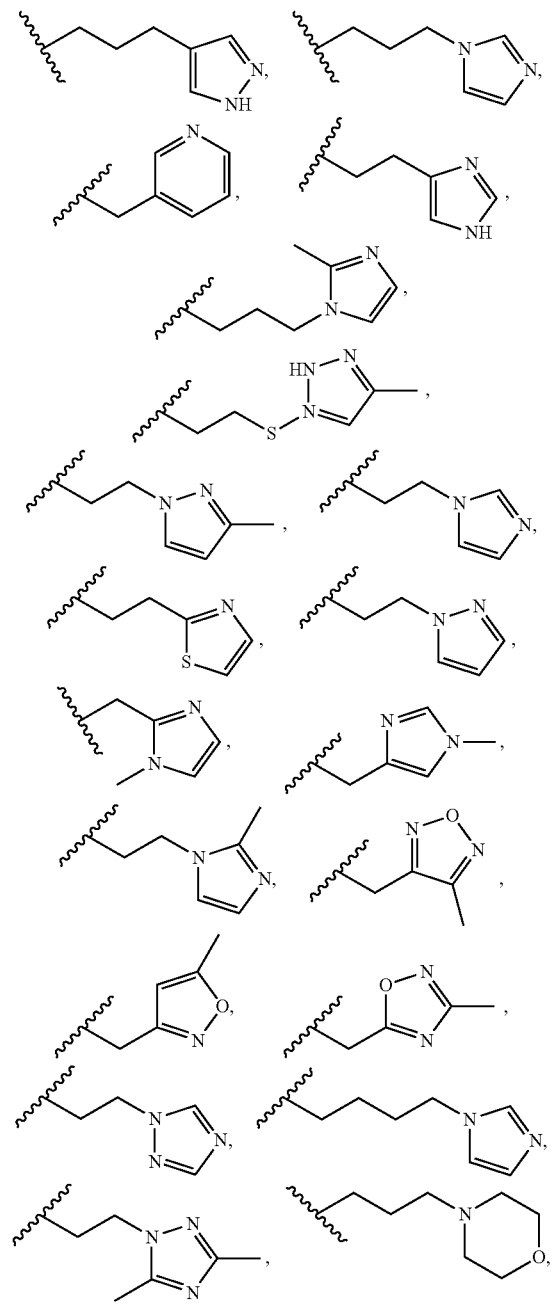
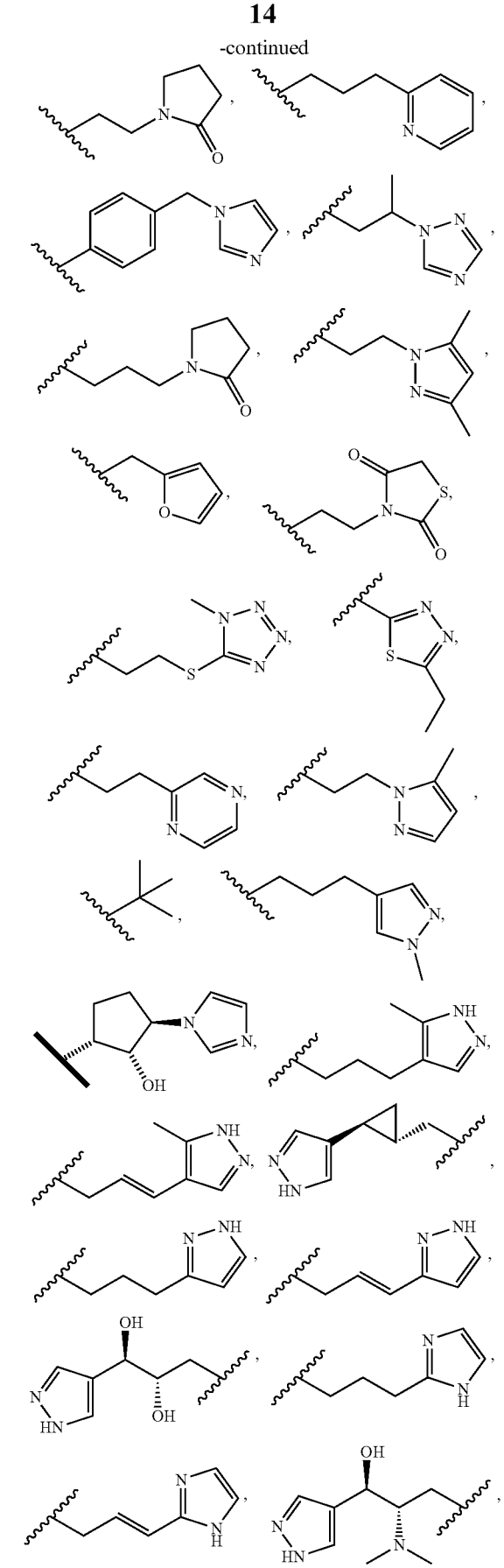

15
-continued

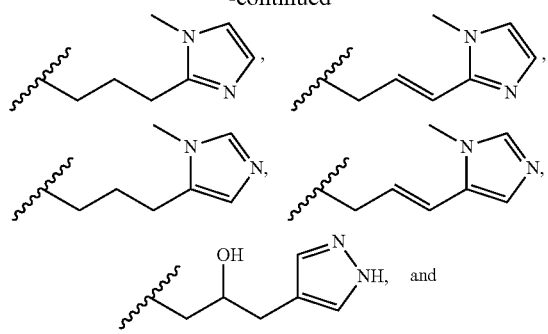

16
-continued

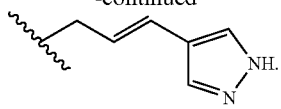

In an embodiment, R⁴ is a hydrogen atom or a methyl group.

In an embodiment, $R^1$ is a substituted or unsubstituted five to eight membered heterocyclic ring. For example, the five to eight membered heterocyclic ring comprises at least one nitrogen atom.

In various embodiments, the compound of the present disclosure is selected from the following structures:

| Structure | StructureID |
|---|---|
| 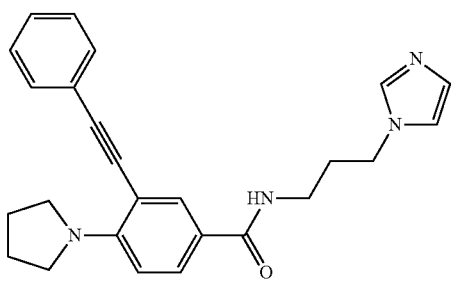 | TT-01901 |
| 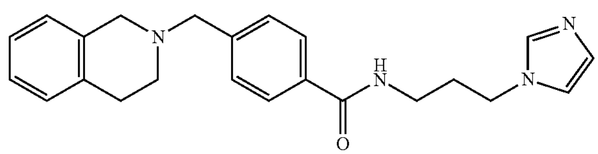 [SMILES: O=C(NCCCn1ccnc1)c1ccc(CN2CCc3ccccc3C2)cc1] | TT-01902 |
| 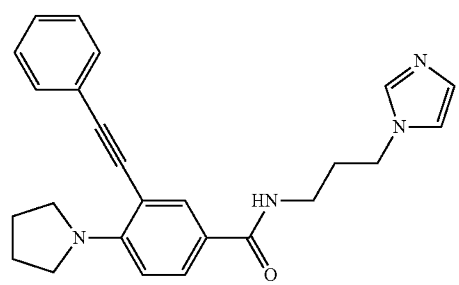 [SMILES: O=C(NCCCn1ccnc1)c1ccc(N2CCCC2)c(C#Cc2ccccc2)c1] | TT-02683 |
| 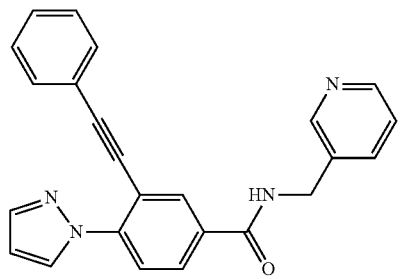 [SMILES: O=C(NCc1cccnc1)c1ccc(-n2cccn2)c(C#Cc2ccccc2)c1] | TT-02684 |

-continued
| Structure | StructureID |
|---|---|
| 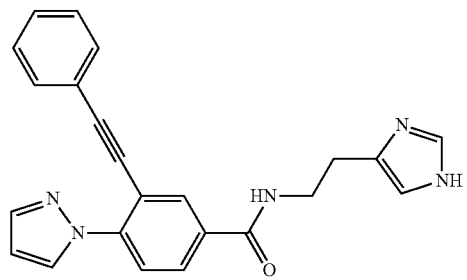 [SMILES: O=C(NCCc1c[nH]cn1)c1ccc(-n2cccn2)c(C#Cc2ccccc2)c1] | TT-02686 |
| 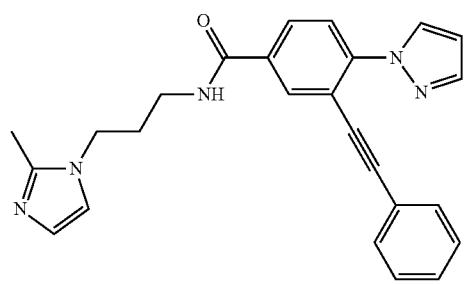 [SMILES: Cc1nccn1CCCNC(=O)c1ccc(-n2cccn2)c(C#Cc2ccccc2)c1] | TT-02689 |
| 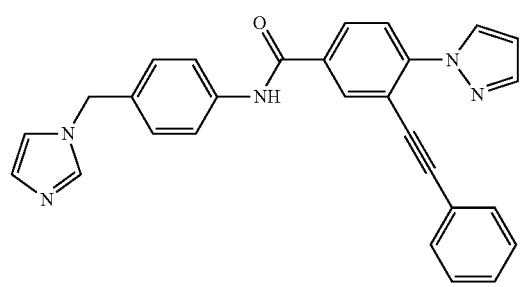 [SMILES: O=C(Nc1ccc(Cn2ccnc2)cc1)c1ccc(-n2cccn2)c(C#Cc2ccccc2)c1] | TT-02690 |
| 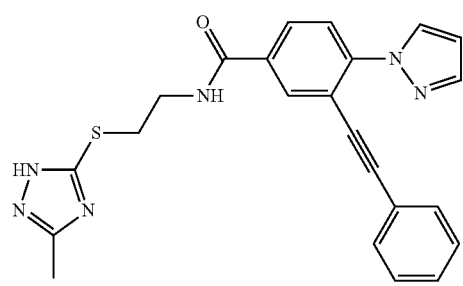 [SMILES: Cc1n[nH]c(SCCNC(=O)c2ccc(-n3cccn3)c(C#Cc3ccccc3)c2)n1] | TT-02691 |
| 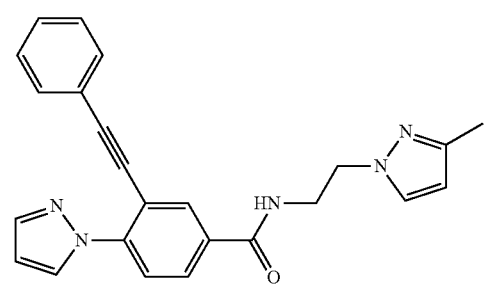 [SMILES: Cc1ccn(CCNC(=O)c2ccc(-n3cccn3)c(C#Cc3ccccc3)c2)n1] | TT-02692 |

-continued
| Structure | StructureID |
|---|---|
| 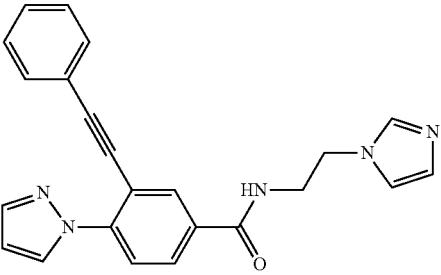 | TT-02694 |
| 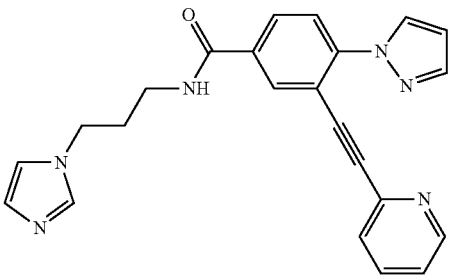 [SMILES: O=C(NCCCn1ccnc1)c1ccc(-n2cccn2)c(C#Cc2ccccn2)c1] | TT-02695 |
| 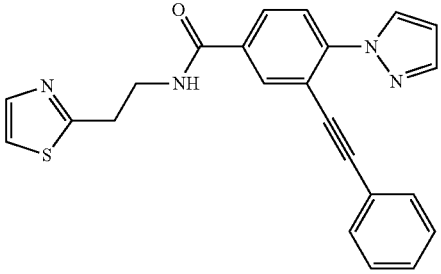 [SMILES: O=C(NCCc1nccs1)c1ccc(-n2cccn2)c(C#Cc2ccccc2)c1] | TT-02707 |
| 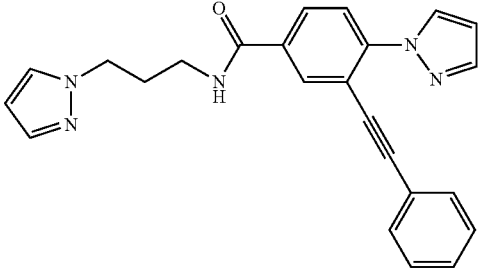 [SMILES: O=C(NCCCn1cccn1)c1ccc(-n2cccn2)c(C#Cc2ccccc2)c1] | TT-02709 |
| 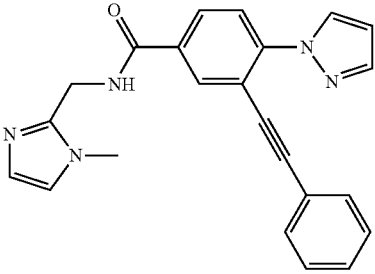 [SMILES: Cn1ccnc1CNC(=O)c1ccc(-n2cccn2)c(C#Cc2ccccc2)c1] | TT-02713 |

-continued
| Structure | StructureID |
|---|---|
| 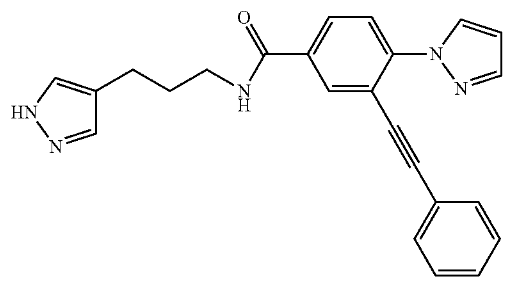 [SMILES: O=C(NCCCc1cn[nH]c1)c1ccc(-n2cccn2)c(C#Cc2ccccc2)c1] | TT-02715 |
| 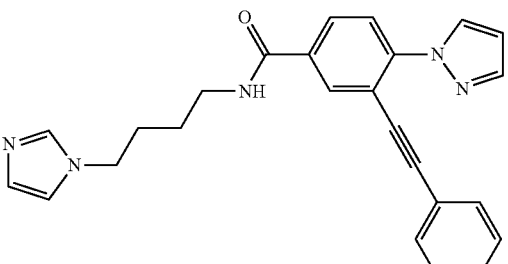 | TT-02717 |
| 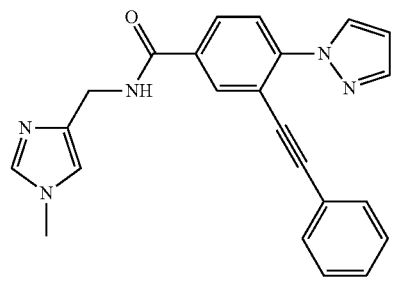 [SMILES: Cn1cnc(CNC(=O)c2ccc(-n3cccn3)c(C#Cc3ccccc3)c2)c1] | TT-02721 |
| 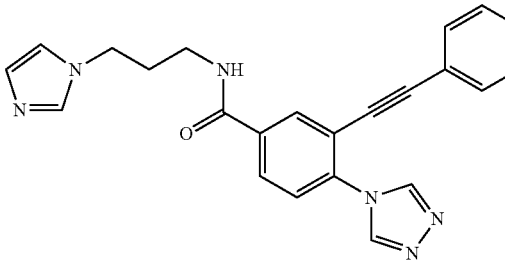 | TT-02731 |
| 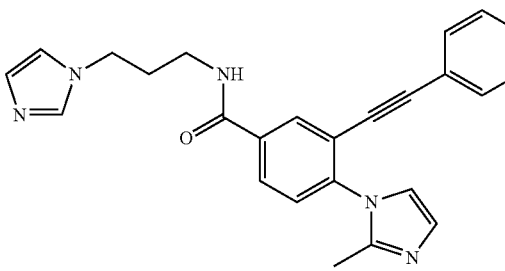 | TT-02732 |

-continued

| Structure | StructureID |
|---|---|
| 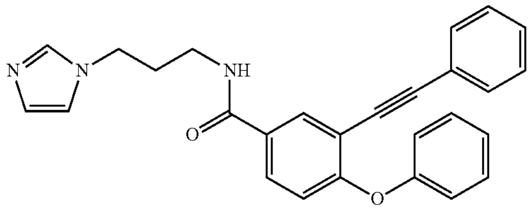 [SMILES: O=C(NCCCn1ccnc1)c1ccc(Oc2ccccc2)c(C#Cc2ccccc2)c1] | TT-02741 |
| 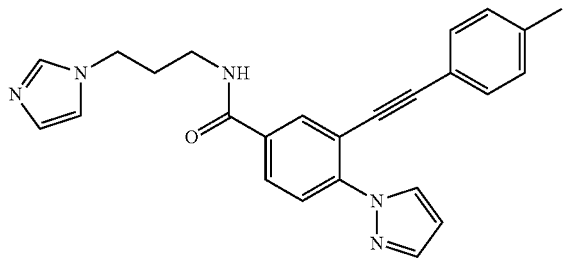 [SMILES: Cc1ccc(C#Cc2cc(C(=O)NCCCn3ccnc3)ccc2-n2cccn2)cc1] | TT-02745 |
| 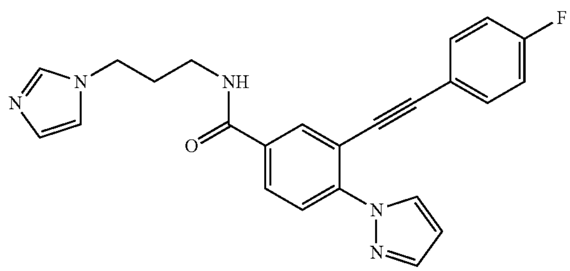 [SMILES: O=C(NCCCn1ccnc1)c1ccc(-n2cccn2)c(C#Cc2ccc(F)cc2)c1] | TT-02746 |
| 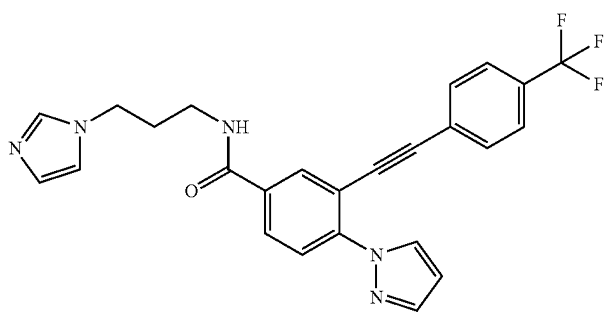 [SMILES: O=C(NCCCn1ccnc1)c1ccc(-n2cccn2)c(C#Cc2ccc(C(F)(F)F)cc2)c1] | TT-02747 |
| 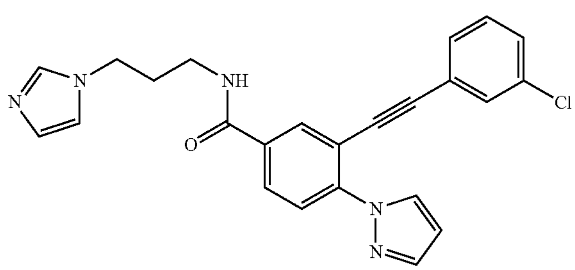 [SMILES: O=C(NCCCn1ccnc1)c1ccc(-n2cccn2)c(C#Cc2cccc(Cl)c2)c1] | TT-02749 |
| 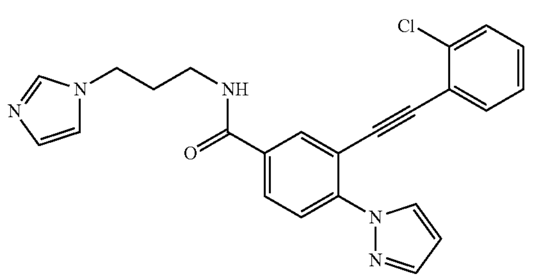 [SMILES: O=C(NCCCn1ccnc1)c1ccc(-n2cccn2)c(C#Cc2ccccc2Cl)c1] | TT-02750 |

-continued

| Structure | StructureID |
|---|---|
| 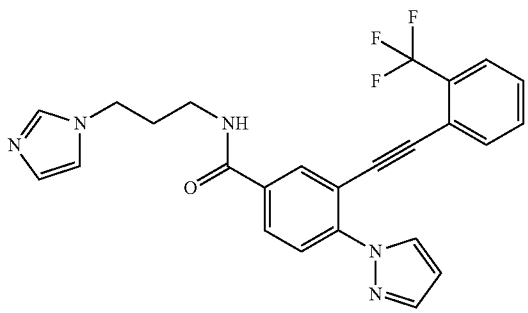 [SMILES: O=C(NCCCn1ccnc1)c1ccc(-n2cccn2)c(C#Cc2ccccc2C(F)(F)F)c1] | TT-02751 |
| 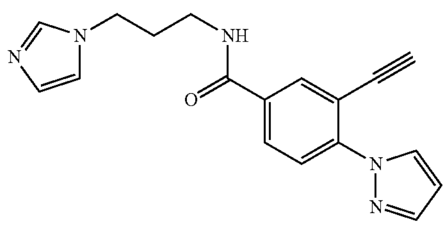 [SMILES: C#Cc1cc(C(=O)NCCCn2ccnc2)ccc1-n1cccn1] | TT-02752 |
| 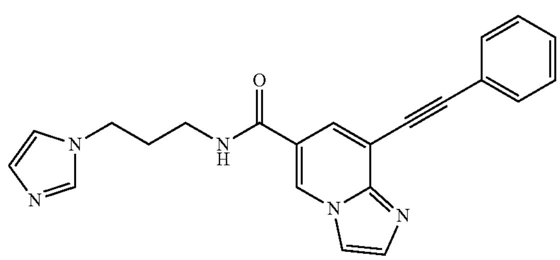 [SMILES: O=C(NCCCn1ccnc1)c1cc(C#Cc2ccccc2)c2nccn2c1] | TT-02760 |
| 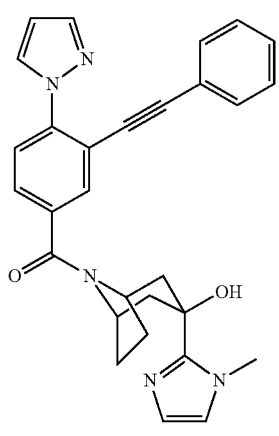 [SMILES: Cn1ccnc1C1(O)CC2CCC(C1)N2C(=O)c1ccc(-n2cccn2)c(C#Cc2ccccc2)c1] | TT-02793 |

| Structure | StructureID |
|---|---|
| 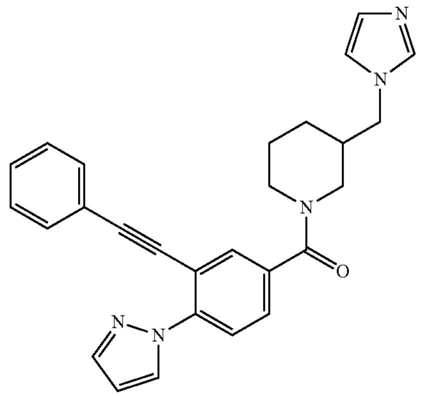 [SMILES: O=C(c1ccc(-n2cccn2)c(C#Cc2ccccc2)c1)N1CCCC(Cn2ccnc2)C1] | TT-02796 |
| 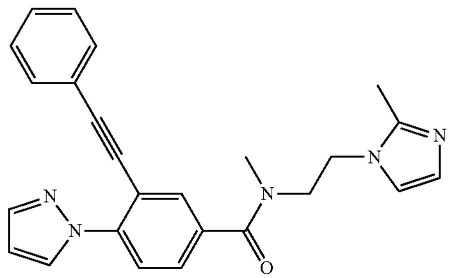 [SMILES: Cc1nccn1CCN(C)C(=O)c1ccc(-n2cccn2)c(C#Cc2ccccc2)c1] | TT-02797 |
| 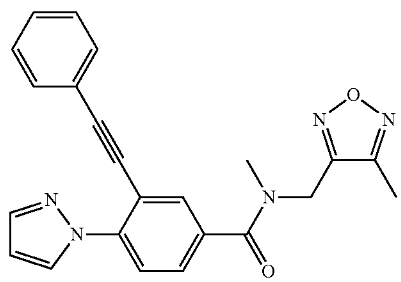 [SMILES: Cc1nonc1CN(C)C(=O)c1ccc(-n2cccn2)c(C#Cc2ccccc2)c1] | TT-02800 |
| 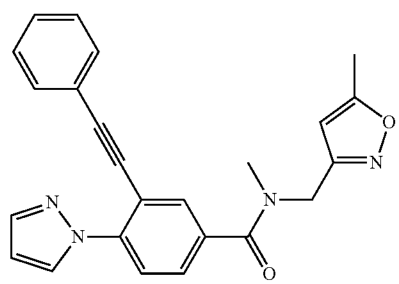 [SMILES: Cc1cc(CN(C)C(=O)c2ccc(-n3cccn3)c(C#Cc3ccccc3)c2)no1] | TT-02801 |
| 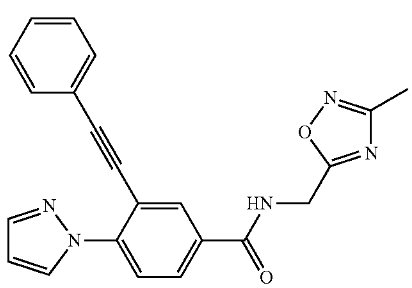 [SMILES: Cc1noc(CNC(=O)c2ccc(-n3cccn3)c(C#Cc3ccccc3)c2)n1] | TT-02802 |

| Structure | StructureID |
|---|---|
| 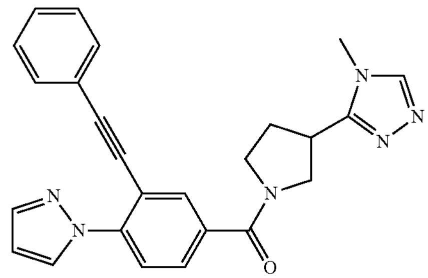 [SMILES: Cn1cnnc1C1CCN(C(=O)c2ccc(-n3cccn3)c(C#Cc3ccccc3)c2)C1] | TT-02803 |
| 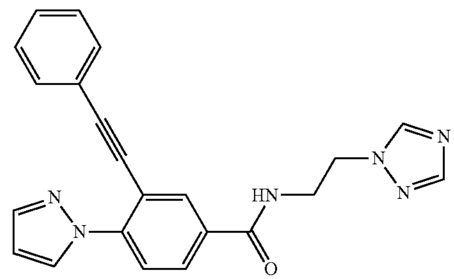 [SMILES: O=C(NCCn1cncn1)c1ccc(-n2cccn2)c(C#Cc2ccccc2)c1] | TT-02804 |
| 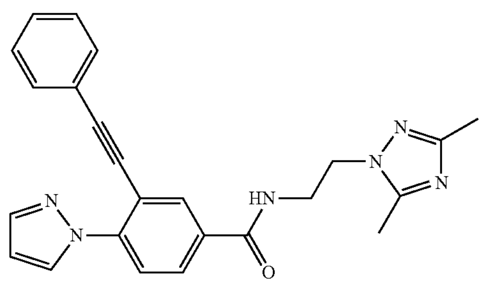 [SMILES: Cc1nc(C)n(CCNC(=O)c2ccc(-n3cccn3)c(C#Cc3ccccc3)c2)n1] | TT-02805 |
| 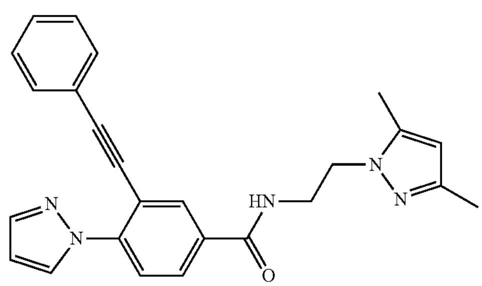 [SMILES: Cc1cc(C)n(CCNC(=O)c2ccc(-n3cccn3)c(C#Cc3ccccc3)c2)n1] | TT-02927 |
| 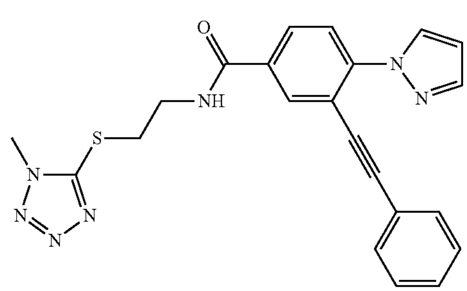 [SMILES: Cn1nnnc1SCCNC(=O)c1ccc(-n2cccn2)c(C#Cc2ccccc2)c1] | TT-02928 |

| Structure | StructureID |
|---|---|
| 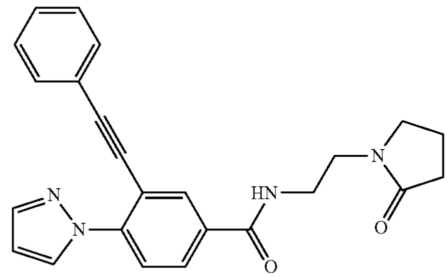 [SMILES: O=C(NCCN1CCCC1=O)c1ccc(-n2cccn2)c(C#Cc2ccccc2)c1] | TT-02929 |
| 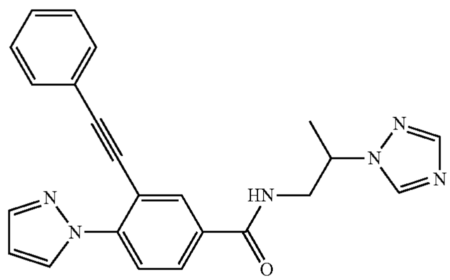 [SMILES: CC(CNC(=O)c1ccc(-n2cccn2)c(C#Cc2ccccc2)c1)n1cncn1] | TT-02930 |
| 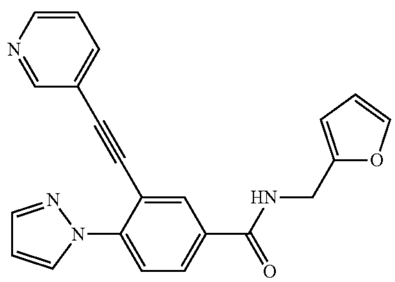 [SMILES: O=C(NCc1ccco1)c1ccc(-n2cccn2)c(C#Cc2cccnc2)c1] | TT-02931 |
| 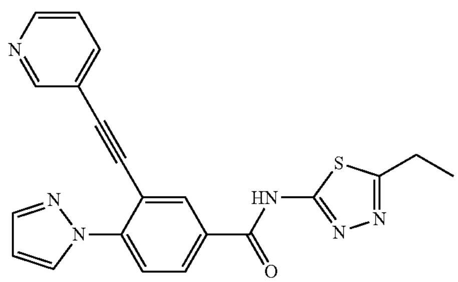 [SMILES: CCc1nnc(NC(=O)c2ccc(-n3cccn3)c(C#Cc3cccnc3)c2)s1] | TT-02932 |
| 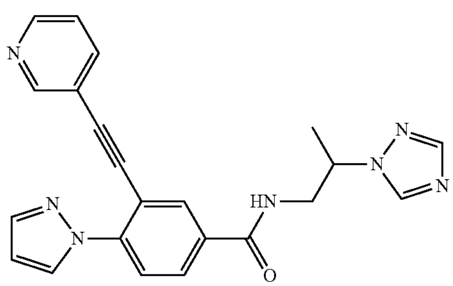 [SMILES: CC(CNC(=O)c1ccc(-n2cccn2)c(C#Cc2cccnc2)c1)n1cncn1] | TT-02933 |

| Structure | StructureID |
|---|---|
| 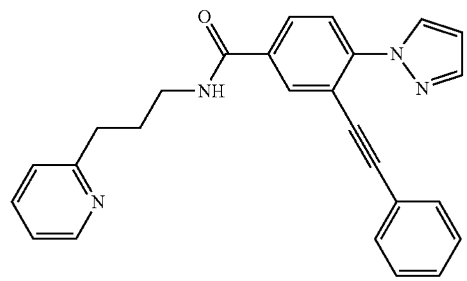 [SMILES: O=C(NCCCc1ccccn1)c1ccc(-n2cccn2)c(C#Cc2ccccc2)c1] | TT-02935 |
| 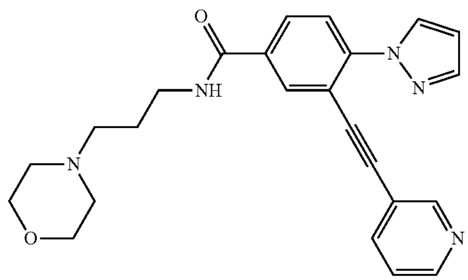 [SMILES: O=C(NCCCN1CCOCC1)c1ccc(-n2cccn2)c(C#Cc2cccnc2)c1] | TT-02936 |
| 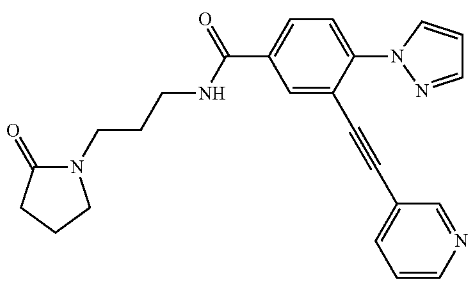 [SMILES: O=C(NCCCN1CCCC1=O)c1ccc(-n2cccn2)c(C#Cc2cccnc2)c1] | TT-02937 |
| 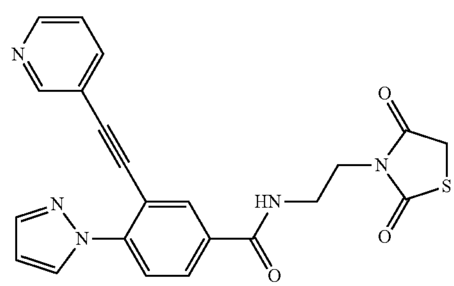 [SMILES: O=C(NCCN1C(=O)CSC1=O)c1ccc(-n2cccn2)c(C#Cc2cccnc2)c1] | TT-02938 |
| 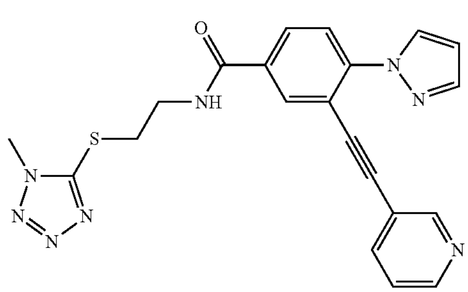 [SMILES: Cn1nnnc1SCCNC(=O)c1ccc(-n2cccn2)c(C#Cc2cccnc2)c1] | TT-02939 |

-continued
| Structure | StructureID |
|---|---|
| 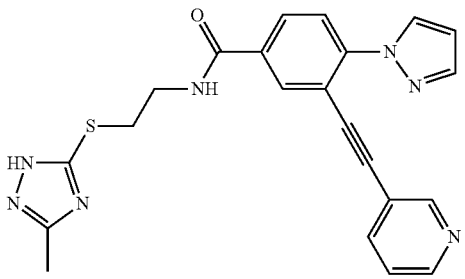 [SMILES: Cc1n[nH]c(SCCNC(=O)c2ccc(-n3cccn3)c(C#Cc3cccnc3)c2)n1] | TT-02940 |
| 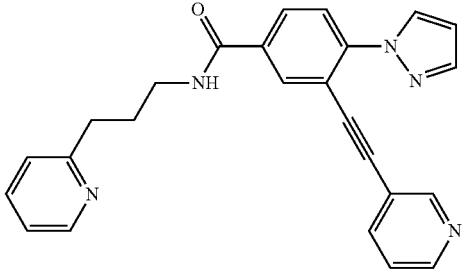 [SMILES: O=C(NCCCc1ccccn1)c1ccc(-n2cccn2)c(C#Cc2cccnc2)c1] | TT-02941 |
| 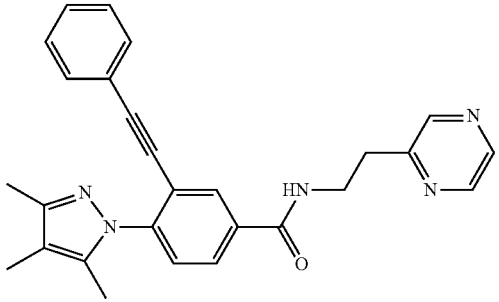 [SMILES: Cc1nn(-c2ccc(C(=O)NCCc3cnccn3)cc2C#Cc2ccccc2)c(C)c1C] | TT-02942 |
| 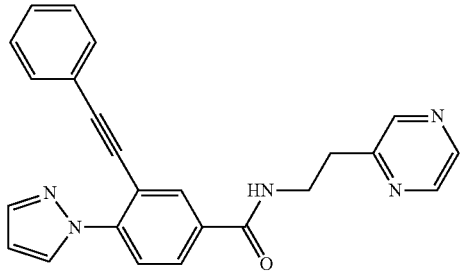 [SMILES: O=C(NCCc1cnccn1)c1ccc(-n2cccn2)c(C#Cc2ccccc2)c1] | TT-02943 |
| 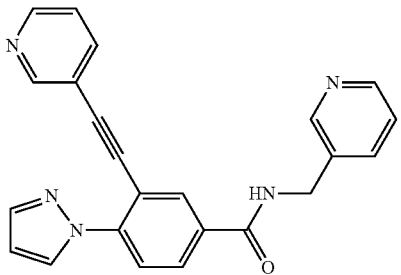 [SMILES: O=C(NCc1cccnc1)c1ccc(-n2cccn2)c(C#Cc2cccnc2)c1] | TT-02944 |

-continued

| Structure | StructureID |
|---|---|
| 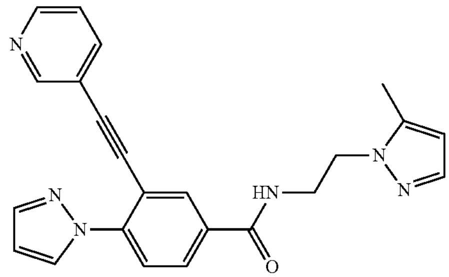 [SMILES: Cc1ccnn1CCNC(=O)c1ccc(-n2cccn2)c(C#Cc2cccnc2)c1] | TT-02945 |
| 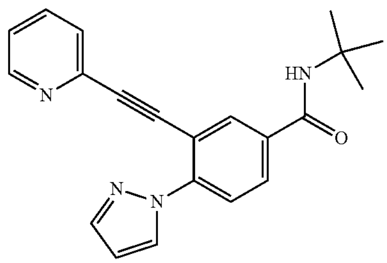 [SMILES: CC(C)(C)NC(=O)c1ccc(-n2cccn2)c(C#Cc2ccccn2)c1] | TT-02946 |
| 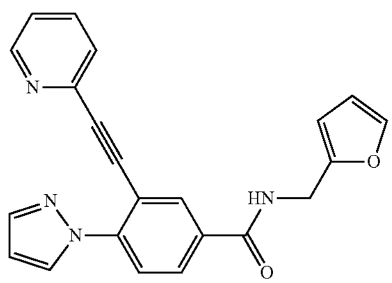 [SMILES: O=C(NCc1ccco1)c1ccc(-n2cccn2)c(C#Cc2ccccn2)c1] | TT-02947 |
| 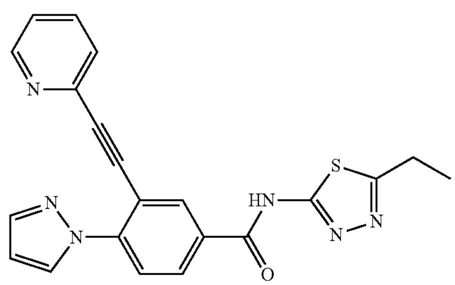 [SMILES: CCc1nnc(NC(=O)c2ccc(-n3cccn3)c(C#Cc3ccccn3)c2)s1] | TT-02948 |
| 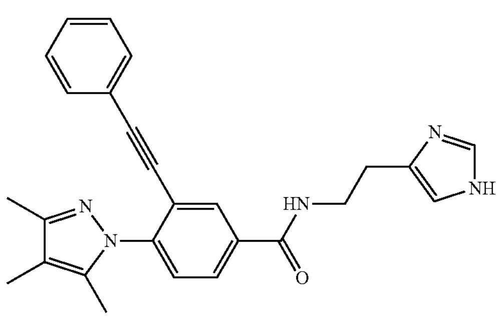 [SMILES: Cc1nn(-c2ccc(C(=O)NCCc3c[nH]cn3)cc2C#Cc2ccccc2)c(C)c1C] | TT-02949 |

-continued
| Structure | StructureID |
|---|---|
| 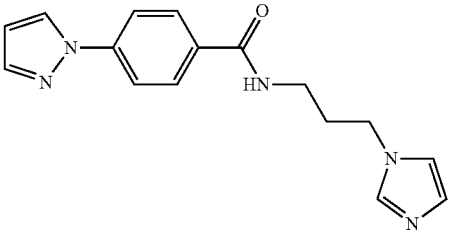 [SMILES: O=C(NCCCn1ccnc1)c1ccc(-n2cccn2)cc1] | TT-03071 |
| 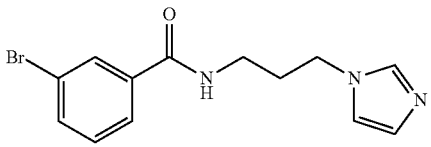 [SMILES: O=C(NCCCn1ccnc1)c1cccc(Br)c1] | TT-03073 |
| 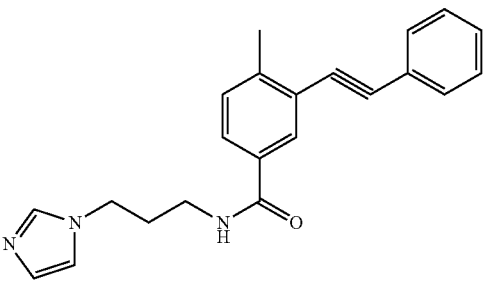 [SMILES: Cc1ccc(C(=O)NCCCn2ccnc2)cc1C#Cc1ccccc1] | TT-03196 |
| 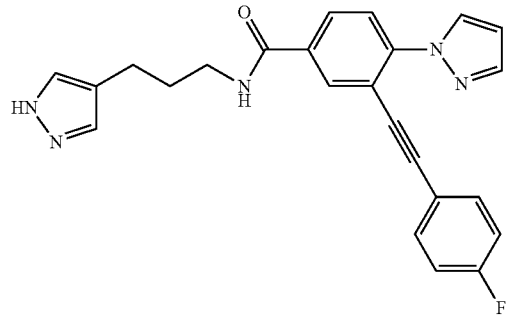 [SMILES: O=C(NCCCc1cn[nH]c1)c1ccc(-n2cccn2)c(C#Cc2ccc(F)cc2)c1] | TT-03197 |
| 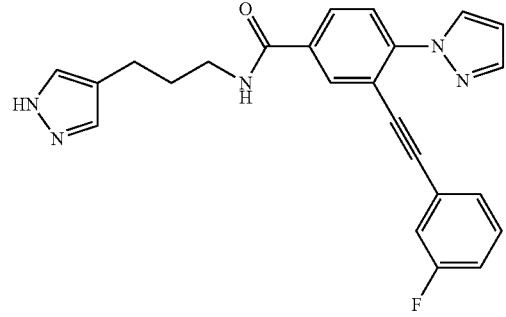 [SMILES: O=C(NCCCc1cn[nH]c1)c1ccc(-n2cccn2)c(C#Cc2cccc(F)c2)c1] | TT-03198 |

-continued

| Structure | StructureID |
|---|---|
| 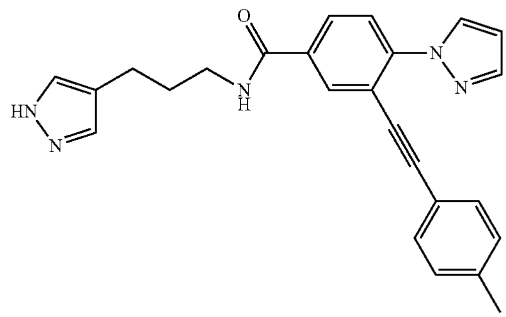 [SMILES: Cc1ccc(C#Cc2cc(C(=O)NCCCc3cn[nH]c3)ccc2-n2cccn2)cc1] | TT-03201 |
| 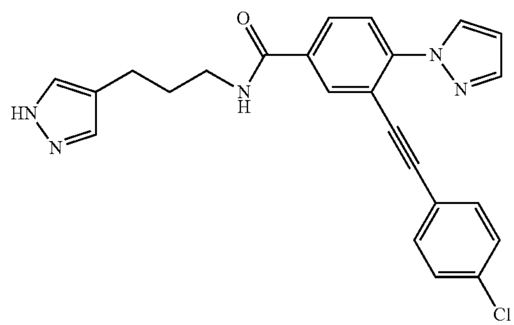 [SMILES: O=C(NCCCc1cn[nH]c1)c1ccc(-n2cccn2)c(C#Cc2ccc(Cl)cc2)c1] | TT-03203 |
| 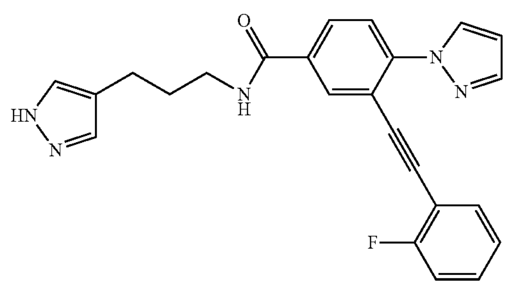 [SMILES: O=C(NCCCc1cn[nH]c1)c1ccc(-n2cccn2)c(C#Cc2ccccc2F)c1] | TT-03211 |
| 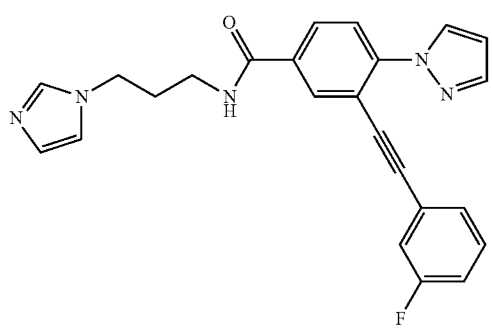 [SMILES: O=C(NCCCn1ccnc1)c1ccc(-n2cccn2)c(C#Cc2cccc(F)c2)c1] | TT-03217 |
| 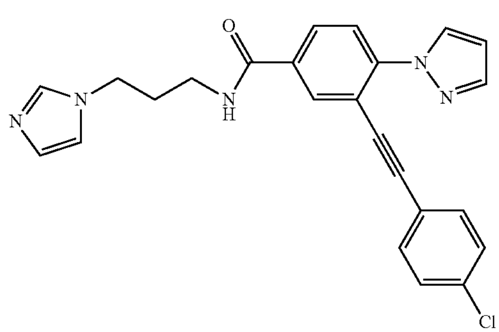 [SMILES: O=C(NCCCn1ccnc1)c1ccc(-n2cccn2)c(C#Cc2ccc(Cl)cc2)c1] | TT-03221 |

-continued
| Structure | StructureID |
|---|---|
| 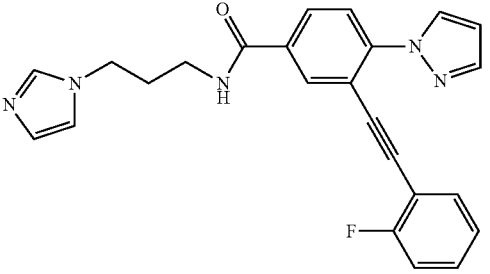 [SMILES: O=C(NCCCn1ccnc1)c1ccc(-n2cccn2)c(C#Cc2ccccc2F)c1] | TT-03225 |
| 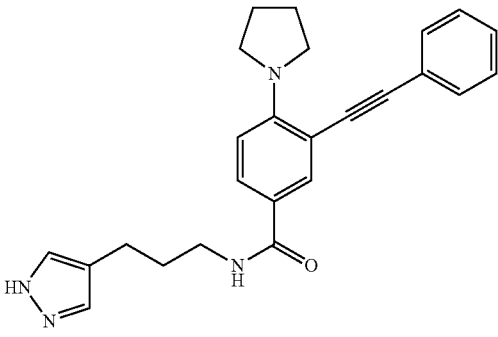 [SMILES: O=C(NCCCc1cn[nH]c1)c1ccc(N2CCCC2)c(C#Cc2ccccc2)c1] | TT-03230 |
| 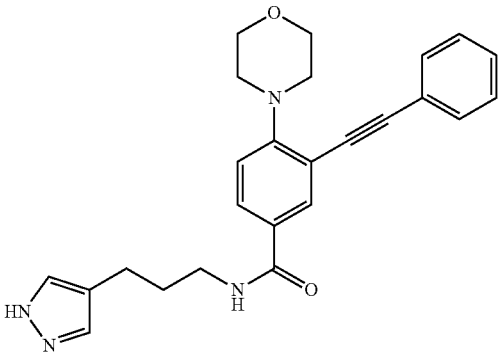 [SMILES: O=C(NCCCc1cn[nH]c1)c1ccc(N2CCOCC2)c(C#Cc2ccccc2)c1] | TT-03232 |
| 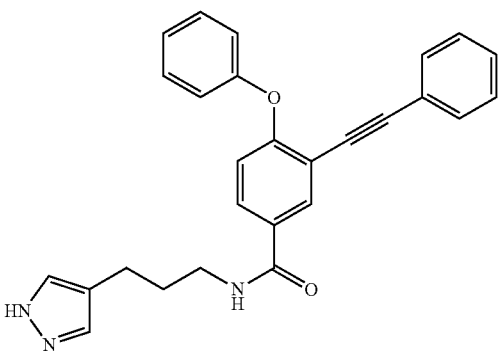 [SMILES: O=C(NCCCc1cn[nH]c1)c1ccc(Oc2ccccc2)c(C#Cc2ccccc2)c1] | TT-03233 |

-continued

| Structure | StructureID |
|---|---|
| 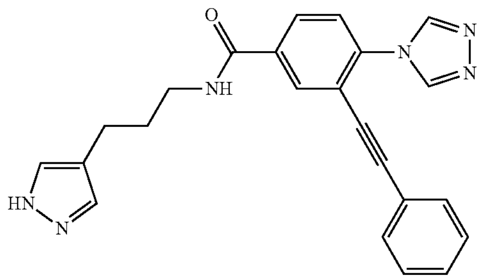 [SMILES: O=C(NCCCc1cn[nH]c1)c1ccc(-n2cnnc2)c(C#Cc2ccccc2)c1] | TT-03237 |
| 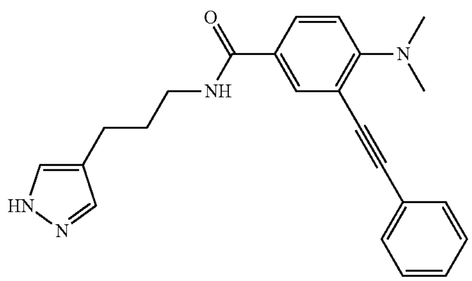 [SMILES: CN(C)c1ccc(C(=O)NCCCc2cn[nH]c2)cc1C#Cc1ccccc1] | TT-03242 |
| 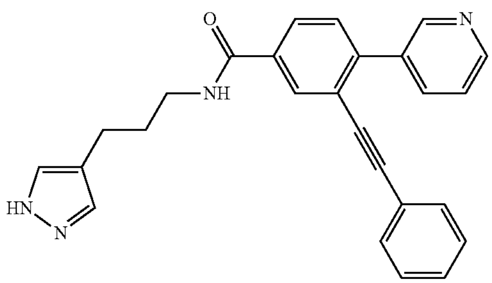 [SMILES: O=C(NCCCc1cn[nH]c1)c1ccc(-c2cccnc2)c(C#Cc2ccccc2)c1] | TT-03245 |
| 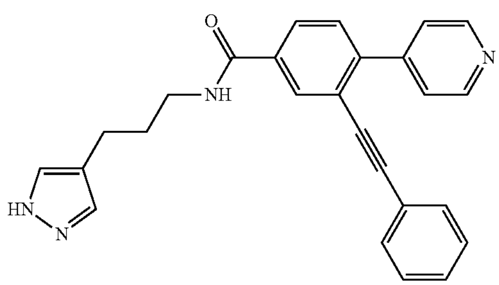 [SMILES: O=C(NCCCc1cn[nH]c1)c1ccc(-c2ccncc2)c(C#Cc2ccccc2)c1] | TT-03246 |
| 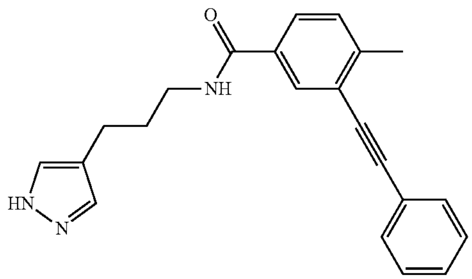 [SMILES: Cc1ccc(C(=O)NCCCc2cn[nH]c2)cc1C#Cc1ccccc1] | TT-03248 |

-continued

| Structure | StructureID |
|---|---|
| 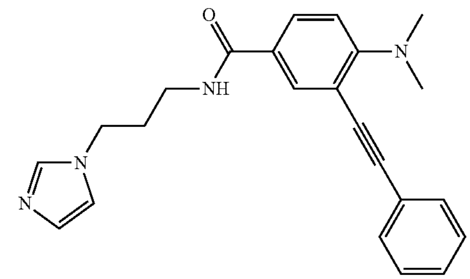 [SMILES: CN(C)c1ccc(C(=O)NCCCn2ccnc2)cc1C#Cc1ccccc1] | TT-03252 |
| 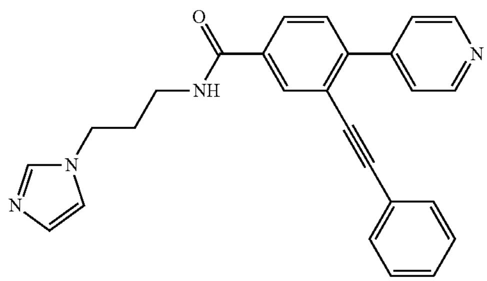 [SMILES: O=C(NCCCn1ccnc1)c1ccc(-c2ccncc2)c(C#Cc2ccccc2)c1] | TT-03256 |
| 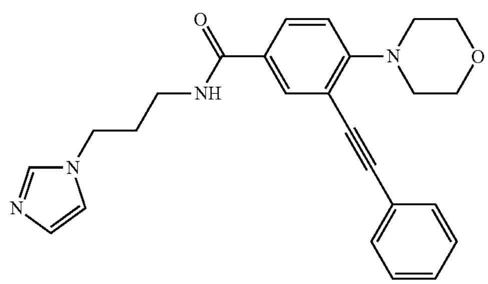 [SMILES: O=C(NCCCn1ccnc1)c1ccc(N2CCOCC2)c(C#Cc2ccccc2)c1] | TT-03261 |
| 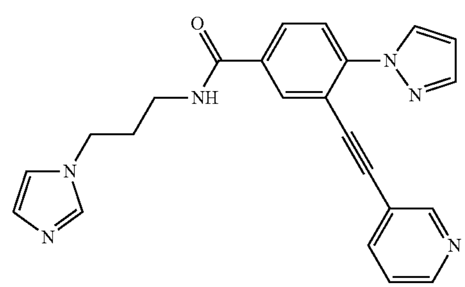 [SMILES: O=C(NCCCn1ccnc1)c1ccc(-n2cccn2)c(C#Cc2cccnc2)c1] | TT-03264 |
| 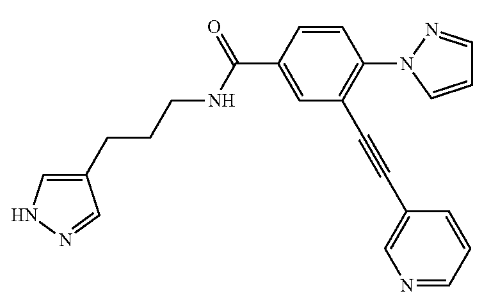 [SMILES: O=C(NCCCc1cn[nH]c1)c1ccc(-n2cccn2)c(C#Cc2cccnc2)c1] | TT-03303 |

-continued
| Structure | StructureID |
|---|---|
| 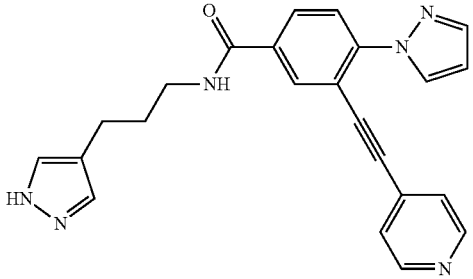 [SMILES: O=C(NCCCc1cn[nH]c1)c1ccc(-n2cccn2)c(C#Cc2ccncc2)c1] | TT-03304 |
| 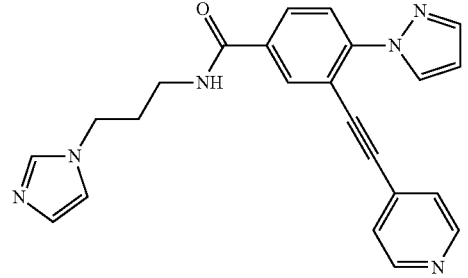 [SMILES: O=C(NCCCn1ccnc1)c1ccc(-n2cccn2)c(C#Cc2ccncc2)c1] | TT-03305 |
| 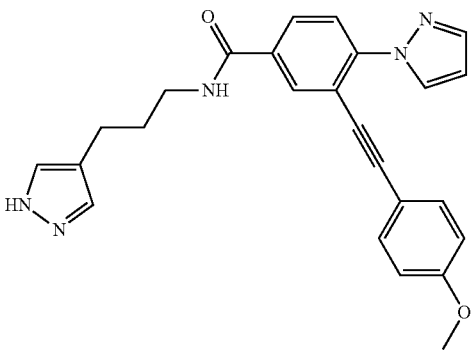 [SMILES: COc1ccc(C#Cc2cc(C(=O)NCCCc3cn[nH]c3)ccc2-n2cccn2)cc1] | TT-03306 |
| 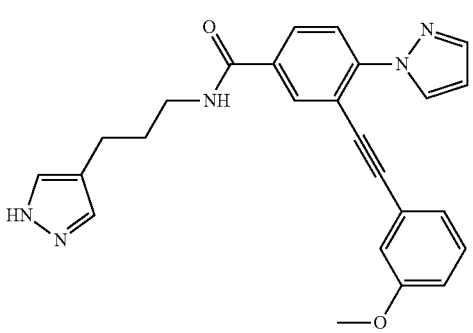 [SMILES: COc1cccc(C#Cc2cc(C(=O)NCCCc3cn[nH]c3)ccc2-n2cccn2)c1] | TT-03308 |
| 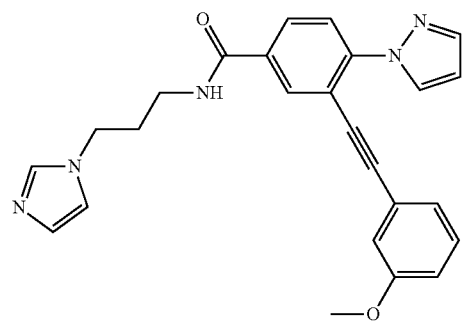 [SMILES: COc1cccc(C#Cc2cc(C(=O)NCCCn3ccnc3)ccc2-n2cccn2)c1] | TT-03309 |

-continued

| Structure | StructureID |
|---|---|
| 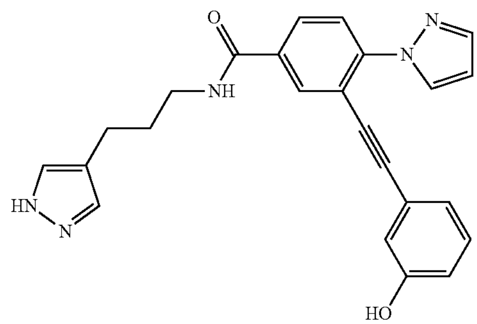 [SMILES: O=C(NCCCc1cn[nH]c1)c1ccc(-n2cccn2)c(C#Cc2cccc(O)c2)c1] | TT-03311 |
| 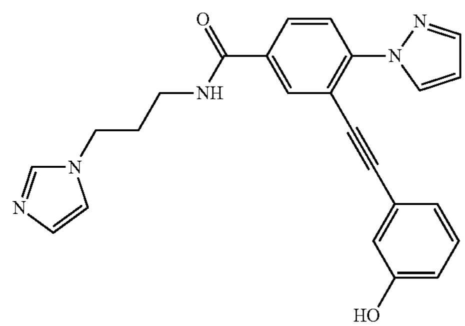 [SMILES: O=C(NCCCn1ccnc1)c1ccc(-n2cccn2)c(C#Cc2cccc(O)c2)c1] | TT-03312 |
| 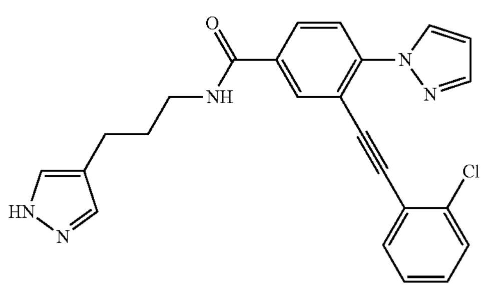 [SMILES: O=C(NCCCc1cn[nH]c1)c1ccc(-n2cccn2)c(C#Cc2ccccc2Cl)c1] | TT-03321 |
| 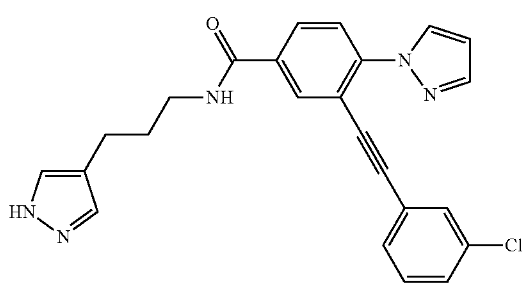 [SMILES: O=C(NCCCc1cn[nH]c1)c1ccc(-n2cccn2)c(C#Cc2cccc(Cl)c2)c1] | TT-03322 |
| 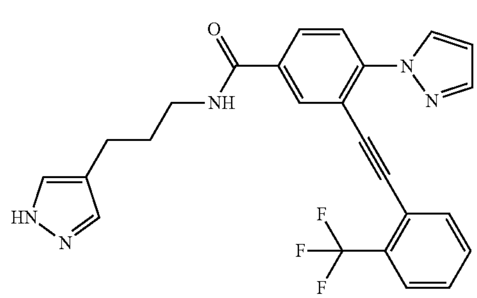 [SMILES: O=C(NCCCc1cn[nH]c1)c1ccc(-n2cccn2)c(C#Cc2ccccc2C(F)(F)F)c1] | TT-03323 |

-continued

| Structure | StructureID |
|---|---|
| 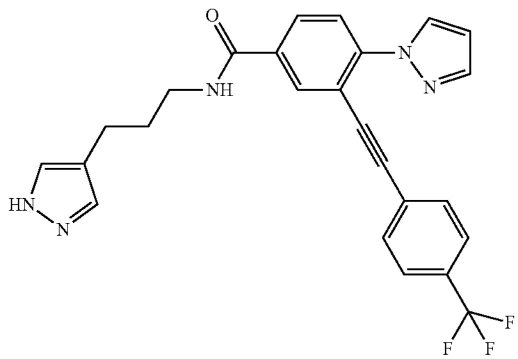 [SMILES: O=C(NCCCc1cn[nH]c1)c1ccc(-n2cccn2)c(C#Cc2ccc(C(F)(F)F)cc2)c1] | TT-03324 |
| 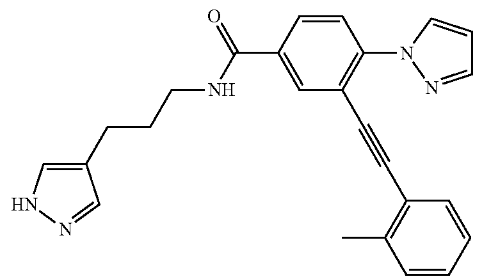 [SMILES: Cc1ccccc1C#Cc1cc(C(=O)NCCCc2cn[nH]c2)ccc1-n1cccn1] | TT-03326 |
| 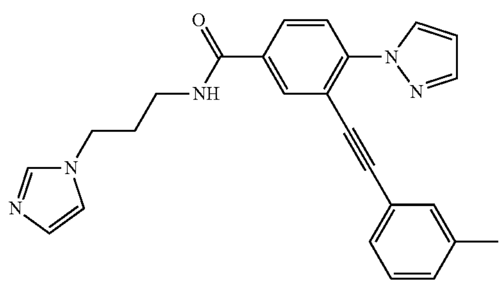 [SMILES: Cc1cccc(C#Cc2cc(C(=O)NCCCn3ccnc3)ccc2-n2cccn2)c1] | TT-03327 |
| 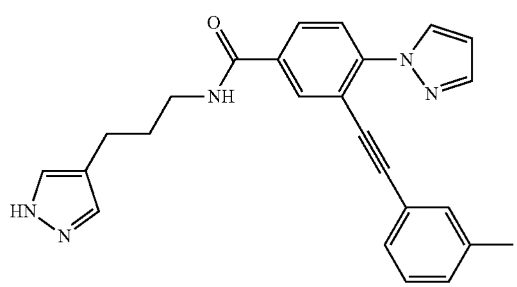 [SMILES: Cc1cccc(C#Cc2cc(C(=O)NCCCc3cn[nH]c3)ccc2-n2cccn2)c1] | TT-03328 |
| 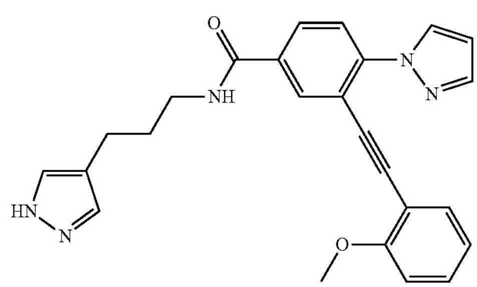 [SMILES: COc1ccccc1C#Cc1cc(C(=O)NCCCc2cn[nH]c2)ccc1-n1cccn1] | TT-03330 |

-continued

| Structure | StructureID |
|---|---|
| 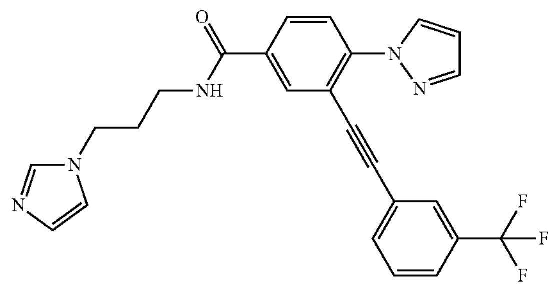 [SMILES: O=C(NCCCn1ccnc1)c1ccc(-n2cccn2)c(C#Cc2cccc(C(F)(F)F)c2)c1] | TT-03331 |
| 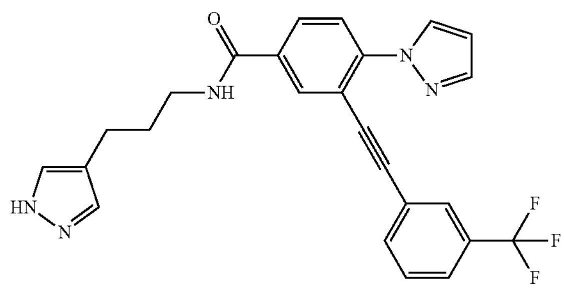 [SMILES: O=C(NCCCc1cn[nH]c1)c1ccc(-n2cccn2)c(C#Cc2cccc(C(F)(F)F)c2)c1] | TT-03332 |
| 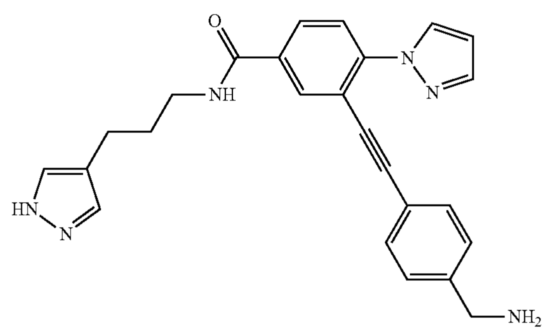 [SMILES: NCc1ccc(C#Cc2cc(C(=O)NCCCc3cn[nH]c3)ccc2-n2cccn2)cc1] | TT-03334 |
| 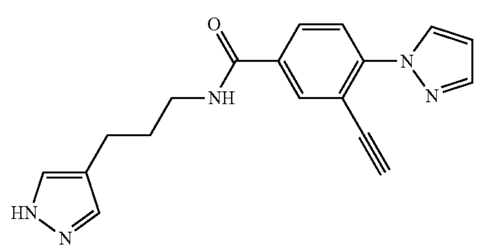 [SMILES: C#Cc1cc(C(=O)NCCCc2cn[nH]c2)ccc1-n1cccn1] | TT-03337 |
| 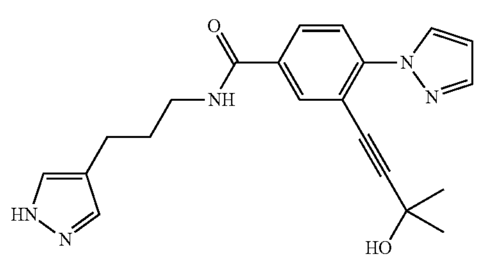 [SMILES: CC(C)(O)C#Cc1cc(C(=O)NCCCc2cn[nH]c2)ccc1-n1cccn1] | TT-03346 |

-continued
| Structure | StructureID |
|---|---|
| 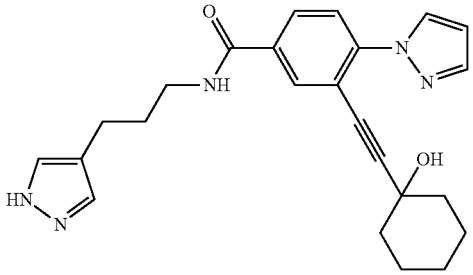 [SMILES: O=C(NCCCc1cn[nH]c1)c1ccc(-n2cccn2)c(C#CC2(O)CCCCC2)c1] | TT-03351 |
| 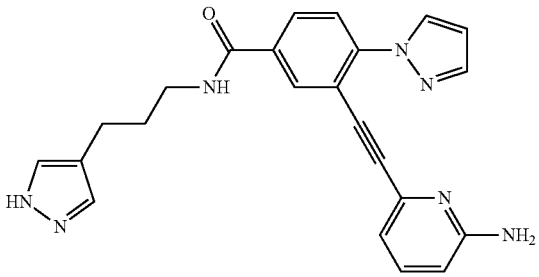 [SMILES: Nc1cccc(C#Cc2cc(C(=O)NCCCc3cn[nH]c3)ccc2-n2cccn2)n1] | TT-03354 |
| 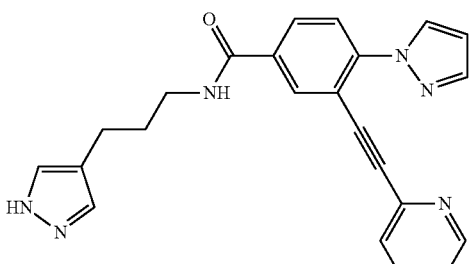 | TT-03355 |
| 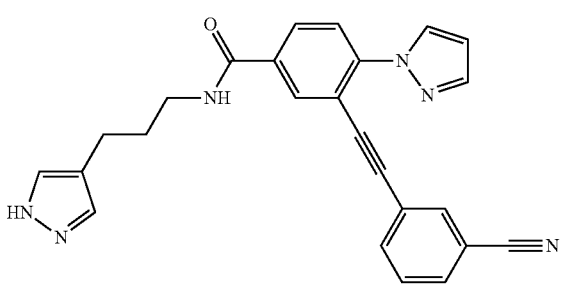 [SMILES: N#Cc1cccc(C#Cc2cc(C(=O)NCCCc3cn[nH]c3)ccc2-n2cccn2)c1] | TT-03357 |
| 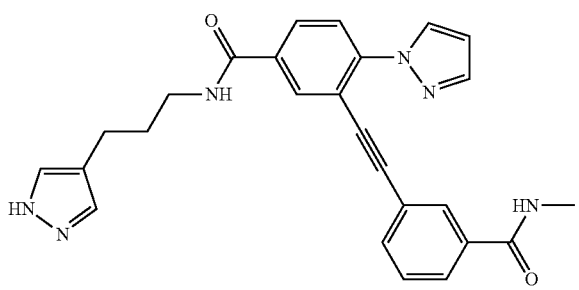 [SMILES: CNC(=O)c1cccc(C#Cc2cc(C(=O)NCCCc3cn[nH]c3)ccc2-n2cccn2)c1] | TT-03359 |

| Structure | StructureID |
|---|---|
| 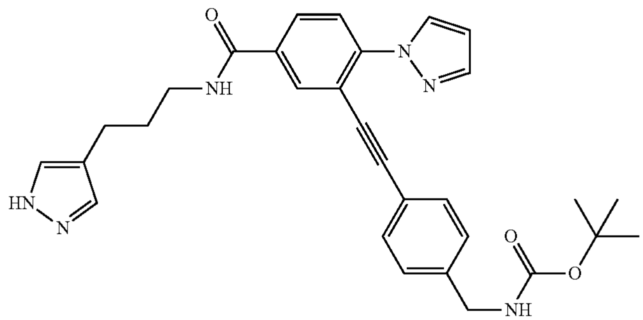 [SMILES: CC(C)(C)OC(=O)NCc1ccc(C#Cc2cc(C(=O)NCCCc3cn[nH]c3)ccc2-n2cccn2)cc1] | TT-03364 |
| 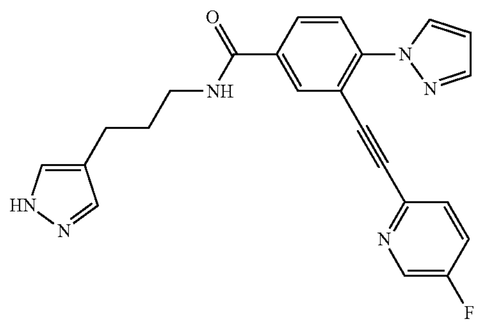 [SMILES: O=C(NCCCc1cn[nH]c1)c1ccc(-n2cccn2)c(C#Cc2ccc(F)cn2)c1] | TT-03569 |
| 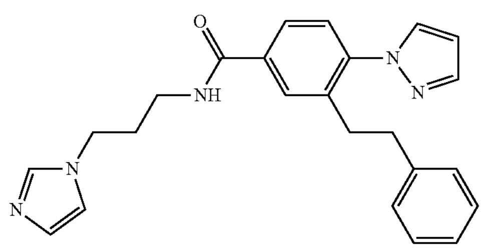 [SMILES: O=C(NCCCn1ccnc1)c1ccc(-n2cccn2)c(CCc2ccccc2)c1] | TT-03574 |
| 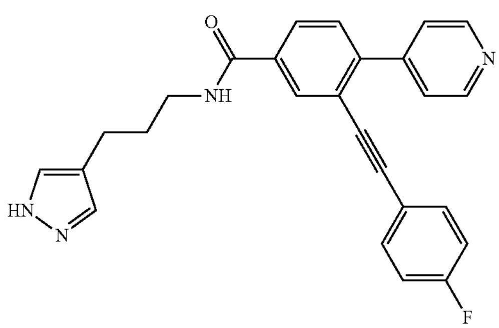 [SMILES: O=C(NCCCc1cn[nH]c1)c1ccc(-c2ccncc2)c(C#Cc2ccc(F)cc2)c1] | TT-03582 |
| 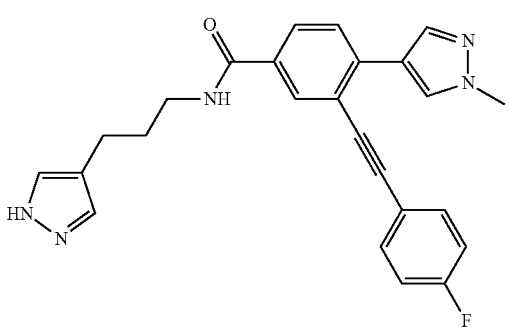 [SMILES: Cn1cc(-c2ccc(C(=O)NCCCc3cn[nH]c3)cc2C#Cc2ccc(F)cc2)cn1] | TT-03585 |

| Structure | StructureID |
|---|---|
| 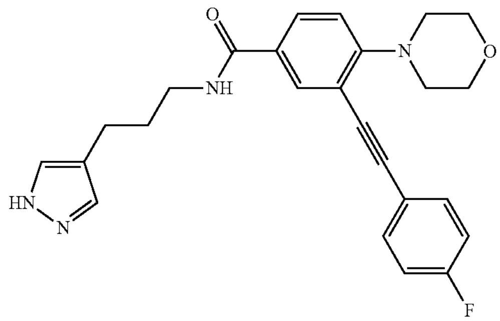 [SMILES: O=C(NCCCc1cn[nH]c1)c1ccc(N2CCOCC2)c(C#Cc2ccc(F)cc2)c1] | TT-03586 |
| 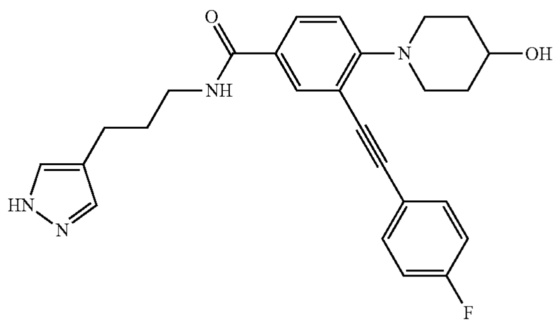 [SMILES: O=C(NCCCc1cn[nH]c1)c1ccc(N2CCC(O)CC2)c(C#Cc2ccc(F)cc2)c1] | TT-03587 |
| 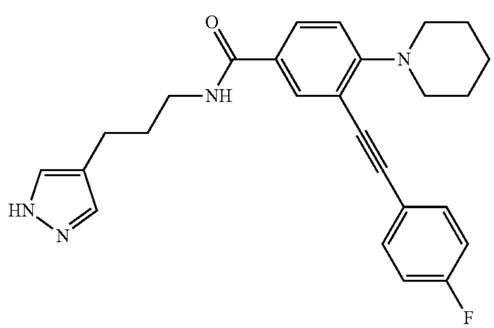 [SMILES: O=C(NCCCc1cn[nH]c1)c1ccc(N2CCCCC2)c(C#Cc2ccc(F)cc2)c1] | TT-03588 |
| 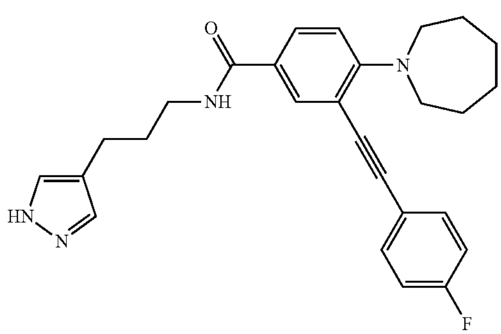 [SMILES: O=C(NCCCc1cn[nH]c1)c1ccc(N2CCCCCC2)c(C#Cc2ccc(F)cc2)c1] | TT-03589 |

-continued
| Structure | StructureID |
|---|---|
| 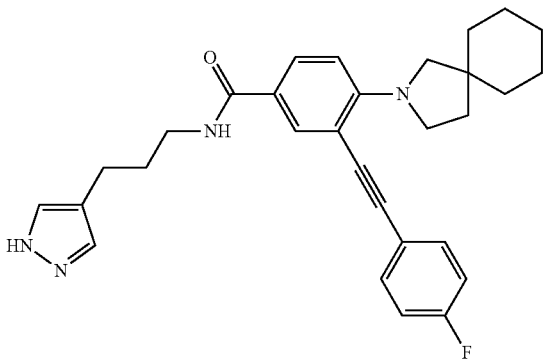 [SMILES: O=C(NCCCc1cn[nH]c1)c1ccc(N2CCC3(CCCCC3)C2)c(C#Cc2ccc(F)cc2)c1] | TT-03590 |
| 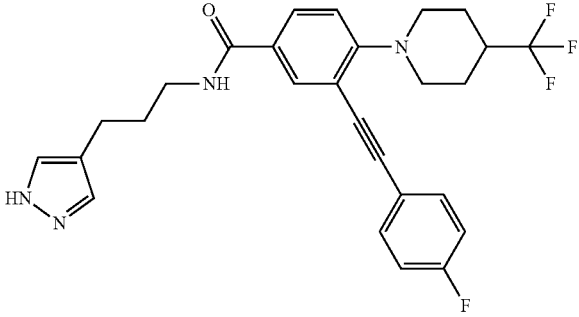 [SMILES: O=C(NCCCc1cn[nH]c1)c1ccc(N2CCC(C(F)(F)F)CC2)c(C#Cc2ccc(F)cc2)c1] | TT-03591 |
| 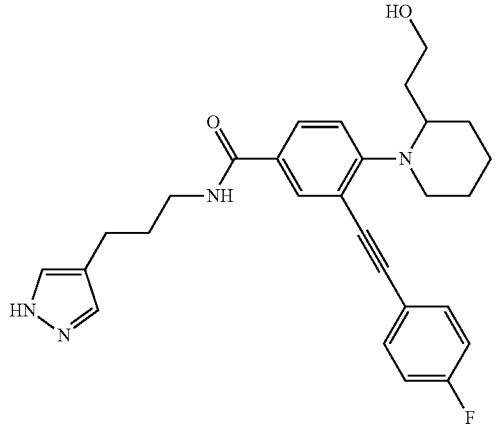 [SMILES: O=C(NCCCc1cn[nH]c1)c1ccc(N2CCCCC2CCO)c(C#Cc2ccc(F)cc2)c1] | TT-03592 |
| 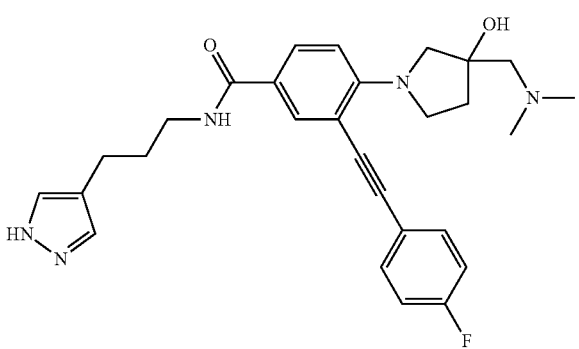 [SMILES: CN(C)CC1(O)CCN(c2ccc(C(=O)NCCCc3cn[nH]c3)cc2C#Cc2ccc(F)cc2)C1] | TT-03594 |

-continued
| Structure | StructureID |
|---|---|
| 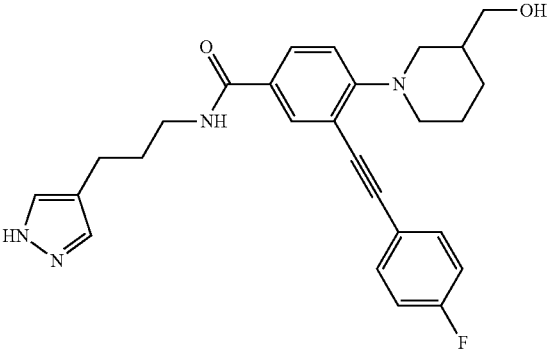 [SMILES: O=C(NCCCc1cn[nH]c1)c1ccc(N2CCCC(CO)C2)c(C#Cc2ccc(F)cc2)c1] | TT-03595 |
| 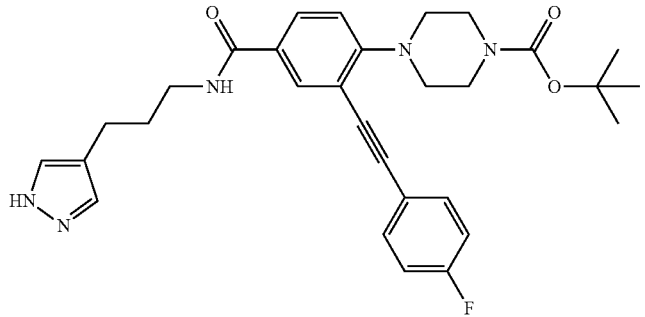 [SMILES: CC(C)(C)OC(=O)N1CCN(c2ccc(C(=O)NCCCc3cn[nH]c3)cc2C#Cc2ccc(F)cc2)CC1] | TT-03596 |
| 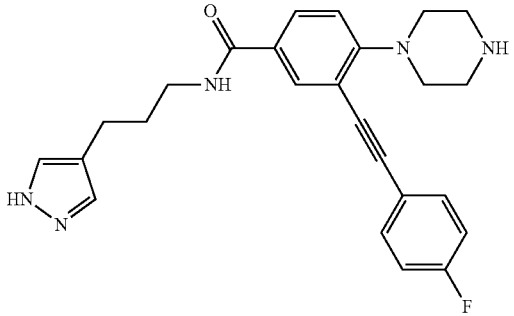 [SMILES: O=C(NCCCc1cn[nH]c1)c1ccc(N2CCNCC2)c(C#Cc2ccc(F)cc2)c1] | TT-03597 |
| 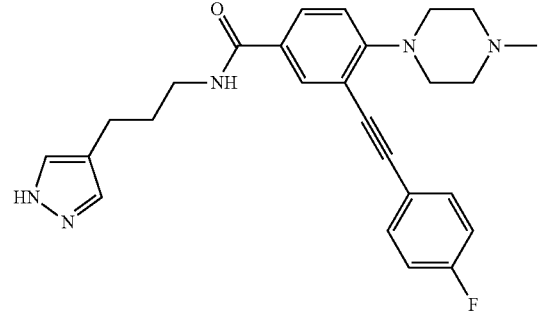 [SMILES: CN1CCN(c2ccc(C(=O)NCCCc3cn[nH]c3)cc2C#Cc2ccc(F)cc2)CC1] | TT-03598 |

-continued

| Structure | StructureID |
|---|---|
| 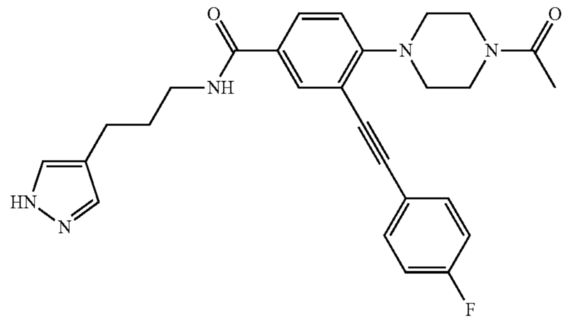 [SMILES: CC(=O)N1CCN(c2ccc(C(=O)NCCCc3cn[nH]c3)cc2C#Cc2ccc(F)cc2)CC1] | TT-03599 |
| 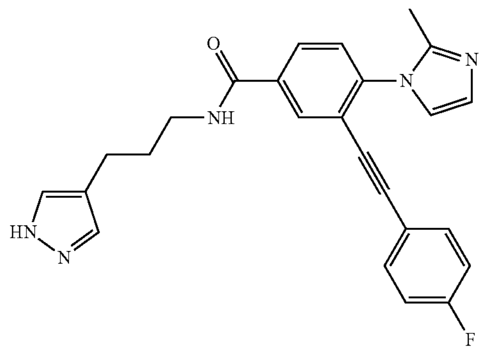 [SMILES: Cc1nccn1-c1ccc(C(=O)NCCCc2cn[nH]c2)cc1C#Cc1ccc(F)cc1] | TT-03602 |
| 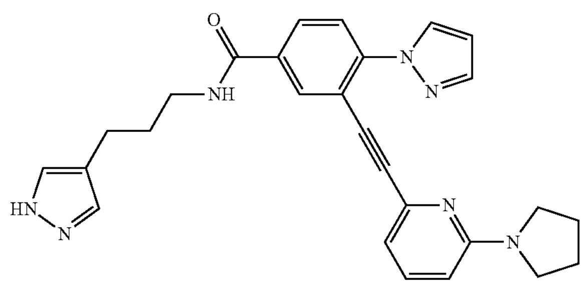 [SMILES: O=C(NCCCc1cn[nH]c1)c1ccc(-n2cccn2)c(C#Cc2cccc(N3CCCC3)n2)c1] | TT-03611 |
| 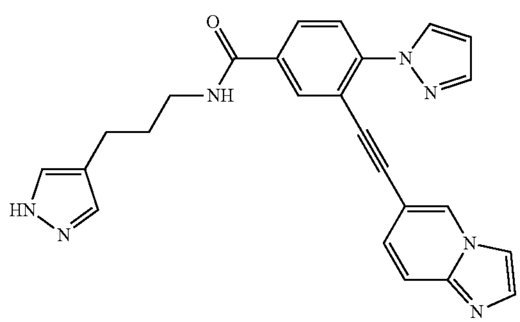 [SMILES: O=C(NCCCc1cn[nH]c1)c1ccc(-n2cccn2)c(C#Cc2ccc3nccn3c2)c1] | TT-03620 |
| 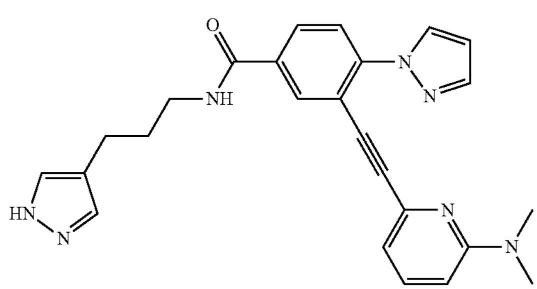 [SMILES: CN(C)c1cccc(C#Cc2cc(C(=O)NCCCc3cn[nH]c3)ccc2-n2cccn2)n1] | TT-03623 |

-continued

| Structure | StructureID |
|---|---|
| 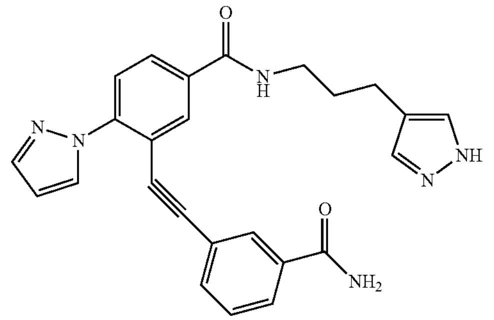 [SMILES: NC(=O)c1cccc(C#Cc2cc(C(=O)NCCCc3cn[nH]c3)ccc2-n2cccn2)c1] | TT-03625 |
| 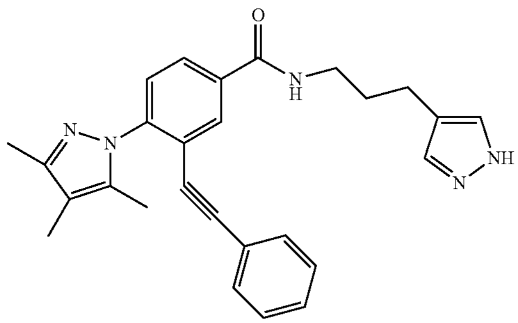 [SMILES: Cc1nn(-c2ccc(C(=O)NCCCc3cn[nH]c3)cc2C#Cc2ccccc2)c(C)c1C] | TT-03626 |
| 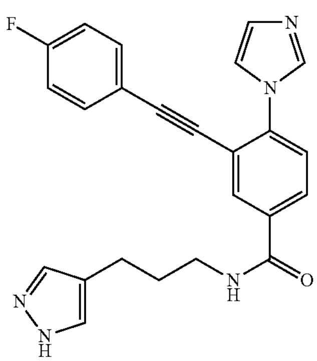 [SMILES: O=C(NCCCc1cn[nH]c1)c1ccc(-n2ccnc2)c(C#Cc2ccc(F)cc2)c1] | TT-03627 |
| 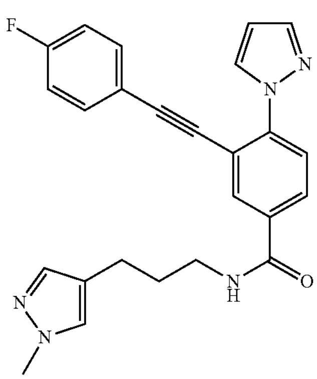 [SMILES: Cn1cc(CCCNC(=O)c2ccc(-n3cccn3)c(C#Cc3ccc(F)cc3)c2)cn1] | TT-03630 |

-continued

| Structure | StructureID |
|---|---|
| 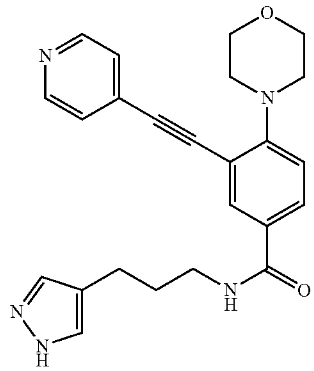 [SMILES: O=C(NCCCc1cn[nH]c1)c1ccc(N2CCOCC2)c(C#Cc2ccncc2)c1] | TT-03631 |
| 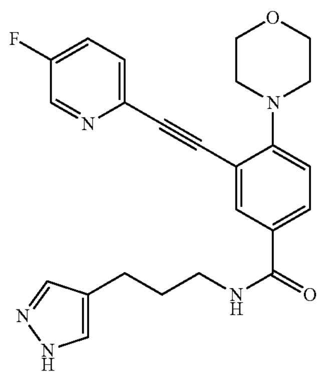 [SMILES: O=C(NCCCc1cn[nH]c1)c1ccc(N2CCOCC2)c(C#Cc2ccc(F)cn2)c1] | TT-03633 |
| 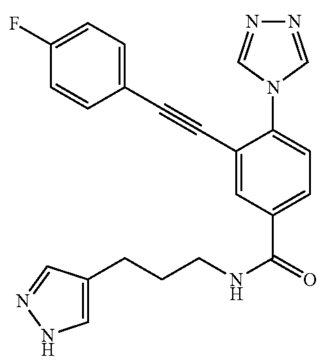 [SMILES: O=C(NCCCc1cn[nH]c1)c1ccc(-n2cnnc2)c(C#Cc2ccc(F)cc2)c1] | TT-03634 |
| 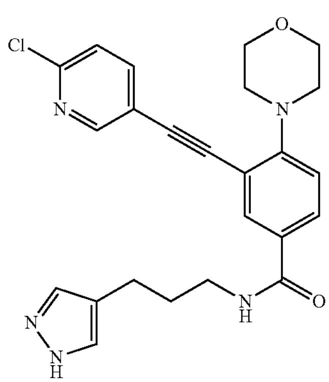 [SMILES: O=C(NCCCc1cn[nH]c1)c1ccc(N2CCOCC2)c(C#Cc2ccc(Cl)nc2)c1] | TT-03655 |

-continued
| Structure | StructureID |
|---|---|
| 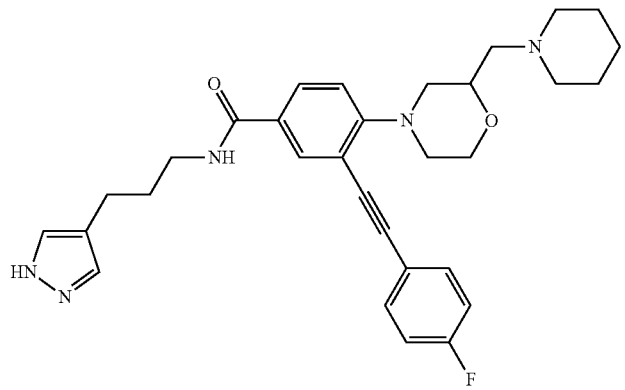 [SMILES: O=C(NCCCc1cn[nH]c1)c1ccc(N2CCOC(CN3CCCCC3)C2)c(C#Cc2ccc(F)cc2)c1] | TT-03669 |
| 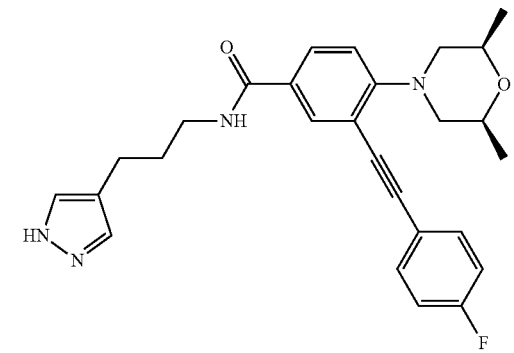 [SMILES: C[C@@H]1CN(c2ccc(C(=O)NCCCc3cn[nH]c3)cc2C#Cc2ccc(F)cc2)C[C@H](C)O1] | TT-03670 |
| 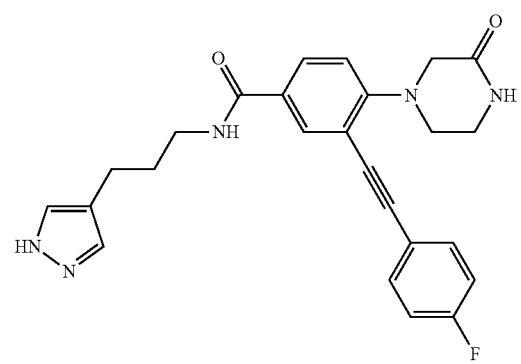 [SMILES: O=C1CN(c2ccc(C(=O)NCCCc3cn[nH]c3)cc2C#Cc2ccc(F)cc2)CCN1] | TT-03671 |
| 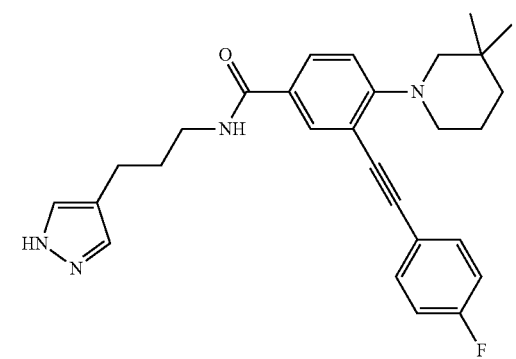 [SMILES: CC1(C)CCCN(c2ccc(C(=O)NCCCc3cn[nH]c3)cc2C#Cc2ccc(F)cc2)C1] | TT-03676 |

-continued
| Structure | StructureID |
|---|---|
| 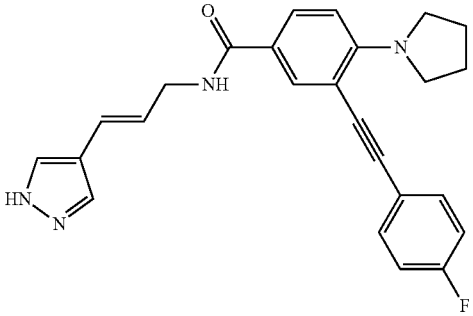 [SMILES: O=C(NC/C=C/c1cn[nH]c1)c1ccc(N2CCCC2)c(C#Cc2ccc(F)cc2)c1] | TT-03717 |
| 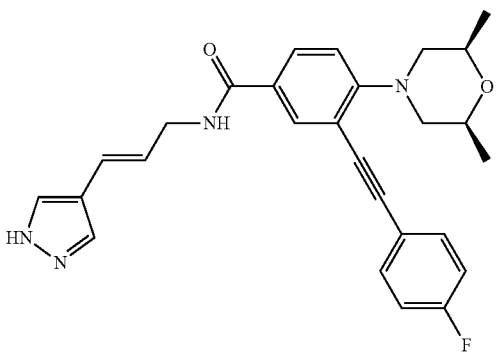 [SMILES: C[C@@H]1CN(c2ccc(C(=O)NC/C=C/c3cn[nH]c3)cc2C#Cc2ccc(F)cc2)C[C@H](C)O1] | TT-03718 |
| 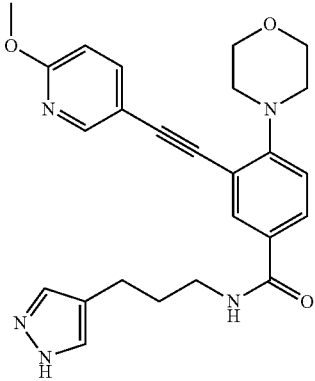 [SMILES: COc1ccc(C#Cc2cc(C(=O)NCCCc3cn[nH]c3)ccc2N2CCOCC2)cn1] | TT-03720 |
| 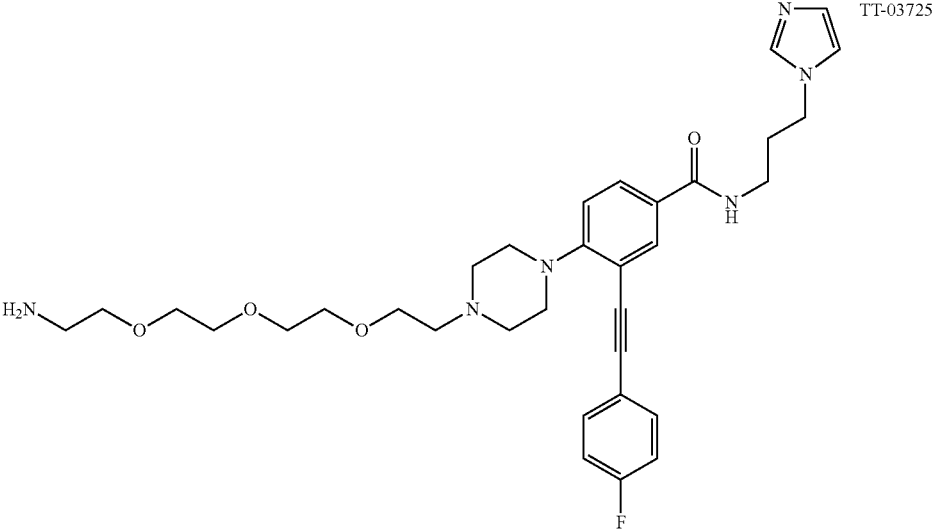 | TT-03725 |

-continued
| Structure | StructureID |
|---|---|
| 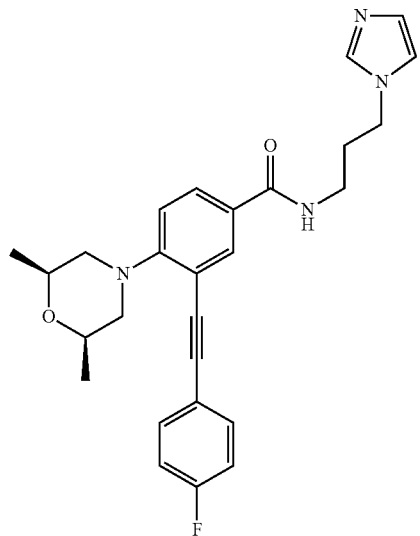 [SMILES: C[C@@H]1CN(c2ccc(C(=O)NCCCn3ccnc3)cc2C#Cc2ccc(F)cc2)C[C@H](C)O1] | TT-03727 |
| 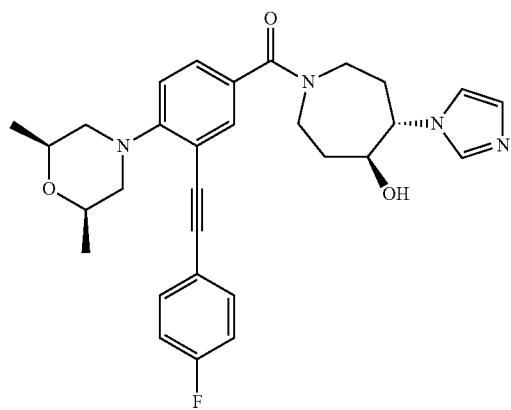 [SMILES: C[C@@H]1CN(c2ccc(C(=O)N3CC[C@H](O)[C@@H](n4ccnc4)CC3)cc2C#Cc2ccc(F)cc2)C[C@H](C)O1] | TT-03732 |
| 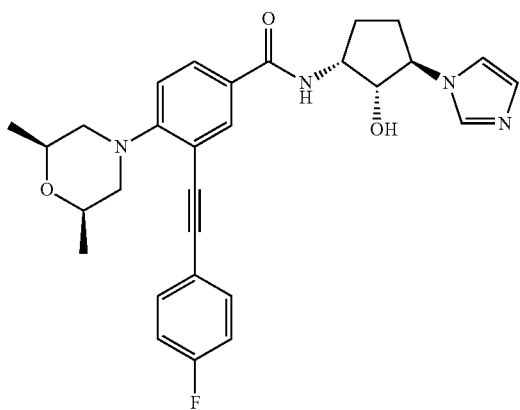 [SMILES: C[C@@H]1CN(c2ccc(C(=O)N[C@@H]3CC[C@@H](n4ccnc4)[C@@H]3O)cc2C#Cc2ccc(F)cc2)C[C@H](C)O1] | TT-03733 |

| Structure | StructureID |
|---|---|
| 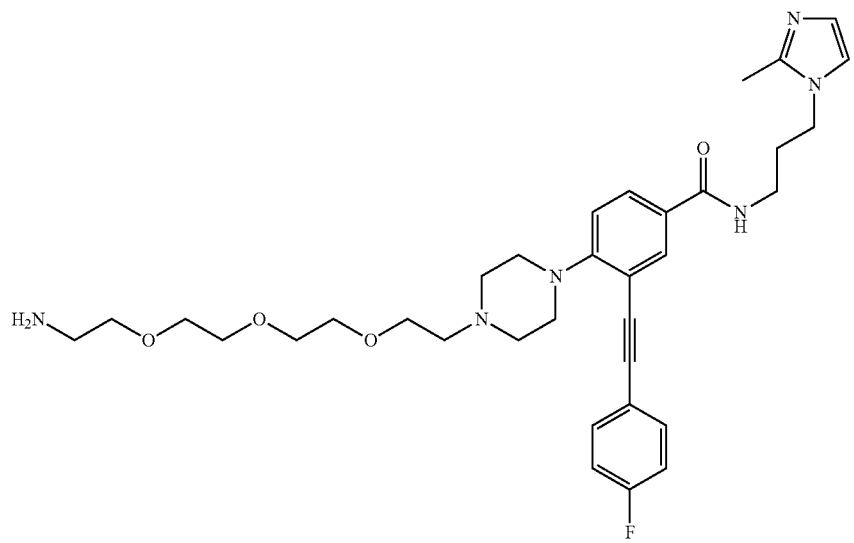 [SMILES: Cc1nccn1CCCNC(=O)c1ccc(N2CCN(CCOCCOCCOCCN)CC2)c(C#Cc2ccc(F)cc2)c1] | TT-03749 |
| 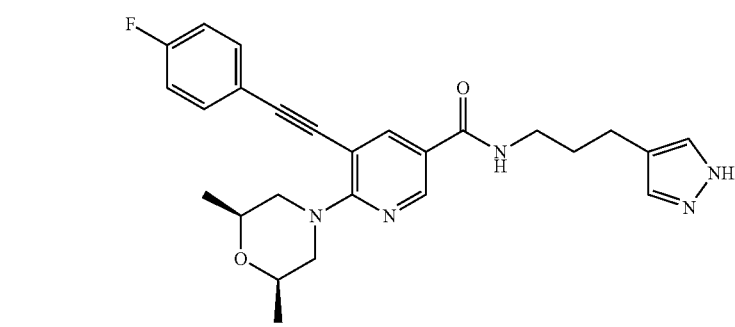 [SMILES: C[C@@H]1CN(c2ncc(C(=O)NCCCc3cn[nH]c3)cc2C#Cc2ccc(F)cc2)C[C@H](C)O1] | TT-03750 |
| 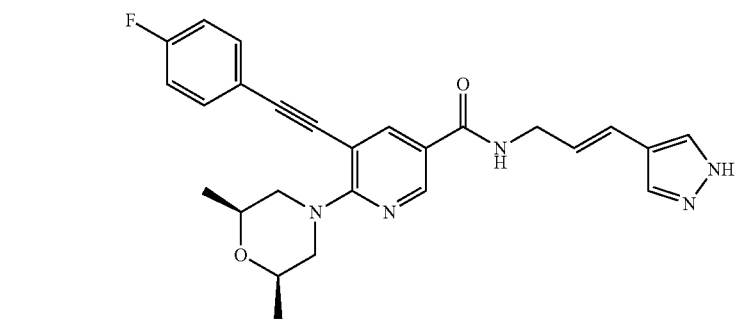 [SMILES: C[C@@H]1CN(c2ncc(C(=O)NC/C=C/c3cn[nH]c3)cc2C#Cc2ccc(F)cc2)C[C@H](C)O1] | TT-03751 |
| 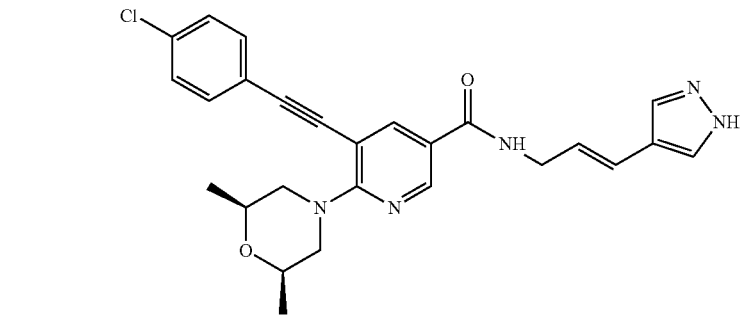 [SMILES: C[C@@H]1CN(c2ncc(C(=O)NC/C=C/c3cn[nH]c3)cc2C#Cc2ccc(Cl)cc2)C[C@H](C)O1] | TT-03752 |

-continued
| Structure | StructureID |
|---|---|
| 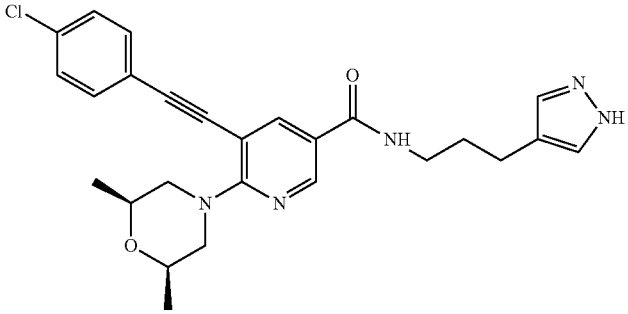 [SMILES: C[C@@H]1CN(c2ncc(C(=O)NCCCc3cn[nH]c3)cc2C#Cc2ccc(Cl)cc2)C[C@H](C)O1] | TT-03753 |
| 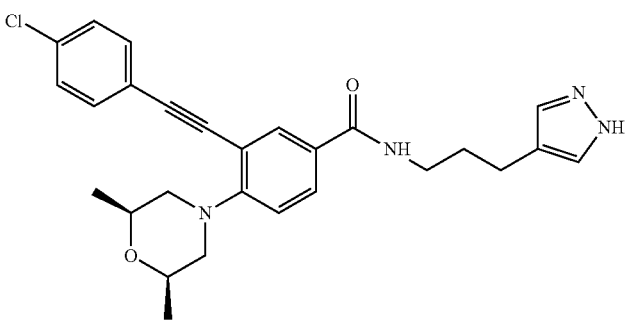 [SMILES: C[C@@H]1CN(c2ccc(C(=O)NCCCc3cn[nH]c3)cc2C#Cc2ccc(Cl)cc2)C[C@H](C)O1] | TT-03754 |
| 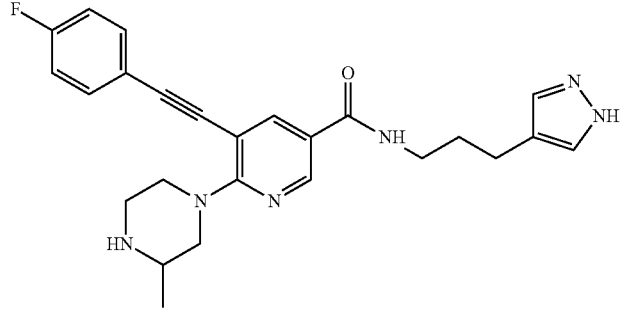 [SMILES: CC1CN(c2ncc(C(=O)NCCCc3cn[nH]c3)cc2C#Cc2ccc(F)cc2)CCN1] | TT-03756 |
| 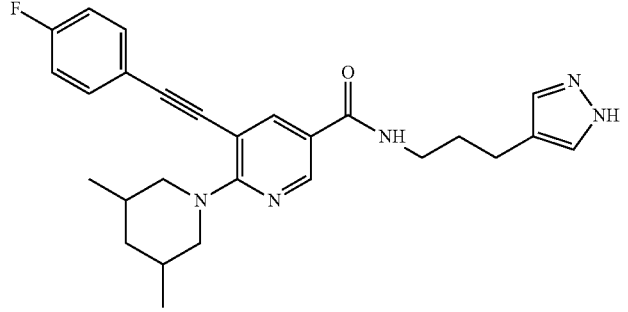 [SMILES: CC1CC(C)CN(c2ncc(C(=O)NCCCc3cn[nH]c3)cc2C#Cc2ccc(F)cc2)C1] | TT-03761 |

| Structure | StructureID |
|---|---|
| 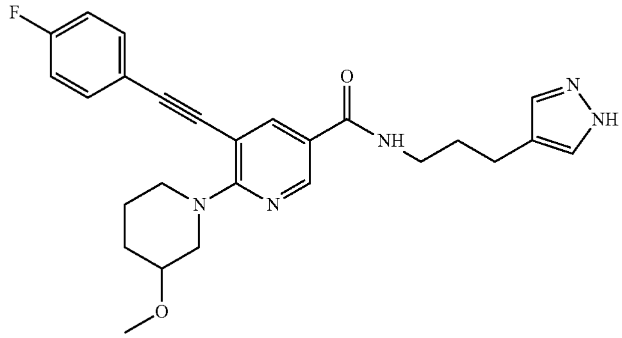 [SMILES: COC1CCCN(c2ncc(C(=O)NCCCc3cn[nH]c3)cc2C#Cc2ccc(F)cc2)C1] | TT-03762 |
| 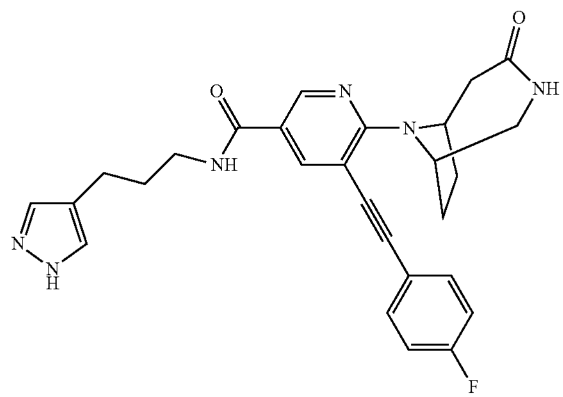 [SMILES: O=C1CC2CCC(CN1)N2c1ncc(C(=O)NCCCc2cn[nH]c2)cc1C#Cc1ccc(F)cc1] | TT-03765 |
| 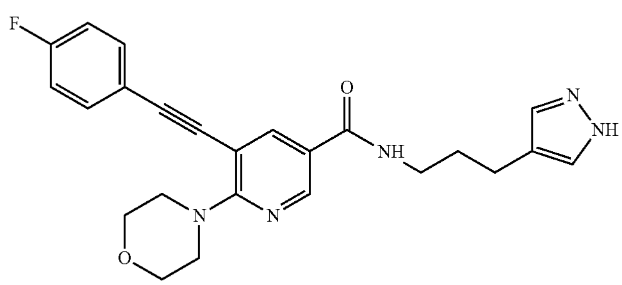 [SMILES: O=C(NCCCc1cn[nH]c1)c1cnc(N2CCOCC2)c(C#Cc2ccc(F)cc2)c1] | TT-03767 |
| 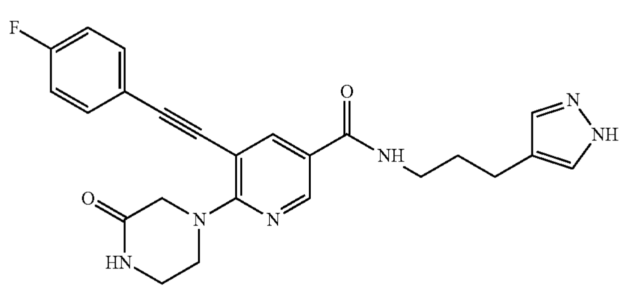 [SMILES: O=C1CN(c2ncc(C(=O)NCCCc3cn[nH]c3)cc2C#Cc2ccc(F)cc2)CCN1] | TT-03768 |

-continued
| Structure | StructureID |
|---|---|
| 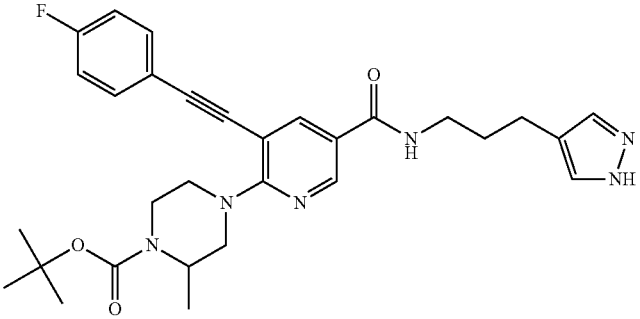 [SMILES: CC1CN(c2ncc(C(=O)NCCCc3cn[nH]c3)cc2C#Cc2ccc(F)cc2)CCN1C(=O)OC(C)(C)C] | TT-03772 |
| 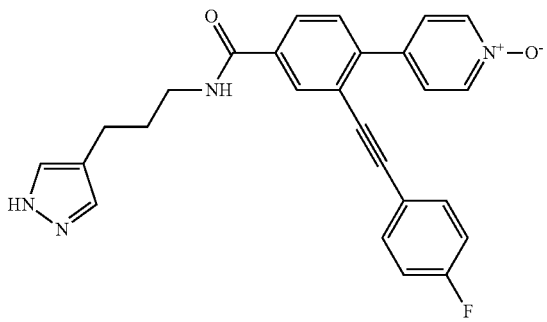 [SMILES: O=C(NCCCc1cn[nH]c1)c1ccc(-c2cc[n+]([O-])cc2)c(C#Cc2ccc(F)cc2)c1] | TT-03773 |
| 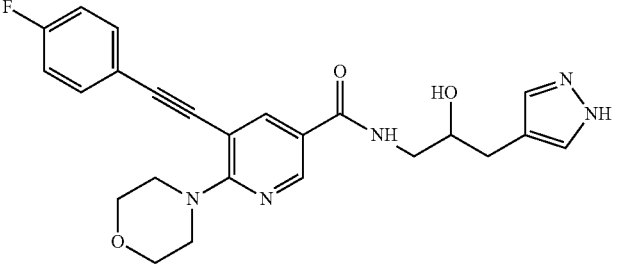 [SMILES: O=C(NCC(O)Cc1cn[nH]c1)c1cnc(N2CCOCC2)c(C#Cc2ccc(F)cc2)c1] | TT-03774 |
| 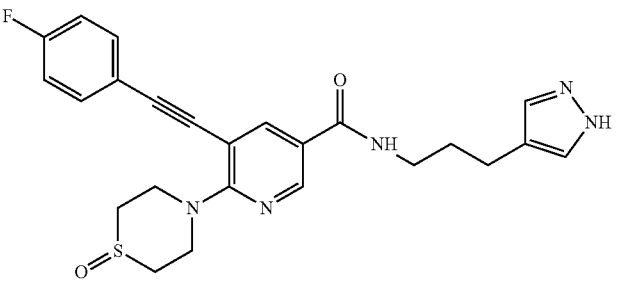 [SMILES: O=C(NCCCc1cn[nH]c1)c1cnc(N2CCS(=O)CC2)c(C#Cc2ccc(F)cc2)c1] | TT-03782 |
| 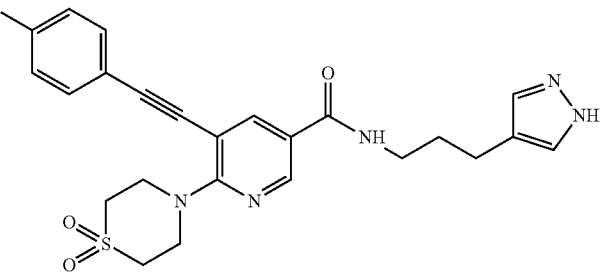 | TT-03783 |

In an embodiment, the compound of the disclosure has the following structure:

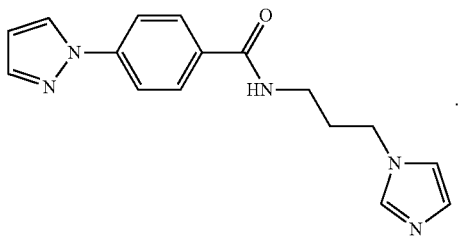 [SMILES: O=C(NCCCn1ccnc1)c1ccc(-n2cccn2)cc1]

In an embodiment, the compound of the disclosure is not N-(3-(1H-imidazol-1-yl)propyl)-3-(phenylethynyl)-4-(1H-pyrazol-1-yl)benzamide:

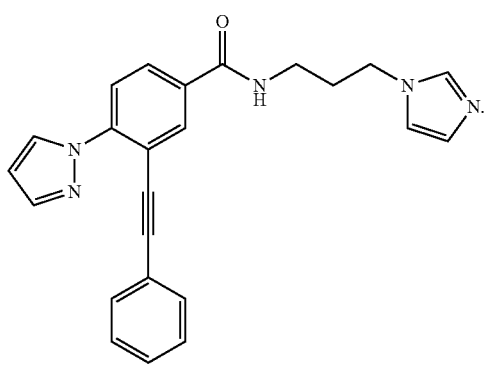 [SMILES: O=C(NCCCn1ccnc1)c1ccc(-n2cccn2)c(C#Cc2ccccc2)c1]

Non-limiting examples of general methods for the preparation of the compounds of the present disclosure are provided in the following schemes (i) and (ii):

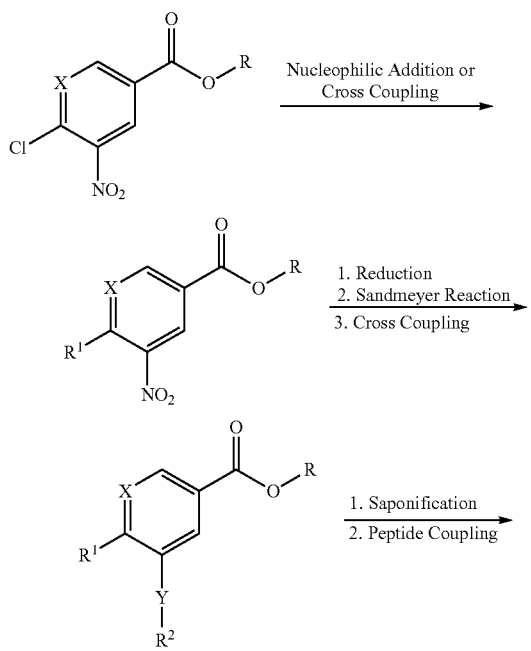

(i)

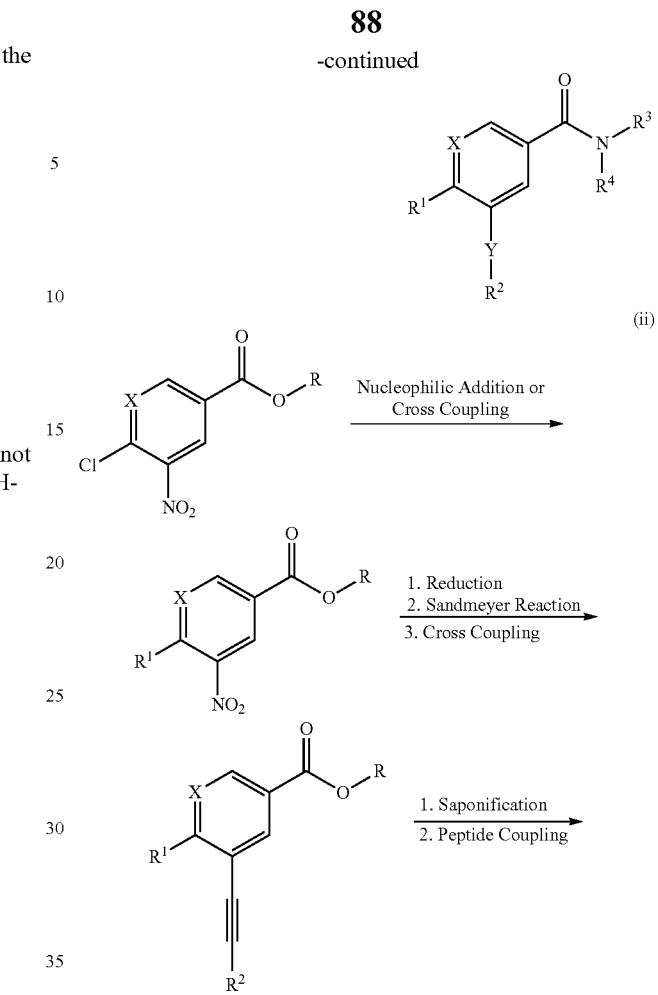

(ii)

More specific, non-limiting, examples of methods to synthesize compounds of the present are illustrated in the examples that follow.

In an aspect, the present disclosure provides a composition comprising at least one compound of the disclosure. Compositions comprising at least one compound of the disclosure include, for example, pharmaceutical preparations.

The present disclosure includes all possible stereoisomers and geometric isomers of the benzamide or nicotinamide compounds (e.g., a compound having the structure (I) to (XII)). The present disclosure includes both racemic compounds and optically active isomers. When the benzamide or nicotinamide compounds (e.g., a compound having the structure (I) to (XII)) is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of benzamide or nicotinamide compounds (e.g., a compound having the structure (I) to (XII)) are possible, the present disclosure is intended to include all tautomeric forms of the compounds.

Prodrugs of the benzamide or nicotinamide compounds (e.g., a compound having the structure (I) to (XII)) also can be used as the compound in a method of the present disclosure. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., Med. Res. Rev., 15, 83 (1995)).

Compounds of the present disclosure can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the disclosure can be in the form of salts. Pharmaceutically acceptable salts of the compounds of the disclosure generally are preferred in the methods of the disclosure. As used herein, the term "pharmaceutically acceptable salts" refers to salts or zwitterionic forms of a benzamide or nicotinamide compound (e.g., a compound having the structure (I) to (XII)). Salts of benzamide or nicotinamide compounds (e.g., a compound having the structure (I) to (XII)) can be prepared during the final isolation and purification of the compounds or separately by reacting the compound with an acid having a suitable cation. In an embodiment, the pharmaceutically acceptable salts of a benzamide or nicotinamide compounds (e.g., a compound having the structure (I) to (XII)) are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present disclosure appearing herein is intended to include benzamide or nicotinamide compounds (e.g., a compound having the structure (I) to (XII)) as well as pharmaceutically acceptable salts, hydrates, or prodrugs thereof.

A benzamide or nicotinamide compound (e.g., a compound having the structure (I) to (XII)) also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamics properties of the compounds, and/or improve the therapeutic index or safety profile of the compounds. Suitable auxiliary moieties include, for example, amino acids, oligopeptides, or polypeptides, e.g., antibodies such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., Clin. Cancer Res. (2001) 7:3229).

In an aspect, the disclosure provides a method of treating cancer in an individual diagnosed with or suspected of having cancer comprising administering to the individual a therapeutically effective amount of a benzamide or nicotinamide compound (e.g., a compound having the structure (I) to (XII)) as described herein. In an embodiment, the cancer is a blood cancer. The blood cancer can be, for example, leukemia.

The language "therapeutically effective amount" of a compound of the disclosure refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment. The exact amount desired or required may vary depending on the particular compound or composition used, its mode of administration, and the like. Appropriate effective amount can be determined by one of ordinary skill in the art informed by the instant disclosure using only routine experimentation.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

Compositions comprising a compound of the disclosure and a pharmaceutical agent can be prepared at a patient's bedside, or by a pharmaceutical manufacture. In the latter case, the compositions can be provided in any suitable container, such as a sealed sterile vial or ampoule, and may be further packaged to include instruction documents for use by a pharmacist, physician or other health care provider. The compositions can be provided as a liquid, or as a lyophilized or powder form that can be reconstituted if necessary when ready for use. The compositions can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents. The compositions described herein can include one or more standard pharmaceutically acceptable carriers. Examples of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art can be used to introduce the compositions of the disclosure to an individual. These methods, for example, of introducing the benzamide or nicotinamide compound, or compositions containing the benzamide or nicotinamide compound, can be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intra-arterial, intracranial, intradermal, subcutaneous, intraperitoneal, subcutaneous, intramuscular, intrathecal, and intraarticular. The benzamide or nicotinamide compound also can be administered in the form of an implant, which allows a slow release of the compound, as well as a slow controlled i.v. infusion.

The dose of the composition comprising a compound of the disclosure and a pharmaceutical agent generally depends upon the needs of the individual to whom the composition of the disclosure is to be administered. These factors include, for example, the weight, age, sex, medical history, and nature and stage of the disease for which a therapeutic or prophylactic effect is desired. The compositions can be used in conjunction with any other conventional treatment modality designed to improve the disorder for which a desired therapeutic or prophylactic effect is intended, non-limiting examples of which include surgical interventions and radiation therapies. The compositions can be administered once, or over a series of administrations at various intervals determined using ordinary skill in the art, and given the benefit of the present disclosure.

Compositions of the disclosure can comprise more than one pharmaceutical agent. For example, a first composition comprising a compound of the disclosure and a first pharmaceutical agent can be separately prepared from a composition which comprises the same compound of the disclosure and a second pharmaceutical agent, and such preparations can be mixed to provide a two-pronged (or more) approach to achieving the desired prophylaxis or therapy in an individual. Further, compositions of the disclosure can be prepared using mixed preparations of any of the compounds disclosed herein.

It is envisioned, therefore, that a benzamide or nicotinamide compound (e.g., a compound having the structure (I) to (XII)) are useful in the treatment of a variety of conditions and diseases. Thus, the present disclosure concerns the use of benzamide or nicotinamide compounds (e.g., a compound having the structure (I) to (XII)), or a pharmaceutically acceptable salt thereof, or a pharmaceutical composition containing either entity, for the manufacture of a medicament for the treatment of such conditions and diseases.

The compounds of the present disclosure can be therapeutically administered as the neat chemical, but it is preferred to administer a benzamide or nicotinamide compound (e.g., a compound having the structure (I) to (XII)) as a pharmaceutical composition or formulation. Thus, the present disclosure provides a pharmaceutical composition comprising a benzamide or nicotinamide compound (e.g., a compound having the structure (I) to (XII)) together with a pharmaceutically acceptable diluent or carrier therefor. Also provided is a process of preparing a pharmaceutical composition comprising admixing a benzamide or nicotinamide compound (e.g., a compound having the structure (I) to (XII)) with a pharmaceutically acceptable diluent or carrier therefor.

Accordingly, the present disclosure further provides pharmaceutical formulations comprising a benzamide or nicotinamide compound (e.g., a compound having the structure (I) to (XII)), or a pharmaceutically acceptable salt, prodrug, or hydrate thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Examples of pharmaceutically-acceptable carrier include pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In an embodiment, the pharmaceutically-acceptable formulation is such that it provides sustained delivery of a benzamide or nicotinamide compound (e.g., a compound having the structure (I) to (XII)) to a subject for at least 3 hours, 6 hours, 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles.

The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of a benzamide or nicotinamide compound (e.g., a compound having the structure (I) to (XII)) which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a benzamide or nicotinamide compound (e.g., a compound having the structure (I) to (XII)) with the carrier and, optionally, one or more accessory ingredients. In general, the formulations are prepared by uniformly and intimately bringing into association a benzamide or nicotinamide compound (e.g., a compound having the structure (I) to (XII)) with liquid carriers, or finely divided solid carriers, or both, and then, if necessary, shaping the product.

Compositions of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a benzamide or nicotinamide compound (e.g., a compound having the structure (I) to (XII)) as an active ingredient. A benzamide or nicotinamide compound (e.g., a compound having the structure (I) to (XII)) may also be administered as a bolus, electuary or paste.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of a benzamide or nicotinamide compound (e.g., a compound having the structure (I) to (XII)) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Pharmaceutical compositions of the disclosure for rectal or vaginal administration may be presented as a suppository, which may be prepared by mixing a benzamide or nicotinamide compound (e.g., a compound having the structure (I) to (XII)) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Dosage forms for the topical or transdermal administration of a benzamide or nicotinamide compound (e.g., a compound having the structure (I) to (XII)) include powders, sprays, ointments, pastes, creams, lotions, gels, solutions, patches and inhalants. A benzamide or nicotinamide compound (e.g., a compound having the structure (I) to (XII)) may be mixed under sterile conditions with a pharmaceutically-acceptable carrier, and with any preservatives, buffers, or propellants which may be required.

The ointments, pastes, creams and gels may contain, in addition to a benzamide or nicotinamide compound (e.g., a compound having the structure (I) to (XII)), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a benzamide or nicotinamide compound (e.g., a compound having the structure (I) to (XII)), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ordinarily, an aqueous aerosol is made by formulating an aqueous solution or suspension of the agent together with conventional pharmaceutically-acceptable carriers and stabilizers. The carriers and stabilizers vary with the requirements of the particular benzamide or nicotinamide compounds (e.g., a compound having the structure (I) to (XII)), but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a benzamide or nicotinamide compound (e.g., a compound having the structure (I) to (XII)) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the disclosure.

Pharmaceutical compositions of the disclosure suitable for parenteral administration comprise a benzamide or nicotinamide compound (e.g., a compound having the structure (I) to (XII)) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a par- enterally-administered drug form is accomplished by dissolving or suspending the drug in an oil vehicle.

Injectable depot forms are made by forming microencapsule matrices of a benzamide or nicotinamide compound (e.g., a compound having the structure (I) to (XII)) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When a benzamide or nicotinamide compound (e.g., a compound having the structure (I) to (XII)) are administered as pharmaceuticals, to individuals (e.g., to humans and non-humans (i.e., animals)), they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, a compound having the structure (I) to (XII), which may be used in a suitable hydrated form, and/or the pharmaceutical compositions of the present disclosure, are formulated into pharmaceutically-acceptable dosage forms by conventional methods known to those of skill in the art.

In certain embodiments, the methods of the disclosure include administering to a subject a therapeutically effective amount of a benzamide or nicotinamide compound (e.g., a compound having the structure (I) to (XII)) in combination with another pharmaceutically active ingredient. Examples of pharmaceutically active ingredients known to treat cell proliferative disorders, e.g., anticancer agent, antiproliferative agent, chemotherapeutic. Other pharmaceutically active ingredients that may be used can be found in Harrison's Principles of Internal Medicine, Thirteenth Edition, Eds. T. R. Harrison et al. McGraw-Hill N.Y., N.Y.; and the Physicians Desk Reference 50th Edition 1997, Oradell N.J., Medical Economics Co., the complete contents of which are expressly incorporated herein by reference. A benzamide or nicotinamide compound (e.g., a compound having the structure (I) to (XII)) and the pharmaceutically active ingredient may be administered to the subject in the same pharmaceutical composition or in different pharmaceutical compositions (at the same time or at different times).

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method). In other methods, the subject is prescreened or identified as in need of such treatment by assessment for a relevant marker or indicator of suitability for such treatment. The identification of those patients who are in need of prophylactic treatment for cell proliferative disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history. The subject may have a cell proliferative disorder, may be at risk of developing a cell proliferative disorder, or may need prophylactic treatment prior to anticipated or unanticipated exposure to a condition(s) capable of increasing susceptibility to a cell proliferative disorder, e.g., exposure to carcinogens or to ionizing radiation.

In an aspect, the disclosure provides a kit for treating a cell proliferative disorder in a subject is provided and includes a benzamide or nicotinamide compound (e.g., a compound having the structure (I) to (XII)), pharmaceutically acceptable esters, salts, and prodrugs thereof, and instructions for use. In further aspects, the disclosure provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In certain embodiments, the disclosure provides: a kit for treating a cell proliferative disorder in a subject, the kit comprising a benzamide or nicotinamide compound (e.g., a compound having the structure (I) to (XII)).

For veterinary use, a benzamide or nicotinamide compound (e.g., a compound having the structure (I) to (XII)), or a pharmaceutically acceptable salt or prodrug, is administered as a suitably acceptable formulation in accordance with normal veterinary practice. The veterinarian can readily determine the dosing regimen and route of administration that is most appropriate for a particular animal. Animals treatable by the present compounds and methods include, but are not limited to, pets, livestock, show animals, and zoo specimens.

When administered in combination with other therapeutics, a present benzamide or nicotinamide compound may be administered at relatively lower dosages. In addition, the use of targeting agents may allow the necessary dosage to be relatively low. Certain compounds may be administered at relatively high dosages due to factors including, but not limited to, low toxicity and high clearance.

For human use, a benzamide or nicotinamide compound (e.g., a compound having the structure (I) to (XII)) can be administered alone, but generally is administered in admixture with a pharmaceutical carrier selected with regard to the intended route of administration and standard pharmaceutical practice. Pharmaceutical compositions for use in accordance with the present disclosure can be formulated in a conventional manner using one or more physiologically acceptable carrier comprising excipients and auxiliaries that facilitate processing of a benzamide or nicotinamide compound (e.g., a compound having the structure (I) to (XII)) into pharmaceutical preparations.

The present benzamide or nicotinamide compounds can be administered simultaneously or metronomically with other anti-cancer treatments, such as chemotherapy and/or radiation therapy. The term "simultaneous" or "simultaneously" means that the other anti-cancer treatment and the benzamide or nicotinamide compound are administered within 6 hours, 3 hours or less, of each other. The term "metronomically" means the administration of the other anti-cancer treatments at times different from the anti-cancer treatments and at a certain frequency relative to repeat administration and/or the anti-cancer treatment regimen.

The benzamide or nicotinamide compounds of the present disclosure can be used to treat a variety of diseases and conditions. For example, compounds of the present disclosure can be used in combination with radiation and/or a chemotherapeutic agent in the treatment of cancers. For example, the benzamide or nicotinamide compounds can be used to enhance treatment of tumors that are customarily treated with an antimetabolite, e.g., methotrexate or 5-fluorouracil (5-FU).

Use of benzamide or nicotinamide compounds of the present disclosure can result in partial or complete regression of cancer cells, i.e., the partial or complete disappearance of such cells from the cell population. For example, a method of the disclosure can be used to slow the rate of tumor growth, decrease the size or number of tumors, or to induce partial or complete tumor regression.

In an embodiment, cancers treated by benzamide or nicotinamide compounds (e.g., a compound having the structure (I) to (XII)) are hematopoietic tumors of lymphoid lineage, including leukemia, acute lymphocytic leukemia, acute lymphoblastic leukemia, 8-celllymphoma, T-cell lymphoma, Hodgkins lymphoma, nonHodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia.

A benzamide or nicotinamide compound (e.g., a compound having the structure (I) to (XII)) can be used for treating a disease or condition in vivo by administration to an individual in need thereof. The disease or condition can be a cancer. A variety of cancers can be treated including, but not limited to: carcinomas, including bladder (including accelerated and metastic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

One method of the present disclosure comprises administration of a therapeutically effective amount of a present benzamide or nicotinamide compound in combination with a chemotherapeutic agent that can effect single- or double-strand DNA breaks or that can block DNA replication or cell proliferation. Alternatively, a method of the present disclosure comprises administration of a therapeutically effective amount of at least one present benzamide or nicotinamide compound in combination with therapies that include use of an antibody, e.g., herceptin, that has activity in inhibiting the proliferation of cancer cells. Accordingly, cancers, for example, colorectal cancers, head and neck cancers, pancreatic cancers, breast cancers, gastric cancers, bladder cancers, vulvar cancers, leukemias, lymphomas, melanomas, renal cell carcinomas, ovarian cancers, brain tumors, osteosarcomas, and lung carcinomas, are susceptible to enhanced treatment by administration of a present benzamide or nicotinamide in combination with a chemotherapeutic agent or an antibody.

Without intending to be bound by any particular theory it is considered that compounds of the present disclosure inhibit NAMPT (Nicotinamide phosphoribosyltransferase). It is considered that based on such inhibition that compounds of the present disclosure have efficacy against diseases related to this target such as acute respiratory distress syndrome (ARDS), aging, atherosclerosis, cancer, diabetes mellitus, rheumatoid arthritis, and sepsis.

Cancers treatable by the present disclosure also include solid tumors, i.e., carcinomas and sarcomas. Carcinomas include malignant neoplasms derived from epithelial cells which infiltrate (i.e., invade) surrounding tissues and give rise to metastases. Adenocarcinomas are carcinomas derived from glandular tissue, or from tissues that form recognizable glandular structures. Another broad category of cancers includes sarcomas, which are tumors whose cells are embedded in a fibrillar or homogeneous substance, like embryonic connective tissue. The present disclosure also enables treatment of cancers of the myeloid or lymphoid systems, including leukemias, lymphomas, and other cancers that typically are not present as a tumor mass, but are distributed in the vascular or lymphoreticular systems.

Additional forms of cancer treatable by the present benzamide or nicotinamide compounds include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscleinvasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Accordingly, administration of a present benzamide or nicotinamide compound is expected to enhance treatment regimens.

In an aspect, a benzamide or nicotinamide compound (e.g., a compound having the structure (I) to (XII)) exhibit anticancer activity. In various embodiments, the compounds of the disclosure are those in which show IC50 values in cytotoxicity experiments towards cells lines MV4-11 and U937 of >20 μM, 10-20 μM, 5-10 μM, 1-5 μM, or <1 μM.

As appreciated by persons skilled in the art, additional active or ancillary agents can be used in the methods described herein. Reference herein to treatment also extends to prophylaxis, as well as to treatment of established diseases or symptoms.

The compound of the present disclosure can be applied to cell populations ex vivo. For example, the present benzamide or nicotinamide compounds can be used ex vivo to determine the optimal schedule and/or dosing of administration of the present benzamide or nicotinamide compound for a given indication, cell type, patient, and other parameter. Information gleaned from such use can be used for experimental purposes or in the clinic to set protocol for in vivo treatment. Other ex vivo uses for which the disclosure is suited are apparent to those skilled in the art.

A present benzamide or nicotinamide compound also can be administered in combination with radiation. Diseases that are treatable with electromagnetic radiation include neoplastic diseases, benign and malignant tumors, and cancerous cells.

Electromagnetic radiation treatment of other diseases not listed herein also is contemplated by the present disclosure. Preferred embodiments of the present disclosure employ the electromagnetic radiation of: gamma-radiation (10-20 to 10-13 m), X-ray radiation (10-12 to 10-9 m), ultraviolet light (10 nm to 400 nm), visible light (400 nm to 700 nm), infrared radiation (700 nm to 1 mm), and microwave radiation (1 mm to 30 nm).

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRINriD, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present benzamide or nicotinamide compound, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUO-SOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a benzamide or nicotinamide compound of the present disclosure can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the disclosure include hormones and antagonists thereof, radioisotopes, antibodies, natural products, and combinations thereof.

A benzamide or nicotinamide compound (e.g., a compound having the structure (I) to (XII)) of this disclosure can be provided in pharmaceutical compositions. In an embodiment, the pharmaceutical composition comprises one or more benzamide or nicotinamide compounds (e.g., a compound having the structure (I) to (XII)) of the present disclosure and a pharmaceutically acceptable carrier. In an embodiment, the kits of the disclosure can comprise one or more benzamide or nicotinamide compounds (e.g., a compound having the structure (I) to (XII)) alone, as pharmaceutical preparations, or separate pharmaceutical preparations with each pharmaceutical preparation comprising a separate benzamide or nicotinamide compound (e.g., a compound having the structure (I) to (XII)).

The following specific examples are to be construed as merely illustrative, and not limitative of the remainder of the disclosure in any way whatsoever.

Example 1

This example provides synthetic procedures for benzamides and nicotinamides of the present disclosure.

Procedure for Synthesis of Compound 24.

A suspension of compound 14 (33.6 g, 156 mmol, 1.0 eq.) and hydrazine hydrate (12 mL, 386 mmol, 2.5 eq.) in ethanol (280 mL) was stirred at room temperature for 20 hours. The formed precipitate was filtered off and dried. The obtained product was purified by column chromatography (silica gel, hexane/ethyl acetate, 2:1) giving compound 24 (10.86 g, 33%) as a yellow-orange solid. APCI-MS (m/z (intensity)): 211.70 ([M+H]$^+$, 90%), 253.13 ([M+MeCN+H]$^+$, 100%).

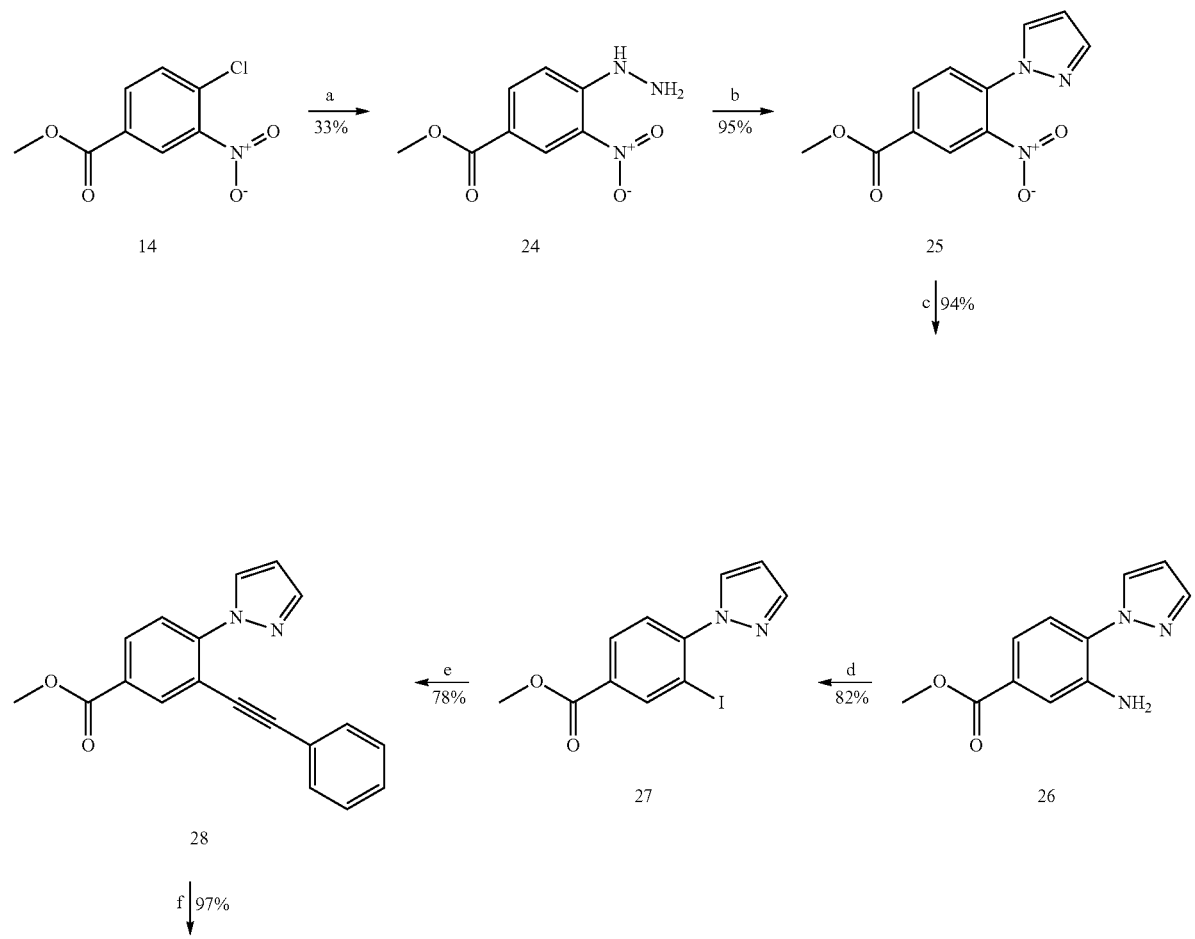

Scheme 1.

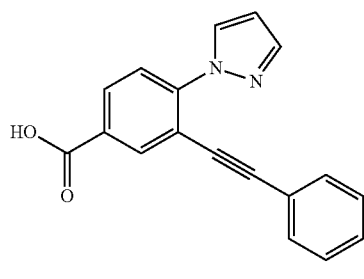

29

-continued

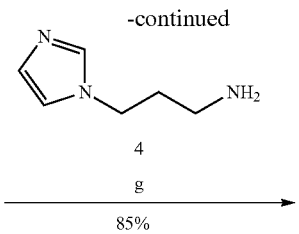

4

↓ g
85%

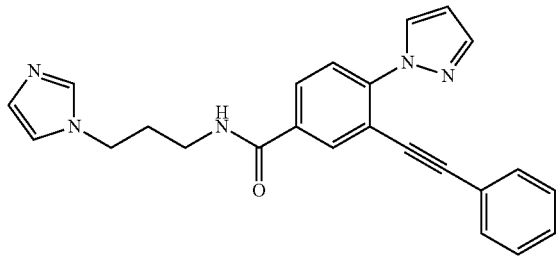

30, TT-01901

(a) N₂H₄*H₂O, EtOH, RT, 20 h; (b) HCl aq. conc., H₂O, (MeO)₂CHCH₂CH(OMe)₂, EtOH, reflux, 2.5 h; (c) H₂, Ra — Ni, MeOH, RT, 16 h; (d) NaNO₂, H₂O, HCl, aq. conc., H₂O, 0° C., KI, RT, 30 min; (e) phenylacetylene, PdCl₂[PPh₃]₂, t-Bu₃P, Et₃N, DMF, Ar, 80° C., 2 h; (f) NaOH, H₂O, MeOH, 55° C., 2.5 h; (g) TBTU, DIPEA, DCM, THF, RT, 2 h Procedure for Synthesis of Compound 25.

A mixture of concentrated aqueous HCl solution (0.75 mL, 8.6 mmol, 0.17 eq.) and water (37 mL) was added to a suspension of compound 24 (10.85 g, 51.38 mmol, 1.0 eq.) and 1,1,3,3-tetramethoxypropane (12.50 g, 76.12 mmol, 1.5 eq.) in EtOH (74 mL) dropwise at room temperature. The reaction mixture was stirred at refluxing for 2.5 hours. The formed precipitate was collected by filtration and dried. The obtained product was purified by column chromatography (silica gel, hexane/ethyl acetate, 4:1) giving compound 25 (12.05 g, 95%) as a yellowish crystals. APCI-MS (m/z (intensity)): 248.10 ([M+H]⁺, 100%), 289.12 ([M+MeCN+H]⁺, 10%).

Procedure for Synthesis of Compound 26.

A mixture of compound 25 (12.05 g. 48.74 mmol, 1.0 eq.), Raney nickel catalyst (2.4 g, 40.89 mmol, 0.84 eq.) and methanol (500 mL) was hydrogenated (2 atm) at room temperature for 16 hours. The catalyst was removed by filtration. The filtrate was concentrated at reduced pressure. The obtained residue was purified by column chromatography (silica gel, hexane/ethyl acetate, 4:1) giving compound 26 (9.91 g, 94%) as a yellowish solid. APCI-MS (m/z (intensity)): 218.10 ([M+H]⁺, 100%). ¹H NMR $\delta_H$ (400 MHz, D₆-DMSO): 3.85 (s, 3H), 5.93 (brs, 2H), 6.54 (t, 1H), 7.23 (dd, 1H), 7.40 (d, 1H), 7.54 (d, 1H), 7.79 (d, 1H), 8.20 (d, 1H).

Procedure for Synthesis of Compound 27.

A solution of sodium nitrite (3.14 g, 45.50 mmol, 1.0 eq.) in water (45 mL) was slowly added to a stirred suspension of compound 26 (9.75 g, 44.88 mmol, 1.0 eq.) in a mixture of concentrated aqueous HCl solution (45 mL) and water (45 mL) at 0° C. By the end of addition of the sodium nitrite solution the reaction mixture became clear. After the addition formation of a precipitate was observed. The reaction mixture was stirred at 0° C. for 10 minutes after the addition. Then a solution of potassium iodide (14.82 g, 89.28 mmol, 2.0 eq.) in water (45 mL) was added to the mixture at 0° C. A very viscous red-brown mixture was formed which turned to dark brown color. The reaction mixture was stirred at room temperature for 30 minutes, treated with saturated aqueous potassium carbonate solution to reach pH>8 and extracted with DCM. The organic layer was washed with an aqueous NaHSO₃ solution, with water, dried over sodium sulfate and concentrated at reduced pressure. The obtained residue was purified by column chromatography (silica gel, hexane/ethyl acetate, 4:1) giving compound 27 (12.04 g, 82%) as a yellowish solid. APCI-MS (m/z (intensity)): 329.07 ([M+H]⁺, 100%), 370.09 ([M+MeCN+H]⁺, 20%).

Procedure for Synthesis of Compound 28.

Triethylamine (10 mL), t-Bu₃P (668 mg, 3.30 mmol, 9 mol %) and PdCl₂[PPh₃]₂ (773 mg, 1.10 mmol, 3 mol %) were added to a solution of compound 27 (12.02 g, 36.63 mmol, 1.0 eq.) in anhydrous DMF (60 mL). The resulting mixture was stirred under argon atmosphere at room temperature for 10 minutes. Then phenyl-acetylene (7.49 g, 73.39 mmol, 2.0 eq.) was added dropwise. The reaction mixture was stirred at 75-80° C. for 2 hours, cooled down to room temperature and filtered through a pad of Celite washing with ethyl acetate. The filtrate was diluted with water (250 mL) and extracted with ethyl acetate. The organic phase was dried over sodium sulfate and concentrated at reduced pressure. The obtained residue was purified by column chromatography (silica gel, hexane/DCM, 4:1), then washed with cold diethyl ether and dried giving compound 28 (8.68 g, 78%) as a yellowish solid. APCI-MS (m/z (intensity)): 303.18 ([M+H]⁺, 100%). ¹H NMR $\delta_H$ (400 MHz, D₆-DMSO): 3.95 (s, 3H), 6.64 (t, 1H), 7.43-7.47 (m, 3H), 7.51-7.55 (m, 2H), 7.86 (d, 1H), 7.89 (d, 1H), 8.09 (dd, 1H), 8.24 (d, 1H), 8.62 (d, 1H).

Procedure for Synthesis of Compound 29.

A solution of NaOH (4.55 g, 113.75 mmol, 5.0 eq.) in water (40 mL) was added to a suspension of compound 28 (6.90 g, 22.82 mmol, 1.0 eq.) in MeOH (350 mL). The reaction mixture was stirred at 50-55° C. for 2.5 hours, cooled down to room temperature, concentrated at reduced pressure, diluted with water (200 mL) and acidified with an aqueous HCl solution (1M) to reach pH 5. The formed precipitate was collected by filtration, dried at reduced pressure with $P_2O_5$, washed with cold ether and dried giving compound 29 (6.38 g, 97%) as a yellowish solid. APCI-MS (m/z (intensity)): 289.12 ([M+H]$^+$, 100%). $^1$H NMR $\delta_H$ (400 MHz, D$_6$-DMSO): 3.50 (brs, 1H+H$_2$O), 6.58 (t, 1H), 7.40-7.44 (m, 3H), 7.46-7.50 (m, 2H), 7.67 (d, 1H), 7.79 (d, 1H), 8.03 (dd, 1H), 8.19 (d, 1H), 8.48 (d, 1H).

Procedure for Synthesis of Compound 30.

A mixture of compound 29 (4.97 g, 17.24 mmol, 1.0 eq.), TBTU (7.75 g, 24.15 mmol, 1.4 eq.), DCM (50 mL) and THF (150 mL) was stirred at room temperature for 50 minutes. Then 3-imidazol-1-yl-propylamine (4) (2.38 g, 18.98 mmol, 1.1 eq.) and DIPEA (6 mL, 34.50 mmol, 2.0 eq.) were added. The reaction mixture was stirred at room temperature for 2 hours, diluted with saturated aqueous NaHCO$_3$ solution (equivalent volume), stirred at room temperature for 1.5 hours and extracted with ethyl acetate. The organic layer was dried over sodium sulfate and concentrated at reduced pressure. The obtained residue was purified by column chromatography (silica gel, ethyl acetate/MeOH/NH$_4$OH, 40:2:1) giving compound 30 (5.78 g, 85%) as a white solid.

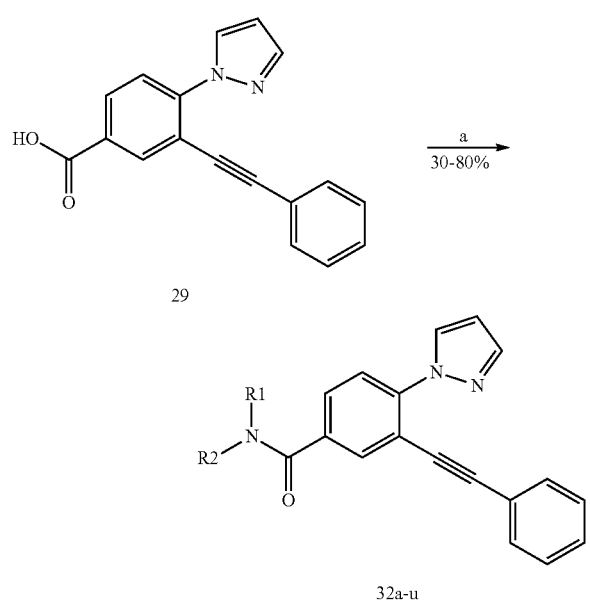

Scheme 2.

(a) R1R2NH, TBTU, Et$_3$N, DCM, THF, RT, 4 h

TABLE 1

| | —NR1R2 | Compound | Yield (%) |
|---|---|---|---|
| 1 | | 32a | 60 |

TABLE 1-continued

| | —NR1R2 | Compound | Yield (%) |
|---|---|---|---|
| 2 | | 32b | 30 |
| 3 | | 32c | 36 |
| 4 | | 32d | 63 |
| 5 | | 32e | 60 |
| 6 | | 32f | 69 |
| 7 | | 32g | 31 |
| 8 | | 32h | 57 |
| 9 | | 32i | 70 |
| 10 | | 32j | 37 |
| 11 | | 32k | 74 |
| 12 | | 32l | 39 |
| 13 | | 32m | 65 |

TABLE 1-continued

| | —NR1R2 | Compound | Yield (%) |
|---|---|---|---|
| 14 | methyl(methyl-furazanyl-methyl)amine | 32n | 54 |
| 15 | methyl(5-methyl-isoxazol-3-yl-methyl)amine | 32o | 74 |
| 16 | (3-methyl-1,2,4-oxadiazol-5-yl-methyl)amine | 32p | 65 |
| 17 | 4-methyl-3-(1-methyl-pyrrolidin-3-yl)-4H-1,2,4-triazole | 32q | 37 |
| 18 | 2-(1H-1,2,4-triazol-1-yl)ethyl-amine | 32r | 68 |
| 19 | 4-(1H-imidazol-1-yl)butyl-amine | 32s | 75 |
| 20 | 1-methyl-3-((1H-imidazol-1-yl)methyl)piperidine | 32t | 57 |
| 21 | 2-(3,5-dimethyl-1H-1,2,4-triazol-1-yl)ethyl-amine | 32u | 80 |

Generic Procedure for Synthesis of Compounds 32a-u.

A suspension of compound 29 (140 mg, 0.48 mmol, 1.0 eq.), TBTU (263 mg, 0.82 mmol, 1.7 eq.) and THF (5 mL) was stirred at room temperature for 2 hours. Then the corresponding amine (R1R2NH) (0.58 mmol, 1.2 eq), triethylamine (0.2 mL, 1.44 mmol, 3.0 eq.) and DCM (3 mL) were added. The reaction mixture was stirred at room temperature for 4 hours, diluted with saturated aqueous NaHCO₃ solution (equivalent volume), stirred at room temperature for 2 hours and extracted with DCM. The organic layer was dried over sodium sulfate and concentrated at reduced pressure. The obtained residue was purified by column chromatography giving a target compounds (32a-u).

Scheme 3.

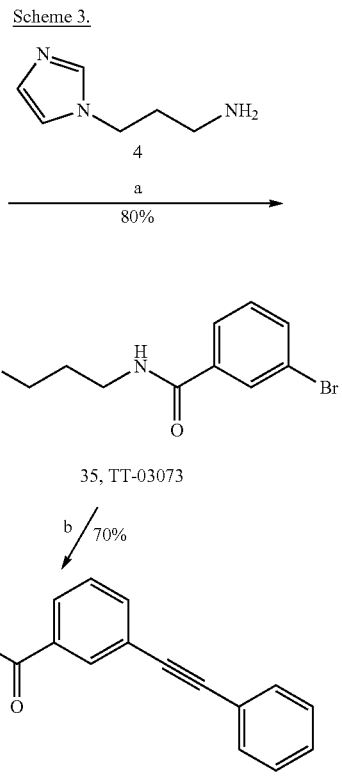

(a) TBTU, Et₃N, DCM, RT, 50 h; (b) phenylacetylene, PdCl₂[PPh₃]₂, t-Bu₃P, Et₃N, DMF, Ar, 80° C., 2 h Procedure for Synthesis of Compound 35.

A mixture of 3-bromo-benzoic acid (34) (700 mg, 3.48 mmol, 1.0 eq.), TBTU (1.680 g, 5.22 mmol, 1.5 eq.), 3-imidazol-1-yl-propylamine (4) (500 mg, 3.99 mmol, 1.1 eq.), triethylamine (0.7 mL, 5.00 mmol, 1.4 eq.) and DCM (15 mL) was stirred at room temperature for 50 hours, diluted with saturated aqueous NaHCO₃ solution (50 mL) and extracted with DCM. The organic layer was dried over sodium sulfate and concentrated at reduced pressure. The obtained residue was purified by column chromatography (silica gel, ethyl acetate/MeOH), washed with diethyl ether and dried giving compound 35 (855 mg, 80%) as a white solid.

Procedure for Synthesis of Compound 36.

A mixture of compound 35 (308 mg, 1.00 mmol, 1.0 eq.), PdCl₂[PPh₃]₂ (30 mg, 0.04 mmol, 4 mol %), t-Bu₃P (30 mg, 0.15 mmol, 15 mol %), triethylamine (3 mL) and DMF (3 mL) was stirred under argon atmosphere at room temperature for 5 minutes. Then phenyl-acetylene (200 mg, 2.00 mmol, 2.0 eq.) was added dropwise. The reaction mixture was stirred at 75-80° C. for 2 hours, cooled down to room temperature, diluted with water (20 mL) and extracted with DCM. The organic phase was dried over sodium sulfate and concentrated at reduced pressure. The obtained residue was purified by column chromatography (silica gel, ethyl acetate/MeOH/NH₄OH, 10:2:1) giving compound 36 (230 mg, 70%) as a white solid.

Experimental part: General experimental methods. LCMS. The LC/MS analysis was done at Surveyor MSQ (Thermo Fisher Scientific) with APCI ionization. 1. Type of HPLC column: Phenomenex Onyx Monolithic C18; 25×4.6 mm; Part No: CHO-7645. 2. Solvent for samples dissolution: 50% DMSO, 50% acetonitrile. 3. Flow rate: 1.5 mL/min; column temperature 25° C. 4. Mobile phase: A=0.1% solution of formic acid in water, B=0.1% solution of formic acid in acetonitrile. 5. Gradient:

| time, min. | A % | B % |
|---|---|---|
| 0.0 | 100 | 0 |
| 0.1 | 100 | 0 |
| 2.1 | 5 | 95 |
| 2.5 | 5 | 95 |
| 2.6 | 100 | 0 |
| 4.0 | 100 | 0 |

6. Detection: diode array (PDA), 200-800 nm; photodiode array detector. Detection was carried out in the full ultraviolet-visible range from 200 to 800 nm. APCI (+ or/and − ions)—atmospheric pressure chemical ionization ELSD (PL-ELS 2100). 7. Total run time of the method: 4.5 min. 8. Injection volume: 2 μL.

NMR: The $^1$H NMR spectra were recorded on a MERCURY plus 400 MHz spectrometer (Varian). Chemical shift values are given in ppm relative to tetramethylsilane (TMS), with the residual solvent proton resonance as internal standard.

HPLC: The HPLC analysis was done at Agilent 1100 instrument. 1. Type of HPLC column: Onyx Monolithic C18, 100×4.6 mm. 2. Flow rate: 1 mL/min; column temperature—ambient. 3. Mobile phase: A=0.1% TFA in water, B=0.1% TFA in acetonitrile.

List of abbreviations: Ac—acetyl, MeCO, APCI—atmospheric-pressure chemical ionization, aq.—aqueous, Ar—aryl or argon, atm—atmosphere(s), brs—broad singlet, Bu—butyl, conc.—concentrated, d—doublet, DABCO—1,4-diazabicyclo[2.2.2]octane, DCM—dichloromethane, dd—doublet of doublets, DIPEA—diisopropylethylamine, DMF—dimethylformamide, DMSO—dimethylsulfoxide, dppf—1,1'-bis(diphenylphosphino)ferrocene, ELSD—evaporative light scattering detector, Et—ethyl, eq.—equivalent, h—hour(s), HPLC—high-performance liquid chromatography, i-—iso-, i-Pr—i-propyl, m—multiplet, Me—methyl, MeCN—acetonitrile, MHz—megahertz, n-—normal-, n-Bu—n-butyl, min—minute(s), MS—mass-spectrometry, MWI—microwave irradiation, NBS—N-bromosuccinimide, NMR—Nuclear magnetic resonance, PDA—photodiode array, Ph—phenyl, Pr—propyl, q—quartet, Ra—Ni—Raney-nickel, RT—room temperature, s—singlet, t—triplet, t-—tert-, TBTU—N,N,N',N'-tetramethyl-O-(benzotriazol-1-yl)uronium tetrafluoroborate, t-Bu—tert-butyl, THF—tetrahydrofuran, TMS (tms)—trimethylsilyl, UV—ultraviolet.

Example 2

This example provides synthetic procedures for benzamides and nicotinamides of the present disclosure.

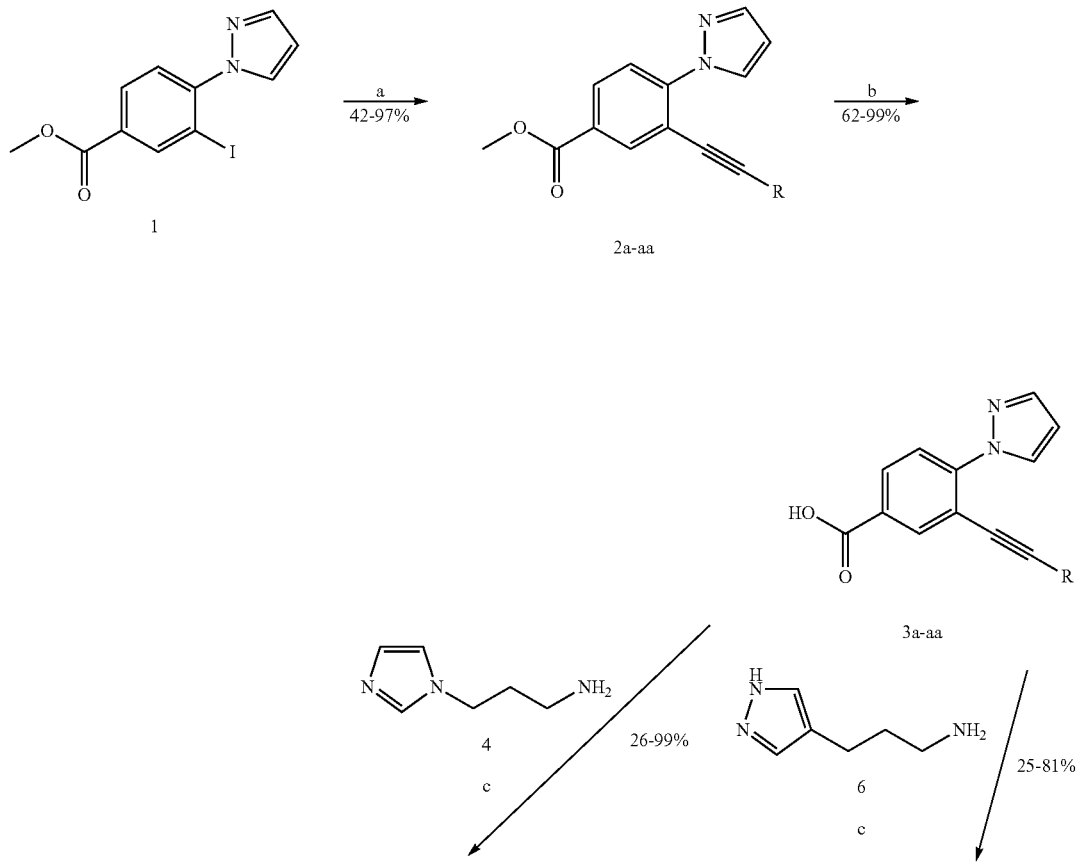

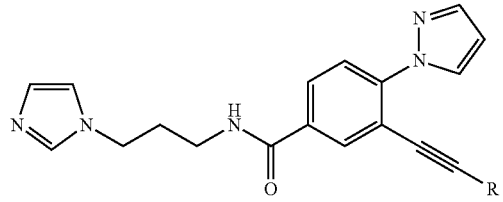

5a-o

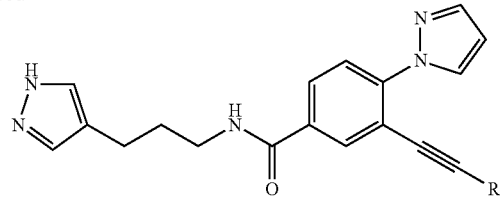

7a-aa (a) acetylene; PdCl₂[PPh₃]₂, CuI, Et₃N, MeCN, Ar, reflux, 4-8 h; (b) NaOH, THF, H₂O, MeOH, 50° C., 1-2 h; (c) TBTU, Et₃N, DMF, RT, 8-12 h

TABLE 2

|   | —R | Product compound | Yield (%) | Product compound | Yield (%) |
|---|---|---|---|---|---|
| 1 | 3-Py— | 2a | 96 | 3a | 87 |
| 2 | 4-Me—C₆H₄— | 2b | 51 | 3b | 88 |
| 3 | 4-F—C₆H₄— | 2c | 70 | 3c | 94 |
| 4 | 4-CF₃—C₆H₄— | 2d | 81 | 3d | 75 |
| 5 | 3-Cl—C₆H₄— | 2e | 76 | 3e | 95 |
| 6 | 2-Cl—C₆H₄— | 2f | 84 | 3f | 96 |
| 7 | 2-CF₃—C₆H₄— | 2g | 84 | 3g | 62 |
| 8 | 3-F—C₆H₄— | 2h | 56 | 3h | 96 |
| 9 | 4-Cl—C₆H₄— | 2i | 79 | 3i | 93 |
| 10 | 2-F—C₆H₄— | 2j | 73 | 3j | 96 |
| 11 | 4-Py— | 2k | 97 | 3k | 83 |
| 12 | 4-MeO—C₆H₄— | 2l | 42 | 3l | 82 |
| 13 | 3-MeO—C₆H₄— | 2m | 75 | 3m | 94 |
| 14 | 3-HO—C₆H₄— | 2n | 44 | 3n | 97 |
| 15 | 2-Me—C₆H₄— | 2o | 86 | 3o | 89 |
| 16 | 3-Me—C₆H₄— | 2p | 59 | 3p | 85 |
| 17 | 2-MeO—C₆H₄— | 2q | 49 | 3q | 67 |
| 18 | 3-CF₃—C₆H₄— | 2r | 68 | 3r | 82 |
| 19 | —CMe₂OH | 2s | 91 | 3s | 73 |
| 20 | HO-cyclohexyl | 2t | 97 | 3t | 98 |
| 21 | 6-amino-2-pyridyl | 2u | 38 | 3u | 52 |
| 22 | 2-Py— | 2v | 64 | 3v | 81 |
| 23 | 5-F-2-pyridyl | 2w | 62 | 3w | 99 |
| 24 | 6-Cl-3-pyridyl | 2x | 52 | 3x | 99 |
| 25 | imidazo[1,2-a]pyridin-6-yl | 2y | 73 | 3y | 71 |
| 26 | 6-(dimethylamino)-2-pyridyl | 2z | 35 | 3z | 99 |
| 27 | 3-MeNHCO—C₆H₄— | 2aa | 61 | 3aa | 99 |

TABLE 3

|   | —R | Starting compound | Product compound | Yield (%) |
|---|---|---|---|---|
| 1 | 3-Py- | 3a | 5a | 62 |
| 2 | 4-Me—C₆H₄— | 3b | 5b | 65 |
| 3 | 4-F—C₆H₄— | 3c | 5c | 69 |
| 4 | 4-CF₃—C₆H₄— | 3d | 5d | 99 |
| 5 | 3-Cl—C₆H₄— | 3e | 5e | 26 |
| 6 | 2-Cl—C₆H₄— | 3f | 5f | 42 |
| 7 | 2-CF₃—C₆H₄— | 3g | 5g | 88 |
| 8 | 3-F—C₆H₄— | 3h | 5h | 53 |
| 9 | 4-Cl—C₆H₄— | 3i | 5i | 69 |
| 10 | 2-F—C₆H₄— | 3j | 5j | 66 |
| 11 | 4-Py- | 3k | 5k | 61 |
| 12 | 3-MeO—C₆H₄— | 3m | 5l | 61 |
| 13 | 3-HO—C₆H₄— | 3n | 5m | 42 |
| 14 | 3-Me—C₆H₄— | 3p | 5n | 81 |
| 15 | 3-CF₃—C₆H₄— | 3r | 5o | 62 |

TABLE 4

|   | —R | Starting compound | Product compound | Yield (%) |
|---|---|---|---|---|
| 1 | 3-Py— | 3a | 7a | 59 |
| 2 | 4-Me—C₆H₄— | 3b | 7b | 62 |
| 3 | 4-F—C₆H₄— | 3c | 7c | 75 |
| 4 | 4-CF₃—C₆H₄— | 3d | 7d | 70 |
| 5 | 3-Cl—C₆H₄— | 3e | 7e | 62 |
| 6 | 2-Cl—C₆H₄— | 3f | 7f | 58 |
| 7 | 2-CF₃—C₆H₄— | 3g | 7g | 56 |
| 8 | 3-F—C₆H₄— | 3h | 7h | 25 |
| 9 | 4-Cl—C₆H₄— | 3i | 7i | 81 |
| 10 | 2-F—C₆H₄— | 3j | 7j | 66 |
| 11 | 4-Py— | 3k | 7k | 46 |
| 12 | 4-MeO—C₆H₄— | 3l | 7l | 54 |
| 13 | 3-MeO—C₆H₄— | 3m | 7m | 68 |
| 14 | 3-HO—C₆H₄— | 3n | 7n | 47 |
| 15 | 2-Me—C₆H₄— | 3o | 7o | 63 |
| 16 | 3-Me—C₆H₄— | 3p | 7p | 62 |
| 17 | 2-MeO—C₆H₄— | 3q | 7q | 73 |

TABLE 4-continued

| | —R | Starting compound | Product compound | Yield (%) |
|---|---|---|---|---|
| 18 | 3-CF$_3$—C$_6$H$_4$— | 3r | 7r | 54 |
| 19 | —CMe$_2$OH | 3s | 7s | 63 |
| 20 | HO-cyclohexyl-* | 3t | 7t | 53 |
| 21 | 6-aminopyridin-2-yl* | 3u | 7u | 46 |
| 22 | 2-Py— | 3v | 7v | 26 |
| 23 | 5-fluoropyridin-2-yl* | 3w | 7w | 56 |
| 24 | 6-chloropyridin-3-yl* | 3x | 7x | 62 |
| 25 | imidazo[1,2-a]pyridin-6-yl* | 3y | 7y | 69 |
| 26 | 6-(methylamino)pyridin-2-yl* | 3z | 7z | 70 |
| 27 | 3-MeNHCO—C$_6$H$_4$— | 3aa | 7aa | 49 |

Generic Procedure for Synthesis of Compounds 2a-aa:

To a solution of compound 1 (656 mg, 2.00 mmol, 1.0 eq.) in MeCN (10 mL) were added triethylamine (0.56 mL, 4.00 mmol, 2.0 eq.), then under argon atmosphere PdCl$_2$[PPh$_3$]$_2$ (70 mg, 0.10 mmol, 5 mol %), CuI (19 mg, 0.10 mmol, 5 mol %) and the corresponding acetylene (3.00 mmol, 1.5 eq.). The mixture was refluxed under argon atmosphere for 4-8 hours, cooled down to room temperature and concentrated at reduced pressure. The obtained residue was purified by column chromatography (silica gel, DCM/ethyl acetate or hexane/ethyl acetate) to give a target compound (2a-aa). Compound 2a: yield 580 mg, 96% as a white solid. APCI-MS (m/z (intensity)): 304.20 ([M+H]', 100%). Compound 2b: yield 320 mg, 51% as a beige solid. APCI-MS (m/z (intensity)): 317.22 ([M+H]$^+$, 100%). Compound 2c: yield 450 mg, 70% as a white solid. APCI-MS (m/z (intensity)): 321.23 ([M+H]$^+$, 100%). Compound 2d: yield 600 mg, 81% as a brown oil. Compound 2e: yield 514 mg, 76% as a white solid. Compound 2f: yield 565 mg, 84% as a beige solid. Compound 2g: yield 625 mg, 84% as a beige solid. Compound 2h: yield 270 mg, 56% as a white solid. APCI-MS (m/z (intensity)): 321.20 ([M+H]$^+$, 100%). Compound 2i: yield 530 mg, 79% as a white solid. APCI-MS (m/z (intensity)): 337.22, 338.44 ([M+H]$^+$, 100%). Compound 2j: yield 465 mg, 73% as a white solid. Compound 2k: yield 586 mg, 97% as a light-beige solid. APCI-MS (m/z (intensity)): 304.20 ([M+H]$^+$, 100%). Compound 2l: yield 140 mg, 42% as a white solid. APCI-MS (m/z (intensity)): 330.10 ([M+H]$^+$, 100%). Compound 2m: yield 500 mg, 75% as a white solid. APCI-MS (m/z (intensity)): 333.20 ([M+H]$^+$, 100%). Compound 2n: yield 280 mg, 44% as a beige solid. Compound 2o: yield 540 mg, 86% as a beige solid. Compound 2p: yield 370 mg, 59% as a colorless oil. Compound 2q: yield 164 mg, 49% as a white solid. APCI-MS (m/z (intensity)): 333.06 ([M+H]$^+$, 100%). Compound 2r: yield 500 mg, 68% as a white solid. Compound 2s: yield 515 mg, 91% as a yellow oil. Compound 2t: yield 630 mg, 97% as a yellow oil. Compound 2u: yield 240 mg, 38% as a yellow solid. APCI-MS (m/z (intensity)): 318.77 ([M+H]$^+$, 100%). Compound 2v: yield 195 mg, 64% as a grey solid. Compound 2w: yield 200 mg, 62% as a beige solid. Compound 2x: yield 175 mg, 52% as a beige solid. Compound 2y: yield 250 mg, 73% as a brown solid. APCI-MS (m/z (intensity)): 343.12 ([M+H]$^+$, 100%). Compound 2z: yield 120 mg, 35% as a yellow solid. APCI-MS (m/z (intensity)): 347.11 ([M+H]$^+$, 100%). Compound 2aa: yield 220 mg, 61% as a white solid.

Generic Procedure for Synthesis of Compounds 3a-aa:

The corresponding ester (2a-aa) (whole amount prepared on the previous stage) was dissolved in hot MeOH or MeOH-THF mixture (2:1, 10-25 mL). Then a solution of NaOH (200 mg, 5.00 mmol) in water (10 mL) was added. The resulting mixture was stirred at 50° C. for 1-2 hours (TLC control), cooled down to room temperature), acidified with concentrated aqueous HCl solution (to adjust pH 4-5). The formed precipitate was collected by filtration, washed with cold water and diethyl ether and dried to give a target compound (3a-aa). Compound 3a: yield 480 mg, 87% as a beige solid. APCI-MS (m/z (intensity)): 290.11 ([M+H]$^+$, 100%). APCI-MS (m/z (intensity)): 288.07 ([M−H]$^−$, 85%), 334.12 ([M−H+formic acid]$^−$, 100%). Compound 3b: yield 270 mg, 88% as a white solid. APCI-MS (m/z (intensity)): 303.17 ([M+H]$^+$, 100%). APCI-MS (m/z (intensity)): 301.11 ([M−H]$^−$, 100%), 347.19 ([M−H+formic acid]$^−$, 90%). Compound 3c: yield 406 mg, 94% as a white solid. APCI-MS (m/z (intensity)): 306.68 ([M+H]$^+$, 100%). APCI-MS (m/z (intensity)): 305.14 ([M−H]$^−$, 100%), 651.22 ([M−H+formic acid]$^−$, 85%). Compound 3d: yield 451 mg, 75% as a beige-green solid. APCI-MS (m/z (intensity)): 357.06 ([M+H]$^+$, 100%). Compound 3e: yield 470 mg, 95% as a light-green solid. APCI-MS (m/z (intensity)): 323.09, 325.10 ([M+H]$^+$, 100%). Compound 3f: yield 520 mg, 96% as a white solid. APCI-MS (m/z (intensity)): 323.09, 325.09 ([M+H]$^+$, 100%). Compound 3g: yield 373 mg, 62% as a white solid. APCI-MS (m/z (intensity)): 357.07 ([M+H]$^+$, 100%). Compound 3h: yield 248 mg, 96% as a white solid. APCI-MS (m/z (intensity)): 305.13 ([M−H]$^−$, 100%), 351.19 ([M−H+formic acid]$^−$, 90%). Compound 3i: yield 470 mg, 93% as a white solid. APCI-MS (m/z (intensity)): 322.64, 323.84 ([M+H]$^+$, 100%). APCI-MS (m/z (intensity)): 321.11, 322.35 ([M−H]$^−$, 100%), 367.19 ([M−H+formic acid]$^−$, 50%). Compound 3j: yield 426 mg, 96% as a white solid. APCI-MS (m/z (intensity)): 306.68 ([M+H]$^+$, 100%). APCI-MS (m/z (intensity)): 305.11 ([M−H]$^−$, 100%), 351.20 ([M−H+formic acid]$^−$, 60%). Compound 3k: yield 466 mg, 83% as a beige solid. APCI-MS (m/z (intensity)): 290.12 ([M+H]$^+$, 100%). Compound 3l: yield 110 mg, 82% as a grey solid. APCI-MS (m/z (intensity)): 319.21 ([M+H]$^+$, 100%). APCI-MS (m/z (intensity)): 317.13 ([M−H]$^−$, 100%), 363.23 ([M−H+formic acid]$^−$, 80%). Compound 3m: yield 448 mg, 94% as a white solid. APCI-MS (m/z (intensity)): 319.23 ([M+H]$^+$, 100%). Compound 3n: yield 260 mg, 97% as a beige solid. APCI-MS (m/z (intensity)): 305.18 ([M+H]$^+$, 100%). APCI-MS (m/z (intensity)): 303.13 ([M−H]$^−$, 45%), 349.17 ([M−H+formic acid]$^−$, 100%). Compound 3o: yield 460 mg, 89% as a white solid.

APCI-MS (m/z (intensity)): 302.51 ([M+H]$^+$, 100%). Compound 3p: yield 300 mg, 85% as a white solid. APCI-MS (m/z (intensity)): 302.45 ([M+H]$^+$, 100%). Compound 3q: yield 105 mg, 67% as a white solid. APCI-MS (m/z (intensity)): 319.07 ([M+H]$^+$, 100%). Compound 3r: yield 386 mg, 80% as a light-green solid. APCI-MS (m/z (intensity)): 357.07 ([M+H]$^+$, 100%). Compound 3s: yield 357 mg, 73% as a beige solid. APCI-MS (m/z (intensity)): 270.45 ([M+H]$^+$, 100%), 253.10 ([M–H$_2$O+H]$^+$, 65%). Compound 3t: yield 590 mg, 98% as a white solid. APCI-MS (m/z (intensity)): 311.19 ([M+H]$^+$, 70%), 293.17 ([M–H$_2$O+H]$^+$, 100%). Compound 3u: yield 120 mg, 52% as a beige solid. APCI-MS (m/z (intensity)): 305.13 ([M+H]$^+$, 100%). Compound 3v: yield 150 mg, 81% as a grey solid. APCI-MS (m/z (intensity)): 290.14 ([M+H]$^+$, 100%). Compound 3w: yield 190 mg, 99% as a beige solid. APCI-MS (m/z (intensity)): 308.13 ([M+H]$^+$, 100%). Compound 3x: yield 165 mg, 99% as a beige solid. APCI-MS (m/z (intensity)): 324.11, 326.10 ([M+H]$^+$, 100%). APCI-MS (m/z (intensity)): 322.01 ([M–H]$^+$, 100%), 367.96 ([M–H+formic acid]$^-$, 60%). Compound 3y: yield 170 mg, 71% as a beige solid. APCI-MS (m/z (intensity)): 329.35 ([M+H]$^+$, 100%). Compound 3z: yield 115 mg, 99% as a beige solid. APCI-MS (m/z (intensity)): 33.07 ([M+H]$^+$, 100%). Compound 3aa: yield 210 mg, 99% as a white solid. APCI-MS (m/z (intensity)): 346.10 ([M+H]$^+$, 100%).

Generic Procedure for Synthesis of Compounds 5a-o:

A mixture of the corresponding acid derivative (3a-k, m,n,p,r) (0.33-0.86 mmol, 1.0 eq.), TBTU (1.2 eq.), triethylamine (3.0 eq.) and dry DMF (5 mL) was stirred at room temperature for 5 minutes. Then 3-imidazol-1-yl-propylamine (4) (1.2 eq.) was added. The resulted mixture was stirred at room temperature for 8-12 hours, diluted with water (100 mL), extracted with ethyl acetate (3×50 mL). The organic layers were combined, washed with an aqueous K$_2$CO$_3$ solution (30 mL), water (3×30 mL), dried over sodium sulfate and concentrated at reduced pressure. The obtained residue was purified by column chromatography (silica gel, DCM/MeOH) to give a target compound (5a-o). Compound 5a: yield 197 mg, 62% as a white solid. Compound 5b: yield 115 mg, 65% as a white solid. Compound 5c: yield 186 mg, 69% as a white solid. Compound 5d: yield 290 mg, 99% as a white solid. Compound 5e: yield 80 mg, 26% as a white solid. Compound 5f: yield 145 mg, 42% as a white solid. Compound 5g: yield 213 mg, 88% as a white solid. Compound 5h: yield 86 mg, 53% as a grey solid. Compound 5i: yield 210 mg, 69% as a white solid. Compound 5j: yield 187 mg, 66% as a white solid. Compound 5k: yield 193 mg, 61% as a beige solid. Compound 5l: yield 180 mg, 61% as a white solid. Compound 5m: yield 70 mg, 42% as a white solid. Compound 5n: yield 167 mg, 81% as a white solid. Compound 5o: yield 153 mg, 62% as a white solid.

Generic Procedure for Synthesis of Compounds 7a-aa:

The same as Generic procedure for synthesis of compounds 5a-o using 3-(1H-pyrazol-4-yl)-propylamine hydrochloride (6) (1.2 eq.) and triethylamine (4.0 eq.). Compound 7a: yield 188 mg, 59% as a white solid. Compound 7b: yield 109 mg, 62% as a beige solid. Compound 7c: yield 200 mg, 75% as a white solid. Compound 7d: yield 204 mg, 70% as a white solid. Compound 7e: yield 188 mg, 62% as a white solid. Compound 7f: yield 200 mg, 58% as a white solid. Compound 7g: yield 134 mg, 56% as a white solid. Compound 7h: yield 40 mg, 25% as a colorless oil. Compound 7i: yield 246 mg, 81% as a white solid. Compound 7j: yield 188 mg, 66% as a yellowish oil. Compound 7k: yield 145 mg, 46% as a beige solid. Compound 7l: yield 80 mg, 54% as a beige solid. Compound 7m: yield 200 mg, 68% as a white solid. Compound 7n: yield 78 mg, 47% as a white solid. Compound 7o: yield 85 mg, 63% as a white solid. Compound 7p: yield 128 mg, 62% as a white solid. Compound 7q: yield 102 mg, 73% as a white solid. Compound 7r: yield 133 mg, 54% as a white solid. Compound 7s: yield 87 mg, 63% as a beige solid. Compound 7t: yield 75 mg, 53% as a white solid. Compound 7u: yield 75 mg, 46% as a white solid. Compound 7v: yield 53 mg, 26% as a brown oil. Compound 7w: yield 143 mg, 56% as a beige solid. Compound 7x: yield 136 mg, 62% as a beige solid. Compound 7y: yield 155 mg, 69% as a white solid. Compound 7z: yield 108 mg, 70% as a white solid. Compound 7aa: yield 135 mg, 49% as a white solid.

Scheme 5.

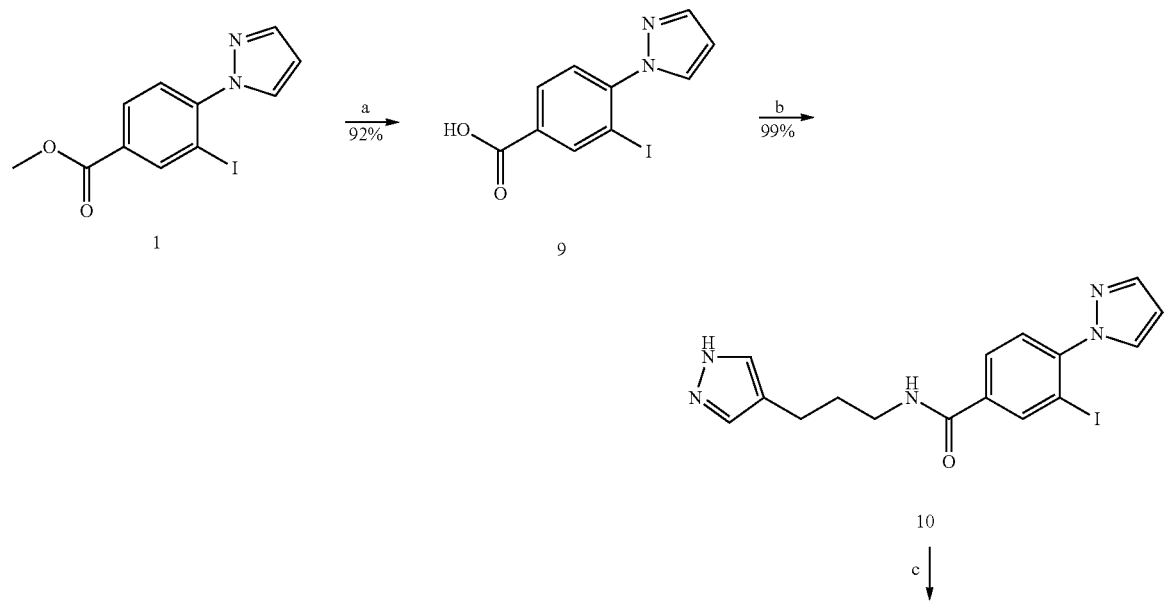

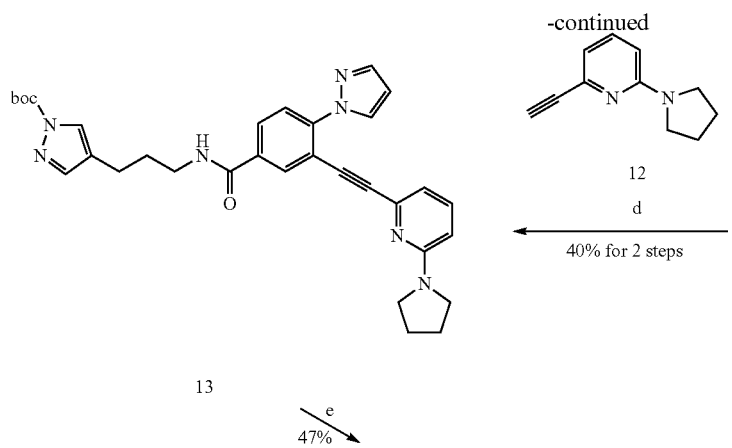

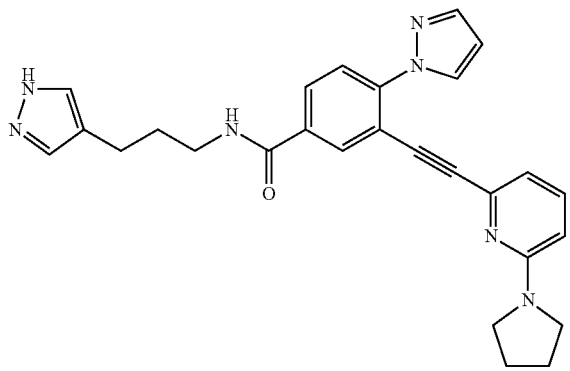

14, TT-03611

(a) NaOH, H₂O, MeOH, 50° C., 1 h; (b) amine 6, TBTU, Et₃N, DMF, RT, 8 h; (c) Boc₂O, Et₃N, DCM, THF, RT, 4 h; (d) PdCl₂[PPh₃]₂, CuI, Et₃N, MeCN, Ar, reflux, 4 h; (e) HCl, MeOH, H₂O, RT, 1 h Procedure for Synthesis of Compound 9.

To a solution of compound 1 (656 mg, 2.00 mmol, 1.0 eq.) in MeOH (20 mL) was added a solution of NaOH (200 mg, 5.00 mmol, 2.5 eq.) in water (10 mL) and the reaction mixture was stirred at 50° C. for 1 hour, cooled down to room temperature, acidified with concentrated aqueous HCl solution to adjust pH 4-5. The formed precipitate was collected by filtration, washed with cold water and diethyl ether and dried to give compound 9 (580 mg, 92%) as a white solid. APCI-MS (m/z (intensity)): 315.00 ([M+H]⁺, 100%). APCI-MS (m/z (intensity)): 312.94 ([M−H]⁻, 100%), 358.91 ([M−H+formic acid]⁻, 80%).

Procedure for Synthesis of Compound 10.

A mixture of compound 9 (580 mg, 1.85 mmol, 1.0 eq.), TBTU (709 mg, 2.20 mmol, 1.2 eq.), triethylamine (0.98 mL, 7.00 mmol, 3.4 eq.) and dry DMF (30 mL) was stirred at room temperature for 5 minutes. Then 3-(1H-pyrazol-4-yl)-propylamine hydrochloride (6) (356 mg, 2.20 mmol, 1.2 eq.) was added. The resulted mixture was stirred at room temperature for 8 hours, diluted with water (300 mL) and extracted with ethyl acetate (3×150 mL). The organic layers were combined, washed with an aqueous K₂CO₃ solution (100 mL), water (3×100 mL), dried over sodium sulfate and concentrated at reduced pressure. The obtained residue was purified by column chromatography (silica gel, DCM/MeOH) to give compound 10 (770 mg, 99%) as a white solid. APCI-MS (m/z (intensity)): 422.02 ([M+H]⁺, 100%).

Scheme 6.

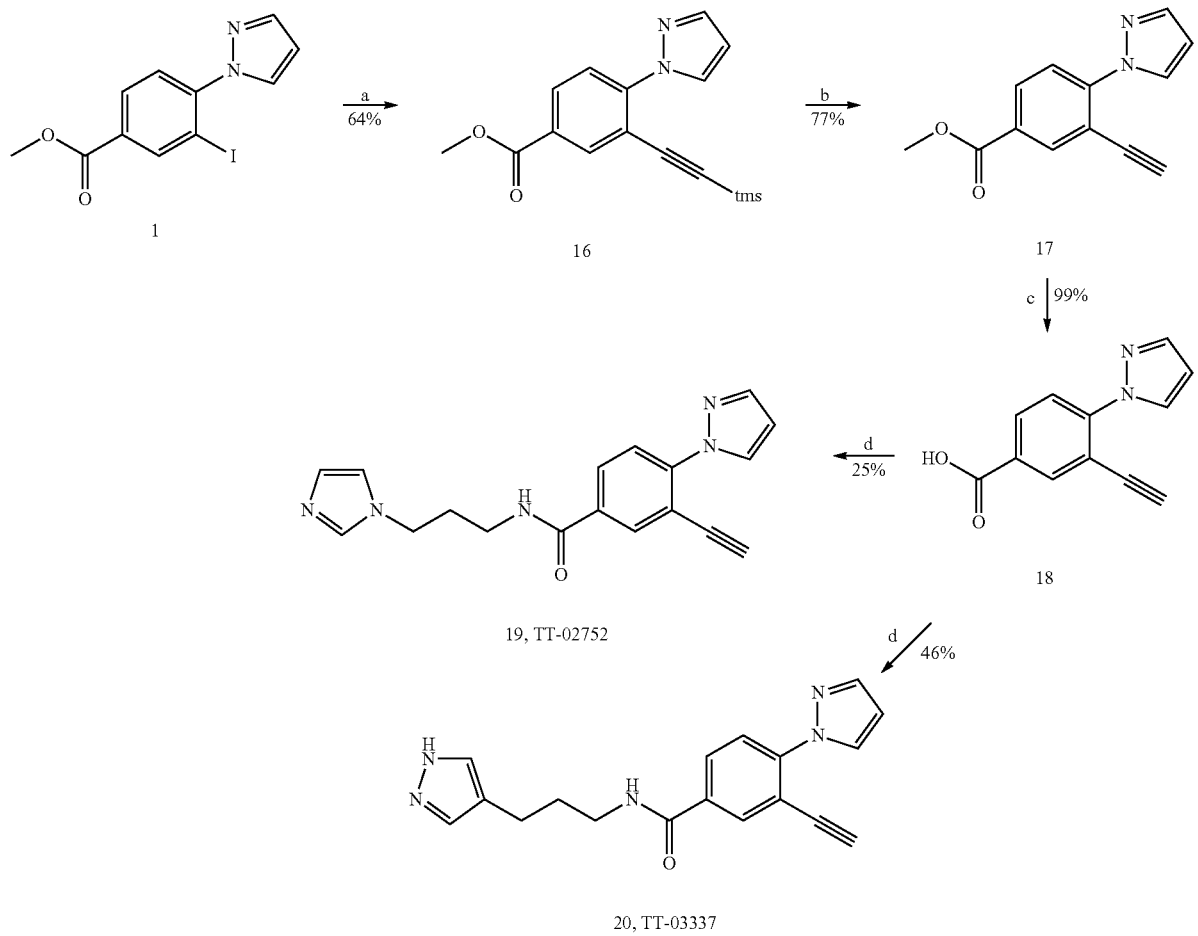

(a) TMS-acetylene; PdCl$_2$[PPh$_3$]$_2$, CuI, Et$_3$N, MeCN, Ar, reflux, 3.5 h; (b) TBAF*3H$_2$O, hexane, ethyl acetate, 0° C., 20 min; (c) NaOH, THF, H$_2$O, MeOH, 40° C., 1 h; (d) amine 4 or 6, TBTU, Et$_3$N, DMF, RT, 8-12 h Procedure for Synthesis of Compound 13.

To a solution of compound 10 (210 mg, 0.50 mmol, 1.0 eq.) in a mixture of DCM (10 mL) and THF (5 mL) were added triethylamine (0.1 mL, 0.71 mmol, 1.4 eq.) and Boc$_2$O (125 mg, 0.58 mmol, 1.16 eq.). The mixture was stirred at room temperature for 4 hours and concentrated at reduced pressure to give crude product 11 as colorless oil, which was used on the next step without purification. The crude product 11 (approx. 0.50 mmol, 1.0 eq.) was dissolved in MeCN (20 mL). Then triethylamine (0.4 mL), PdCl$_2$[PPh$_3$]$_2$ (10 mg, 0.015 mmol, 3 mol %), CuI (10 mg, 0.05 mmol, 10 mol %) and 2-ethynyl-6-pyrrolidin-1-yl-pyridine (12) (125 mg, 0.73 mmol, 1.46 eq.) were added under argon atmosphere. The reaction mixture was refluxed for 4 hours, cooled down to room temperature and concentrated at reduced pressure. The obtained residue was purified by column chromatography (silica gel, DCM/ethyl acetate, 2:1) to give compound 13 (112 mg, 40%) as a colorless oil. APCI-MS (m/z (intensity)): 566.53 ([M+H]$^+$, 100%), 466.43 ([M−Boc+H]$^+$, 20%).

Procedure for Synthesis of Compound 14.

To a solution of compound 13 (112 mg, 0.20 mmol, 1.0 eq.) in MeOH (10 mL) was added an aqueous HCl solution (15%, 2 mL). The resulted mixture was stirred at room temperature for 1 hour, neutralized with an aqueous K$_2$CO$_3$ solution and extracted with DCM (2×50 mL). The combined organic layers were dried over sodium sulfate and concentrated. The obtained residue was purified by column chromatography (silica gel, DCM/MeOH, 20:1) to give compound 14 (43 mg, 47%) as a beige solid.

Procedure for Synthesis of Compound 16.

A mixture of compound 1 (3.28 g, 10.00 mmol, 1.0 eq.), triethylamine (4.2 mL, 30.00 mmol, 3.0 eq.), PdCl$_2$[PPh$_3$]$_2$ (0.35 g, 0.50 mmol, 5 mol %), CuI (0.19 g, 1.00 mmol, 10 mol %) and TMS-acetylene (1.96 g, 20.00 mmol, 2.0 eq.) and MeCN (25 mL) was refluxed for 3.5 hours under argon atmosphere and concentrated at reduced pressure. The obtained residue was purified by column chromatography (silica gel, hexane/ethyl acetate, 10:1) to give compound 16 (1.90 g, 64%) as a yellow oil. APCI-MS (m/z (intensity)): 299.15 ([M+H]$^+$, 100%).

Procedure for Synthesis of Compound 17.

To a solution of compound 16 (1.90 g, 6.38 mmol, 1.0 eq.) in hexane (50 mL) was added dropwise a solution of TBAF trihydrate (0.85 g, 3.19 mmol, 0.50 eq.) in ethyl acetate (10 mL) at 0° C. The reaction mixture was stirred for 20 minutes at 0° C., washed with water (2×20 mL), dried over sodium sulfate and concentrated at reduced pressure. The obtained residue was purified by column chromatography (silica gel, DCM) to give compound 17 (1.11 g, 77%) as a yellowish solid. APCI-MS (m/z (intensity)): 227.16 ([M+H]$^+$, 100%).

Procedure for Synthesis of Compound 18.

To a solution of compound 17 (470 mg, 2.08 mmol, 1.0 eq.) in MeOH (10 mL) was added a solution of NaOH (200 mg, 5.00 mmol, 2.4 eq.) in water (10 mL). The resulted mixture was stirred at 40° C. for 1 hour, cooled down to room temperature, acidified with concentrated aqueous HCl solution to adjust pH 4-5. The formed precipitate was collected by filtration, washed with cold water and diethyl ether and dried to give compound 18 (435 mg, 99%) as a beige solid. APCI-MS (m/z (intensity)): 213.19 ([M+H]$^+$, 100%).

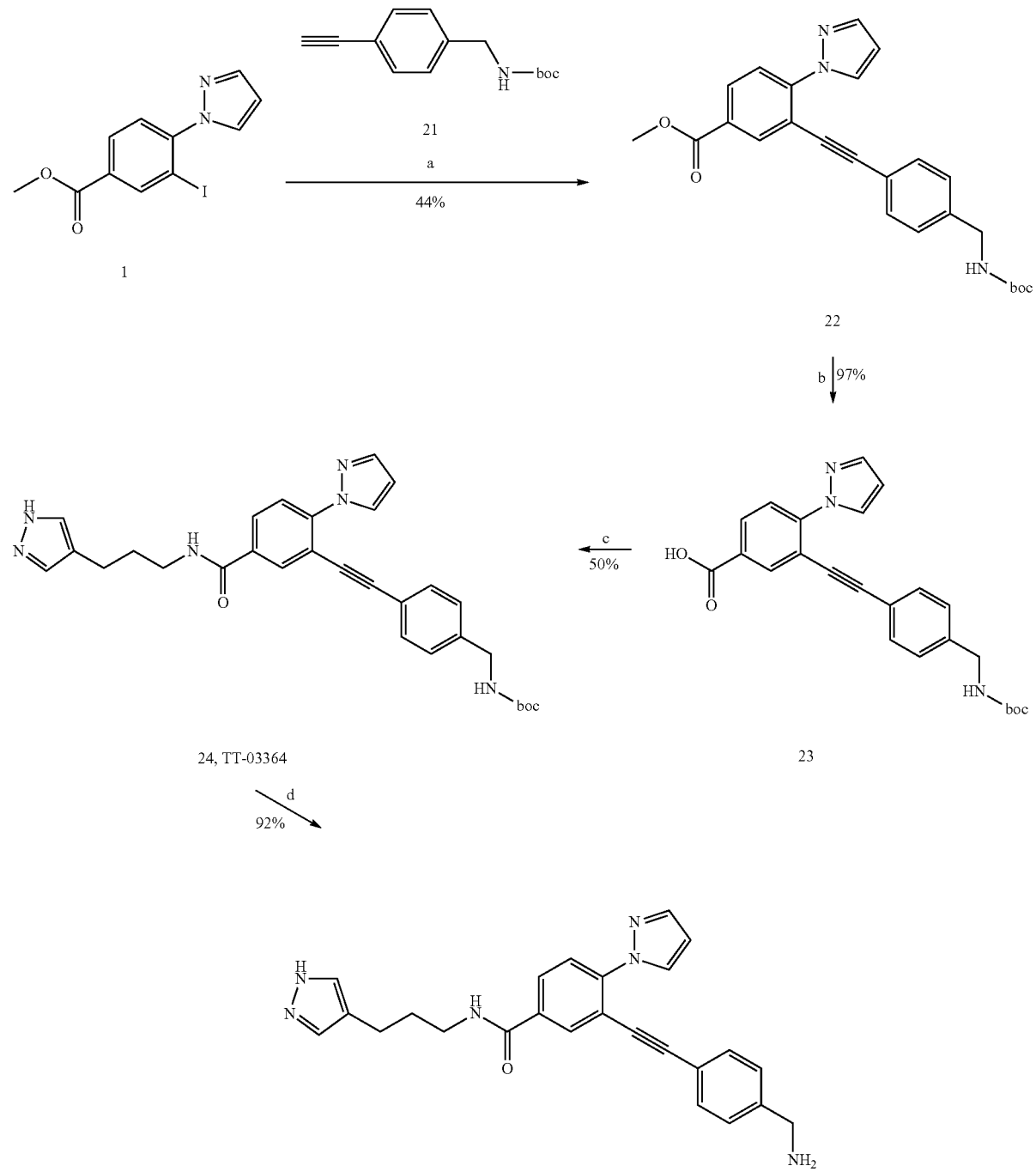

Scheme 7.

(a) PdCl$_2$[PPh$_3$]$_2$, CuI, Et$_3$N, MeCN, Ar, reflux, 7 h; (b) NaOH, THF, H$_2$O, MeOH, 50° C., 1 h; (c) amine 6, TBTU, Et$_3$N, DMF, RT, 12 h; (d) HCl, H$_2$O, MeOH, RT, 8 h Procedure for Synthesis of Compound 19.

Compound 19 was prepared according to Generic procedure for synthesis of compounds 5a-o using compound 18 (210 mg, 0.99 mmol). Yield 78 mg, 25% as a beige solid.

Procedure for Synthesis of Compound 20.

Compound 20 was prepared according to Generic procedure for synthesis of compounds 7a-aa using compound 18 (210 mg, 0.99 mmol). Yield 144 mg, 46% as a white solid.

Procedure for Synthesis of Compound 22.

Compound 22 was prepared according to Generic procedure for synthesis of compounds 2a-aa using compound 1 (328 mg, 1.00 mmol, 1.0 eq.) and (4-ethynyl-benzyl)-carbamic acid tert-butyl ester (21) (300 mg, 1.30 mmol, 1.3 eq.). Yield 188 mg, 44% as a yellowish solid.

Procedure for Synthesis of Compound 23.

Compound 23 was prepared according to Generic procedure for synthesis of compounds 3a-aa using compound 22 (188 mg, 0.44 mmol). Yield 177 mg, 97% as a beige solid. APCI-MS (m/z (intensity)): 418.19 ([M+H]$^+$, 100%).

Procedure for Synthesis of Compound 24.

Compound 24 was prepared according to Generic procedure for synthesis of compounds 7a-aa using compound 23 (177 mg, 0.42 mmol). Yield 133 mg, 50% as a white solid.

Procedure for Synthesis of Compound 25.

To a solution of compound 24 (93 mg, 0.18 mmol, 1.0 eq.) in MeOH (5 mL) was added an aqueous HCl solution (15%, 2 mL). The reaction mixture was stirred at room temperature for 8 hours, neutralized with an aqueous $K_2CO_3$ solution and extracted with DCM (2×50 mL). The combined organic layers were dried over sodium sulfate and concentrated. The obtained residue was purified by column chromatography (silica gel, DCM/MeOH, 10:1) to give compound 25 (70 mg, 92%) as a beige solid Procedure for Synthesis of Compound 27.

Compound 27 was prepared according to Generic procedure for synthesis of compounds 2a-aa using compound 1 (656 mg, 2.00 mmol, 1.0 eq.) and 4-ethynyl-benzonitrile (26) (380 mg, 3.00 mmol, 1.5 eq.). Yield 437 mg, 67% as a beige-yellow solid. APCI-MS (m/z (intensity)): 328.14 ([M+H]$^+$, 100%), 369.11 ([M+MeCN+H]$^+$, 100%).

Procedure for Synthesis of Compounds 30 and 31.

A mixture of intermediates 28 and 29 (420 mg, with 2:3: ratio according to LCMS) was prepared according to Generic procedure for synthesis of compounds 3a-aa using compound 27 (437 mg, 1.34 mmol). The obtained mixture was used for next step without separation. A part of the mixture (150 mg, approx. 0.48 mmol), TBTU (225 mg, 0.70 mmol, 1.5 eq.), triethylamine (0.28 mL, 2.0 mmol, 4.2 eq.) and DMF dry (5 mL) were stirred at room temperature for 5 minutes. Then 3-(1H-pyrazol-4-yl)-propylamine hydrochloride (6) (113 mg, 0.70 mmol, 1.5 eq.) was added. The resulted mixture was stirred at room temperature for 12 hours, diluted with water (100 mL) and extracted with ethyl acetate (3×50 mL). The organic layers were combined, washed with an aqueous $K_2CO_3$ solution (30 mL), water (3×30 mL), dried over sodium sulfate and concentrated at reduced pressure. The obtained residue was purified by column chromatography (silica gel, DCM/MeOH) to give separated compounds 30 (76 mg, 38% for 2 steps) as a white solid and 31 (63 mg, 30% for 2 steps) as a white solid.

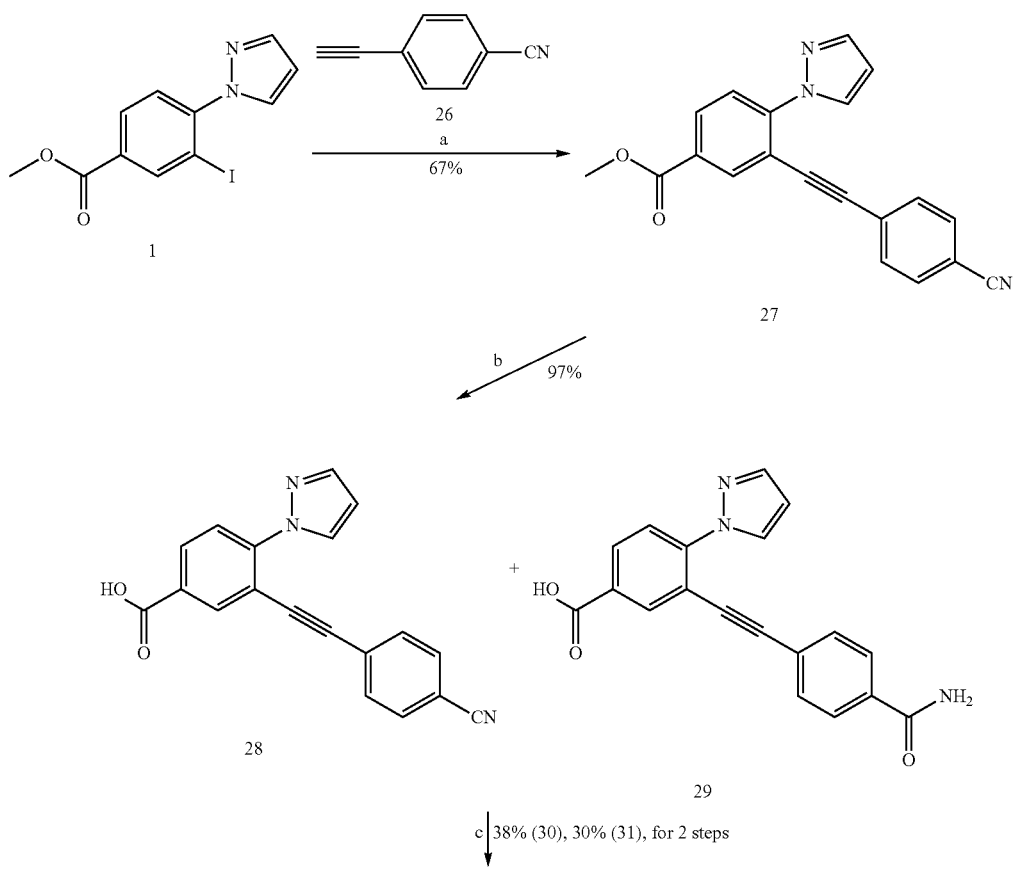

Scheme 8.

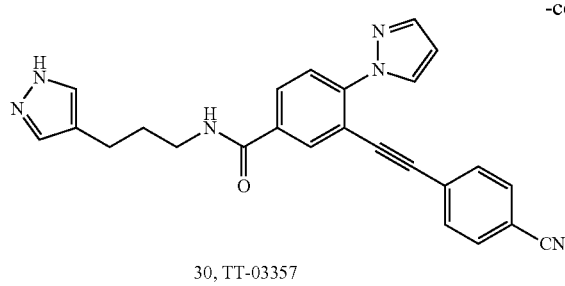

30, TT-03357

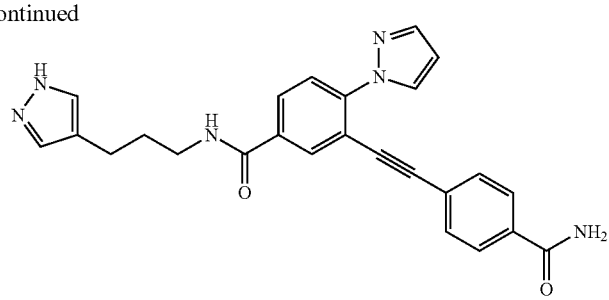

31, TT-03625

(a) PdCl$_2$[PPh$_3$]$_2$, CuI, Et$_3$N, MeCN, Ar, reflux, 8 h;
(b) NaOH, THF, H$_2$O, MeOH, 50° C., 2 h;
(c) amine 6, TBTU, Et$_3$N, DMF, RT, 12 h Procedure for Synthesis of Compound 34.

A mixture of compound 33 (300 mg, 0.76 mmol, 1.0 eq.), 10% Pd/C catalyst (100 mg, 0.094 mmol, 9 mol %) and MeOH (50 mL).) was stirred under hydrogen atmosphere at room temperature for 3 hours. The catalyst was removed by filtration. The filtrate was concentrated at reduced pressure. The obtained residue was purified by column chromatography (silica gel, ethyl acetate/MeOH/NH$_4$OH, 40:2:1) giving compound 34 (252 mg, 83%) as a white solid.

Procedure for Synthesis of Compound 36.

A mixture of 4-(1H-pyrazol-1-yl)benzoic acid (35) (278 mg, 1.48 mmol, 1.00 eq.), 3-(1H-imidazol-1-yl)propan-1-amine (4) (200 mg, 1.60 mmol, 1.08 eq.), TBTU (622 mg, 2.00 mmol, 1.35 eq.), triethylamine (0.28 mL, 2.00 mmol, 1.35 eq.) and DCM (10 mL) was stirred at room temperature for 20 hours, diluted with equal volume of saturated aqueous NaHCO$_3$ solution and stirred at room temperature for 2 hours. The resulting mixture was extracted with DCM. The organic phase was dried over sodium sulfate and concentrated at reduced pressure. The obtained residue was purified by column chromatography (silica gel, ethyl acetate/MeOH, 20:1), then was recrystallized from DCM/hexane giving compound 36 (101 mg, 23%) as a yellow solid.

Scheme 9.

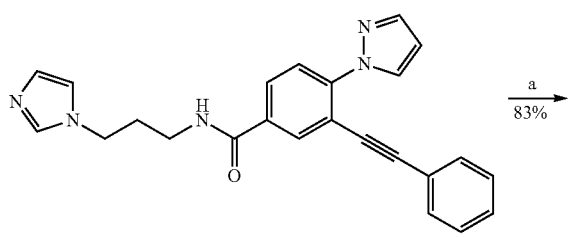

33, TT-01901

-continued

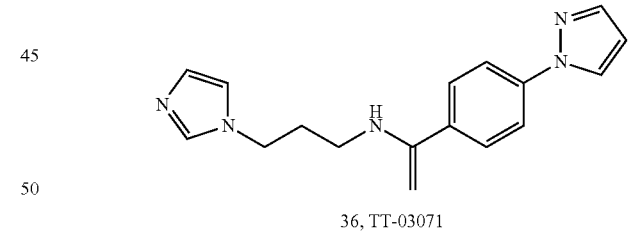

34, TT-03574

(a) H$_2$, Pd/C, MeOH, RT, 3 h

Scheme 10.

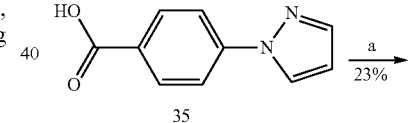

35

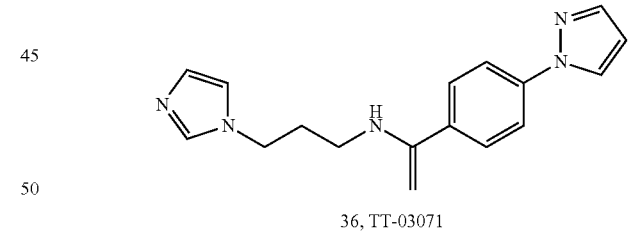

36, TT-03071

(a) amine 4, TBTU, Et$_3$N, DCM, RT, 20 h

TABLE 5

| —NR1R2 | Comp. | Conditions | Yield (%)$^a$ | Comp. | Conditions | Yield (%) | Comp. | Yield (%) |
|---|---|---|---|---|---|---|---|---|
| 1  *—N(piperidine) | 43a | a, c | 91 | 44a | d | 78 | 45a | 99 |

TABLE 5-continued

| —NR1R2 | Comp. | Conditions | Yield (%)[a] | Comp. | Conditions | Yield (%) | Comp. | Yield (%) |
|---|---|---|---|---|---|---|---|---|
| 2 azepane (N-*) | 43b | a, c | 75 | 44b | d | 70 | 45b | 92 |
| 3 3,3-dimethylpiperidine (N-*) | 43c | a, c | 95 | 44c | d | 70 | 45c | 93 |
| 4 2-azaspiro[4.5]decane (N-*) | 43d | a, c | 84 | 44d | d | 59 | 45d | 93 |
| 5 4-(trifluoromethyl)piperidine (N-*) | 43e | a, c | 60 | 44e | d | 71 | 45e | 94 |
| 6 2-(2-hydroxyethyl)piperidine (N-*) | 43f | b, c | 48 | 44f | d | 56 | 45f | 91 |
| 7 4-boc-piperazine (N-*) | 43g | a, c | 86 | 44g | e | 30 | 45g | 49 |

[a] yield for 2 steps

TABLE 6

| —NR1R2 | Starting compound | Product compound | Conditions | Yield (%) |
|---|---|---|---|---|
| 1 piperidine (N-*) | 45a | 46a | g | 99 |
| 2 azepane (N-*) | 45b | 46b | g | 79 |
| 3 3,3-dimethylpiperidine (N-*) | 45c | 46c | g | 70 |
| 4 2-azaspiro[4.5]decane (N-*) | 45d | 46d | g | 80 |
| 5 4-(trifluoromethyl)piperidine (N-*) | 45e | 46e | g | 89 |
| 6 2-(2-hydroxyethyl)piperidine (N-*) | 45f | 46f | g | 78 |
| 7 4-boc-piperazine (N-*) | 46g | 46g | j | 64 |

TABLE 7

| —NR1R2 | Starting compound | Product compound | Yield (%) |
|---|---|---|---|
| 1 piperidine (N-*) | 46a | 49a | 38 |
| 2 azepane (N-*) | 46b | 49b | 78 |

TABLE 7-continued

| | —NR1R2 | Starting compound | Product compound | Yield (%) |
|---|---|---|---|---|
| 3 | piperidine with gem-dimethyl | 46c | 49c | 98 |
| 4 | spiro[4.5]decane-N | 46d | 49d | 56 |
| 5 | 4-(trifluoromethyl)piperidine | 46e | 49e | 90 |
| 6 | 2-(2-hydroxyethyl)piperidine | 46f | 49f | 61 |
| 7 | N-boc-piperazine | 46g | 49g | 39 |
| 8 | N-methylpiperazine | 46h | 49h | 48 |

Generic Procedure for Synthesis of Compounds 43a-e.

A mixture of 4-chloro-3-nitro-benzoic acid methyl ester (41) (5.39 g, 25.00 mmol, 1.0 eq.), corresponding amine (37.50 mmol, 1.5 eq.), DIPEA (4.35 mL, 25.00 mmol, 1.0 eq.) and ethanol (50 mL) was heated at reflux for 6 hours, then cooled to room temperature, and concentrated at reduced pressure. The obtained residue was purified by column chromatography (silica gel, ethyl acetate/hexane) to give an intermediate (42a-e) used on the next stage without additional characterization. Nickel powder (10% weight to an intermediate 42a-e) was added to a solution of the corresponding intermediate (42a-e) in methanol. The obtained mixture was stirred at room temperature under H$_2$ (3-4 atm) for 8 hours, filtered and concentrated at reduced pressure. The obtained residue was purified by column chromatography (silica gel, ethyl acetate/hexane) to give a target compound (43a-e). Compound 43a: yield 5.33 g, 91% (for 2 steps) as a yellow solid. APCI-MS (m/z (intensity)): 235.23 ([M+H]$^+$, 100%). Compound 43b: yield 4.63 g, 75% (for 2 steps) as a yellow solid. APCI-MS (m/z (intensity)): 279.20 ([M+H]$^+$, 100%). Compound 43c: yield 2.15 g, 95% (for 2 steps) as a yellow solid. APCI-MS (m/z (intensity)): 456.08 ([M+H]$^+$, 100%). Compound 43d: yield 6.04 g, 84% (for 2 steps) as a yellowish solid. APCI-MS (m/z (intensity)): 289.21 ([M+H]$^+$, 100%). Compound 43e: yield 0.51 g, 30% (for 2 steps) as a yellowish solid. APCI-MS (m/z (intensity)): 302.80 ([M+H]$^+$, 100%).

Procedure for Synthesis of Compound 43f.

A mixture of 4-chloro-3-nitro-benzoic acid methyl ester (41) (5.39 g, 25.00 mmol, 1.0 eq.), 3-hydroxymethylpiperidine (3.23 g, 25.00 mmol, 1.0 eq.), DIPEA (3.51 mL, 25.00 mmol, 1.0 eq.) and DMF (50 mL) was heated at 100° C. for 5 hours, then the second portion of 3-hydroxymethylpiperidine (323 mg, 2.50 mmol, 0.1 eq.) was added. The mixture was stirred at 100° C. for 8 hours, cooled to room temperature, poured to water and extracted with ethyl acetate. The organic phase was washed with brine and concentrated at reduced pressure. The obtained residue was purified by column chromatography (silica gel, ethyl acetate/hexane) to give the intermediate 42f as a yellow oil (4.13 g) used on the next stage without additional characterization. Nickel powder (413 mg, 10% weight) was added to a solution of the intermediate 42f in methanol (10%, 40 mL). The obtained mixture was stirred at room temperature under H$_2$ (3-4 atm) for 8 hours filtered and concentrated at reduced pressure. The obtained residue was purified by column chromatography (silica gel, ethyl acetate/hexane) to give compound 43f as a yellow oil (3.34 g, 48% for 2 steps). APCI-MS (m/z (intensity)): 279.21 ([M+H]$^+$, 100%).

Procedure for Synthesis of Compound 43g.

A mixture of 4-chloro-3-nitro-benzoic acid methyl ester (41) (5.39 g, 25.00 mmol, 1.0 eq.), N-boc-piperazine (5.12 g, 27.50 mmol, 1.1 eq.), DIPEA (4.35 mL, 25.00 mmol, 1.0 eq.) and ethanol (50 mL) was heated at reflux for 4 hours, then cooled to room temperature, and concentrated at reduced pressure. The obtained residue was purified by chromatography (silica gel, ethyl acetate/hexane) to give the intermediate 42g as a yellowish oil (8.77 g). Nickel powder (877 mg, 10% weight) was added to a solution of the intermediate 42g in methanol (10%, 90 mL). The obtained mixture was stirred at room temperature under H$_2$ (3-4 atm) for 8 hours, filtered and concentrated at reduced pressure. The obtained residue was purified by column chromatography (silica gel, ethyl acetate/hexane) to give compound 43g as a yellow solid (7.21 g, 86% for 2 steps). APCI-MS (m/z (intensity)): 336.18 ([M+H]$^+$, 100%).

Scheme 11.

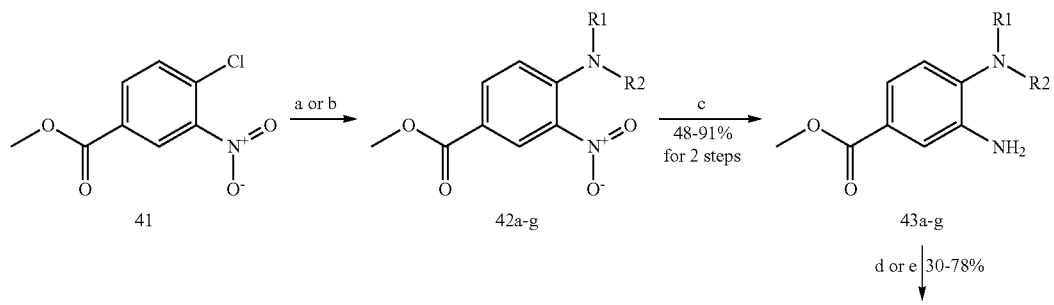

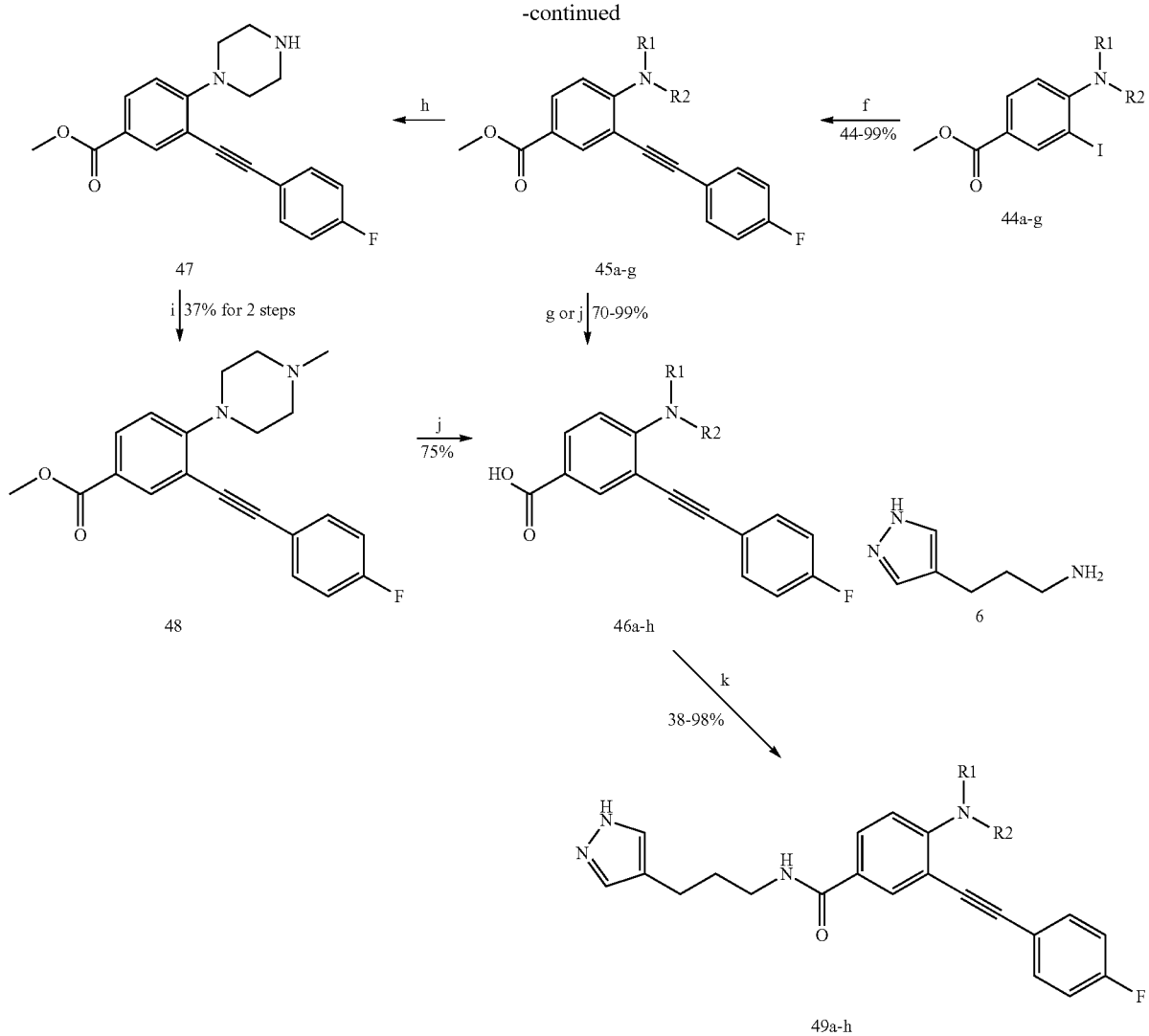

(a) amine, DIPEA, EtOH, reflux, 4-6 h;
(b) amine, DIPEA, DMF, 100° C., 13 h;
(c) H₂, Ni, RT, 8 h;
(d) HCl, NaNO₂, H₂O, KI, -5° C. to RT, 30 min;
(e) HCl, NaNO₂, H₂O, KI, -5° C. to RT, 30 min, then Boc₂O, EtOH, RT, 16 h;
(f) 4-fluorophenylacetylene; PdCl₂[PPh₃]₂, CuI, Et₃N, MeCN, Ar, 60° C., 1.5 h;
(g) NaOH, THF, H₂O, MeOH, RT, 16 h;
(h) HCl*dioxane, THF, RT, 21 h;
(i) formic acid, paraform and formaldehyde, EtOH, reflux, 14 h;
(j) LiOH, H₂O, THF, MeOH, RT, 16 h;
(k) TBTU, Et₃N, DCM, RT, 5-16 h Generic Procedure for Synthesis of Compounds 44a-f:

A solution of sodium nitrite (1.58 g, 23.00 mmol, 1.02 eq.) in water (23 mL) was slowly added to a stirred solution of the corresponding amine (43a-f) (22.62 mmol, 1.00 eq.) in a mixture of concentrated aqueous HCl solution (23 mL) and water (23 mL) at −5° C. By the end of addition of the sodium nitrite solution the reaction mixture became clear. The reaction mixture was stirred at −5° C.÷−2° C. for 10 minutes after the addition. Then a solution of potassium iodide (7.51 g, 43.00 mmol, 1.90 eq.) in water (23 mL) was added to the mixture at −2° C. Then the reaction mixture was stirred at room temperature for 30 minutes, diluted with DCM, treated with saturated aqueous potassium carbonate solution to reach pH>8 and extracted with DCM. The organic layer was washed with an aqueous Na₂S₂O₅ solution, with water, dried over sodium sulfate and concentrated at reduced pressure. The obtained residue was purified by column chromatography (silica gel, ethyl acetate/hexane) to give a target compound (44a-f). Compound 44a: yield 6.11 g, 78% as a red oil. APCI-MS (m/z (intensity)): 346.04 ([M+H]⁺, 100%). Compound 44b: yield 4.70 g, 70% as a yellow oil. APCI-MS (m/z (intensity)): 360.02 ([M+H]⁺, 100%). Compound 44c: yield 2.16 g, 70% as reddish oil. APCI-MS (m/z (intensity)): 374.04 ([M+H]⁺, 100%). Compound 44d: yield 4.97 g, 59% as red solid. APCI-MS (m/z (intensity)): 400.00 ([M+H]⁺, 100%). Compound 44e: yield 0.50 g, 71% as an orange oil. APCI-MS (m/z (intensity)): 413.59 ([M+H]⁺, 100%). Compound 44f: yield 2.60 g, 56% as a red oil. APCI-MS (m/z (intensity)): 390.04 ([M+H]⁺, 100%).

Procedure for Synthesis of Compound 44g.

A solution of sodium nitrite (1.51 g, 21.93 mmol, 1.05 eq.) in water (23 mL) was slowly added to a stirred solution of compound 43g (7.21 g, 21.50 mmol, 1.00 eq.) in a mixture of concentrated aqueous HCl solution (23 mL) and water (23 mL) at −8° C. By the end of the addition of the sodium nitrite solution the reaction mixture became clear. The reaction mixture was stirred at −8° C. to −2° C. for 10 minutes after the addition. Then a solution of potassium iodide (7.14 g, 43.00 mmol, 2.00 eq.) in water (23 mL) was added to the mixture at −2° C. Then the reaction mixture was stirred at room temperature for 30 minutes, diluted with DCM, treated with saturated aqueous potassium carbonate solution to reach pH>8 and extracted with DCM. The organic layer was washed with an aqueous $Na_2S_2O_5$ solution, water, dried over sodium sulfate and concentrated at reduced pressure. The obtained residue was purified by column chromatography (silica gel, ethyl acetate/hexane) to yield a mixture of compound 44g and end a byproduct—a derivative of compound 44g with cleaved Boc protecting group (1:1, 2.03 g). The resulted mixture was dissolved in EtOH (30 mL). $Boc_2O$ (0.5 eq.) was added, and the mixture was stirred at room temperature for 16 hours, poured to water and extracted with ethyl acetate. The organic phase was concentrated. The obtained residue was purified by column chromatography (silica gel, ethyl acetate/hexane) to give compound 44g as a colorless oil (2.85 g, 30%). APCI-MS (m/z (intensity)): 446.59 ([M+H]+, 100%).

Generic Procedure for Synthesis of Compounds 45a-g.

A mixture of the corresponding iodide (44a-g) (3.24 mmol, 1.0 eq.), 4-fluorophenylacetylene (0.584 g, 4.86 mmol, 1.5 eq.), $PdCl_2[PPh_3]_2$ (0.070 g, 0.10 mmol, 3 mol %), copper iodide (0.019 g, 0.10 mmol, 3 mol %), triethylamine (0.910 mL, 6.48 mmol, 2.0 eq.) and anhydrous acetonitrile (20 mL) was stirred under argon atmosphere at 60° C. for 1.5 hours, cooled to room temperature, poured to water and extracted with ethyl acetate. The organic phase was, washed with brine and concentrated at reduced pressure. The obtained residue was purified by column chromatography (silica gel, ethyl acetate/hexane) to give a target compound (45a-g). Compound 45a: yield 1.08 g, 99% as a yellowish oil. APCI-MS (m/z (intensity)): 338.16 ([M+H]+, 100%). Compound 45b: yield 0.58 g, 92% as a yellowish oil. APCI-MS (m/z (intensity)): 352.16 ([M+H]+, 100%). Compound 45c: yield 0.51 g, 93% as a yellowish oil. APCI-MS (m/z (intensity)): 365.68 ([M+H]+, 100%). Compound 45d: yield 0.55 g, 93% as a yellowish oil. APCI-MS (m/z (intensity)): 392.22 ([M+H]+, 100%). Compound 45e: yield 0.43 g, 94% as a yellowish oil. APCI-MS (m/z (intensity)): 406.14 ([M+H]+, 100%). Compound 45f: yield 0.52 g, 91% as a yellowish oil. APCI-MS (m/z (intensity)): 439.19 ([M+H]+, 100%). Compound 45g: yield 1.36 g, 49% as a yellowish oil. APCI-MS (m/z (intensity)): 439.19 ([M+H]+, 100%).

Generic Procedure for Synthesis of Compounds 46a-f.

To a solution of the corresponding ester (45a-f) (1.66 mmol, 1.0 eq.) in THF (4 mL) and MeOH (4 mL) an aqueous solution of sodium hydroxide (50%, 250 µL, 5.00 mmol, 3.0 eq.) was added, and the reaction mixture was stirred at room temperature for 16 hours, concentrated at reduced pressure, diluted with water, treated with an aqueous HCl solution (1M) to reach pH 5 and extracted with ethyl acetate. The combined organic layers were washed with water, and concentrated at reduced pressure. The obtained residue was purified by chromatography (silica gel, ethanol/DCM) to give a target compound (46a-f). Compound 46a: yield 1.08 g, 99% as a beige solid. APCI-MS (m/z (intensity)): 324.18 ([M+H]+, 100%). Compound 46b: yield 0.44 g, 79% as a brown solid. APCI-MS (m/z (intensity)): 338.19 ([M+H]+, 100%). Compound 46c: yield 0.35 g, 70% as a brownish solid. APCI-MS (m/z (intensity)): 352.18 ([M+H]+, 100%). Compound 46d: yield 0.42 g, 80% as a brownish solid. APCI-MS (m/z (intensity)): 378.24 ([M+H]+, 100%). Compound 46e: yield 0.37 g, 89% as a brownish solid. APCI-MS (m/z (intensity)): 392.13 ([M+H]+, 100%). Compound 46f: yield 0.39 g, 78% as a white solid. APCI-MS (m/z (intensity)): 368.12 ([M+H]+, 100%).

Procedure for Synthesis of Compound 46g.

To a solution of compound 45g (1.088 g, 2.48 mmol, 1.0 eq.) in THF (15 mL) and MeOH (18 mL) a solution of $LiOH*H_2O$ (420 mg, 10.00 mmol, 4.0 eq.) in water (16 mL) was added, and the reaction mixture was stirred at room temperature for 16 hours, diluted with water, treated with an aqueous solution of HCl to reach pH 5 and extracted with ethyl acetate. The combined organic layers were washed with water, and concentrated at reduced pressure. The obtained residue was purified by column chromatography (silica gel, ethanol/DCM) to give compound 46g (676 mg, 64%) as a beige solid. APCI-MS (m/z (intensity)): 425.16 ([M+H]+, 100%).

Procedure for Synthesis of Compound 48.

A solution of compound 45g (272 mg, 0.62 mmol, 1.0 eq.) in THF (5 mL) was treated with a solution of HCl in dioxane (16%, 4.7 mL). The reaction mixture was stirred at room temperature for 21 hour, poured to an aqueous $NaHCO_3$ solution and extracted with ethyl acetate. The organic phase was concentrated at reduced pressure. The obtained residue was dried giving the intermediate 47 (238 mg) as a beige solid, which was used on the next stage without additional purification and characterization. The intermediate 47 (238 mg), $HCO_2H$ (380 µL, 10.00 mmol), paraform (93 mg, 3.10 mmol) and EtOH (3 mL) was stirred at reflux for 5 hours, then an aqueous solution of formaldehyde (40%, 430 µL) was added. The resulted mixture was stirred at reflux for 9 hours, cooled to room temperature, poured to an aqueous $NaHCO_3$ solution and extracted with ethyl acetate. The organic phase was concentrated at reduced pressure. The obtained residue was purified by column chromatography (silica gel, ethanol/DCM) to give of compound 48 (81 mg, 37% for 2 steps) as dark brown oil. APCI-MS (m/z (intensity)): 353.16 ([M+H]+, 100%).

Procedure for Synthesis of Compound 46h.

To a solution of compound 48 (81 mg, 0.23 mmol, 1.0 eq.) in MeOH (4 mL) a solution of $LiOH*H_2O$ (28 mg, 0.69 mmol, 3.0 eq.) in water (4 mL) was added, and the reaction mixture was stirred at room temperature for 16 hours, diluted with water, treated with an aqueous HCl solution to reach pH 6 and extracted with ethyl acetate. The combined organic layers were washed with water and concentrated at reduced pressure. The obtained residue was dried giving compound 46h (58 mg, 75%) as a white solid. APCI-MS (m/z (intensity)): 339.18 ([M+H]+, 100%).

Scheme 12.

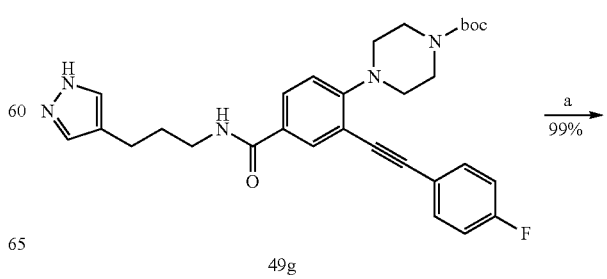

49g

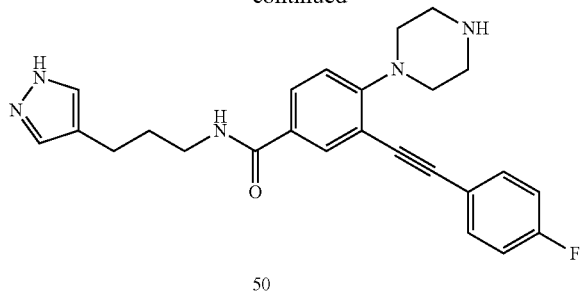

50

(a) HCl*dioxane, THF, RT, 16 h eq.) was added. The reaction mixture was stirred at room temperature for 5-16 hours, poured to an aqueous NaOH solution (1N) and extracted with ethyl acetate. The organic phase was washed with water and concentrated. The obtained residue was purified by column chromatography (silica gel, ethanol/DCM) to give a target compound (49a-h). Compound 49a: yield 41 mg, 38% as a yellow solid. Compound 49b: yield 139 mg, 78% as a yellow solid. Compound 49c: yield 181 mg, 98% as a white solid. Compound 49d: yield 110 mg, 56% as a yellow solid. Compound 49e: yield 179 mg, 90% as a yellow solid. Compound 49f: yield 146 mg, 61% as a white solid. Compound 49g: yield 67 mg, 39% as a white solid Compound 49h: yield 36 mg, 48% as a white solid Scheme 13.

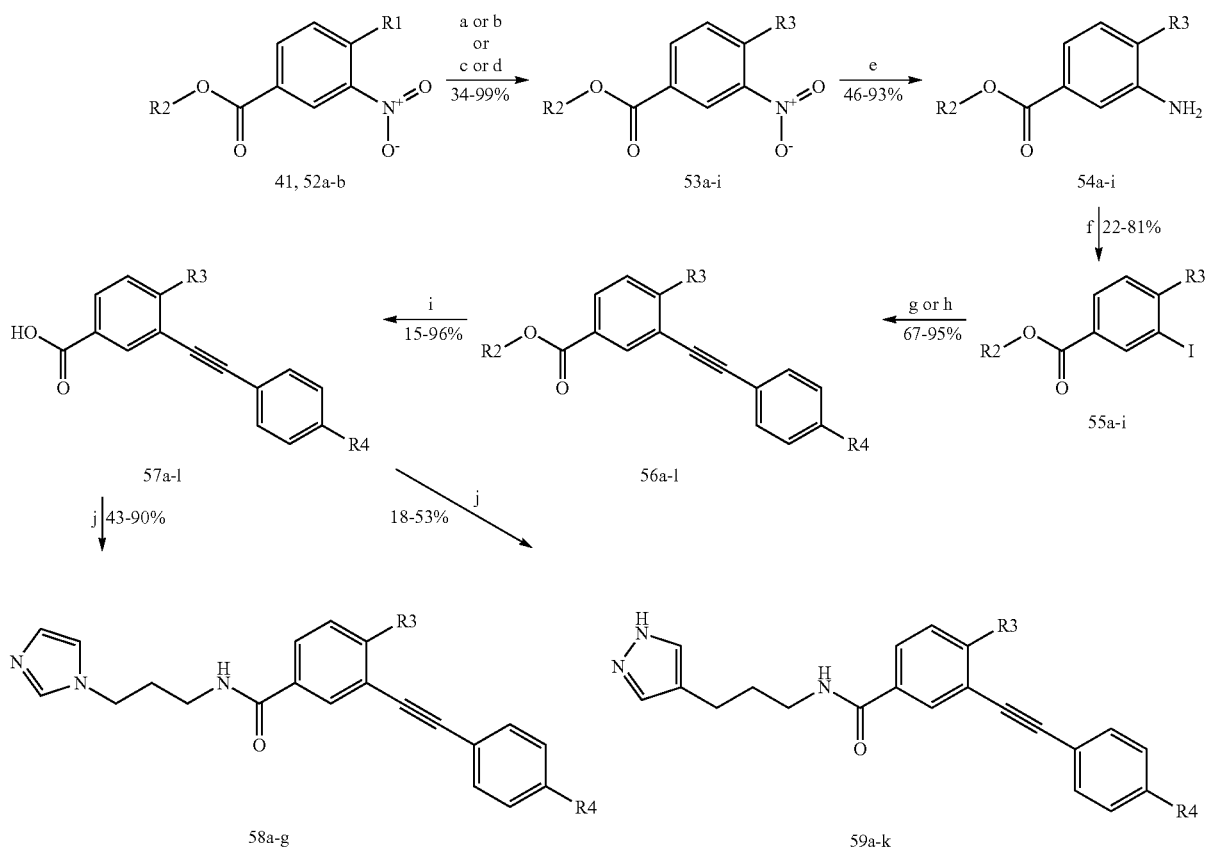

(a) amine, Et$_3$N, EtOH, reflux, 1-10 h;
(b) PhOH, K$_2$CO$_3$, CuI, DMF, Ar, 100° C., 2 h;
(c) R3-H, DIPEA, MeCN, reflux, 6-22 h;
(d) R3B(OH)$_2$, [PPh$_3$]$_4$Pd, Na$_2$CO$_3$, EtOH, toluene, H$_2$O, reflux, 2-4 h:
(e) H$_2$, Ni, EtOH, RT, 8-70 h;
(f) NaNO$_2$, KI, HCl, H$_2$O, 0° C. to RT, 30 min;
(g) phenylacetylene; PdCl$_2$[PPh$_3$]$_2$, t-Bu$_3$P, Et$_3$N, DMF, Ar, 80° C., 1-4.5 h;
(h) 4-fluorophenylacetylene; PdCl$_2$[PPh$_3$]$_2$, CuI, Et$_3$N, MeCN, Ar, reflux, 2.5-4 h;
(i) NaOH, EtOH or MeOH, H$_2$O, 55-60° C., 30 min-5.5 h;
(j) amine 4 or 6, TBTU, Et$_3$N, DCM, RT, 3-15 h Generic Procedure for Synthesis of Compounds 49a-h.

A mixture of the corresponding acid (46a-h) (0.40 mmol, 1.0 eq.), TBTU (180 mg, 0.56 mmol, 1.4 eq.), triethylamine (0.126 µL, 0.90 mmol, 2.2 eq.) and DMF (3 mL) was stirred at room temperature for 30 minutes. Then 3-(1H-pyrazol-4-yl)-propylamine hydrochloride (6) (78 mg, 0.48 mmol, 1.2

Procedure for Synthesis of Compound 50.

A solution of compound 49g (52 mg, 0.098 mmol) in THF (5 mL) was treated with a solution of HCl in dioxane (16%, 0.5 mL) and stirred at room temperature for 16 hours, poured to an aqueous NaHCO$_3$ solution, diluted with EtOH, and extracted with ethyl acetate. The organic phase was concentrated at reduced pressure. The obtained residue was dried giving compound 50 (48 mg, 99%) as a beige solid.

TABLE 8

| Starting comp. | R1 | R2 | Product compound | R3 | Conditions | Yield (%) |
|---|---|---|---|---|---|---|
| 1 | 41 | Cl | Me | 53a | Me₂N— | a | 93 |
| 2 | 52a | Cl | Et | 53b | pyrrolidin-1-yl | a | 66 |
| 3 | 52a | Cl | Et | 53c | morpholin-4-yl | a | 99 |
| 4 | 41 | Cl | Me | 53d | PhO— | b | 70 |
| 5 | 52b | F | Et | 53e | imidazol-1-yl | c | 90 |
| 6 | 52b | F | Et | 53f | 1,2,4-triazol-1-yl | c | 86 |
| 7 | 41 | Cl | Me | 53g[a] | 3-Py— | d | 43 |
| 8 | 41 | Cl | Me | 53h[a] | 4-Py— | d | 34 |
| 9 | 41 | Cl | Me | 53i[a] | pyrazol-4-yl | d | 70 |

[a] compounds were obtained as a Et esters

TABLE 9

| | R3 | R2 | Starting comp. | Product comp. | Yield (%) | Product comp. | Yield (%) |
|---|---|---|---|---|---|---|---|
| 1 | Me₂N— | Me | 53a | 54a | 59 | 55a | 25 |
| 2 | pyrrolidin-1-yl | Et | 53b | 54b | 51 | 55b | 70 |
| 3 | morpholin-4-yl | Et | 53c | 54c | 46 | 55c | 65 |
| 4 | PhO— | Me | 53d | 54d | 93 | 55d | 50 |
| 5 | imidazol-1-yl | Et | 53e | 54e | 93 | 55e | 22 |
| 6 | 1,2,4-triazol-1-yl | Et | 53f | 54f | 72 | 55f | 77 |
| 7 | 3-Py— | Et | 53g | 54g | 60 | 55g | 56 |
| 8 | 4-Py | Et | 53h | 54h | 92 | 55h | 59 |
| 9 | pyrazol-4-yl | Et | 53i | 54i | 90 | 55i | 81 |

TABLE 10

| | R3 | R2 | Starting comp. | R4 | Conditions | Product comp. | Yield (%) | Product comp. | Yield (%) |
|---|---|---|---|---|---|---|---|---|---|
| 1 | Me₂N— | Me | 55a | H | a | 56a | 83 | 57a | 48 |
| 2 | pyrrolidin-1-yl | Et | 55b | H | a | 56b | 72 | 57b | 60 |
| 3 | morpholin-4-yl | Et | 55c | H | a | 56c | 89 | 57c | 90 |
| 4 | PhO— | Me | 55d | H | a | 56d | 78 | 57d | 15 |
| 5 | imidazol-1-yl | Et | 55e | H | a | 56e | 67 | 57e | 83 |
| 6 | imidazol-1-yl | Et | 55e | F | b | 56f | 72 | 57f | 95 |
| 7 | 1,2,4-triazol-1-yl | Et | 55f | H | a | 56g | 85 | 57g | 94 |

TABLE 10-continued

| | R3 | R2 | Starting comp. | R4 | Conditions | Product comp. | Yield (%) | Product comp. | Yield (%) |
|---|---|---|---|---|---|---|---|---|---|
| 8 | [triazole, *—N linked] | Et | 55f | F | b | 56h | 95 | 57h | 89 |
| 9 | 3-Py— | Et | 55g | H | a | 56i | 92 | 57i | 94 |
| 10 | 4-Py | Et | 55h | H | a | 56j | 95 | 57j | 96 |
| 11 | 4-Py | Et | 55h | F | b | 56k | 80 | 57k | 90 |
| 12 | [pyrazole, N-Me, 4-linked] | Et | 55i | F | b | 56l | 70 | 57i | 95 |

TABLE 11

| | R3 | R4 | Starting comp. | Product comp. | Yield (%) |
|---|---|---|---|---|---|
| 1 | $Me_2N-$ | H | 57a | 58a | 69 |
| 2 | [pyrrolidine, *—N] | H | 57b | 58b | 80 |
| 3 | [morpholine, *—N] | H | 57c | 58c | 79 |
| 4 | PhO— | H | 57d | 58d | 80 |
| 5 | [2-methylimidazole, *—N] | H | 57e | 58e | 90 |
| 6 | [triazole, *—N] | H | 57g | 58f | 43 |
| 7 | 4-Py | H | 57j | 58g | 60 |

TABLE 12

| | R3 | R4 | Starting comp. | Product comp. | Yield (%) |
|---|---|---|---|---|---|
| 1 | $Me_2N-$ | H | 57a | 59a | 41 |
| 2 | [pyrrolidine, *—N] | H | 57b | 59b | 18 |
| 3 | [morpholine, *—N] | H | 57c | 59c | 52 |
| 4 | PhO— | H | 57d | 59d | 42 |
| 5 | [2-methylimidazole, *—N] | F | 57f | 59e | 35 |
| 6 | [triazole, *—N] | H | 57g | 59f | 37 |
| 7 | [triazole, *—N] | F | 57h | 59g | 52 |
| 8 | 3-Py— | H | 57i | 59h | 53 |
| 9 | 4-Py | H | 57j | 59i | 28 |
| 10 | 4-Py | F | 57k | 59j | 48 |
| 11 | [pyrazole, N-Me, 4-linked] | F | 57l | 59k | 43 |

Generic Procedure for Synthesis of Compounds 53a-c.

A suspension of 4-chloro-3-nitro-benzoic acid methyl ester (41) or 4-chloro-3-nitro-benzoic acid ethyl ester (52a) (31.57 mmol, 1.0 eq.), the corresponding amine (35.00 mmol, 1.1 eq.) and triethylamine (5.6 mL, 40.00 mmol, 1.3 eq.) in ethanol (200 mL) was stirred at reflux for 1-10 hours, cooled down to room temperature and concentrated at reduced pressure. The obtained residue was purified by column chromatography (silica gel; hexane/ethyl acetate) giving a target compound (53a-c). Compound 53a: yield 6.89 g, 93% as a yellow solid. APCI-MS (m/z (intensity)): 225.14 ([M+H]$^+$, 100%). Compound 53b: yield 7.02 g, 66% as a yellow solid. $^1$H NMR $\delta_H$ (400 MHz, D$_6$-DMSO): 1.28 (t, 3H), 1.90-1.94 (m, 4H), 3.17-3.24 (m, 4H), 4.27 (q, 2H), 7.08 (d, 1H), 7.90 (dd, 1H), 8.21 (d, 1H). APCI-MS (m/z (intensity)): 265.16 ([M+H]$^+$, 100%). Compound 53c: yield 8.80 g, 99% as a yellow solid. $^1$H NMR $\delta_H$ (400 MHz, D$_6$-DMSO): 1.39 (t, 3H), 3.16 (t, 4H), 3.85 (t, 4H), 4.38 (q, 2H), 7.09 (d, 1H), 8.10 (dd, 1H), 8.44 (d, 1H). APCI-MS (m/z (intensity)): 281.14 ([M+H]$^+$, 100%).

Procedure for Synthesis of Compound 53d.

A mixture of 4-chloro-3-nitro-benzoic acid methyl ester (41) (9.92 g, 46.00 mmol. 1.0 eq.), phenol (5.20 g, 55.20 mmol, 1.2 eq.), K$_2$CO$_3$ (7.63 g, 55.20 mmol, 1.2 eq.), CuI (0.26 g, 1.37 mmol, 3 mol %) and DMF (20 mL) was stirred at 110° C. for 1.8 hours under argon atmosphere. The cooled reaction mixture was diluted with water (100 mL). The formed solid was collected by filtration, dried and purified by column chromatography (silica gel; hexane/ethyl acetate)

giving compound 53d (8.85 g, 70%) as a yellow solid. $^1$H NMR $\delta_H$ (400 MHz, D$_6$-DMSO): 3.87 (s, 3H), 6.98 (d, 1H), 7.09-7.13 (m, 2H), 7.24-7.29 (m, 1H), 7.40-7.46 (m, 2H), 8.11 (dd, 1H), 8.59 (d, 1H). APCI-MS (m/z (intensity)): 273.10 ([M+H]$^+$, 100%).

Generic Procedure for Synthesis of Compounds 53e,f.

A mixture of 4-fluoro-3-nitro-benzoic acid ethyl ester (52b) (6.39 g, 30.0 mmol, 1.0 eq.), the corresponding amine (30.0 mmol, 1.0 eq.), DIPEA (7.8 mL, 81.6 mmol, 2.7 eq.) and MeCN (60 mL) was stirred at reflux for 6-22 hours, cooled down to room temperature and concentrated at reduced pressure. The obtained residue was purified by column chromatography (silica gel; hexane/ethyl acetate) giving a target compound (53e,f). Compound 53e: yield 7.43 g, 90% as a yellow solid. $^1$H NMR $\delta_H$ (400 MHz, D$_6$-DMSO): 1.35 (t, 3H), 2.11 (s, 3H), 4.41 (q, 2H), 6.93 (d, 1H), 7.21 (d, 1H), 7.83 (d, 1H), 8.35 (dd, 1H), 8.58 (d, 1H). APCI-MS (m/z (intensity)): 275.69 ([M+H]$^+$, 100%). Compound 53f: yield 6.40 g, 86% as an orange solid. $^1$H NMR $\delta_H$ (400 MHz, D$_6$-DMSO): 1.36 (t, 3H), 4.40 (q, 2H), 8.05 (d, 1H), 8.28 (s, 1H), 8.37 (dd, 1H), 8.53 (d, 1H), 9.17 (s, 1H). APCI-MS (m/z (intensity)): 263.10 ([M+H]$^+$, 100%), 304.17 ([M+MeCN+H]$^+$, 20%).

Generic Procedure for Synthesis of Compounds 53g-i.

To a mixture of 4-chloro-3-nitro-benzoic acid methyl ester (41) (6.26 g, 29.07 mmol, 1.0 eq.) and the corresponding boronic acid (R3-B(OH)$_2$) (43.60 mmol, 1.5 eq.) in toluene (80 mL) and EtOH (80 mL) a mixture of Pd[PPh$_3$]$_4$ (725 mg, 0.63 mmol, 0.2 eq.) and an aqueous solution of Na$_2$CO$_3$ (2M, 35 mL, 70.00 mmol, 2.4 eq.) in toluene (60 mL) and EtOH (60 mL) was added rapidly. Then water (35 mL) was added. The reaction mixture was stirred at reflux under argon atmosphere for 1 hour, then an addition portion of Pd[PPh$_3$]$_4$ (725 mg, 0.63 mmol, 0.2 eq.) was added. The resulted mixture was stirred at reflux for 1-3 hours, cooled down to room temperature and concentrated at reduced pressure. The obtained residue was diluted with water and DCM and filtered through Celite. The organic phase was dried over sodium sulfate and concentrated at reduced pressure. The obtained residue was purified by column chromatography (silica gel, hexane/ethyl acetate) giving a target compound (53g-i). Compound 53g: yield 3.37 g, 43% as a yellow solid. APCI-MS (m/z (intensity)): 273.14 ([M+H]$^+$, 100%), 314.22 ([M+MeCN+H]$^+$, 21%). Compound 53h: yield 2.44 g, 34% as a yellow solid. APCI-MS (m/z (intensity)): 273.13 ([M+H]$^+$, 100%). Compound 53i: yield 1.89 g, 70% as a yellow solid. APCI-MS (m/z (intensity)): 275.75 ([M+H]$^+$, 100%), 317.20 ([M+MeCN+H]$^+$, 16%).

Generic Procedure for Synthesis of Compounds 54a-i.

A mixture of the corresponding nitro derivative (53a-i) (29.21 mmol, 1.0 eq.), Raney nickel catalyst (3.00 g, 51.12 mmol, 1.75 eq.) and EtOH (450 mL).) was stirred under hydrogen atmosphere (1-20 atm.) at room temperature for 8-70 hours. The catalyst was removed by filtration. The filtrate was concentrated at reduced pressure. The obtained residue was purified by column chromatography (silica gel, hexane/ethyl acetate) giving a target compound (54a-i). Compound Ma: yield 3.37 g, 59% as a white solid. APCI-MS (m/z (intensity)): 194.80 ([M+H]$^+$, 100%). Compound 54b: yield 2.86 g, 51% as a brownish solid. $^1$H NMR $\delta_H$ (400 MHz, CDCl$_3$): 1.30 (t, 3H), 1.82-1.95 (m, 4H), 3.13-3.20 (m, 4H), 3.72 (brs, 2H), 4.30 (q, 2H), 6.87 (d, 1H), 7.24 (s, 1H), 7.41 (d, 1H). APCI-MS (m/z (intensity)): 235.23 ([M+H]$^+$, 100%). Compound 54c: yield 3.59 g, 46% as a white solid. APCI-MS (m/z (intensity)): 257.17 ([M+H]$^+$, 100%). $^1$H NMR $\delta_H$ (400 MHz, D$_6$-DMSO): 1.35 (t, 3H), 2.95 (t, 4H), 3.87 (t, 4H), 3.96 (brs, 2H), 4.32 (q, 2H), 6.96 (d, 1H), 7.25 (s, 1H), 7.41 (s, 1H), 7.47 (d, 1H). Compound 54d: yield 7.03 g, 93% as a white solid. $^1$H NMR $\delta_H$ (400 MHz, CDCl$_3$): 3.83 (s, 3H), 3.94 (brs, 2H), 6.80 (d, 1H), 7.00-7.05 (m, 2H), 7.10-7.16 (m, 1H), 7.327.40 (m, 3H), 7.51 (d, 1H). APCI-MS (m/z (intensity)): 243.71 ([M+H]$^+$, 100%), 285.17 ([M+MeCN+H]$^+$, 53%). Compound 54e: yield 6.18 g, 93% as a yellowish solid. $^1$H NMR $\delta_H$ (400 MHz, CDCl$_3$): 1.37 (t, 3H), 2.22 (s, 3H), 3.71 (brs, 2H), 4.38 (q, 2H), 6.92 (s, 1H), 7.12 (d, 1H), 7.24 (s, 1H), 7.48 (dd, 1H), 7.52 (d, 1H). APCI-MS (m/z (intensity)): 246.14 ([M+H]$^+$, 100%). Compound 54f: yield 3.91 g, 72% as a yellowish solid. APCI-MS (m/z (intensity)): 233.14 ([M+H]$^+$, 100%), 274.19 ([M+MeCN+H]$^+$, 19%). Compound Mg: yield 1.80 g, 60% as a yellow oil. APCI-MS (m/z (intensity)): 243.77 ([M+H]$^+$, 100%). Compound 54h: yield 1.99 g, 92% as a yellowish solid. APCI-MS (m/z (intensity)): 242.81 ([M+H]$^+$, 100%), 284.19 ([M+MeCN+H]$^+$, 42%). Compound 54i: yield 1.50 g, 90% as a yellowish solid. APCI-MS (m/z (intensity)): 246.19 ([M+H]$^+$, 100%), 286.56 ([M+MeCN+H]$^+$, 22%).

Generic Procedure for Synthesis of Compounds 55a-i.

A solution of sodium nitrite (0.895 g, 12.97 mmol, 1.0 eq.) in water (13 mL) was slowly added to a stirred suspension of the corresponding amine derivative (54a-i) (12.78 mmol, 1.0 eq.) in a mixture of concentrated aqueous HCl solution (13 mL) and water (13 mL) at 0° C. By the end of addition of the sodium nitrite solution the reaction mixture became clear. After the addition formation of a precipitate was observed. The reaction mixture was stirred at 3° C. for 10 minutes after the addition. Then a solution of potassium iodide (4.22 g, 25.42 mmol, 2.0 eq.) in water (13 mL) was added to the mixture at 3° C. A very viscous red-brown mixture was formed which turned to dark brown color. The reaction mixture was stirred at room temperature for 30 minutes, treated with saturated aqueous potassium carbonate solution to reach pH>8 and extracted with DCM. The organic layer was washed with an aqueous NaHSO$_3$ solution, with water, dried over sodium sulfate and concentrated at reduced pressure. The obtained residue was purified by column chromatography (silica gel, hexane/ethyl acetate, 10:1) giving a target compound (55a-i). Compound 55a: yield 1.30 g, 25% as a yellow oil. APCI-MS (m/z (intensity)): 306.01 (M+H]$^+$, 100%). Compound 55b: yield 2.78 g, 70% as a yellowish solid. $^1$H NMR $\delta_H$ (400 MHz, D$_6$-DMSO): 1.27 (t, 3H), 1.85-1.91 (m, 4H), 3.41-3.47 (m, 4H), 4.23 (q, 2H), 6.84 (d, 1H), 7.76 (dd, 1H), 8.30 (s, 1H). APCI-MS (m/z (intensity)): 346.14 ([M+H]$^+$, 100%). Compound 55c: yield 3.00 g, 65% as a yellow solid. APCI-MS (m/z (intensity)): 348.04 ([M+H]$^+$, 100%). Compound 55d: yield 4.39 g, 50% as a yellow solid. APCI-MS (m/z (intensity)): 354.15 (82%), 396.09 ([M+MeCN+H]$^+$, 100%). Compound 55e: yield 1.40 g, 22% as a yellowish solid. $^1$H NMR $\delta_H$ (400 MHz, CDCl$_3$): 1.43 (t, 3H), 2.20 (s, 3H), 4.44 (q, 2H), 6.87 (d, 1H), 7.08 (d, 1H), 7.36 (d, 1H), 8.13 (dd, 1H), 8.62 (d, 1H). APCI-MS (m/z (intensity)): 357.07 ([M+H]$^+$, 100%). Compound 55f: yield 4.40 g, 77% as a yellow solid. $^1$H NMR $\delta_H$ (400 MHz, CDCl$_3$): 1.43 (t, 3H), 4.43 (q, 2H), 7.48 (d, 1H), 8.13-8.16 (m, 2H), 8.48 (s, 1H), 8.65 (d, 1H). APCI-MS (m/z (intensity)): 343.99 ([M+H]$^+$, 100%), 384.97 ([M+MeCN+H]$^+$, 85%). Compound 55g: yield 1.48 g, 56% as a yellow oil. APCI-MS (m/z (intensity)): 354.08 ([M+H]$^+$, 100%), 395.10 ([M+MeCN+H]$^+$, 23%). Compound 55h: yield 1.71 g, 59% as a yellowish solid. APCI-MS (m/z (intensity)): 354.00 ([M+H]$^+$, 100%), 394.96 ([M+MeCN+H]$^+$, 39%). Compound 55i: yield 1.76 g, 81% as a yellow oil. APCI-MS (m/z (intensity)): 357.05 ([M+H]$^+$, 100%), 398.12 ([M+MeCN+H]$^+$, 48%).

Generic Procedure for Synthesis of Compounds 56a-e,g, i,j.

Triethylamine (5 mL), t-Bu$_3$P (200 mg, 1.00 mmol, 10 mol %) and PdCl$_2$[PPh$_3$]$_2$ (202 mg, 0.29 mmol, 3 mol %) were added to a solution of the corresponding iodide derivative (55a-h) (8.17 mmol, 1.0 eq.) in anhydrous DMF (10 mL). The resulting mixture was stirred under argon atmosphere at room temperature for 10 minutes. Then phenylacetylene (1.25 g, 12.25 mmol, 1.5 eq.) was added. The reaction mixture was stirred at 80° C. for 1-4.5 hours, cooled down to room temperature, diluted with water (30 mL) and extracted with DCM. The organic phase was dried over sodium sulfate and concentrated at reduced pressure. The obtained residue was purified by column chromatography (silica gel, hexane/ethyl acetate) giving a target compound (56a-e,g,i,j). Compound 56a: yield 0.98 g, 83% as a yellowish oil. APCI-MS (m/z (intensity)): 280.19 ([M+H]$^+$, 100%). Compound 56b: yield 1.84 g, 72% as a yellowish solid. $^1$H NMR $\delta_H$ (400 MHz, CDCl$_3$): 1.38 (t, 3H), 1.97-2.03 (m, 4H), 3.73-3.78 (m, 4H), 4.34 (q, 2H), 6.60 (d, 1H), 7.29-7.37 (m, 3H), 7.45-7.48 (m, 2H), 7.82 (dd, 1H), 8.12 (d, 1H). APCI-MS (m/z (intensity)): 320.15 ([M+H]$^+$, 100%). Compound 56c: yield 2.44 g, 89% as a yellowish solid. $^1$H NMR $\delta_H$ (400 MHz, CDCl$_3$: 1.40 (t, 3H), 3.38 (t, 4H), 3.92 (t, 4H), 4.37 (q, 2H), 6.92 (d, 1H), 7.33-7.39 (m, 3H), 7.48-7.53 (m, 2H), 7.94 (dd, 1H), 8.18 (d, 1H). APCI-MS (m/z (intensity)): 366.30 ([M+H]$^+$, 100%). Compound 56d: yield 3.18 g, 78% as a yellowish solid. APCI-MS (m/z (intensity)): 329.25 ([M+H]$^+$, 100%), 370.29 ([M+MeCN+H]$^+$, 80%). Compound 56e: yield 0.33 g, 67% as a yellowish solid. APCI-MS (m/z (intensity)): 331.29 ([M+H]$^+$, 100%). Compound 56g: yield 1.55 g, 85% as a yellowish solid. APCI-MS (m/z (intensity)): 318.24 ([M+H]$^+$, 100%), 359.26 ([M+MeCN+H]$^+$, 13%). Compound 56i: yield 1.18 g, 92% as a yellowish solid. APCI-MS (m/z (intensity)): 328.21 ([M+H]$^+$, 100%), 369.23 ([M+MeCN+H]$^+$, 20%). Compound 56j: yield 1.00 g, 95% as a yellowish solid. APCI-MS (m/z (intensity)): 328.26 ([M+H]$^+$, 100%).

Generic Procedure for Synthesis of Compounds 56f,h,k,l.

Triethylamine (5 mL), CuI (16 mg, 0.084 mmol, 4 mol %) and PdCl$_2$[PPh$_3$]$_2$ (50 mg, 0.071 mmol, 3 mol %) were added to a solution of the corresponding iodide derivative (55e,f,h,i) (2.00 mmol, 1.0 eq.) in MeCN (20 mL). The resulting mixture was stirred under argon atmosphere at room temperature for 5 minutes. Then 4-fluorophenyl-acetylene (360 mg, 3.00 mmol, 1.5 eq.) was added. The reaction mixture was stirred at refluxing for 2.5-4 hours, cooled down to room temperature and concentrated at reduced pressure. The obtained residue was purified by column chromatography (silica gel, hexane/ethyl acetate) giving a target compound (56f,h,k,l). Compound 56f: yield 0.25 g, 72% as a yellowish solid. APCI-MS (m/z (intensity)): 349.20 ([M+H]$^+$, 100%). Compound 56h: yield 0.64 g, 95% as a yellowish solid. APCI-MS (161) (m/z (intensity)): 336.20 ([M+H]$^+$, 100%), 377.22 ([M+MeCN+H]$^+$, 52%). Compound 56k: yield 0.49 g, 80% as a yellowish solid. APCI-MS (m/z (intensity)): 346.21 ([M+H]$^+$, 100%). Compound 56l: yield 0.36 g, 70% as a yellowish solid. APCI-MS (m/z (intensity)): 349.24 ([M+H]$^+$, 100%), 390.29 ([M+MeCN+H]$^+$, 15%).

Generic Procedure for Synthesis of Compounds 57a-l.

A solution of NaOH (1.48 g, 37.00 mmol, 5.3 eq.) in water (15 mL) was added to a suspension of the corresponding ester (56a-l) (7.24 mmol, 1.0 eq.) in EtOH (150 mL). The reaction mixture was stirred at 55-60° C. for 30 minutes-5.5 hours, cooled down to room temperature, concentrated at reduced pressure, diluted with water (100 mL) and acidified with an aqueous HCl solution (1M) to reach pH 5. The formed precipitate was collected by filtration and dried giving a target compound (57a-l). Compound 57a: yield 442 mg, 48% as a yellow solid. Compound 57b: yield 314 mg, 60% as a white solid. APCI-MS (m/z (intensity)): 291.80 ([M+H]$^+$, 100%). Compound 57c: yield 2.00 g, 90% as a white solid. APCI-MS (m/z (intensity)): 307.90 ([M+H]$^+$, 100%). Compound 57d: yield 457 mg, 15% as a yellowish solid. APCI-MS (m/z (intensity)): 315.20 ([M+H]$^+$, 13%), 355.89 ([M+MeCN+H]$^+$, 100%). Compound 57e: yield 265 mg, 83% as a light-brownish solid. APCI-MS (m/z (intensity)): 303.23 ([M+H]$^+$, 100%). Compound 57f: yield 218 mg, 95% as a yellowish solid. APCI-MS (m/z (intensity)): 321.22 ([M+H]$^+$, 100%). Compound 57g: yield 1.30 g, 94% as a yellowish solid. $^1$H NMR $\delta_H$ (400 MHz, D$_6$-DMSO): 3.22 (brs, 1H), 7.41-7.48 (m, 5H), 7.79 (d, 1H), 8.10 (dd, 1H), 8.24 (d, 1H), 8.30 (s, 1H), 9.24 (s, 1H). APCI-MS (m/z (intensity)): 290.18 ([M+H]$^+$, 100%), 331.23 ([M+MeCN+H]$^+$, 7%). Compound 57h: yield 524 mg, 89% as a yellowish solid. $^1$H NMR (18f) $\delta_H$ (400 MHz, D$_6$-DMSO): 3.2 (brs, 1H), 7.41-7.48 (m, 5H), 7.79-7.55 (d, 1H), 8.10 (dd, 1H), 8.24 (d, 1H), 8.30 (s, 1H), 9.24 (s, 1H). Compound 57i: yield 1.01 g, 94% as a white solid. APCI-MS (m/z (intensity)): 300.15 ([M+H]$^+$, 100%), 341.18 ([M+MeCN+H]$^+$, 17%). Compound 57j: yield 880 mg, 96% as a white solid. APCI-MS (m/z (intensity)): 300.18 ([M+H]$^+$, 100%), 341.03 ([M+MeCN+H]$^+$, 10%). Compound 57k: yield 420 mg, 90% as a white solid. APCI-MS (m/z (intensity)): 318.17 ([M+H]$^+$, 100%). Compound 57l: yield 320 mg, 95% as a white solid. APCI-MS (m/z (intensity)): 321.19 ([M+H]$^+$, 100%), 362.27 ([M+MeCN+H]$^+$, 8%).

Generic Procedure for Synthesis of Compounds 58a-g, 59a-k.

TBTU (411 mg, 1.28 mmol, 1.5 eq.), triethylamine (0.26 mL, 1.85 mmol, 2.2 eq.) and 3-imidazol-1-yl-propylamine (4) or 3-(1H-pyrazol-4-yl)-propylamine (6) (0.94 mmol, 1.1 eq.) were added to a solution of the corresponding acid (57a-l) (258 mg, 0.85 mmol, 1.0 eq.) in DCM (10 mL). The reaction mixture was stirred at room temperature for 3-15 hours, then diluted with a saturated aqueous NaHCO$_3$ solution (equivalent volume), again stirred at room temperature for 1 hour and extracted with DCM. The organic phase was dried over sodium sulfate and concentrated at reduced pressure. The obtained residue was purified by column chromatography (silica gel; ethyl acetate/MeOH/NH$_4$OH) giving a target compound (58a-g, 59a-k). Compound 58a: yield 210 mg, 69% as a yellowish solid. Compound 58b: yield 320 mg, 80% as a yellowish solid. Compound 58c: yield 230 mg, 79% as a yellowish solid. Compound 58d: yield 250 mg, 80% as a yellowish solid. Compound 58e: yield 315 mg, 90% as a yellowish solid. Compound 58f: yield 147 mg, 43% as a yellowish solid. Compound 58g: yield 170 mg, 60% as a yellowish solid. Compound 59a: yield 125 mg, 41% as a yellowish solid. Compound 59b: yield 65 mg, 18% as a yellowish solid. Compound 59c: yield 150 mg, 52% as a yellowish solid. Compound 59d: yield 130 mg, 42% as a yellowish solid. Compound 59e: yield 60 mg, 35% as a yellowish solid. Compound 59f: yield 125 mg, 37% as a yellowish solid. Compound 59g: yield 85 mg, 52% as a yellowish solid. Compound 59h: yield 173 mg, 53% as a yellowish solid. Compound 59i: yield 80 mg, 28% as a yellowish solid. Compound 59j: yield 115 mg, 48% as a yellowish solid. Compound 59k: yield 110 mg, 43% as a yellowish solid.

Scheme 14.

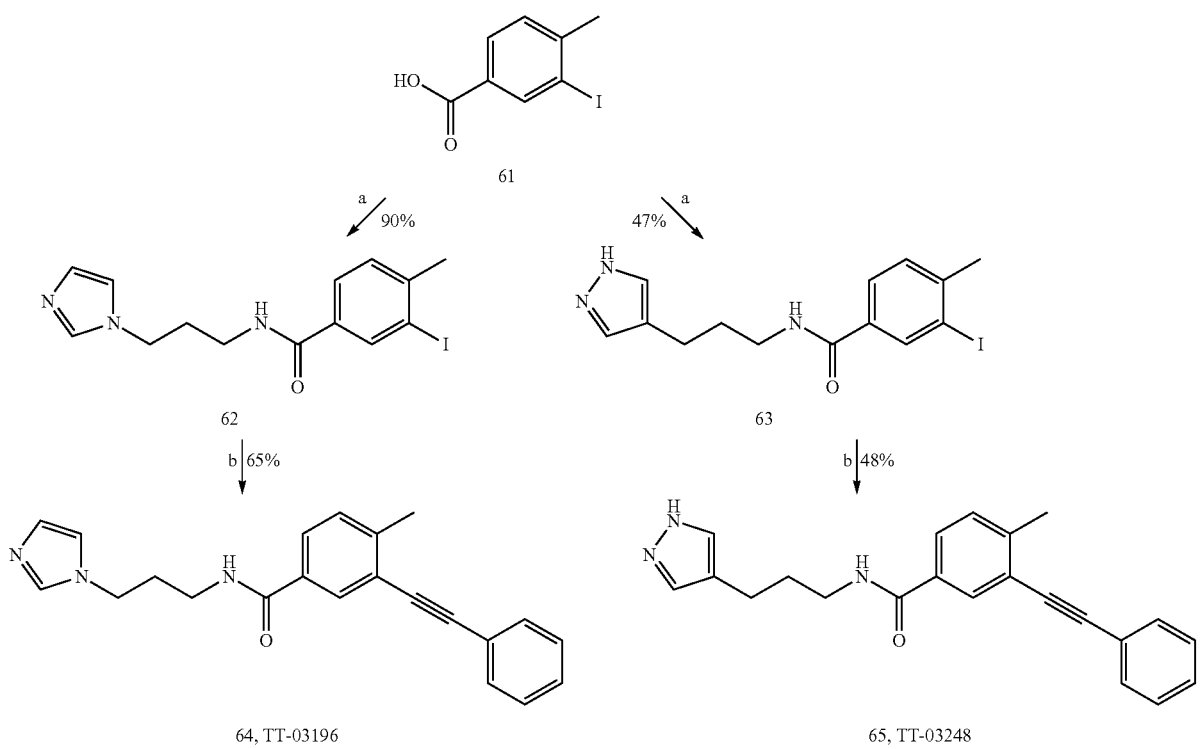

64, TT-03196

65, TT-03248

(a) amine 4 or 6, TBTU, Et₃N, DCM, RT, 20 h;
(b) phenylacetylene; PdCl₂[PPh₃]₂, t-Bu₃P, Et₃N, DMF, Ar, 70-80° C., 2 h Procedure for Synthesis of Compound 62.

TBTU (920 mg, 2.86 mmol, 1.5 eq.), triethylamine (0.42 mL, 3.00 mmol, 1.6 eq.) and 3-imidazol-1-yl-propylamine (4) (263 mg, 2.10 mmol, 1.1 eq.) were added to a solution of 3-iodo-4-methyl-benzoic acid (61) (500 mg, 1.91 mmol, 1.0 eq.) in DCM (20 mL) and DMF (3 mL). The reaction mixture was stirred at room temperature for 20 hours, then diluted with a saturated aqueous NaHCO₃ solution (15 mL), again stirred at room temperature for 1.5 hour and extracted with DCM. The organic phase was dried over sodium sulfate and concentrated at reduced pressure. The obtained residue was purified by column chromatography (silica gel; ethyl acetate/MeOH/NH₄OH, 40:2:1) giving compound 62 (635 mg, 90%) as a yellowish oil. $^1$H NMR $\delta_H$ (400 MHz, CDCl₃): 2.12 (m, 2H), 2.45 (s, 3H), 3.47 (q, 2H), 4.05 (t, 2H), 6.25 (brs, 1H), 6.96 (s, 1H), 7.09 (s, 1H), 7.27 (d, 1H), 7.52 (s, 1H), 7.60 (dd, 1H), 8.17 (d, 1H). APCI-MS (m/z (intensity)): 370.19 ([M+H]$^+$, 100%).

Procedure for Synthesis of Compound 63.

Compound 63 was prepared according to Procedure for synthesis of compound 62 using 3-(1H-pyrazol-4-yl)-propylamine dihydrochloride (6) (340 mg, 1.72 mmol, 0.90 eq.) and triethylamine (1.5 mL, 10.67 mmol, 5.6 eq.). Yield 300 mg, 47% as a yellowish oil. APCI-MS (m/z (intensity)): 370.15 ([M+H]$^+$, 100%), 411.17 ([M+MeCN+H]$^+$, 20%).

Procedure for Synthesis of Compound 64.

Triethylamine (2 mL), t-Bu₃P (43 mg, 0.21 mmol, 10 mol %) and PdCl₂[PPh₃]₂ (43 mg, 0.06 mmol, 3 mol %) were added to a solution of compound 62 (630 mg, 1.71 mmol, 1.0 eq.) in DMF (4 mL). The resulted mixture was stirred under argon atmosphere at room temperature for 10 minutes. Then phenyl-acetylene (261 mg, 2.56 mmol, 1.5 eq.) was added. The reaction mixture was stirred at 75-80° C. for 2 hours, cooled down to room temperature, diluted with water (20 mL) and extracted with DCM. The organic phase was dried over sodium sulfate and concentrated at reduced pressure. The obtained residue was purified by column chromatography (silica gel, ethyl acetate) giving compound 64 (380 mg, 65%) as a yellowish solid.

Scheme 15.

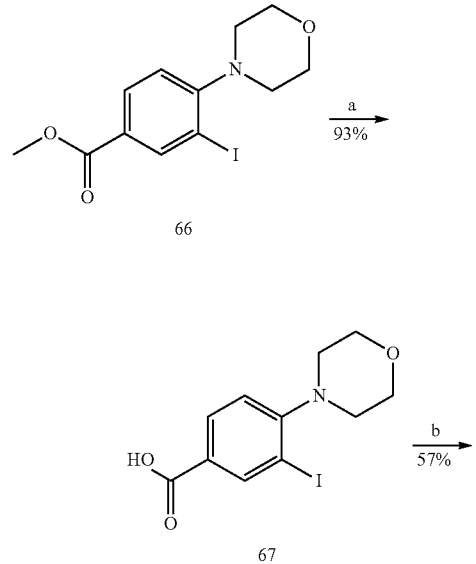

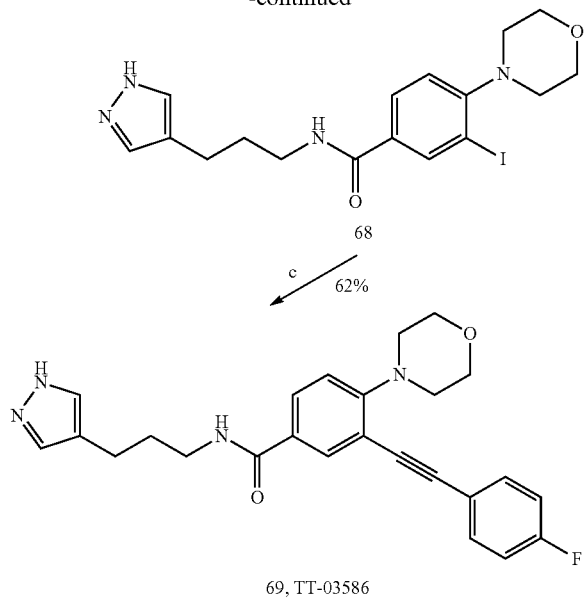

68 c ↓ 62%

69, TT-03586

(a) NaOH, MeOH, H₂O, 55-60° C., 2 h;
(b) amine 6, TBTU, Et₃N, DCM, RT, 12 h:
(c) 4-fluorophenylacetylene; PdCl₂[PPh₃]₂, CuI, Et₃N, MeCN, Ar, reflux, 3 h Procedure for Synthesis of Compound 65.

Compound 65 was prepared according to Procedure for synthesis of compound 64 using compound 63 (290 mg, 0.78 mmol 1.0 eq.), phenyl-acetylene (120 mg, 1.17 mmol, 1.5 eq.), t-Bu₃P (20 mg, 0.1 mmol, 10 mol %), PdCl₂[PPh₃]₂ (20 mg, 0.03 mmol, 3 mol %), triethylamine (1 mL) and DMF (3 mL). Yield 130 mg, 48% as a yellow solid.

Procedure for Synthesis of Compound 66.

Compound 66 was prepared in the same way as its ethyl ester analog 55c.

Procedure for Synthesis of Compound 67.

A solution of NaOH (1.09 g, 27.00 mmol, 5.0 eq.) in water (5 mL) was added to a suspension of compound 66 (1.88 g, 5.41 mmol, 1.0 eq.) in MeOH (110 mL). The reaction mixture was stirred at 50-55° C. for 2 hours, cooled down to room temperature, concentrated at reduced pressure, diluted with water (70 mL) and acidified with an aqueous HCl solution (1M) to reach pH 5. The formed precipitate was collected by filtration and dried giving compound 67 (1.66 g, 93%) as a light yellowish solid. APCI-MS (m/z (intensity)): 334.11 ([M+H]⁺, 100%).

Procedure for Synthesis of Compound 68.

TBTU (1.93 g, 6.00 mmol, 1.5 eq.), triethylamine (2.1 mL, 15.00 mmol, 3.7 eq.), 3-(1H-pyrazol-4-yl)-propylamine dihydrochloride (6) (1.03 g, 5.20 mmol, 1.3 eq.) were added to a solution of compound 67 (1.33 g, 4.00 mmol, 1.0 eq.) in DCM (40 mL). The reaction mixture was stirred at room temperature for 12 hours, then diluted with a saturated aqueous NaHCO₃ solution (40 mL), again stirred at room temperature for 1.5 hour and extracted with DCM. The organic phase was dried over sodium sulfate and concentrated at reduced pressure. The obtained residue was purified by column chromatography (silica gel; ethyl acetate/MeOH/NH₄OH, 40:2:1) giving compound 68 (1.00 g, 57%) as a yellowish oil. APCI-MS (m/z (intensity)): 441.31 ([M+H]⁺, 100%).

Procedure for Synthesis of Compound 69.

Triethylamine (0.2 mL, 1.42 mmol, 3.5 eq.), CuI (7 mg, 0.037 mmol, 4 mol %) and PdCl₂[PPh₃]₂ (12 mg, 0.017 mmol, 2 mol %) were added to a solution of compound 68 (686 mg, 2.00 mmol, 1.0 eq.) in MeCN (20 mL). The resulting mixture was stirred under argon atmosphere at room temperature for 5 minutes. Then 4-fluorophenyl-acetylene (75 mg, 0.6 mmol, 1.5 eq.) was added. The reaction mixture was stirred at refluxing for 3 hours, cooled down to room temperature and concentrated at reduced pressure. The obtained residue was purified by column chromatography (silica gel, ethyl acetate/MeOH, 10:1) giving compound 69 (108 mg, 62%) as a white solid.

Scheme 16.

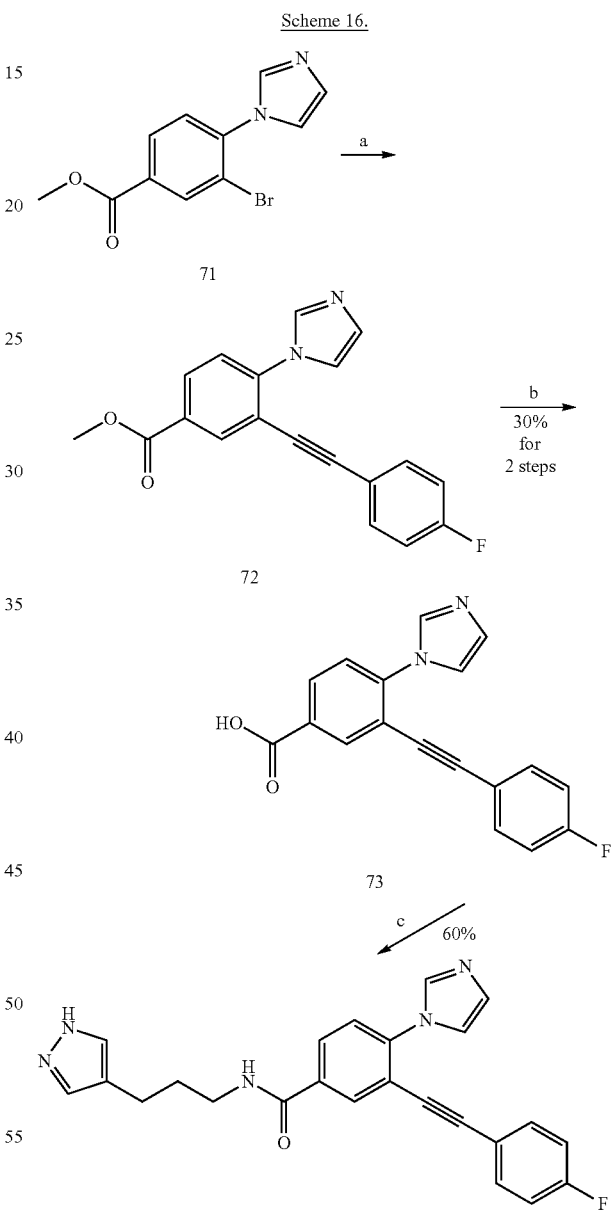

71 a →

72 b →
30%
for
2 steps

73 c ↓ 60%

74, TT-03627

(a) 4-fluorophenylacetylene; PdCl₂[PPh₃]₂, CuI, Et₃N, MeCN, Ar, reflux, 8 h;
(b) NaOH, MeOH, H₂O, 50° C., 1 h;
(c) amine 6, TBTU, Et₃N, DMF, RT, 8 h Procedure for Synthesis of Compound 73.

A mixture of 3-bromo-4-imidazol-1-yl-benzoic acid methyl ester (71) (280 mg, 1.00 mmol, 1.0 eq.), 4-fluoro-phenylacetylene (160 mg, 1.33 mmol, 1.3 eq.), PdCl₂

[PPh₃]₂ (35 mg, 0.05 mmol, 5 mol %), CuI (10 mg, 0.05 mmol, 5 mol %) and triethylamine (0.5 mL) in MeCN (7 mL) was refluxed under argon atmosphere for 4 hours. Then an additional amount of PdCl₂[PPh₃]₂ (35 mg, 0.05 mmol, 5 mol %), CuI (10 mg, 0.05 mmol, 5 mol %) and 4-fluorophenylacetylene (60 mg, 0.50 mmol, 0.5 eq.) were added. The resulted mixture was refluxed for 4 hours, cooled down to room temperature and concentrated at reduced pressure. The obtained residue was purified by column chromatography (silica gel, DCM/ethyl acetate) to give the intermediate 72 (165 mg) as white solid used on the next stage without characterization. To a solution of the intermediate 72 (165 mg, 0.52 mmol) in MeOH (20 mL) was added a solution of NaOH (200 mg, 5.00 mmol) in water (10 mL). The reaction mixture was stirred at 50° C. for 1 hour, cooled down to room temperature, acidified with concentrated aqueous HCl solution to reach pH 4-5. The formed precipitate was collected by filtration, washed with cold water and diethyl ether and dried to give compound 73 (90 mg, 30% for 2 steps) as beige solid. APCI-MS (m/z (intensity)): 307.12 ([M+H]⁺, 100%).

Procedure for Synthesis of Compound 74.

A mixture of compound 73 (90 mg, 0.29 mmol, 1.0 eq.), TBTU (113 mg, 0.35 mmol, 1.2 eq.), triethylamine (0.21 mL, 1.45 mmol, 5.0 eq.) was stirred at room temperature in dry DMF (5 mL) for 5 minutes. Then 3-(1H-pyrazol-4-yl)-propylamine hydrochloride (6) (57 mg, 0.35 mmol, 1.2 eq.) was added. The resulted mixture was stirred at room temperature for 8 hours, diluted with water (100 mL) and extracted with ethyl acetate (3×50 mL). The organic layers were combined, washed with an aqueous K₂CO₃ solution (30 mL), water (3×30 mL), dried over sodium sulfate and concentrated at reduced pressure. The obtained residue was purified by column chromatography (silica gel, DCM/MeOH) to give compound 74 (72 mg, 60%) as a white solid.

Scheme 17.

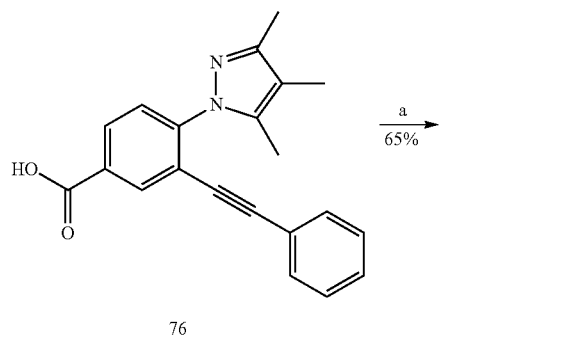

76

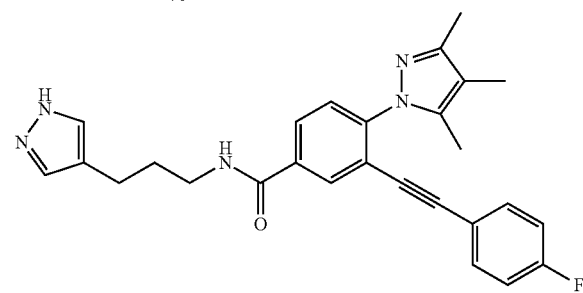

77, TT-03626

(a) amine 6, TBTU, Et₃N, DMF, RT, 12 h

Scheme 18.

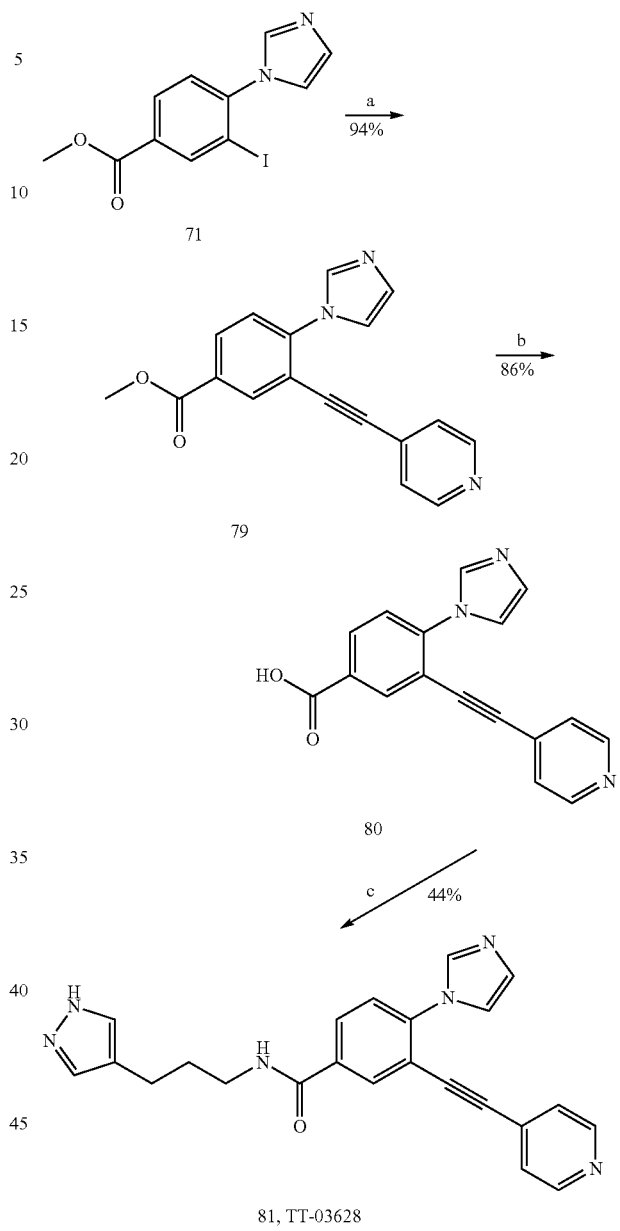

81, TT-03628

(a) 4-pyridylacetylene; PdCl₂[PPh₃]₂, CuI, Et₃N, MeCN, Ar, reflux, 6 h;
(b) NaOH, MeOH, H₂O, 50° C., 1 h;
(c) amine 6, TBTU, Et₃N, DMF, RT, 8 h Procedure for Synthesis of Compound 77.

A mixture of 3-phenylethynyl-4-(3,4,5-trimethyl-pyrazol-1-yl)-benzoic acid (76) (100 mg, 0.30 mmol, 1.0 eq.), TBTU (126 mg, 0.39 mmol, 1.3 eq.), triethylamine (0.23 mL, 1.65 mmol, 5.5 eq.) in dry DMF (5 mL) was stirred at room temperature for 5 minutes. Then 3-(1H-pyrazol-4-yl)-propylamine hydrochloride (6) (63 mg, 0.39 mmol, 1.3 eq.) was added. The resulted mixture was stirred at room temperature for 12 hours, diluted with water (100 mL), extracted with ethyl acetate (3×50 mL). The organic layers were combined, washed with an aqueous K₂CO₃ solution (30 mL), water (3×30 mL), dried over sodium sulfate and concentrated at reduced pressure. The obtained residue was purified by column chromatography (silica gel, DCM/MeOH) to give compound 77 (85 mg, 65%) as a beige solid.

Procedure for Synthesis of Compound 79.

A mixture of 3-iodo-4-imidazol-1-yl-benzoic acid methyl ester (71) (492 mg, 1.50 mmol, 1.0 eq.), 4-pyridylacetylene (206 mg, 2.00 mmol, 1.3 eq.), PdCl$_2$[PPh$_3$]$_2$ (53 mg, 0.075 mmol, 5 mol %), CuI (14 mg, 0.075 mmol, 5 mol %), triethylamine (0.5 mL) and MeCN (10 mL) was refluxed under argon atmosphere for 6 hours, cooled down to room temperature and concentrated at reduced pressure. The obtained residue was purified by column chromatography (silica gel, DCM/EtOH, 40:1) to give compound 79 (430 mg, 94%) as a brownish-grey solid. APCI-MS (m/z (intensity)): 304.07 ([M+H]$^+$, 100%).

Procedure for Synthesis of Compound 80.

To a solution of compound 79 (430 mg, 1.42 mmol) in MeOH (30 mL) was added a solution of NaOH (200 mg, 5.00 mmol) in water (10 mL). The reaction mixture was stirred at 50° C. for 1 hour, cooled down to room temperature, acidified with concentrated aqueous HCl solution to reach pH 4-5. The formed precipitate was collected by filtration, washed with cold water and diethyl ether and dried to give compound 80 (349 mg, 86%) as a grey solid. APCI-MS (m/z (intensity)): 290.09 ([M+H]$^+$, 100%). APCI-MS (m/z (intensity)): 288.04 ([M−H]$^-$, 100%).

Procedure for Synthesis of Compound 81.

Compound 81 was prepared according to Procedure for synthesis of compound 74 using compound 80 (150 mg, 0.52 mmol, 1.0 eq.), TBTU (200 mg, 0.62 mmol, 1.2 eq.), triethylamine (0.36 mL, 2.60 mmol, 5.0 eq.) and 3-(1H-pyrazol-4-yl)-propylamine hydrochloride (6) (100 mg, 0.62 mmol, 1.2 eq.). Yield 91 mg, 44% as a white solid.

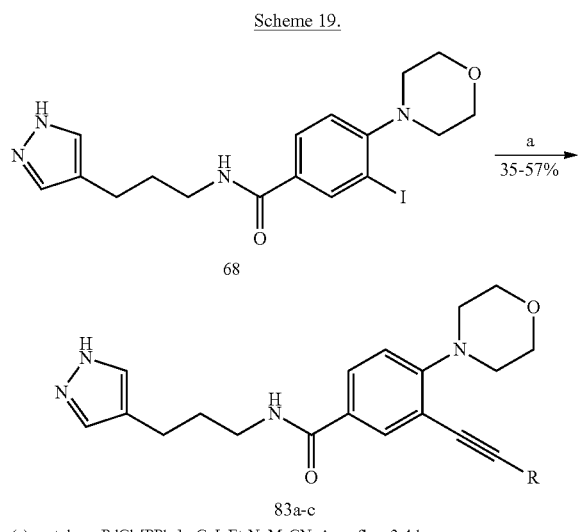

Scheme 19.

83a-c
(a) acetylene; PdCl$_2$[PPh$_3$]$_2$, CuI, Et$_3$N, MeCN, Ar, reflux, 3-4 h

TABLE 13

| R- | Product compound | ASE code | TH code | Yield (%) |
|---|---|---|---|---|
| 1    4-Py— | 83a | ASE 51126871 | TH-03631-1 | 57 |

TABLE 13-continued

| | R- | Product compound | ASE code | TH code | Yield (%) |
|---|---|---|---|---|---|
| 2 | [pyridyl-Cl] | 83b | ASE 51130785 | TH-03655-1 | 36 |
| 3 | [pyridyl-F] | 83c | ASE 51126873 | TH-03633-1 | 35 |

Procedure for Synthesis of Compounds 83a-c.

Compounds 83a-c were prepared according to Procedure for synthesis of compound 69 using the corresponding acetylenes. Compound 83a: yield 85 mg, 57% as a brownish solid. Compound 83b: yield 65 mg, 36% as a brownish solid. Compound 83c: yield 60 mg, 35% as a brownish solid.

Scheme 20.

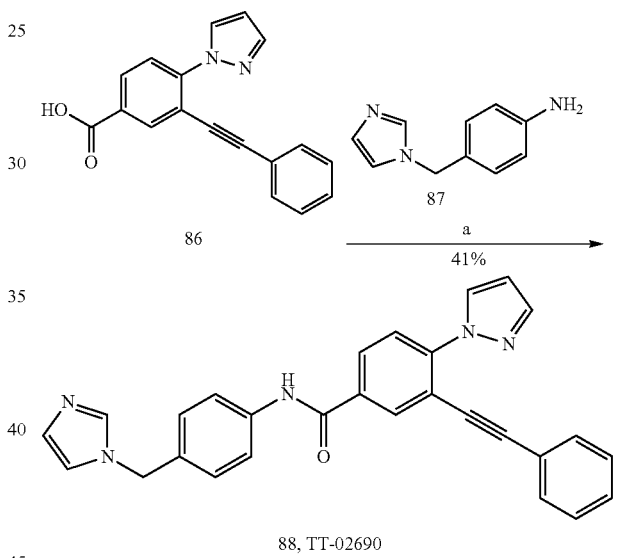

88, TT-02690

(a) TBTU, Et$_3$N, DCM, RT, 20 h

Procedure for Synthesis of Compound 88.

A mixture of compound 86 (128 mg, 0.44 mmol, 1.00 eq.), 4-imidazol-1-ylmethyl-phenylamine (87) (92 mg, 0.53 mmol, 1.2 eq.), TBTU (241 mg, 0.75 mmol, 1.7 eq.), triethylamine (0.2 mL, 1.44 mmol, 3.3 eq.), DCM (3 mL) and THF (5 mL) was stirred at room temperature for 4 hours, diluted with equal volume of saturated aqueous NaHCO$_3$ solution and stirred at room temperature for 2 hours. The resulting mixture was extracted with DCM. The organic phase was dried over sodium sulfate and concentrated at reduced pressure. The obtained residue was purified by column chromatography (silica gel, ethyl acetate/MeOH, 20:1) giving compound 88 (80 mg, 41%) as a yellowish solid.

To a solution of compound 7c (173 mg, 0.42 mmol, 1.0 eq.) in dry DMF (2 mL) were added K$_2$CO$_3$ (87 mg, 0.63 mmol, 1.5 eq.) and MeI (239 mg, 1.68 mmol, 4.0 eq.). The mixture was stirred at 40° C. for 24 hours, diluted with water (100 mL) and extracted with ethyl acetate (3×50 mL). The organic layers were combined, washed with water (3×30 mL), dried over sodium sulfate and concentrated at reduced pressure. The obtained residue was purified by column chromatography (silica gel, DCM/ethyl acetate) to give compound 89 (55 mg, 31%) as a yellowish solid.

Scheme 21.

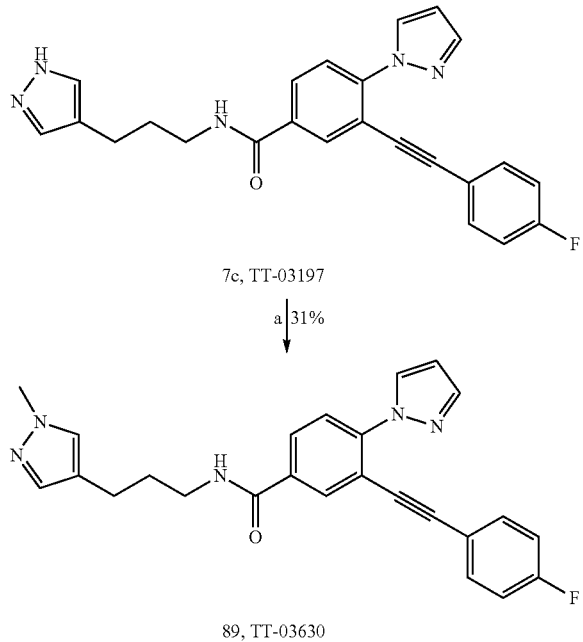

7c, TT-03197 a | 31%

89, TT-03630

(a) MeI, K₂CO₃, DMF, 40° C., 24 h

Experimental part: General experimental methods. LCMS. The LC/MS analysis was done at Surveyor MSQ (Thermo Fisher Scientific) with APCI ionization. 1. Type of HPLC column: Phenomenex Onyx Monolithic C18; 25×4.6 mm; Part No: CHO-7645. 2. Solvent for samples dissolution: 50% DMSO, 50% acetonitrile. 3. Flow rate: 1.5 mL/min; column temperature 25° C. 4. Mobile phase: A=0.1% solution of formic acid in water, B=0.1% solution of formic acid in acetonitrile. 5. Gradient:

| time, min. | A % | B % |
|---|---|---|
| 0.0 | 100 | 0 |
| 0.1 | 100 | 0 |
| 2.1 | 5 | 95 |
| 2.5 | 5 | 95 |
| 2.6 | 100 | 0 |
| 4.0 | 100 | 0 |

6. Detection: diode array (PDA), 200-800 nm; photodiode array detector. Detection was carried out in the full ultraviolet-visible range from 200 to 800 nm. APCI (+ or/and − ions)—atmospheric pressure chemical ionization ELSD (PL-ELS 2100). 7. Total run time of the method: 4.5 min. 8. Injection volume: 2 μL.

NMR: The ¹H NMR spectra were recorded on a MERCURY plus 400 MHz spectrometer (Varian). Chemical shift values are given in ppm relative to tetramethylsilane (TMS), with the residual solvent proton resonance as internal standard.

HPLC: The HPLC analysis was done at Agilent 1100 instrument. 1. Type of HPLC column: Onyx Monolithic C18, 100×4.6 mm. 2. Flow rate: 1 mL/min; column temperature—ambient. 3. Mobile phase: A=0.1% TFA in water, B=0.1% TFA in acetonitrile.

List of abbreviations: Ac—acetyl, MeCO, APCI—atmospheric-pressure chemical ionization, aq.—aqueous, Ar—aryl or argon, atm—atmosphere(s), brs—broad singlet, Bu—butyl, conc.—concentrated, d—doublet, DABCO—1,4-diazabicyclo[2.2.2]octane, DCM—dichloromethane, dd—doublet of doublets, DIPEA—diisopropylethylamine, DMF—dimethylformamide, DMSO—dimethylsulfoxide, dppf—1,1'-bis(diphenylphosphino)ferrocene, ELSD—evaporative light scattering detector, Et—ethyl, eq.—equivalent, h—hour(s), HPLC—high-performance liquid chromatography, i-—iso-, i-Pr—i-propyl, m—multiplet, Me—methyl, MeCN—acetonitrile, MHz—megahertz, n-—normal-, n-Bu—n-butyl, min—minute(s), MS—mass-spectrometry, MWI—microwave irradiation, NBS—N-bromosuccinimide, NMR—Nuclear magnetic resonance, PDA—photodiode array, Ph—phenyl, Pr—propyl, q—quartet, Ra—Ni—Raney-nickel, RT—room temperature, s—singlet, t—triplet, t-—tert-, TBTU—N,N,N',N'-tetramethyl-O-(benzotriazol-1-yl)uronium tetrafluoroborate, t-Bu—tert-butyl, THF—tetrahydrofuran, TMS (tms)—trimethylsilyl, UV—ultraviolet.

Example 3

This example shows a table of compounds of the present disclosure and their activity towards two different cell lines (i.e., MV4-11 and U-397). The IC50 is divided into 5 categories: A<1 μM, B 1-5 μM, C 5-10 μM, D 10-20 μM, and E>20 μM.

| Compound ID | MV4-11 IC50, uM | U-937 IC50, uM |
|---|---|---|
| TT-01901 | A | A |
| TT-01902 | D | C |
| TT-02683 | A | A |
| TT-02684 | A | A |
| TT-02686 | C | D |
| TT-02689 | B | B |
| TT-02690 | C | D |
| TT-02691 | D | C |
| TT-02692 | E | A |
| TT-02694 | E | A |
| TT-02695 | A | A |
| TT-02707 | E | A |
| TT-02709 | E | A |
| TT-02713 | E | A |
| TT-02715 | A | A |
| TT-02717 | A | A |
| TT-02721 | E | E |
| TT-02731 | A | A |
| TT-02732 | A | A |
| TT-02741 | A | A |
| TT-02745 | A | A |
| TT-02746 | A | A |
| TT-02747 | D | C |
| TT-02749 | A | A |
| TT-02750 | A | A |
| TT-02751 | A | A |
| TT-02752 | C | D |
| TT-02760 | D | D |
| TT-02793 | E | C |
| TT-02796 | D | D |
| TT-02797 | E | E |
| TT-02800 | D | B |
| TT-02801 | D | B |
| TT-02802 | E | B |
| TT-02803 | E | A |
| TT-02804 | E | A |
| TT-02805 | B | A |

| Compound ID | MV4-11\|IC50, uM | U-937\|IC50, uM |
|---|---|---|
| TT-02927 | D | C |
| TT-02928 | D | C |
| TT-02929 | E | E |
| TT-02930 | E | E |
| TT-02931 | E | D |
| TT-02932 | E | E |
| TT-02933 | E | E |
| TT-02935 | D | C |
| TT-02936 | E | E |
| TT-02937 | E | E |
| TT-02938 | E | E |
| TT-02939 | E | C |
| TT-02940 | E | D |
| TT-02941 | D | C |
| TT-02942 | E | C |
| TT-02943 | D | B |
| TT-02944 | E | D |
| TT-02945 | E | E |
| TT-02946 | E | C |
| TT-02947 | E | A |
| TT-02948 | E | E |
| TT-02949 | D | C |
| TT-03071 | B | B |
| TT-03073 | E | E |
| TT-03196 | A | A |
| TT-03197 | A | A |
| TT-03198 | A | A |
| TT-03201 | A | A |
| TT-03203 | A | A |
| TT-03211 | A | A |
| TT-03217 | A | A |
| TT-03221 | A | A |
| TT-03225 | A | A |
| TT-03230 | A | A |
| TT-03232 | A | A |
| TT-03233 | A | A |
| TT-03237 | E | E |
| TT-03242 | A | A |
| TT-03245 | A | A |
| TT-03246 | A | A |
| TT-03248 | A | A |
| TT-03252 | A | A |
| TT-03256 | A | A |
| TT-03261 | A | A |
| TT-03264 | A | A |
| TT-03303 | A | A |
| TT-03304 | A | A |
| TT-03305 | A | A |
| TT-03306 | A | A |
| TT-03308 | A | A |
| TT-03309 | A | A |
| TT-03311 | A | A |
| TT-03312 | A | A |
| TT-03321 | A | A |
| TT-03322 | A | A |
| TT-03323 | A | A |
| TT-03324 | B | B |
| TT-03326 | A | A |
| TT-03327 | A | A |
| TT-03328 | A | A |
| TT-03330 | A | A |
| TT-03331 | A | A |
| TT-03332 | A | A |
| TT-03334 | A | A |
| TT-03337 | D | E |
| TT-03346 | C | E |
| TT-03351 | C | C |
| TT-03354 | A | A |
| TT-03355 | A | A |
| TT-03357 | A | A |
| TT-03359 | A | A |
| TT-03364 | B | B |
| TT-03569 | A | A |
| TT-03569 | A | A |
| TT-03574 | C | C |
| TT-03582 | A | A |
| TT-03585 | A | A |
| TT-03586 | A | A |
| TT-03587 | A | A |
| TT-03588 | A | A |
| TT-03588 | A | A |
| TT-03589 | A | A |
| TT-03590 | A | A |
| TT-03591 | A | A |
| TT-03592 | A | A |
| TT-03594 | A | A |
| TT-03595 | A | A |
| TT-03596 | A | A |
| TT-03596 | A | A |
| TT-03597 | A | A |
| TT-03598 | A | A |
| TT-03599 | A | A |
| TT-03602 | A | A |
| TT-03611 | A | A |
| TT-03620 | A | A |
| TT-03623 | A | A |
| TT-03625 | A | A |
| TT-03626 | A | A |
| TT-03627 | A | A |
| TT-03630 | A | A |
| TT-03631 | A | A |
| TT-03633 | A | A |
| TT-03634 | A | A |
| TT-03655 | A | A |
| TT-03669 | A | A |
| TT-03670 | A | A |
| TT-03671 | A | A |
| TT-03676 | A | A |
| TT-03717 | A | A |
| TT-03718 | A | A |
| TT-03720 | A | A |
| TT-03725 | A | A |
| TT-03727 | A | A |
| TT-03732 | A | B |
| TT-03733 | A | B |
| TT-03749 | B | D |
| TT-03750 | A | A |
| TT-03751 | A | A |
| TT-03752 | A | A |
| TT-03753 | A | A |
| TT-03754 | A | A |
| TT-03756 | A | |
| TT-03761 | A | |
| TT-03762 | A | |
| TT-03765 | A | A |
| TT-03767 | A | |
| TT-03768 | A | |
| TT-03772 | A | |
| TT-03773 | A | A |
| TT-03774 | A | B |
| TT-03782 | A | A |
| TT-03783 | A | A |

Example 4

This example provides data related to the efficacy of the instant compounds in xenograft models of human leukemia cells.

Efficacy of compounds was tested in two types of xenograft models of leukemia: subcutaneous (SC) (development of tumors after SC inoculation of cells) and systemic and disseminated (development of tumors on different organs after intravenous inoculation of cells). MV4-11 cells (ATCC CRL-9591) of acute myelomonocytic leukemia (AML) were used.

Treatment of SCID mice inoculated SC with MV4-11 cells with compounds TT-03197 and TT-03203 resulted in a dose-dependent reduction of tumor growth (FIGS. 1 and 2).

The maximum suppression of tumor growth (calculated using formula: STG %=(volume control-volume treated)/volume control*100) was 28% for mice treated with 10 mg/kg of TT-03197 and 55% for mice treated with 40 mg/kg of TT-03203 (FIG. 1). For TT-03203 the maximum STG was 27% for mice treated PO with 10 mg/kg of TT-03203 and 46% for mice treated with 25 mg/kg of TT-03203 (FIG. 2).

Systemic (disseminated) leukemia model was shown to be a more accurate representation of human disease. In this model leukemia cells either from patient of from cell lines are administered intravenously into mice and leukemia cells are engrafted into blood and blood-forming organs (bone marrow, thymus, spleen).

In systemic model of AML SCID mice were irradiated with 3 Gy and inoculated intravenously with MV4-11 cells 24 h after irradiation. Mice were treated with vehicle control, TT-01901 and TT-03586 during days 4-58 (FIG. 3). 30 days after cells implantation mice treated with vehicle were gradually becoming sick, scruffy and were losing weight. Necropsy performed on sick mice revealed multiple tumors on internal organs, enlargement of spleen and liver in some mice. Mice treated with compounds survived significantly longer. The ratio of survival of treated mice versus survival of control mice in percent (T/C) was calculated using formula: T/C %=average survival time for treated mice/average survival time for control mice*100. Increase in the survival (IS) was calculated using formula: IS=(average survival time of treated mice−average survival time of control mice)/average survival time of control mice*100. The survival of mice treated with TT-01901 was 135% and with TT-03586 148% of that for mice treated with vehicle. The corresponding increase in survival was 35% and 48%.

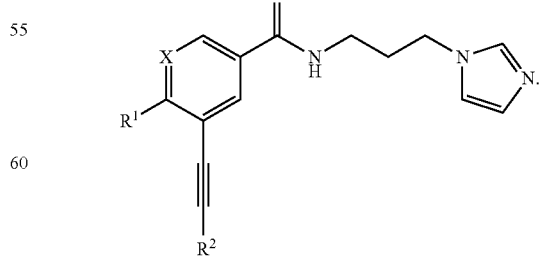

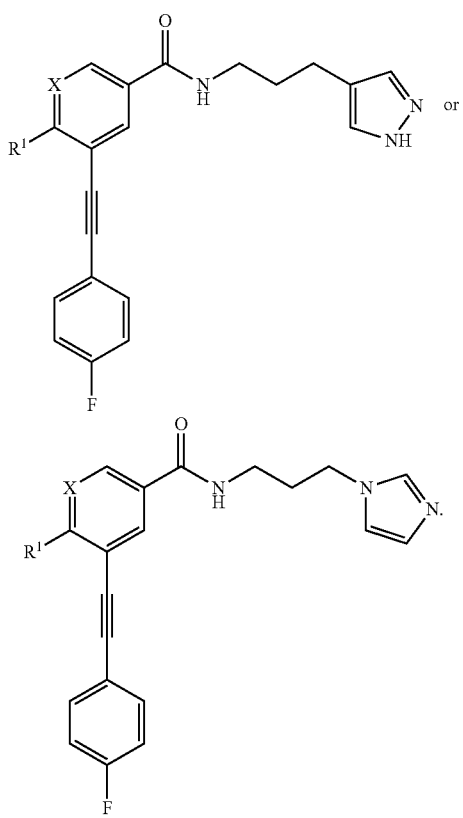
6. The compound of claim 1, wherein the compound has the following structure:
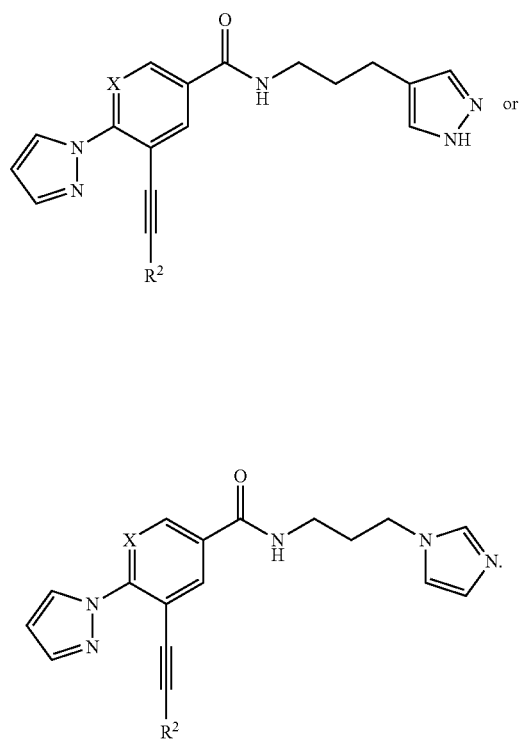
7. The compound of claim 1, wherein R¹ is
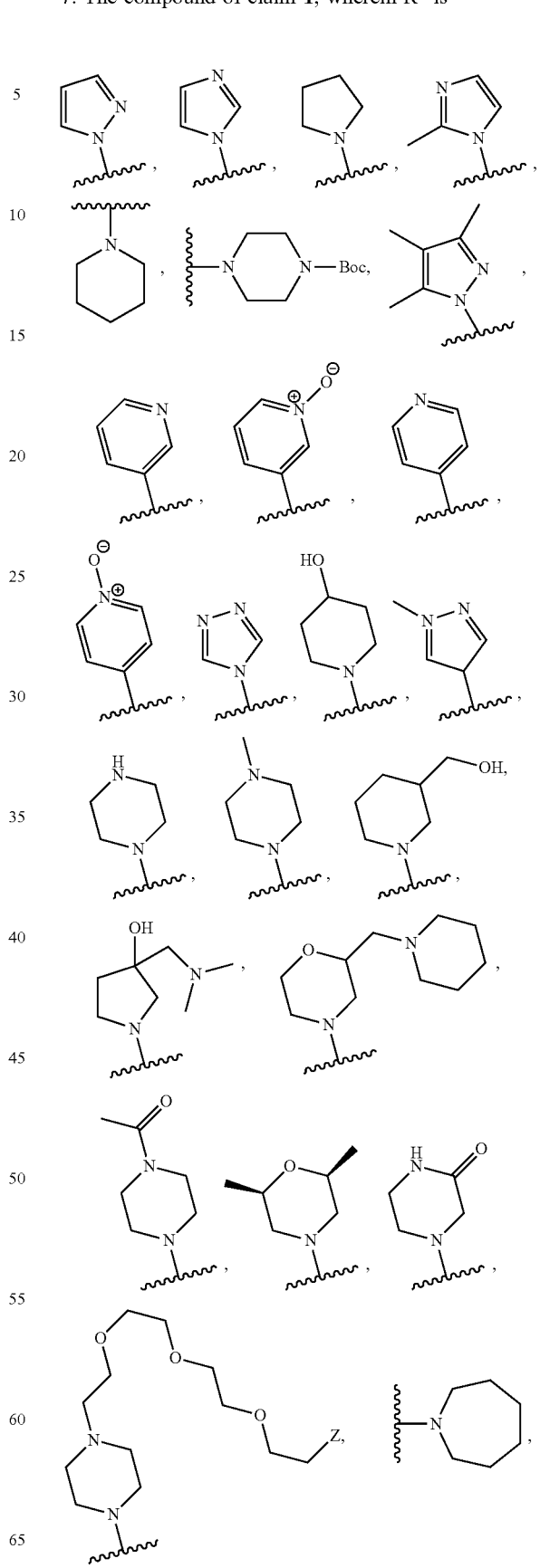

-continued
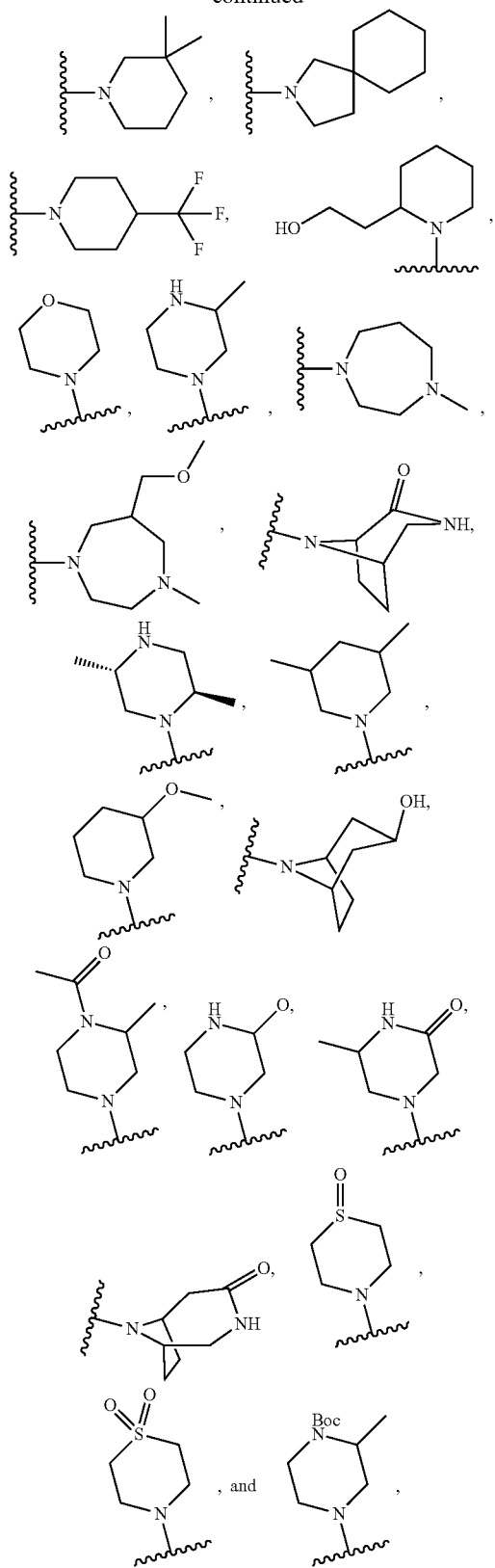
wherein Z is N(R⁶)₂ or OR⁶, where each $R^6$ is independently a hydrogen atom or substituted or unsubstituted $C_1$ to $C_6$ alkyl group.
8. The compound of claim 1, wherein $R^2$ is
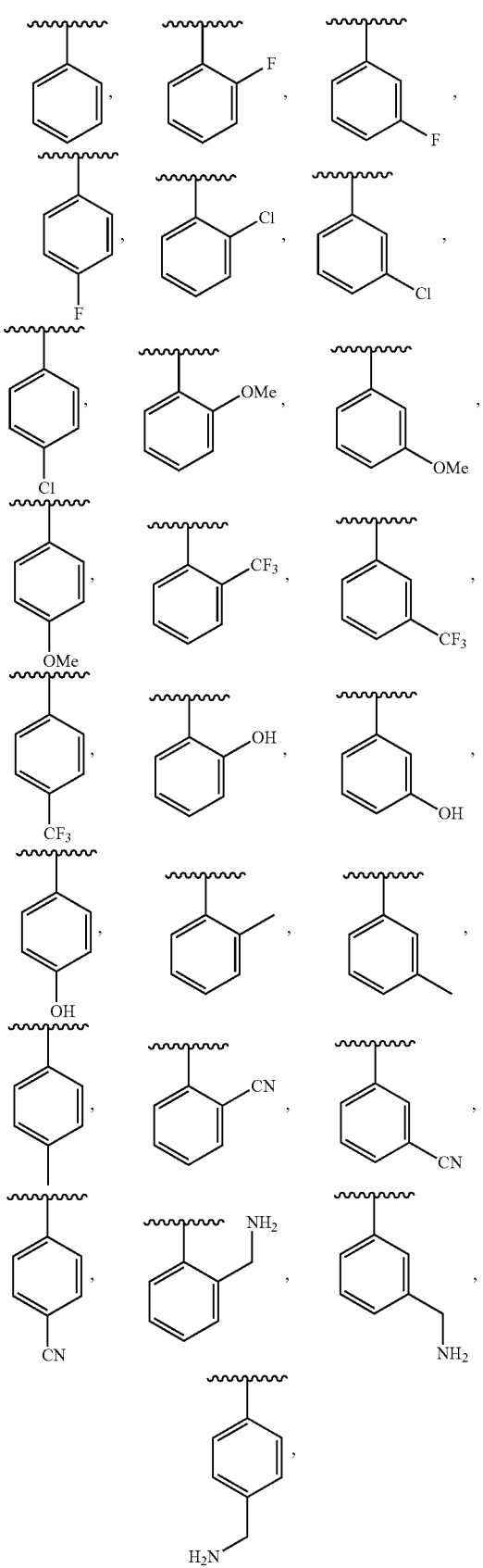

-continued
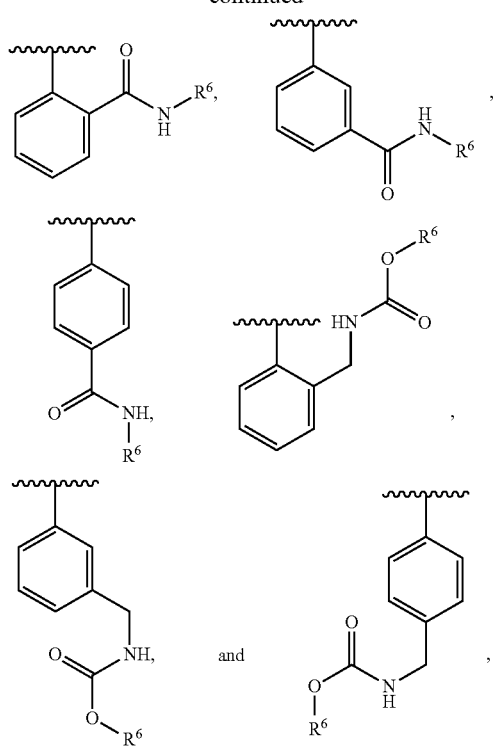
wherein each $R^6$ is independently a hydrogen atom or substituted or unsubstituted $C_1$ to $C_6$ alkyl group.
9. The compound of claim 1, wherein $R^3$ is selected from the following structures:
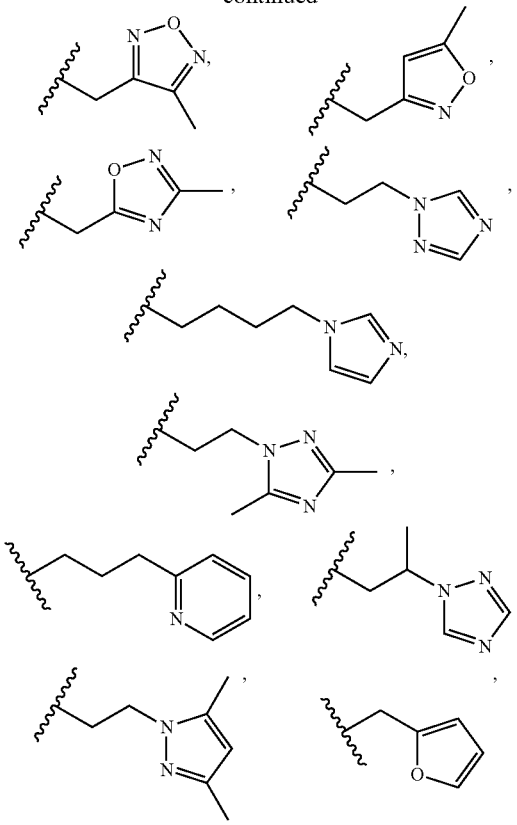
-continued
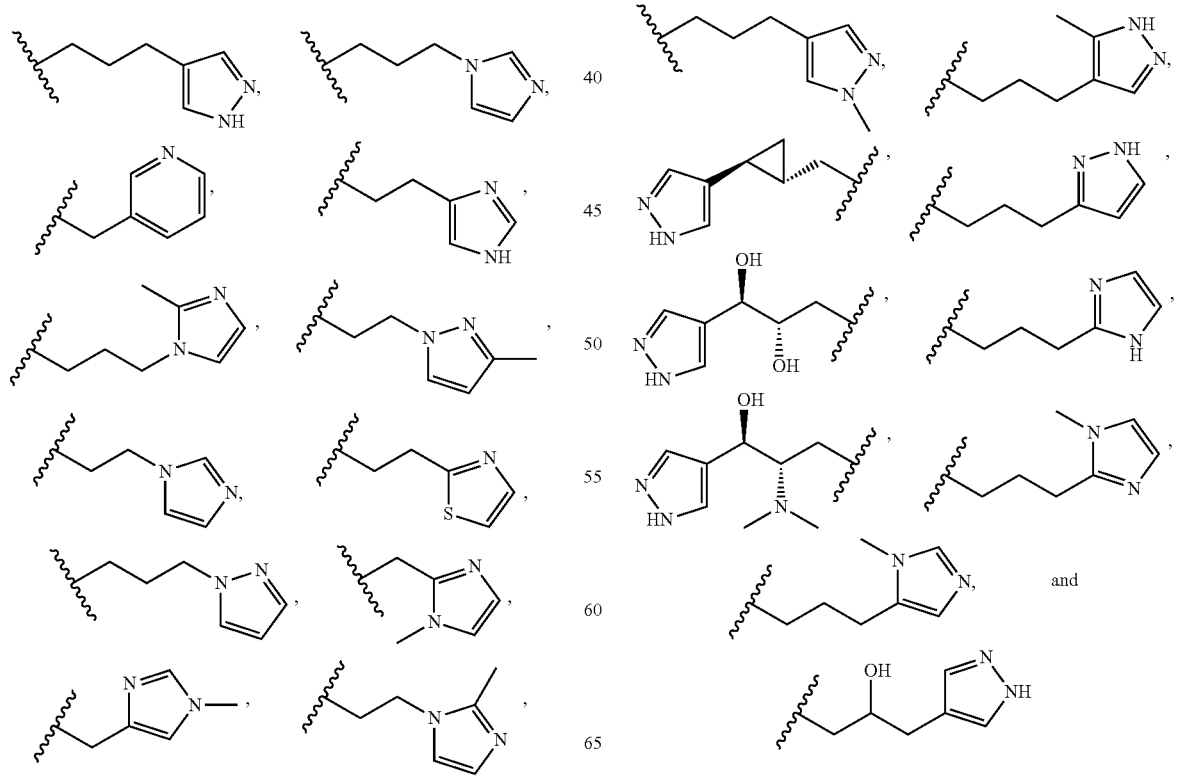

10. The compound of claim 1, wherein $R^1$ is a substituted or unsubstituted five to eight membered heterocyclic ring.
11. The compound of claim 10, wherein the unsubstituted five to eight membered heterocyclic ring comprises at least one nitrogen atom.
12. The compound of claim 1, wherein the compound is selected from the group consisting of:
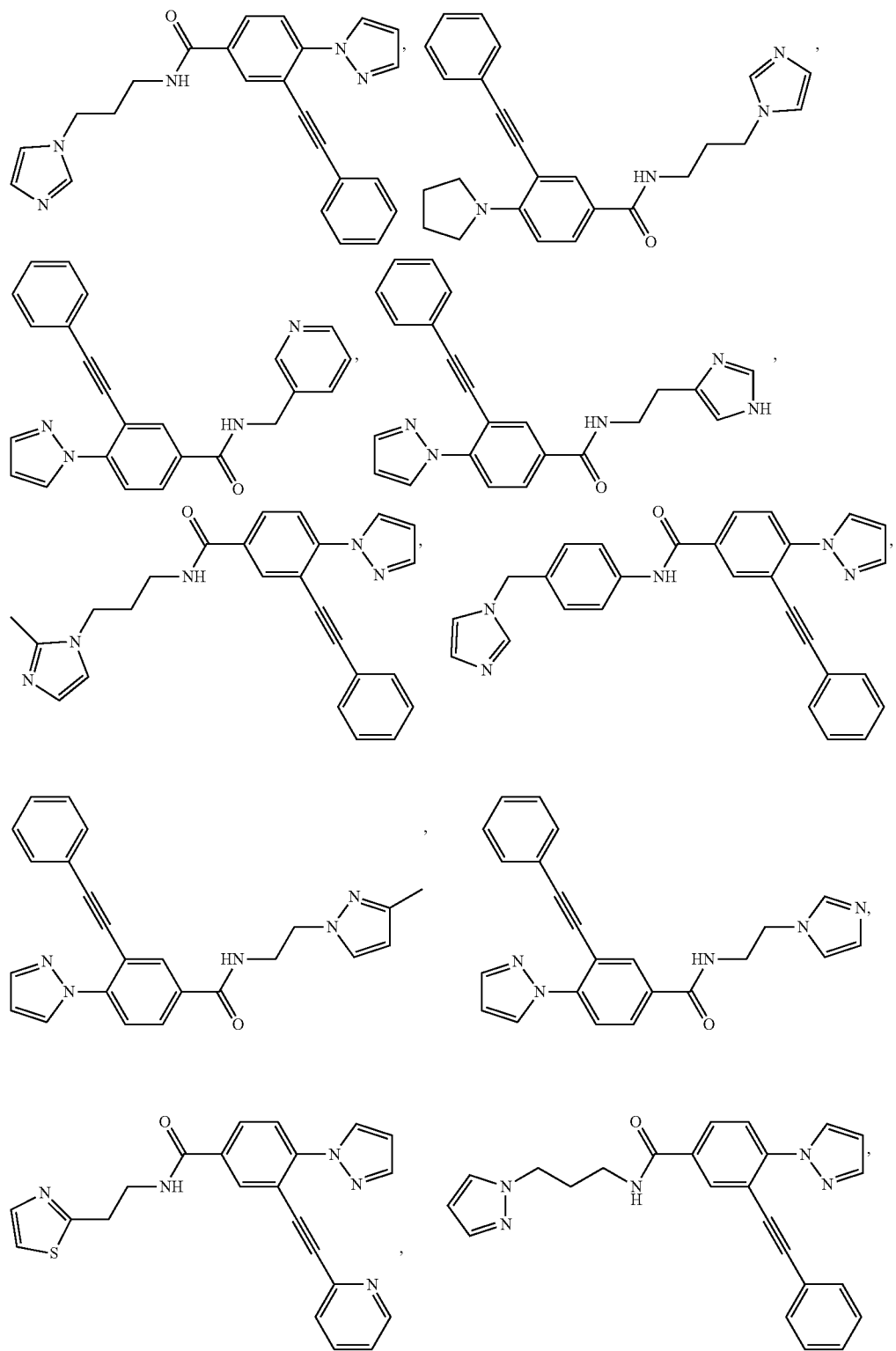

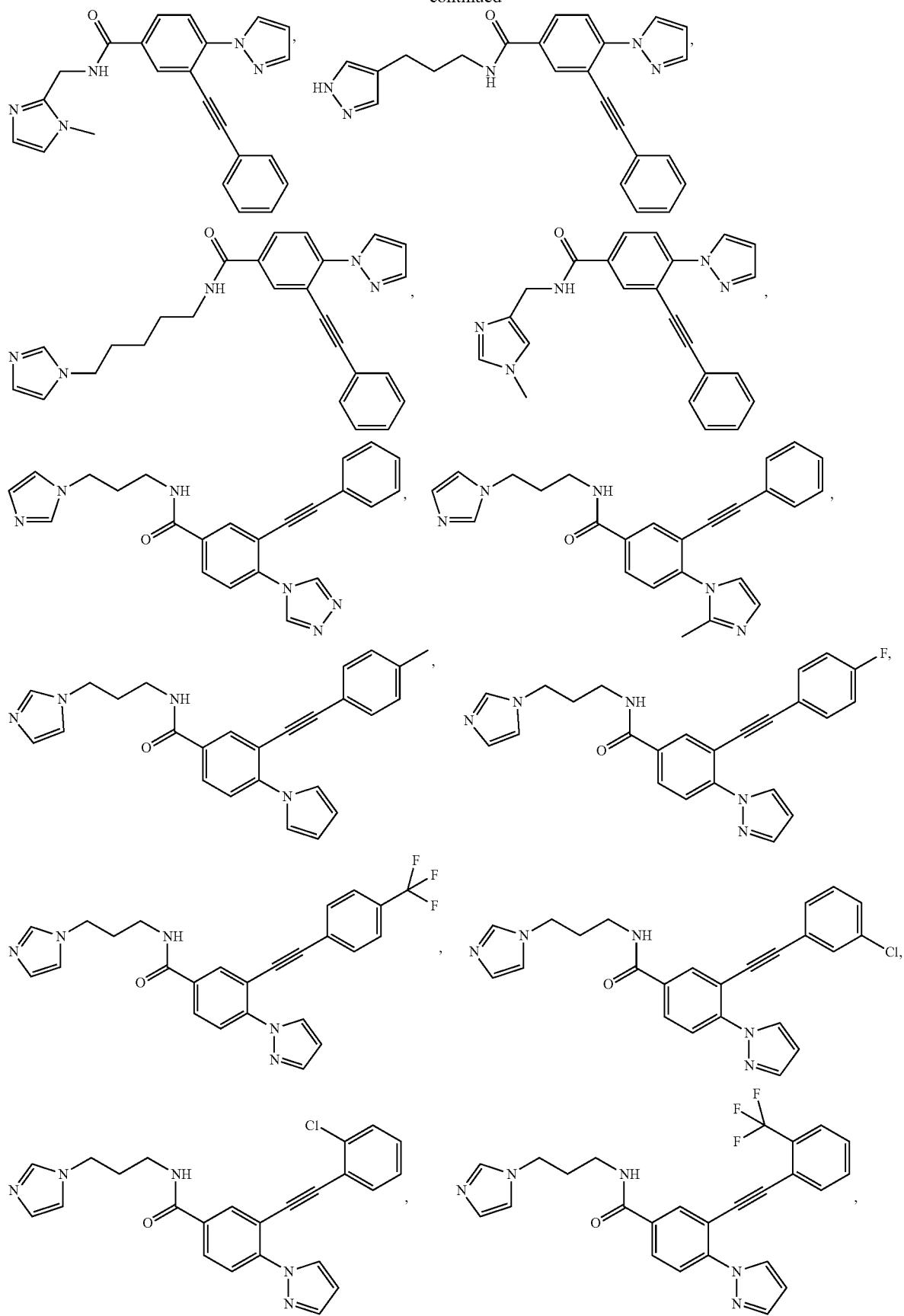

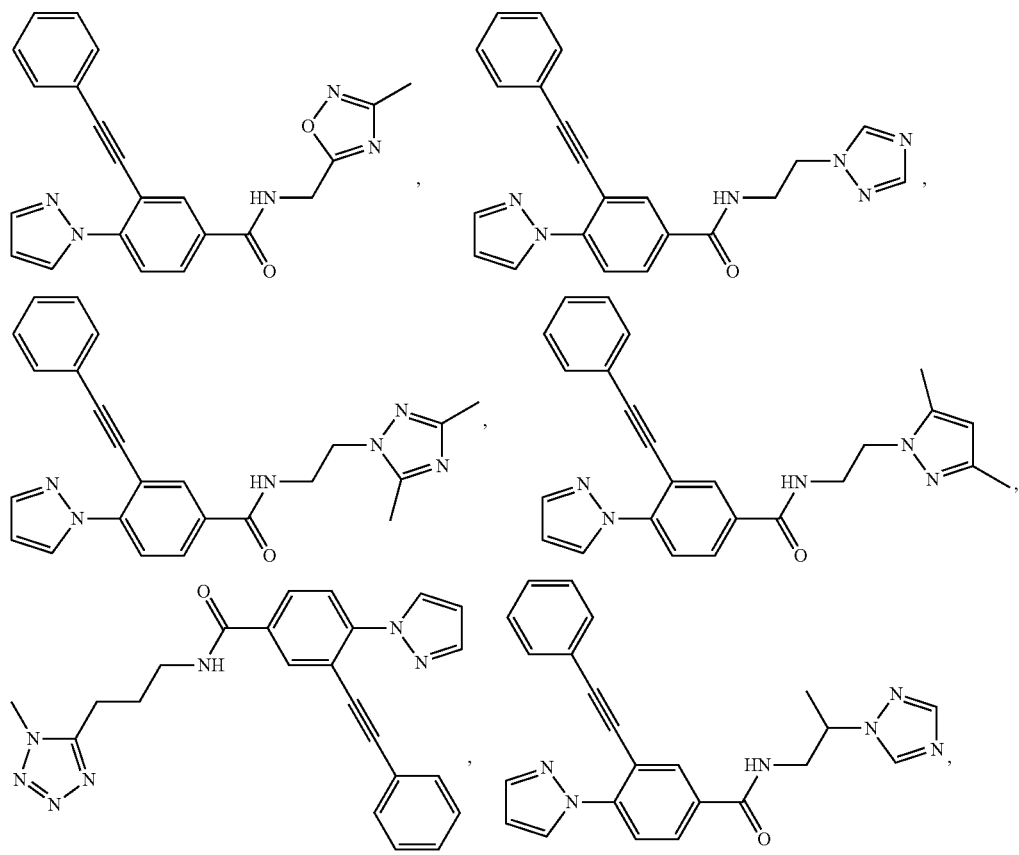
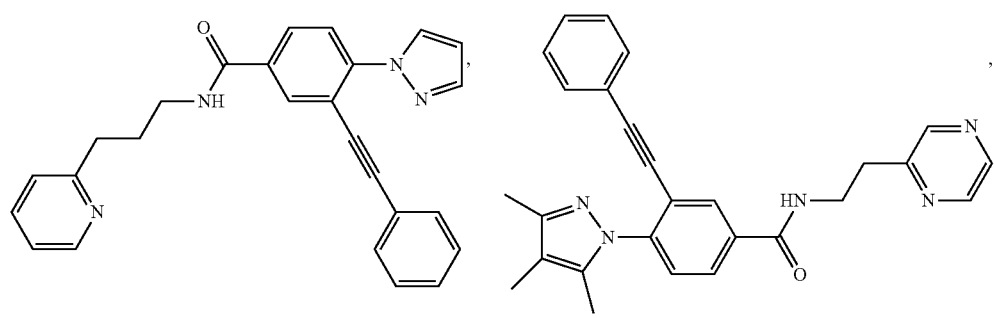
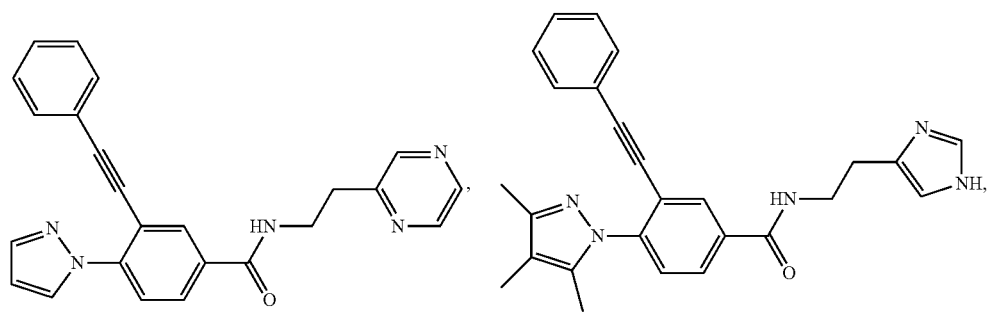

-continued
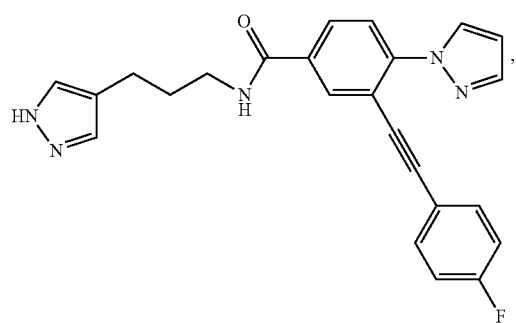 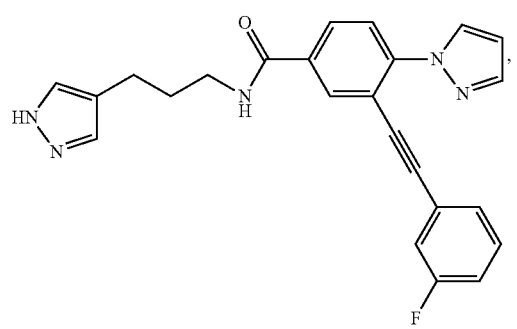
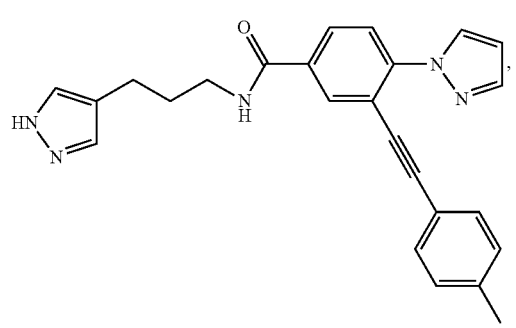 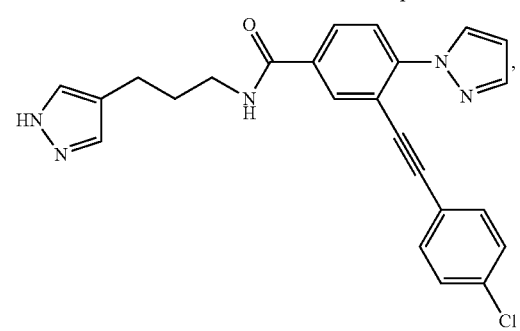
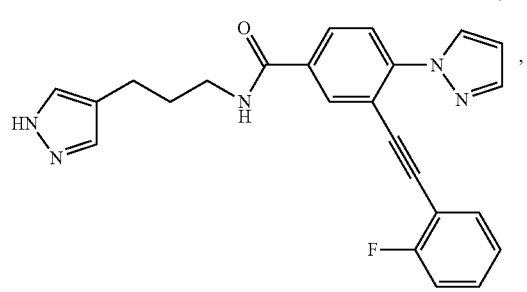 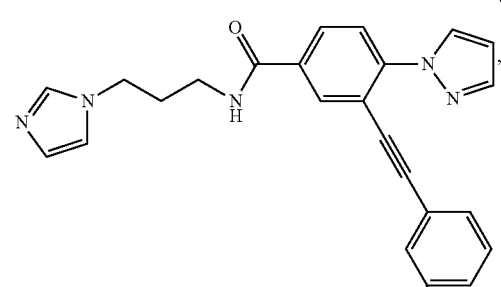
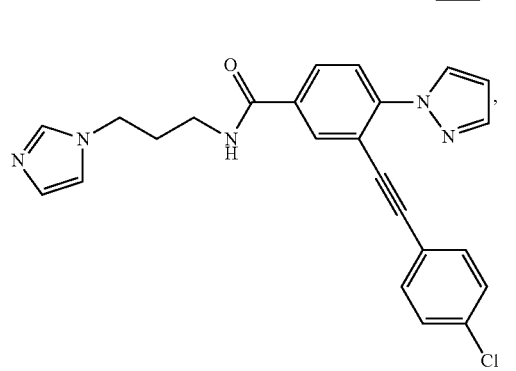 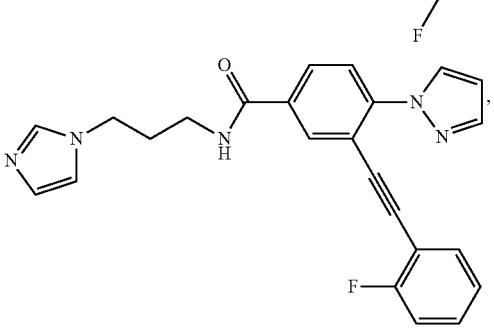
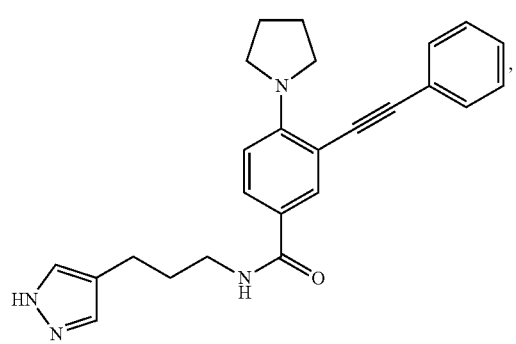 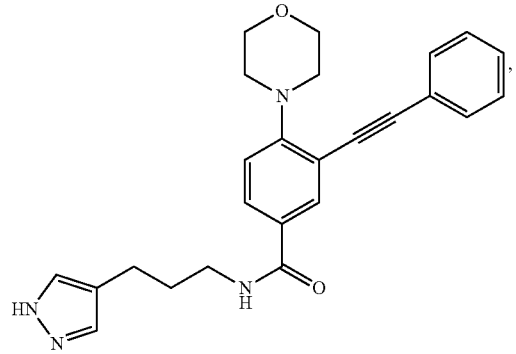

173 174
-continued
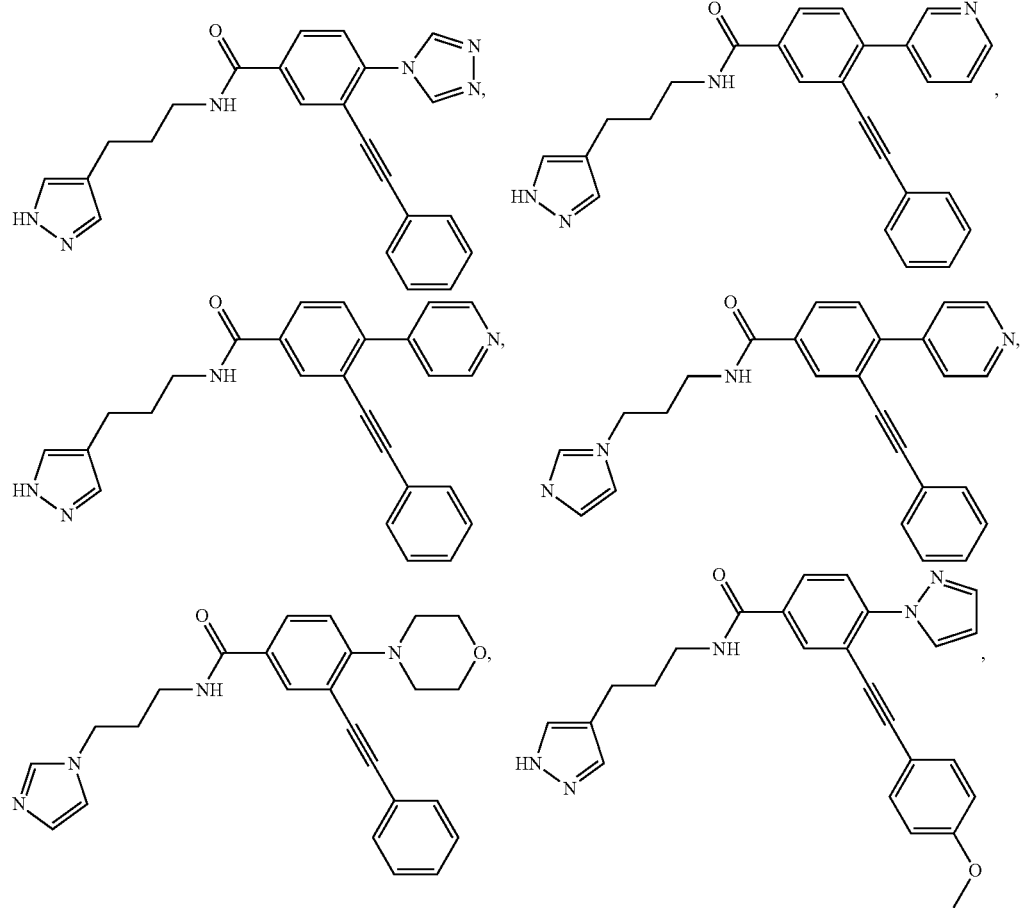
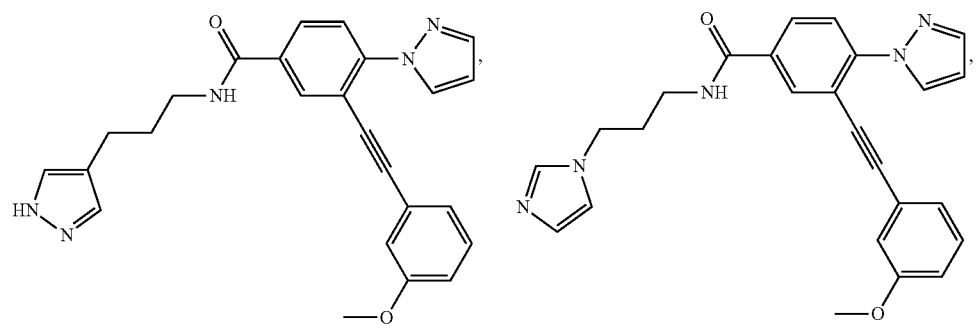
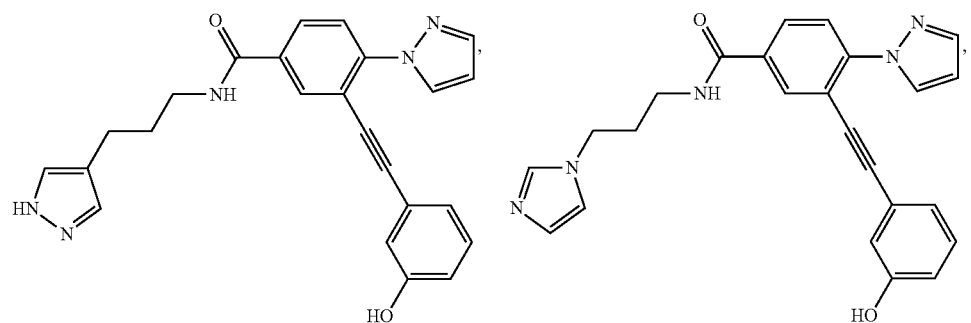

175 176
-continued
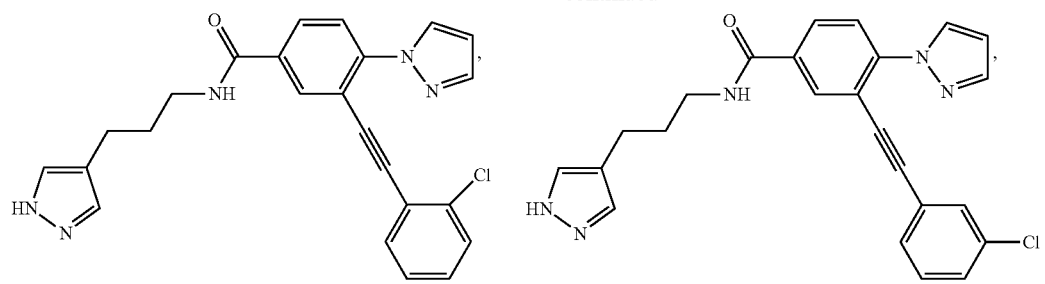
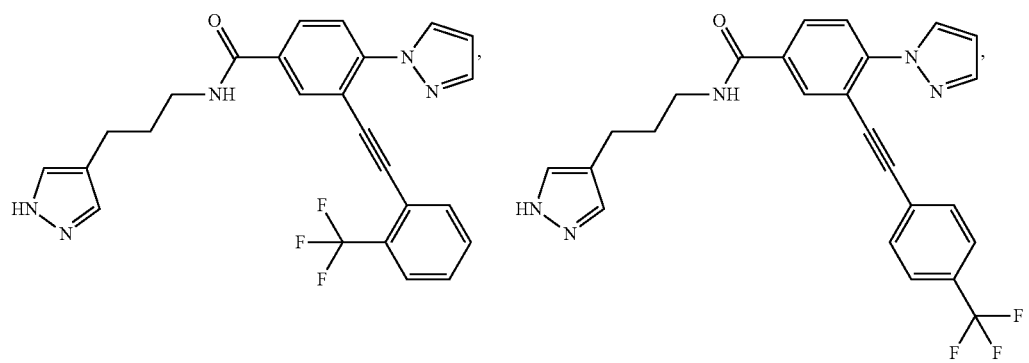
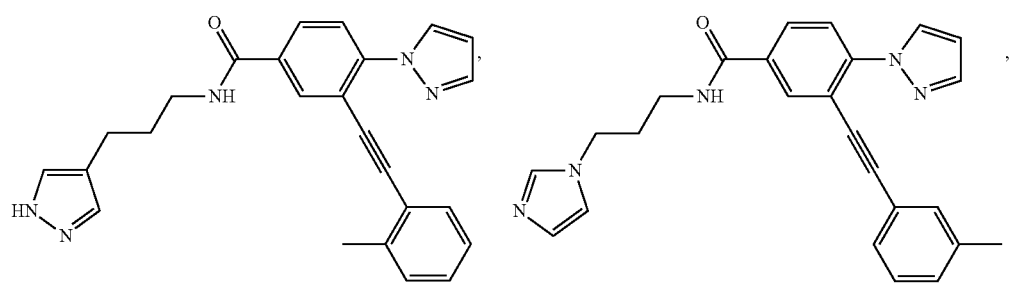
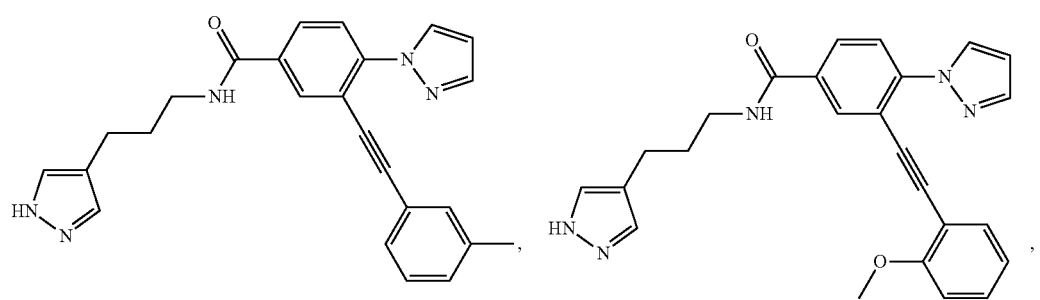
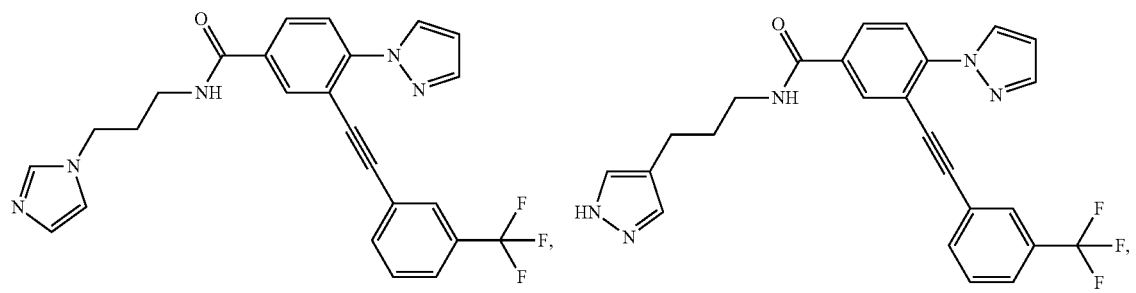

-continued
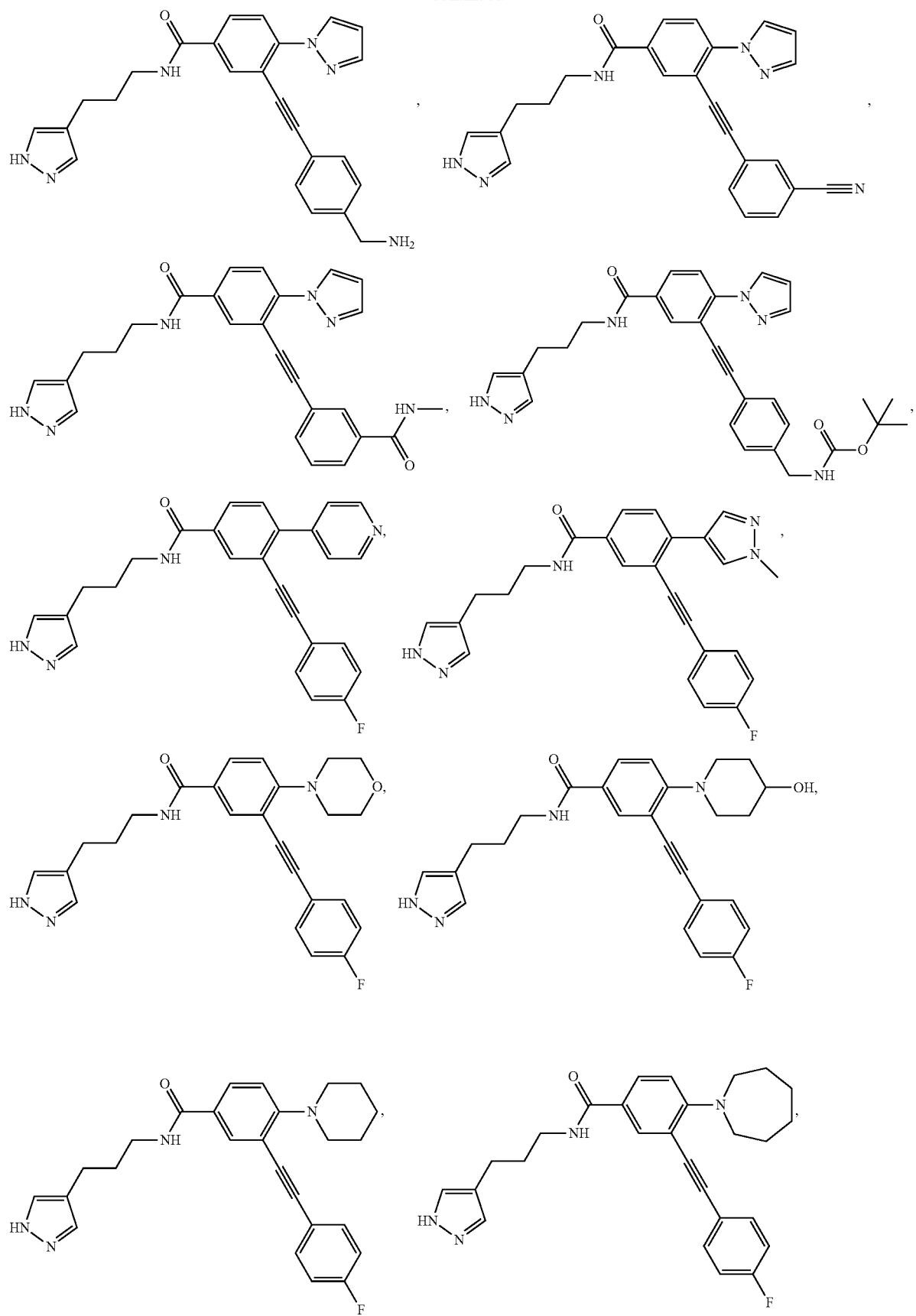

179 180
-continued
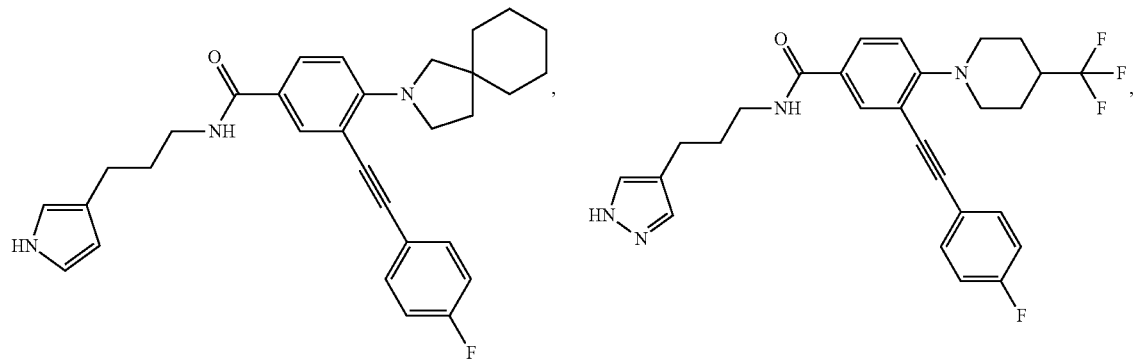
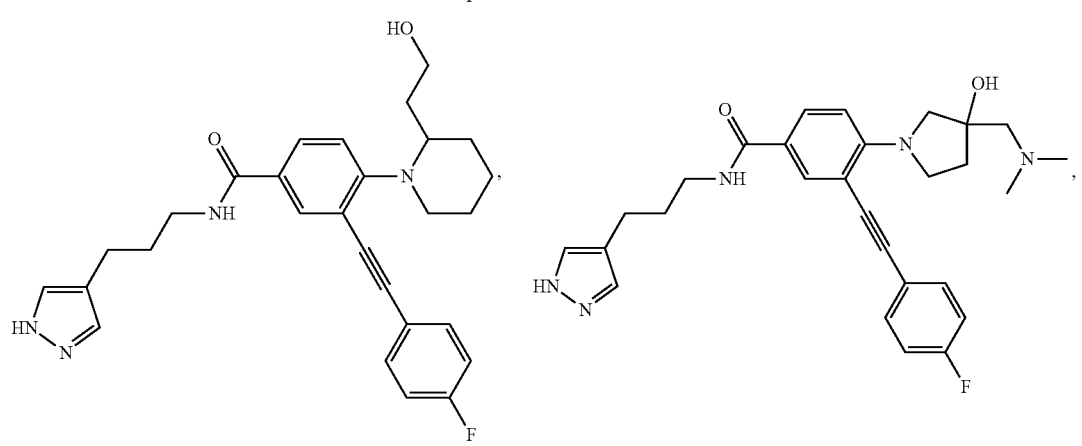
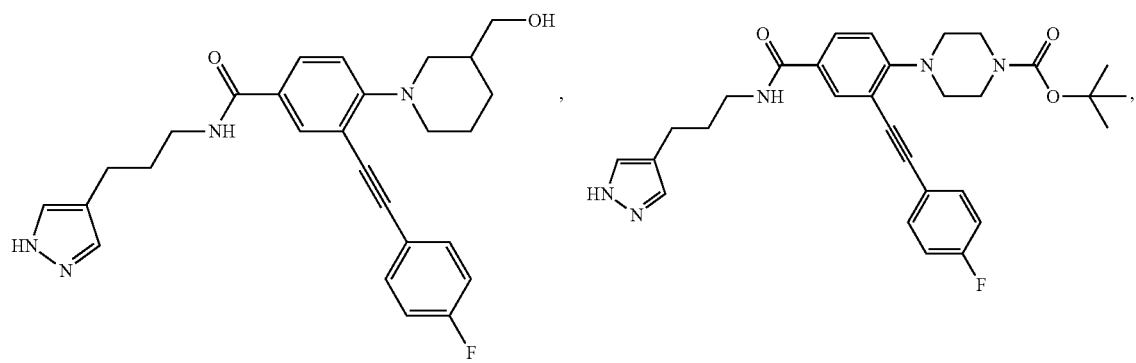
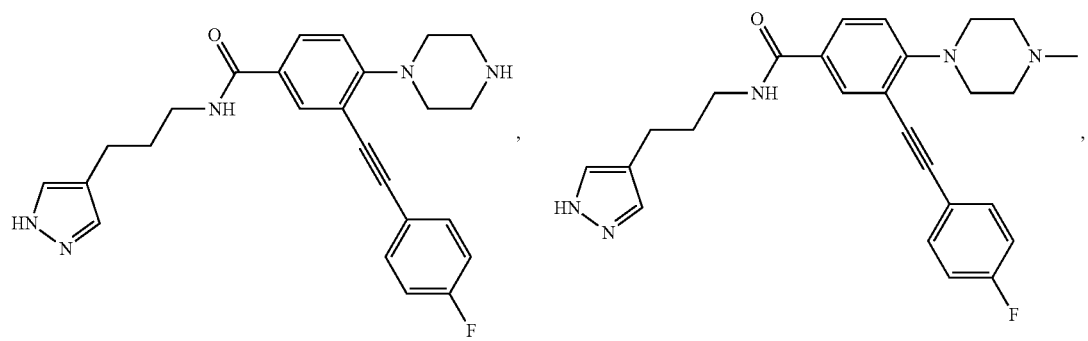

181 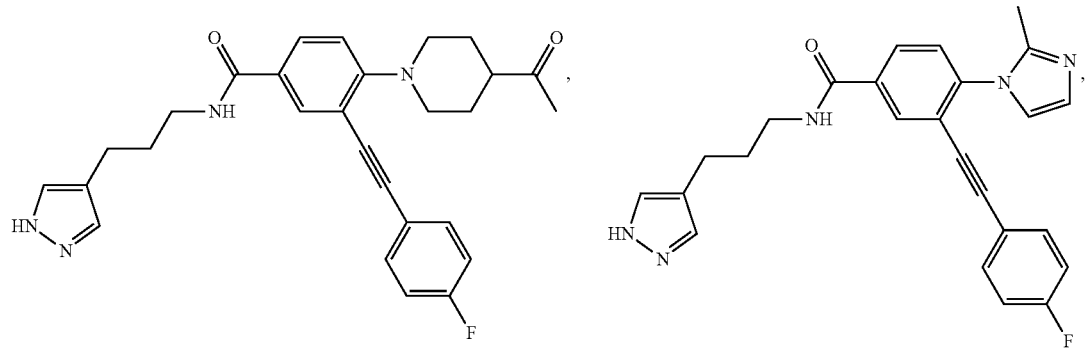 182
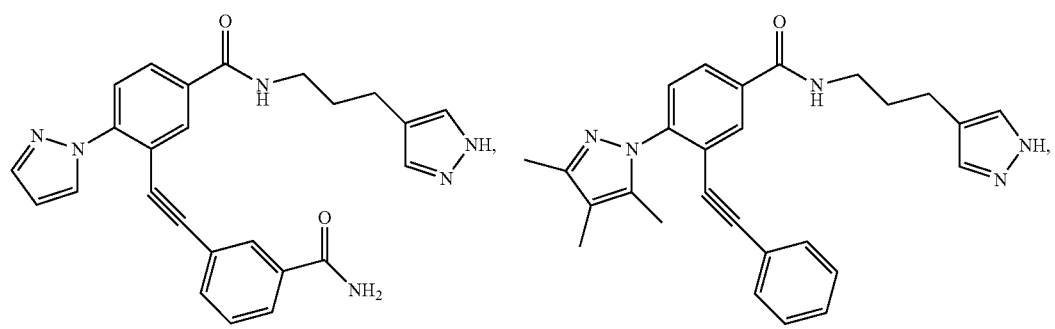
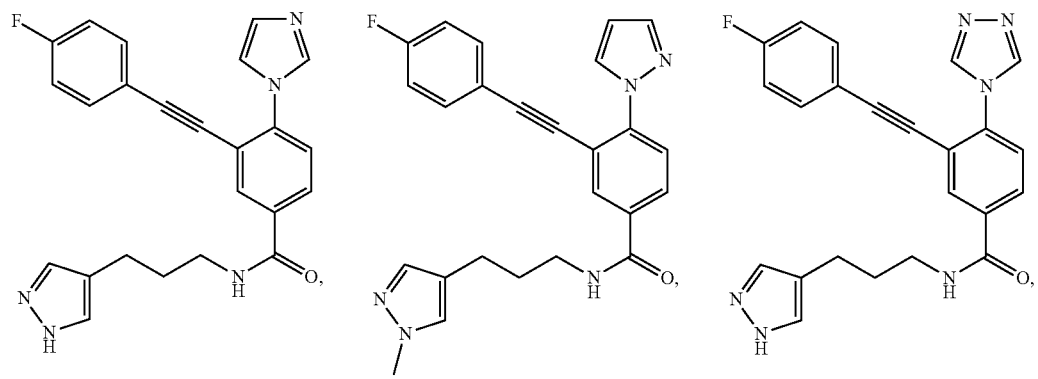
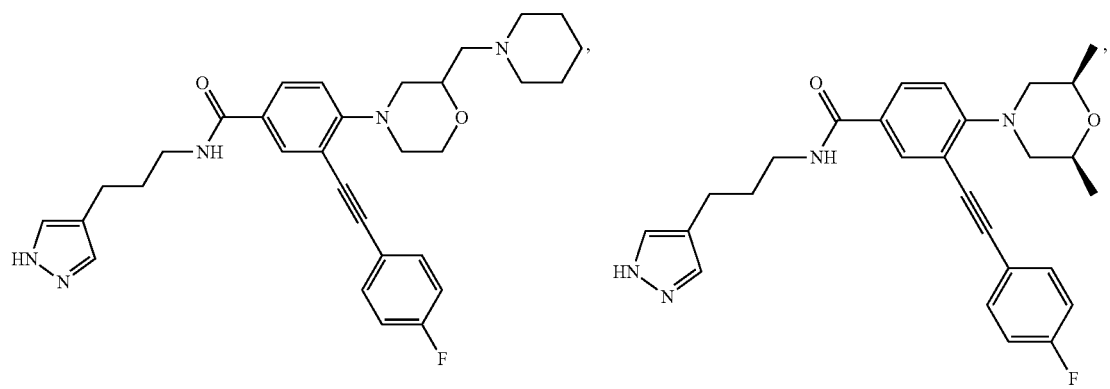

183 184
-continued
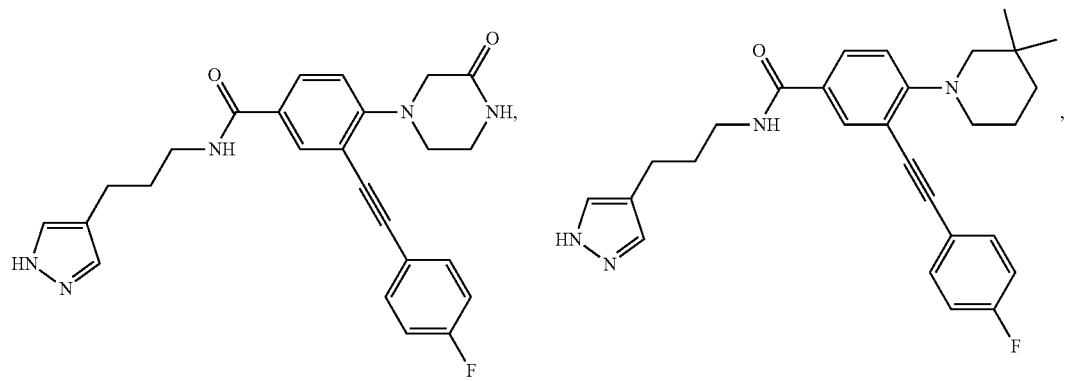
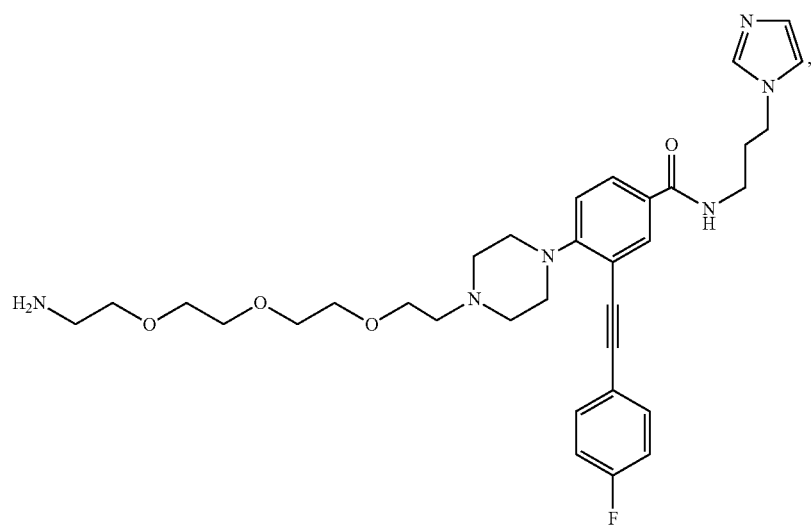
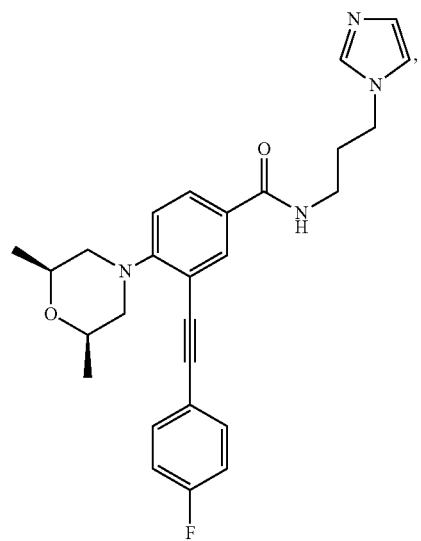

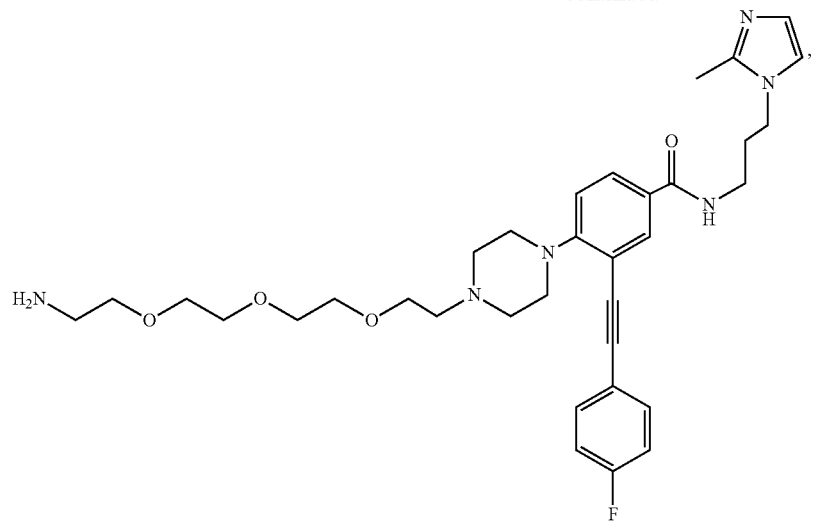
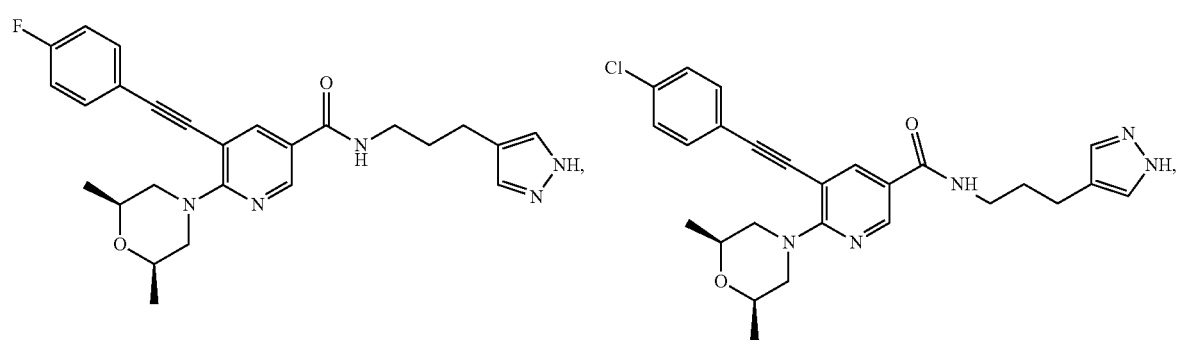
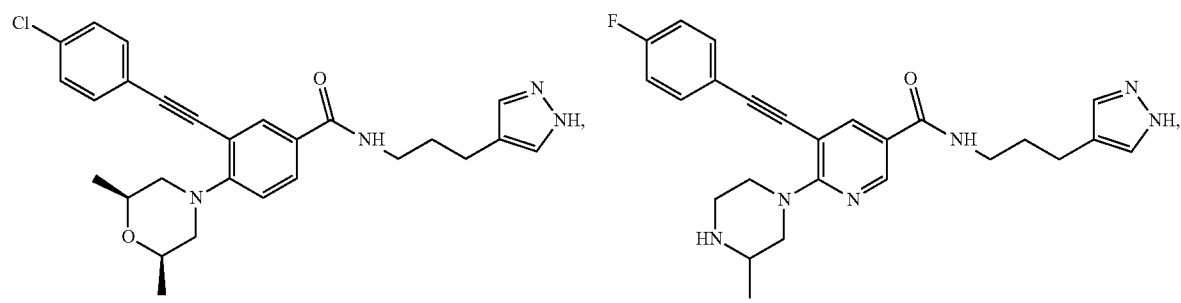
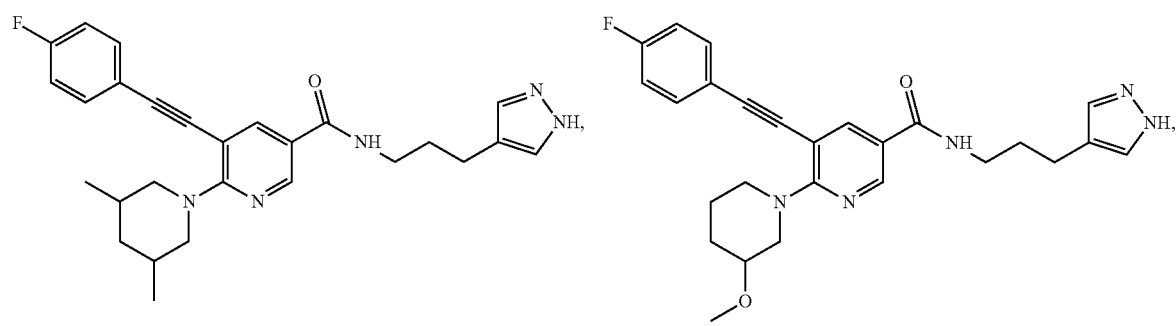

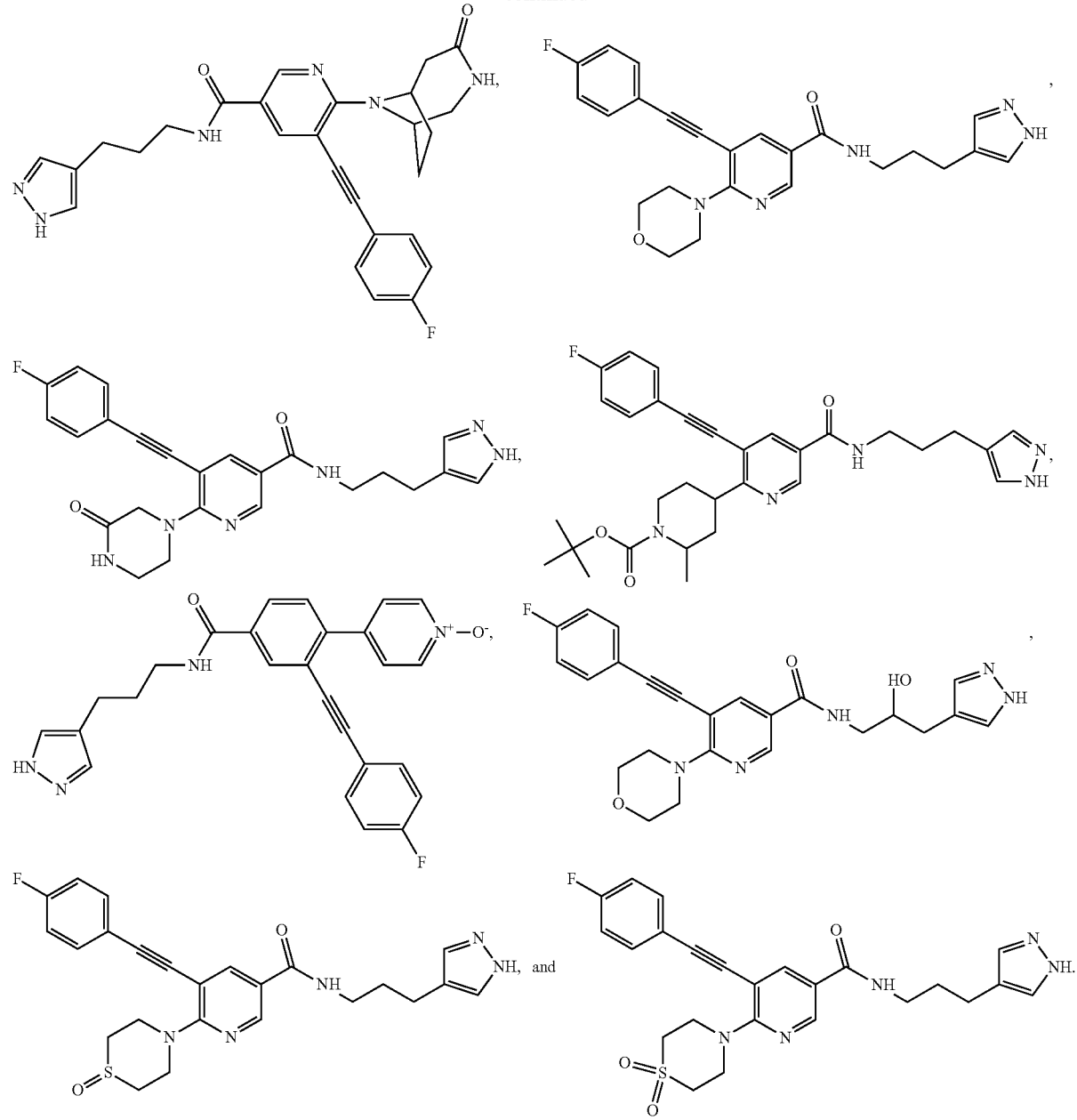

What is claimed is:

1. A compound having the following structure:

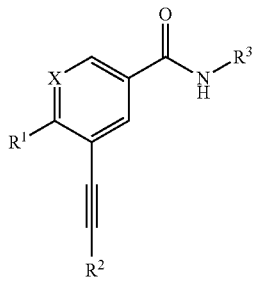

wherein X is a carbon atom or nitrogen atom, $R^1$ is selected from the group consisting of a substituted or unsubstituted five to eight membered heterocyclic ring and a five or six membered heteroaryl ring; $R^2$ is a substituted or unsubstituted phenyl ring; and $R^3$ is a substituted or unsubstituted $C_2$ to $C_8$ alkylheteroaryl group.

2. The compound of claim 1, wherein the compound has the following structure:

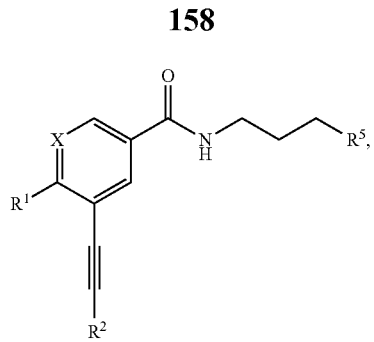

wherein $R^5$ is a $C_2$ to $C_8$ heteroaryl group.

3. The compound of claim 1, wherein the compound has the following structure:

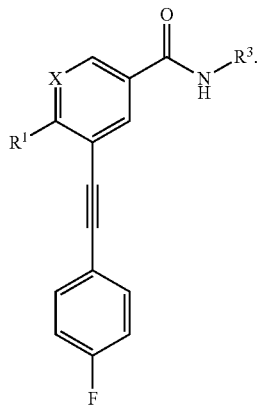

4. The compound of claim 1, wherein the compound has the following structure:

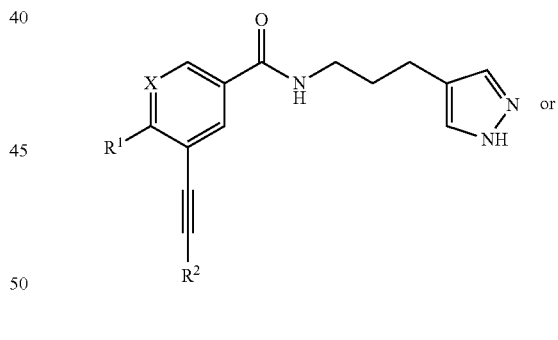

5. The compound of claim 1, wherein the compound has the following structure: